(12) United States Patent
Dadino et al.

(10) Patent No.: US 11,976,074 B1
(45) Date of Patent: May 7, 2024

(54) CRYSTALLINE SALTS OF LINSITINIB

(71) Applicant: Sling Therapeutics, Inc., Ann Arbor, MI (US)

(72) Inventors: Ronald Dadino, Ann Arbor, MI (US); Ryan Zeidan, Ann Arbor, MI (US)

(73) Assignee: SLING THERAPEUTICS, INC., Ann Arbor, MI (US)

( * ) Notice: Subject to any disclaimer, the term of this patent is extended or adjusted under 35 U.S.C. 154(b) by 0 days.

(21) Appl. No.: 18/341,620

(22) Filed: Jun. 26, 2023

Related U.S. Application Data

(60) Provisional application No. 63/509,248, filed on Jun. 20, 2023.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .......................... C07D 487/04; C07B 2200/13
See application file for complete search history.

(56) References Cited

U.S. PATENT DOCUMENTS

| 7,534,797 | B2 | 5/2009 | Arnold et al. |
| 8,101,613 | B2 | 1/2012 | Arnold et al. |
| 2013/0158264 | A1* | 6/2013 | Castelhano ........ A61K 31/4985 544/350 |

OTHER PUBLICATIONS

Barbesino et al., Future projections in thyroid eye disease, The Journal of Clinical Endocrinology & Metabolism, vol. 107, S47-S56, Aug. 8, 2022 (Year: 2022).*

* cited by examiner

*Primary Examiner* — Sarah Pihonak
*Assistant Examiner* — Padmaja S Rao
(74) *Attorney, Agent, or Firm* — Seed IP Law Group LLP

(57) ABSTRACT

The present invention provides salts and crystalline forms of Linsitinib (OSI-906; cis-3-[8-amino-1-(2-phenyl-7-quinolinyl)imidazo[1,5-a]pyrazin-3-yl]-1-methyl-cyclobutanol). These forms of Linsitinib provide increased solubility and improved pharmacokinetic profiles for orally administered pharmaceutical formulations. Accordingly, the invention enables improved methods for treating human insulin-like growth factor-1 receptor (IGF-1R) and insulin receptor (IR) mediated conditions.

27 Claims, 90 Drawing Sheets

CRYSTALLINE SALTS OF LINSITINIB

BACKGROUND

Technical Field

Cis-3-[8-amino-1-(2-phenyl-7-quinolinyl)imidazo[1,5-a]pyrazin-3-yl]-1-methyl-cyclobutanol, also known as OSI-906 and hereinafter referred to as Linsitinib, has the following chemical structure:

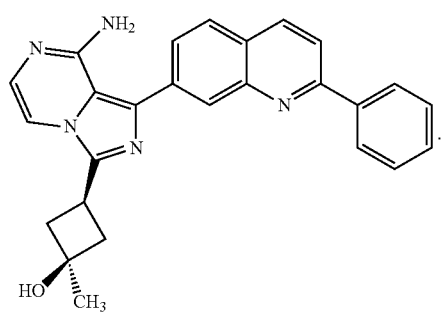

(I)

Linsitinib is a small-molecule inhibitor of the human insulin-like growth factor-1 receptor (IGF-1R) and insulin receptor (IR) and has previously been investigated as an anti-proliferative agent. For example, Linsitinib was granted orphan drug designation for adrenocortical carcinoma and clinical trials have been conducted against a variety of cancers, including myeloma and ovarian cancer. These studies, however, were discontinued due to a lack of efficacy in the studied cancers.

The preparation of Linsitinib in the form of a solid free base is disclosed in U.S. Pat. Nos. 7,534,797 and 8,101,613 to OSI Pharmaceuticals, LLC (see Example 31). While any number of acid and base addition salts are listed (see col. 154 and col. 164, respectively), formic and hydrochloric acid addition salts are identified as being particularly preferred acid addition salts of the generically disclosed compounds.

More recently, Linsitinib has been advanced for the treatment of thyroid eye disease (TED) by oral administration in the form of anhydrous/non-solvated free base. While this form of Linsitinib has proved promising, it suffers from poor pH related solubility. Accordingly, improved forms of Linsitinib are needed to enhance pH related solubility. For example, improved dissolution and pharmacokinetic profiles provided by new forms may enhance efficacy, may enhance tolerability, and may enable advantageous dosage forms. The present invention addresses these and other goals as disclosed in greater detail herein below.

SUMMARY OF THE INVENTION

In one aspect, the present invention provides solid salts forms of Linsitinib.

In one embodiment, provided is a crystalline esylate salt of linsitinib having the structure of Formula II:

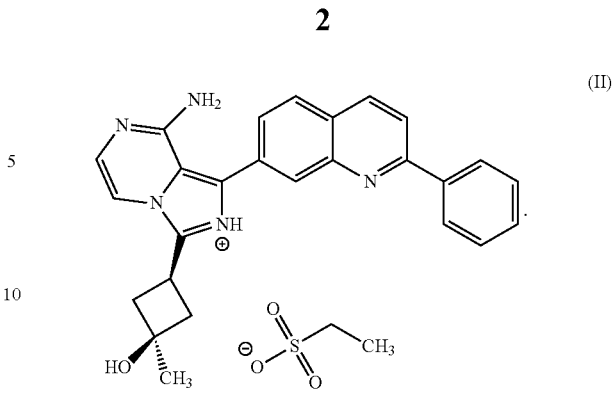

(II)

In one embodiment, provided is a crystalline L-malate salt of linsitinib having the structure of Formula III:

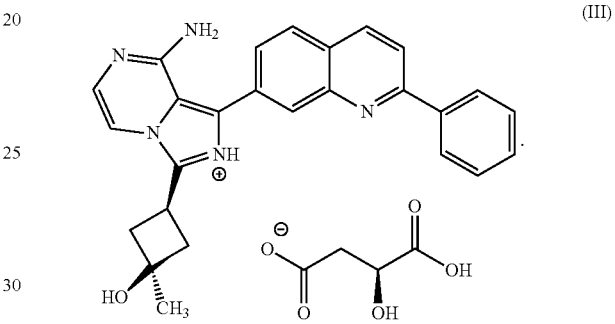

(III)

In one embodiment, provided is a pharmaceutical composition comprising a crystalline esylate salt of linsitinib or a crystalline L-malate salt of linsitinib and a pharmaceutically acceptable excipient.

In one embodiment, provided is a combination therapy comprising a crystalline esylate salt of linsitinib or a crystalline L-malate salt of linsitinib and a TSHR inhibitor.

In one embodiment, provided is a method of treating a condition mediated by human insulin-like growth factor-1 receptor (IGF-IR) or insulin receptor (IR), comprising administering to a subject in need thereof a therapeutically effective amount of a crystalline esylate salt of linsitinib or a crystalline L-malate salt of linsitinib or a pharmaceutical composition thereof.

In one embodiment, provided is a method of treating thyroid eye disease (TED) in a subject in need thereof, comprising administering to a subject in need thereof a therapeutically effective amount of a crystalline esylate salt of linsitinib or a crystalline L-malate salt of linsitinib or a pharmaceutical composition thereof. In one embodiment, the thyroid eye disease is chronic thyroid eye disease.

DETAILED DESCRIPTION

Figure 1:
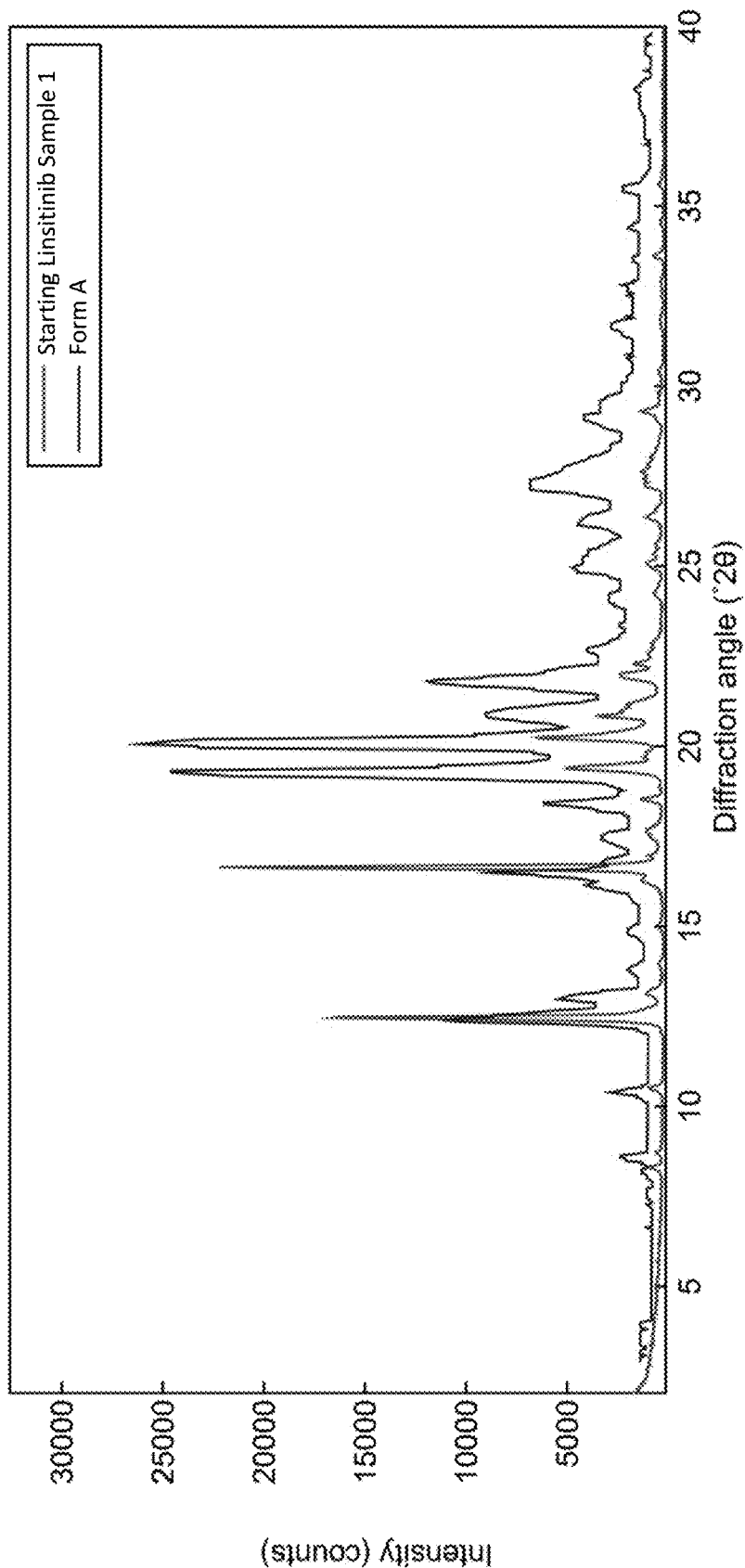
FIG. 1 shows the PXRD of Linsitinib Sample 1 (starting material).

The present invention provides novel salts and crystalline forms of Linsitinib (OSI-906; cis-3-[8-amino-1-(2-phenyl-7-quinolinyl)imidazo[1,5-a]pyrazin-3-yl]-1-methyl-cyclobutanol). These new forms of Linsitinib provide a number of advantages, including increased solubility and absorption for orally administered pharmaceutical formulations. Accordingly, the invention enables improved methods for treating human insulin-like growth factor-1 receptor (IGF-1R) and insulin receptor (IR) mediated conditions.

Definitions

"Linsitinib" refers to the compound cis-3-[8-amino-1-(2-phenyl-7-quinolinyl)imidazo[1,5-a]pyrazin-3-yl]-1-methyl-cyclobutanol as shown in Formula I.

"Salt" refers to an acid addition salt prepared by combining Linsitinib free base with a pharmaceutically acceptable acid.

"Pharmaceutically acceptable" is art-recognized and, as used herein to refer to a composition, excipient, adjuvant, or other material and/or dosage form, refers to a substance which, within the scope of sound medical judgment, is suitable for use in contact with the tissues of human beings and animals without excessive toxicity, irritation, allergic response, or other problems or complications, commensurate with a reasonable benefit/risk ratio. Examples of pharmaceutically acceptable acid addition salts include, but are not limited to hydrochloride, sulfate, phosphate, acetate, L-lactate, maleate, fumarate, succinate, L-malate, adipate, L-tartrate, equine urate, citrate, mucate, glycolate, D-glucuronic acid salt, benzoate, cholate, nicotinic acid, ethanesulfonate, ethanedisulfonate, oxalate, mesylate, benzenesulfonate, 2-hydroxyethanesulfonate, and hydrobromate.

"Esylate" refers to the pharmaceutically acceptable ethansulfonate acid addition salt. Other terms for esylate include ethanesulfonate, ethanesulfonic acid, and esylic acid. Esylate has the following structure:

"L-malate" refers to the pharmaceutically acceptable L-malate acid addition salt. Other terms for L-malate include L-malic acid, (−)-Malic acid, L-hydroxybutanedioic acid, (S)-hydroxybutanedioic acid. L-malate has the following structure:

"Edisylate" refers to the pharmaceutically acceptable ethanedisulfonate acid addition salt. Other terms for edisylate include ethanedisulfonate, ethanedisulfonic acid, and edisylic acid. Edisylate has the following structure:

"Maleate" refers to refers to the pharmaceutically acceptable maleate acid addition salt. Other terms for maleate include (2Z)-but-2-enedioic acid, cis-butenedioic acid, and maleic acid. Maleate has the following structure:

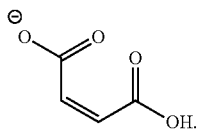

"Napsylate" refers to the pharmaceutically acceptable naphthalene-2-sulfonate acid addition salt. Other terms for napsylate include naphthalene-2-sulfonic acid and napsylic acid. Napsylate has the following structure:

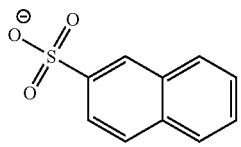 [SMILES: O=S(=O)([O-])c1ccc2ccccc2c1]

"Phosphate" refers to the pharmaceutically acceptable phosphate acid addition salt. Other terms for phosphate include phosphoric acid. Phosphate has the following structure:

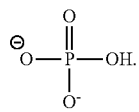

"Fumarate" refers to the pharmaceutically acceptable (E)-3-carboxyacrylate acid addition alt. Other terms for fumarate include (2E)-but-2-enedioic acid, trans-1,2-ethylenedicarboxylic acid, allomaleic acid, boletic acid, donitic acid, lichenic acid, and fumaric acid. Fumarate has the following structure:

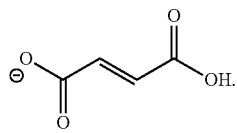

"Crystalline form" refers to a solid form of a compound wherein the constituent molecules are packed in a regularly ordered, repeating pattern. A crystalline form can be triclinic, monoclinic, orthorhombic, tetragonal, trigonal, hexagonal, or cubic. A crystalline form can contain one or more regions, i.e., grains, with distinct crystal boundaries. A crystalline solid can contain two or more crystal geometries.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, refers to the act of treating as "treating" is defined immediately above.

A "therapeutically effective amount" is the amount of Linsitinib, or a crystalline form thereof, that is needed to provide a desired level of drug in the tissues, bloodstream, or other physical compartment of a patient, the desired level giving rise to an anticipated physiological response or biological effect when the Linsitinib salt or crystalline form is administered by the chosen route of administration. The precise amount will depend upon numerous factors including, for example, the particular Linsitinib salt or crystalline form; the specific pharmaceutical formulation or delivery device employed; the severity of the disease state; and patient adherence to a treatment regimen. Therapeutically effective amounts of Linsitinib salts and crystalline forms can be readily determined by one skilled in the art based upon the information provided herein.

"About" and "around," as used herein to modify a numerical value, indicate a defined range around that value. If "X" were the value, "about X" or "around X" would generally indicate a value from 0.95X to 1.05X including, for example, from 0.98X to 1.02X or from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X." When the quantity "X" only includes whole-integer values (e.g., "X carbons"), "about X" or "around X" indicates from (X−1) to (X+1). In such cases, "about X" or "around X" specifically indicates at least the values X, X−1, and X+1.

Linsitinib Salts

One of skill in the art will appreciate that a number of pharmaceutically acceptable acids can be used to prepare Linsitinib salts. Pharmaceutically acceptable acids include, but are not limited to, hydrochloric, acetic, benzenesulfonic, benzoic, camphorsulfonic, citric, ethanesulfonic (esylic), ethanedisulfonic (edisylic), formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, napsylic, and the like. In certain embodiments, the Linsitinib salt comprises an anion derived from a pharmaceutically acceptable acid selected from edisylic, esylic, hydrochloric, maleic, L-malic, napsylic, and phosphoric.

Esylate Salt

In another embodiment, the invention provides an esylate salt of a compound of Formula I:

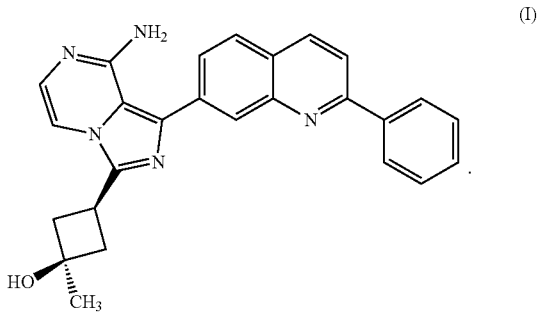 [SMILES: C[C@]1(O)C[C@@H](c2nc(-c3ccc4ccc(-c5ccccc5)nc4c3)c3c(N)nccn32)C1]

(I)

As described above, Formula I corresponds to Linsitinib. Ethanesulfonic acid is a monoprotic acid with the conjugate base ethanesulfonate. As used herein, "esylate" refers to ethanesulfonate. As used herein, "esylate salt" refers to a salt containing at least one ethanesulfonate anion. In certain embodiments, the esylate salt of Linsitinib is a salt according to Formula II:

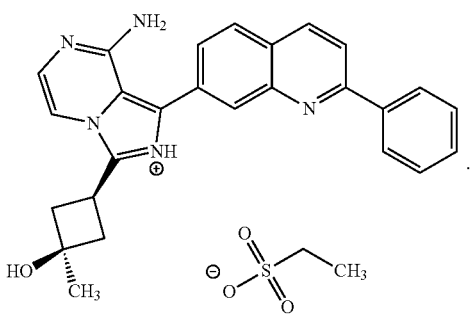

(II)

In one aspect, the invention provides a crystalline form of an esylate salt of a compound of Formula I:

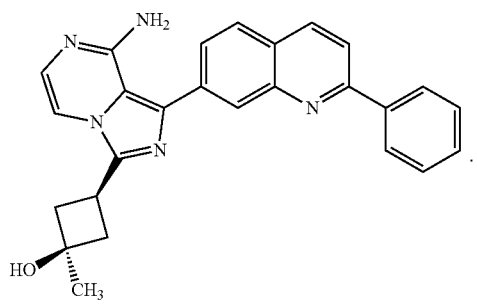

(I)

Esylate 1

Figure 5:
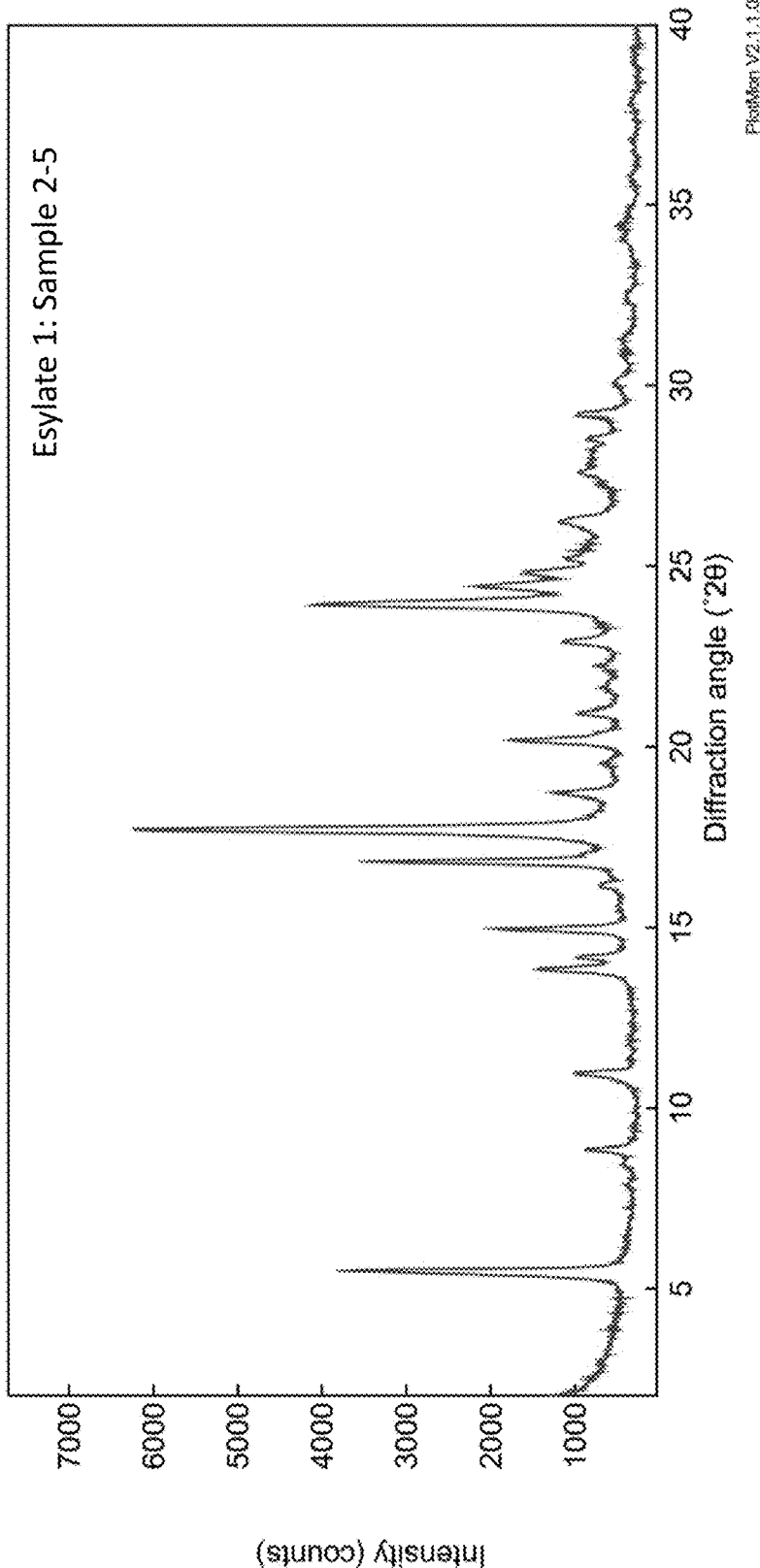
FIG. 5 shows the PXRD of Esylate 1 (Sample 2-5).

In one embodiment, provided is a crystalline linsitinib esylate salt comprising crystalline form Esylate 1. In one embodiment, the crystalline form Esylate 1 of a linsitinib esylate salt is characterized by a powder x-ray diffraction (PXRD) pattern substantially resembling that of FIG. 5, as determined on a diffractometer using Cu-Kα radiation.

Figure 7:
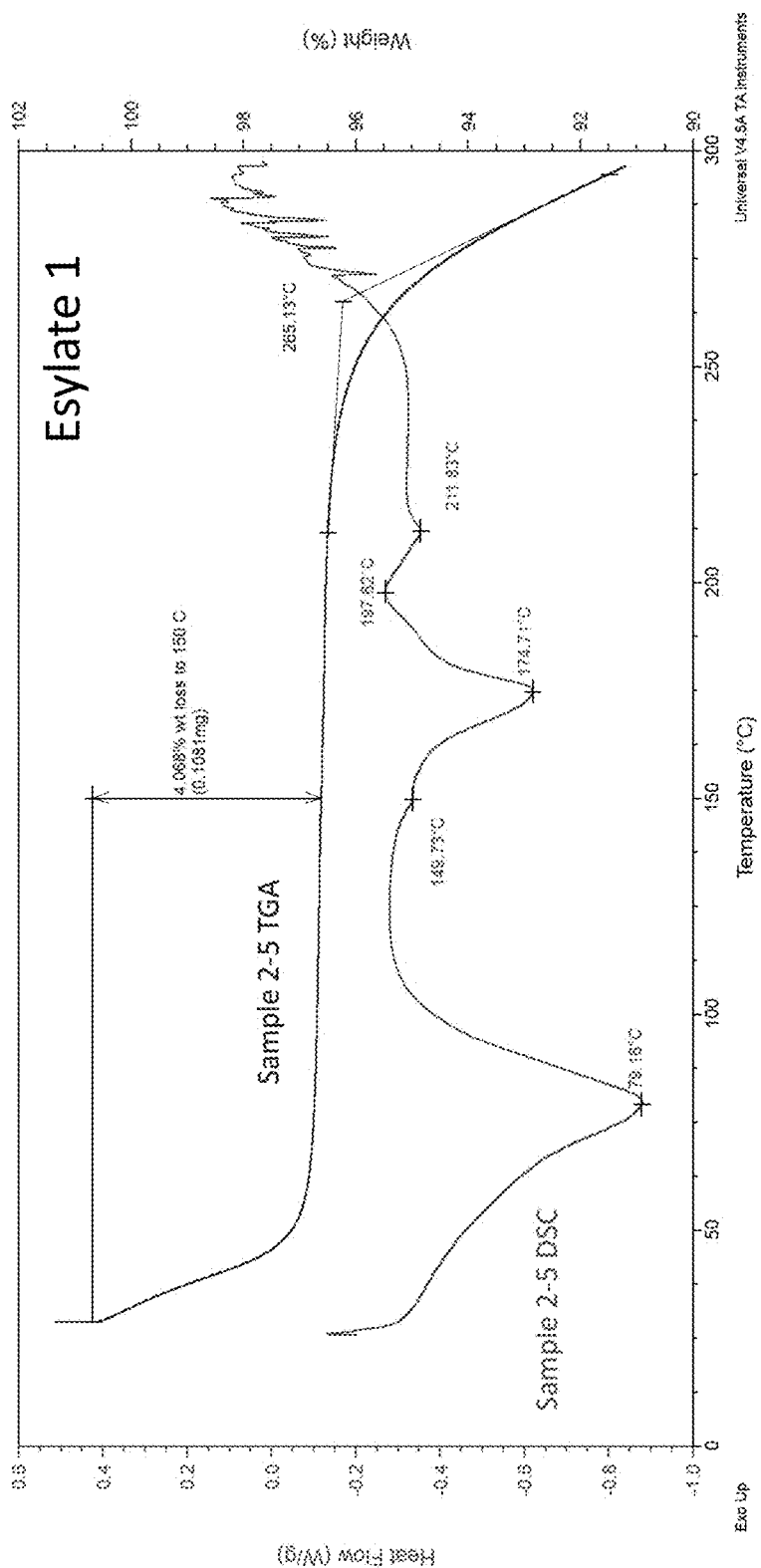
FIG. 7 shows the DSC thermogram of Esylate 1 (Sample 2-5) and the TGA thermogram of Esylate 1 (Sample 2-5).

In one embodiment, the crystalline form Esylate 1 of a linsitinib esylate salt is characterized by a DSC thermogram substantially resembling that of FIG. 7.

In one embodiment, the crystalline form Esylate 1 of a linsitinib esylate salt is characterized by a TGA signal substantially resembling that of FIG. 7.

In one embodiment, provided is a crystalline form Esylate 1 of a linsitinib esylate salt according as characterized by any aspect of the present invention, which is present as a material comprising at least about 95% or more by weight of crystalline form Esylate 1 based of the total amount of linsitinib esylate salt in the material. In one embodiment, the crystalline form Esylate 1 comprises at least about 98% or more by weight of crystalline form Esylate 1 based of the total amount of linsitinib esylate salt in the material. In one embodiment, the crystalline form Esylate 1 comprises at least about 99% or more by weight of crystalline form Esylate 1 based of the total amount of linsitinib esylate salt in the material. In one embodiment, the crystalline form Esylate 1 comprises at least about 99.5% or more by weight of crystalline form Esylate 1 based of the total amount of linsitinib esylate salt in the material.

Esylate 2

In one embodiment, provided is a crystalline linsitinib esylate salt comprising crystalline form Esylate 2. In one embodiment, crystalline form Esylate 2 of a linsitinib esylate salt is characterized by a powder x-ray diffraction (PXRD) pattern comprising at least three peaks selected from the group consisting of 6.74, 8.92, 10.26, 11.04, 14.76, 16.80, 17.60, 17.90, 18.56, 20.24, 20.56, 20.74, 24.58, 25.80, 26.12, and 27.34±0.20 020, as determined on a diffractometer using Cu-Kα radiation. In another embodiment, the crystalline form Esylate 2 of a linsitinib esylate salt is characterized by a powder x-ray diffraction (PXRD) pattern comprising at least six peaks selected from the group consisting of 6.74, 8.92, 10.26, 11.04, 14.76, 16.80, 17.60, 17.90, 18.56, 20.24, 20.56, 20.74, 24.58, 25.80, 26.12, and 27.34±0.2 020, as determined on a diffractometer using Cu-Kα radiation. In another embodiment, the crystalline form Esylate 2 of a linsitinib esylate salt is characterized by a powder x-ray diffraction (PXRD) pattern comprising at least ten peaks selected from the group consisting of 6.74, 8.92, 10.26, 11.04, 14.76, 16.80, 17.60, 17.90, 18.56, 20.24, 20.56, 20.74, 24.58, 25.80, 26.12, and 27.34±0.2 020, as determined on a diffractometer using Cu-Kα radiation. In still another embodiment, the crystalline form Esylate 2 of a linsitinib esylate salt is characterized by a powder x-ray diffraction (PXRD) pattern with peaks substantially the same as Table 8. In one embodiment, the crystalline form Esylate 2 of a linsitinib esylate salt is characterized by a powder x-ray diffraction (PXRD) pattern substantially resembling that of FIG. 8, as determined on a diffractometer using Cu-Kα radiation.

Figure 10:
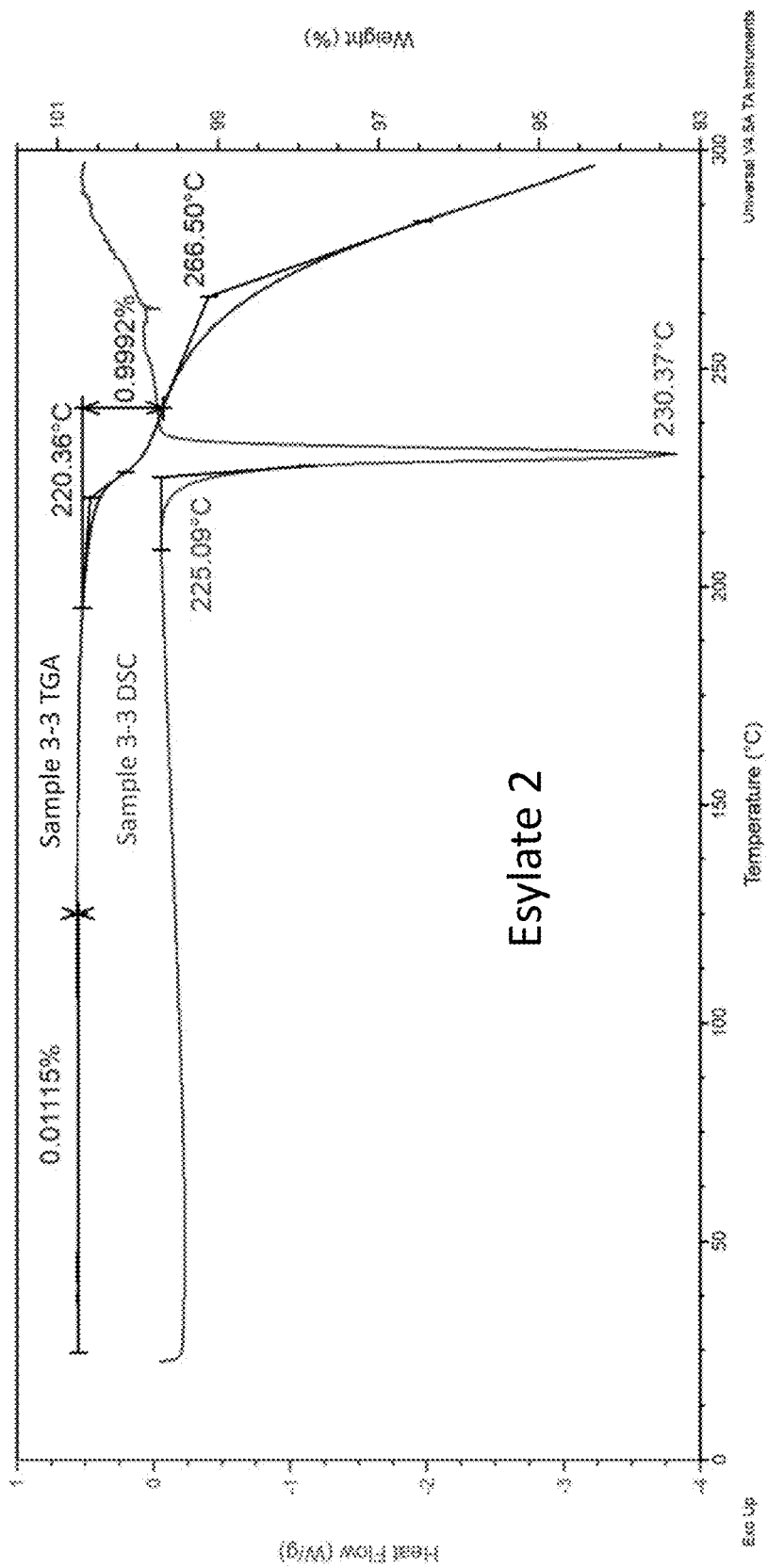
FIG. 10 shows the DSC thermogram of Esylate 2 (Sample 3-3) and the TGA thermogram of Esylate 2 (Sample 3-3).

In one embodiment, crystalline form Esylate 2 of a linsitinib esylate salt is characterized by a DSC thermogram substantially resembling that of FIG. 10. In one embodiment, crystalline form Esylate 2 of a linsitinib esylate salt is characterized by a TGA signal substantially resembling that of FIG. 10.

In one embodiment, provided is a crystalline form Esylate 2 of a linsitinib esylate salt, wherein a single crystal structure of Esylate 2 comprises an orthorhombic crystal structure. In one embodiment, the single crystal structure of Esylate 2 comprises a $P_12_12_1$ space group.

In one embodiment, provided is a crystalline form Esylate 2 of a linsitinib esylate salt, wherein a single crystal structure of Esylate 2 comprises a unit cell with the parameters shown in Table 1:

TABLE 1

| Esylate 2 Single Crystal Unit Cell Parameters | |
|---|---|
| a (Å) | 7.4100(8) |
| b (Å) | 17.4900(17) |
| c (Å) | 19.769(2) |
| α (°) | 90 |
| β (°) | 90 |
| γ (°) | 90 |
| volume (Å3) | 2562.0(5). |

Figure 11:
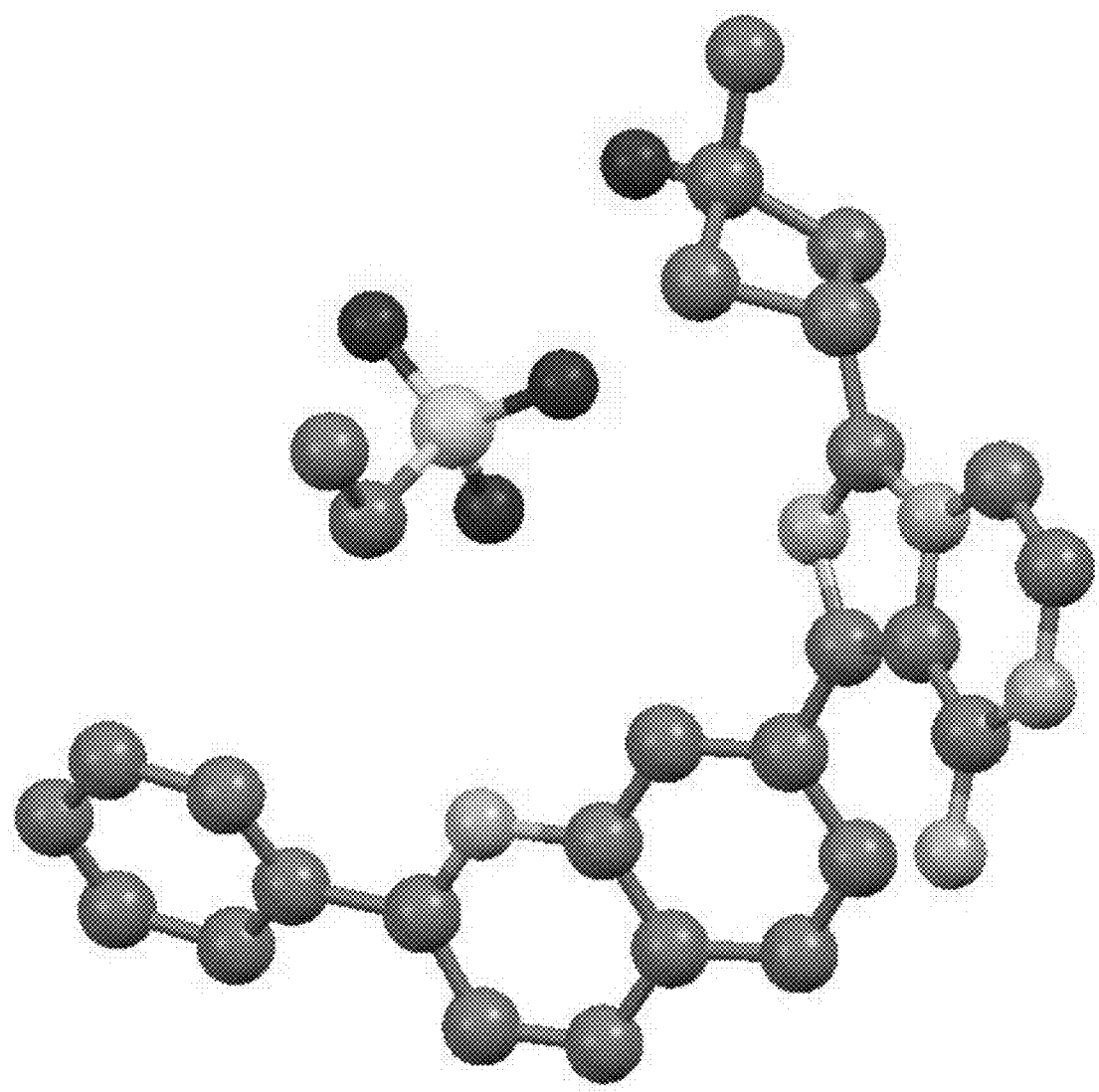
FIG. 11 shows the asymmetric unit cell from the Esylate 2 single crystal structure. Carbon atoms are gray, nitrogen atoms are blue, oxygen atoms are red, and sulfur atoms are yellow. Hydrogen atoms were omitted for clarity.
Figure 12:
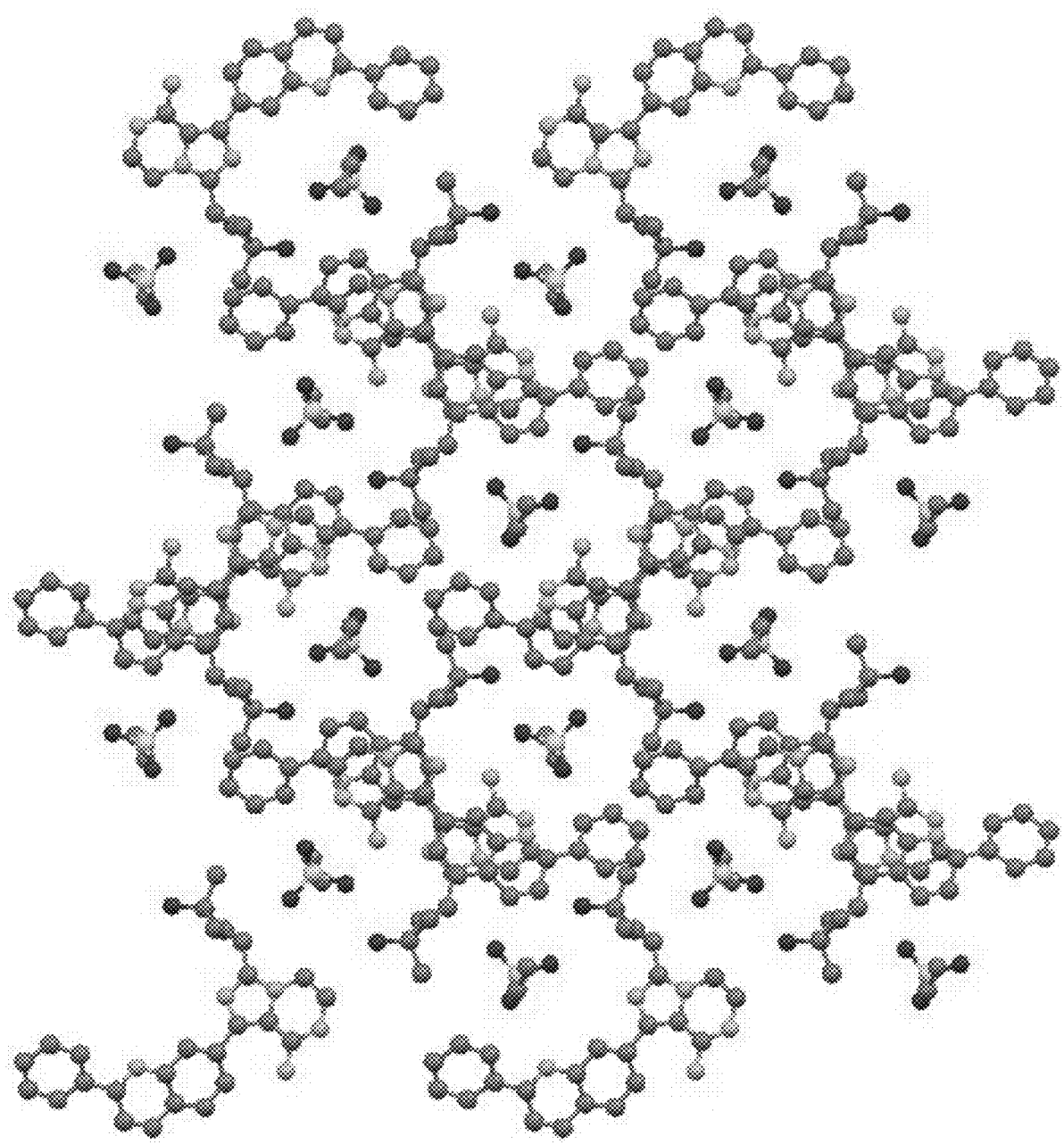
FIG. 12 shows a packing diagram of the Esylate 2 single crystal looking down the a axis.
Figure 13:
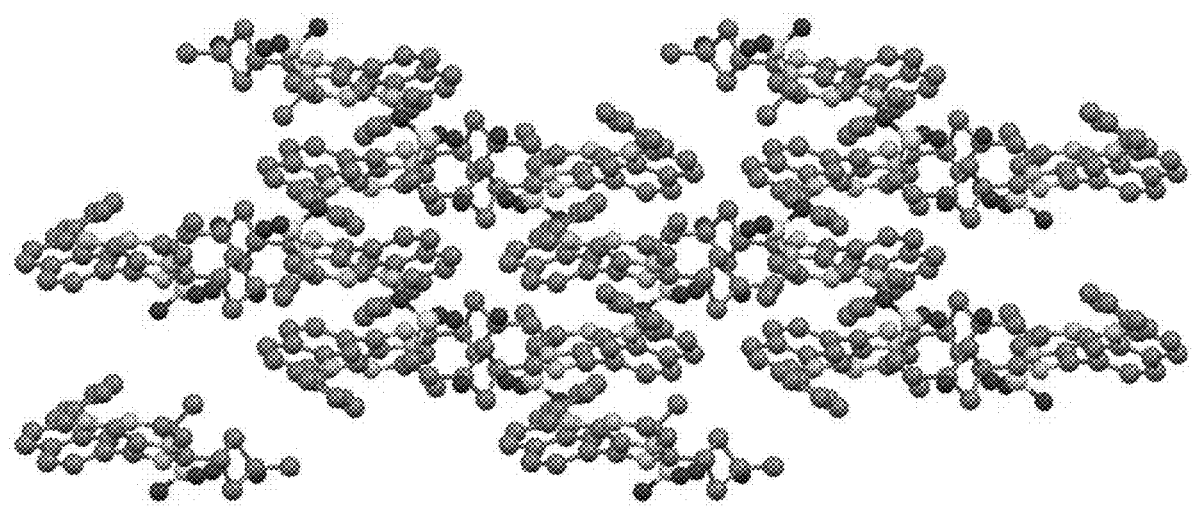
FIG. 13 shows a packing diagram of the Esylate 2 single crystal looking down the b axis.
Figure 14:
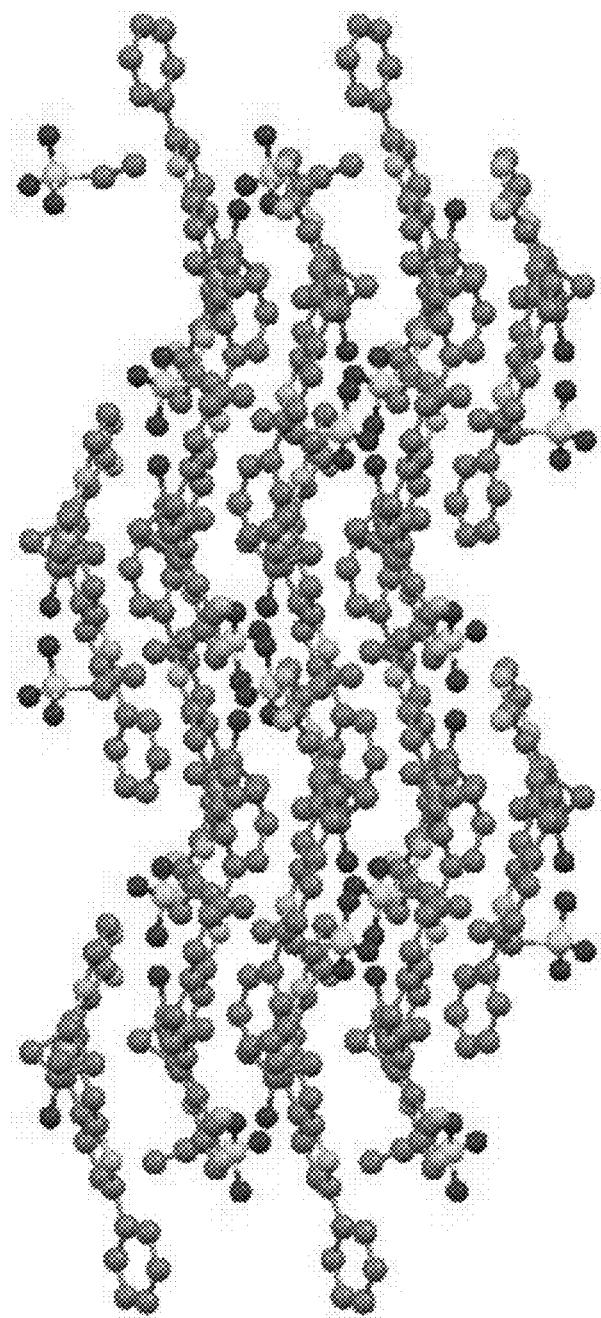
FIG. 14 shows a packing diagram of the Esylate 2 single crystal looking down the c axis.
Figure 15:
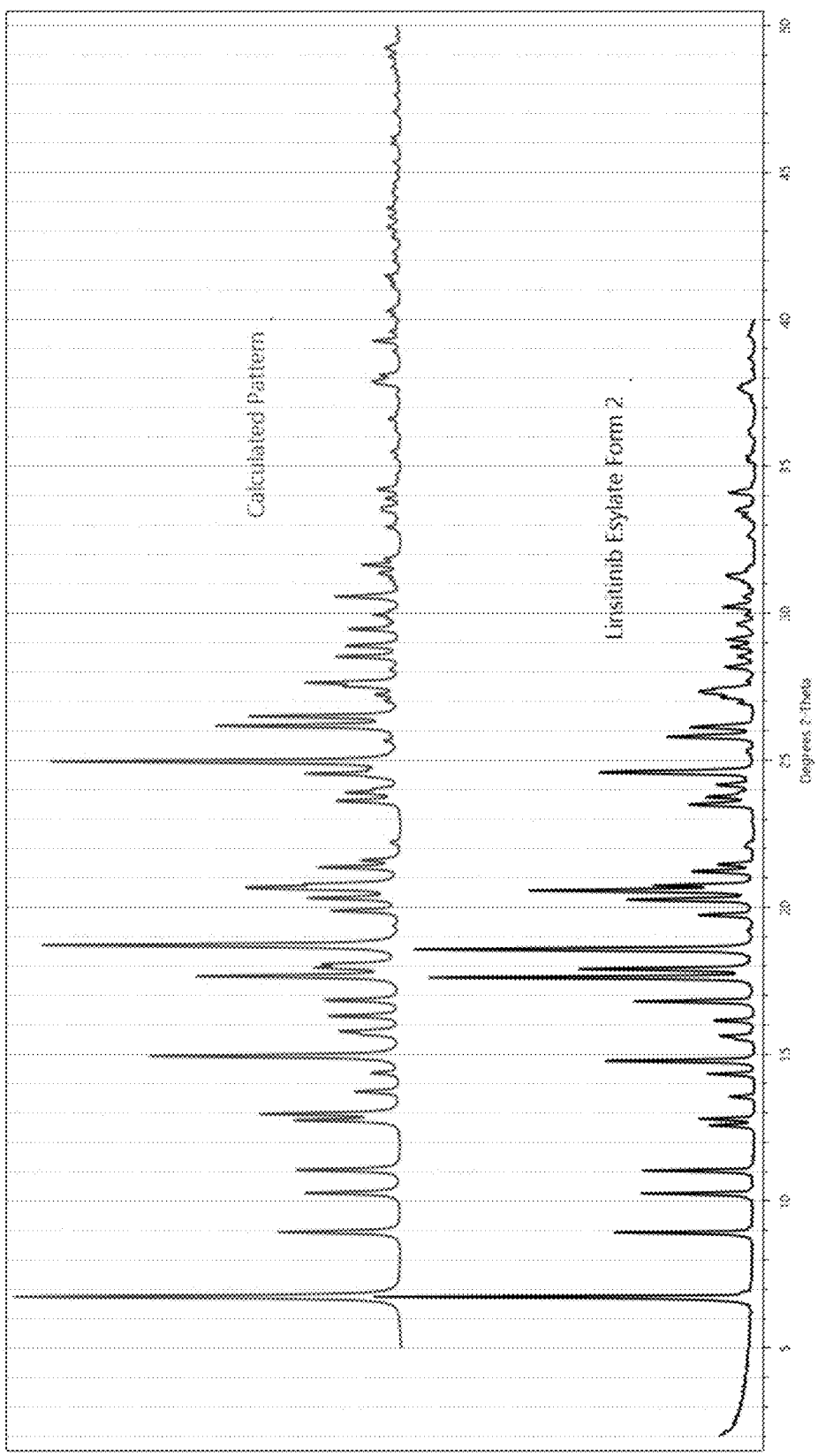
FIG. 15 shows an XRPD pattern calculated from the Esylate 2 single-crystal data, overlaid with a reference XRPD pattern of linsitinib Esylate 2. The patterns overlay well, indicating that they represent the same crystalline phase. The observed peak shifting is due to the temperature difference at which the single crystal and X-ray powder diffraction data were collected.

The asymmetric unit is shown in FIG. 11 Packing diagrams along the a, b, and c axes are shown in FIG. 12, FIG. 13, and FIG. 14. The PXRD pattern calculated from the single-crystal data is overlaid with the reference PXRD pattern of Esyalte 2 in FIG. 15.

In one embodiment, provided is a crystalline form Esylate 2 of a linsitinib esylate salt according as characterized by any aspect of the present invention, which is present as a material comprising at least about 95% or more by weight of crystalline form Esylate 2 based of the total amount of linsitinib esylate salt in the material. In one embodiment, the crystalline form Esylate 2 comprises at least about 98% or more by weight of crystalline form Esylate 2 based of the total amount of linsitinib esylate salt in the material. In one embodiment, the crystalline form Esylate 2 comprises at least about 99% or more by weight of crystalline form Esylate 2 based of the total amount of linsitinib esylate salt in the material. In one embodiment, the crystalline form Esylate 2 comprises at least about 99.5% or more by weight of crystalline form Esylate 2 based of the total amount of linsitinib esylate salt in the material.

Esylate 3

Figure 22:
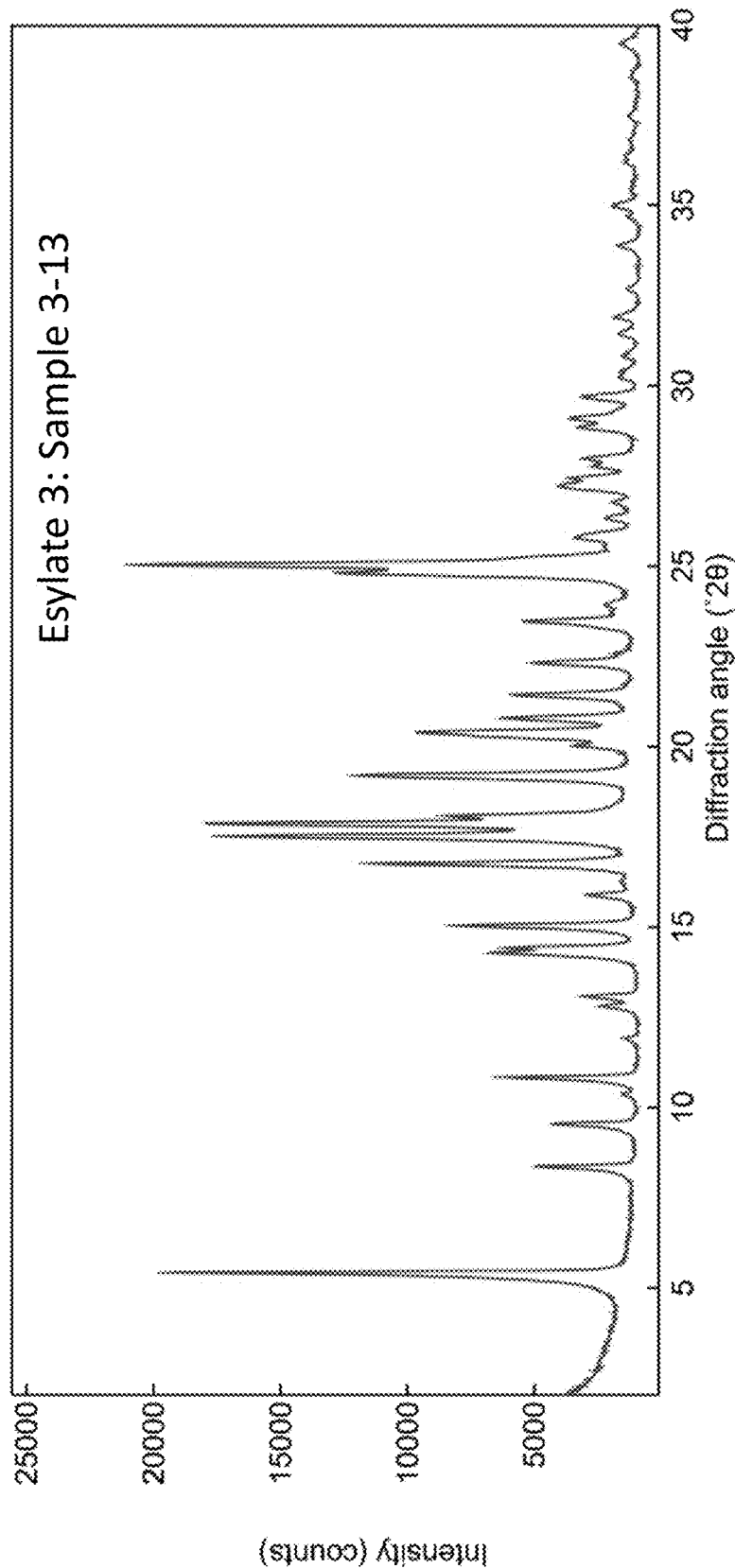
FIG. 22 shows the PXRD of Esylate 3 (Sample 3-13).

In one embodiment, provided is a crystalline linsitinib esylate salt comprising crystalline form Esylate 3. In one embodiment, the crystalline form Esylate 3 of a linsitinib esylate salt is characterized by a powder x-ray diffraction (PXRD) pattern substantially resembling that of FIG. 22, as determined on a diffractometer using Cu-Kα radiation.

Figure 24:
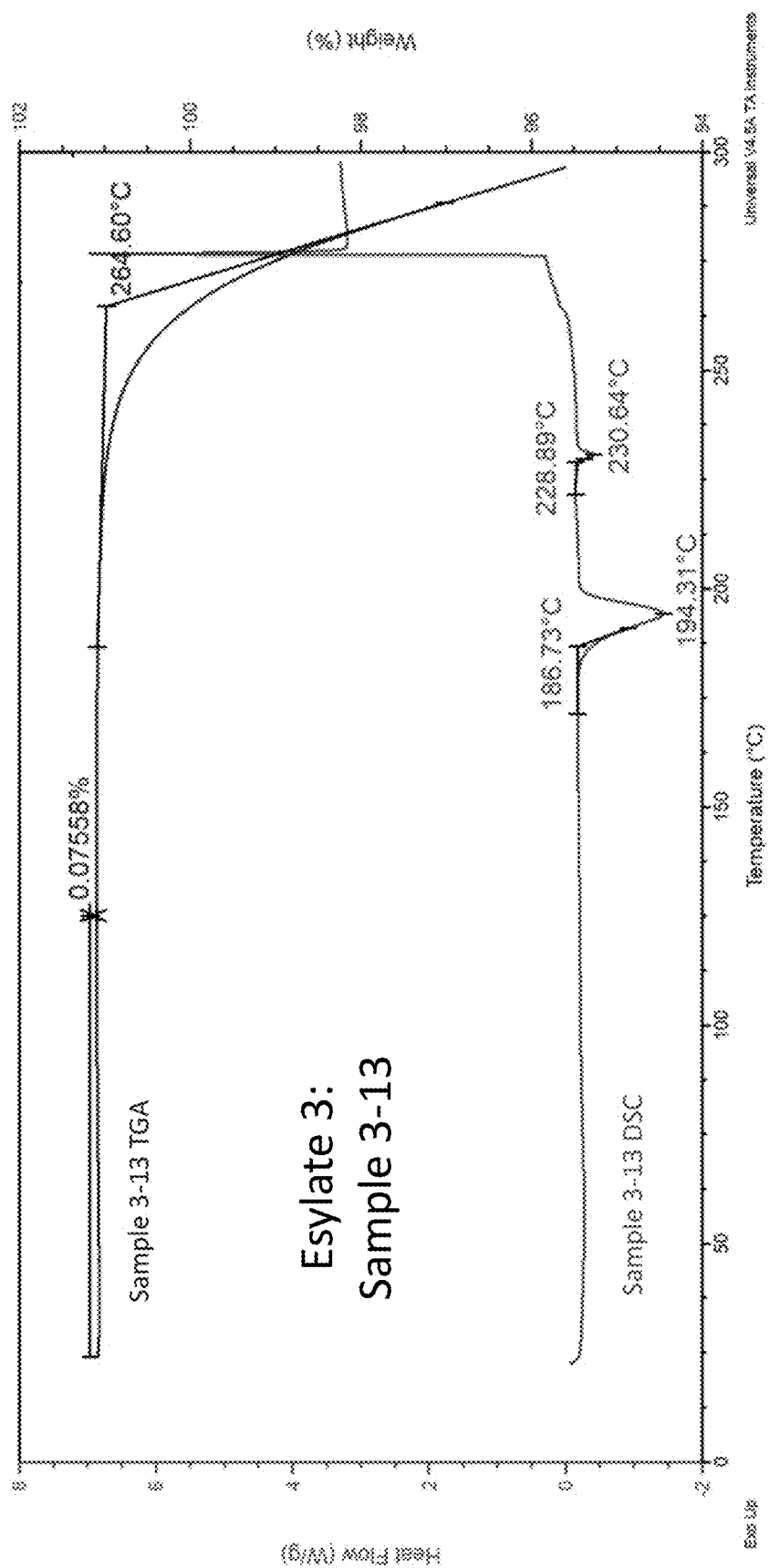
FIG. 24 shows the DSC thermogram of Esylate 3 (Sample 3-13) and the TGA thermogram of Esylate 3 (Sample 3-13)

In one embodiment, the crystalline form Esylate 3 of a linsitinib esylate salt is characterized by a DSC thermogram substantially resembling that of FIG. 24.

In one embodiment, the crystalline form Esylate 3 of a linsitinib esylate salt is characterized by a TGA signal substantially resembling that of FIG. 24.

In one embodiment, provided is a crystalline form Esylate 3 of a linsitinib esylate salt according as characterized by any aspect of the present invention, which is present as a material comprising at least about 95% or more by weight of crystalline form Esylate 3 based of the total amount of linsitinib esylate salt in the material. In one embodiment, the crystalline form Esylate 3 comprises at least about 98% or more by weight of crystalline form Esylate 3 based of the total amount of linsitinib esylate salt in the material. In one embodiment, the crystalline form Esylate 3 comprises at least about 99% or more by weight of crystalline form Esylate 3 based of the total amount of linsitinib esylate salt in the material. In one embodiment, the crystalline form Esylate 3 comprises at least about 99.5% or more by weight of crystalline form Esylate 3 based of the total amount of linsitinib esylate salt in the material.

Esylate 4

In one embodiment, provided is a crystalline linsitinib esylate salt comprising crystalline form Esylate 4. In one embodiment, the crystalline form Esylate 4 of a linsitinib esylate salt is characterized by a powder x-ray diffraction (PXRD) pattern substantially resembling that of FIG. 25, as determined on a diffractometer using Cu-Kα radiation.

Figure 27:
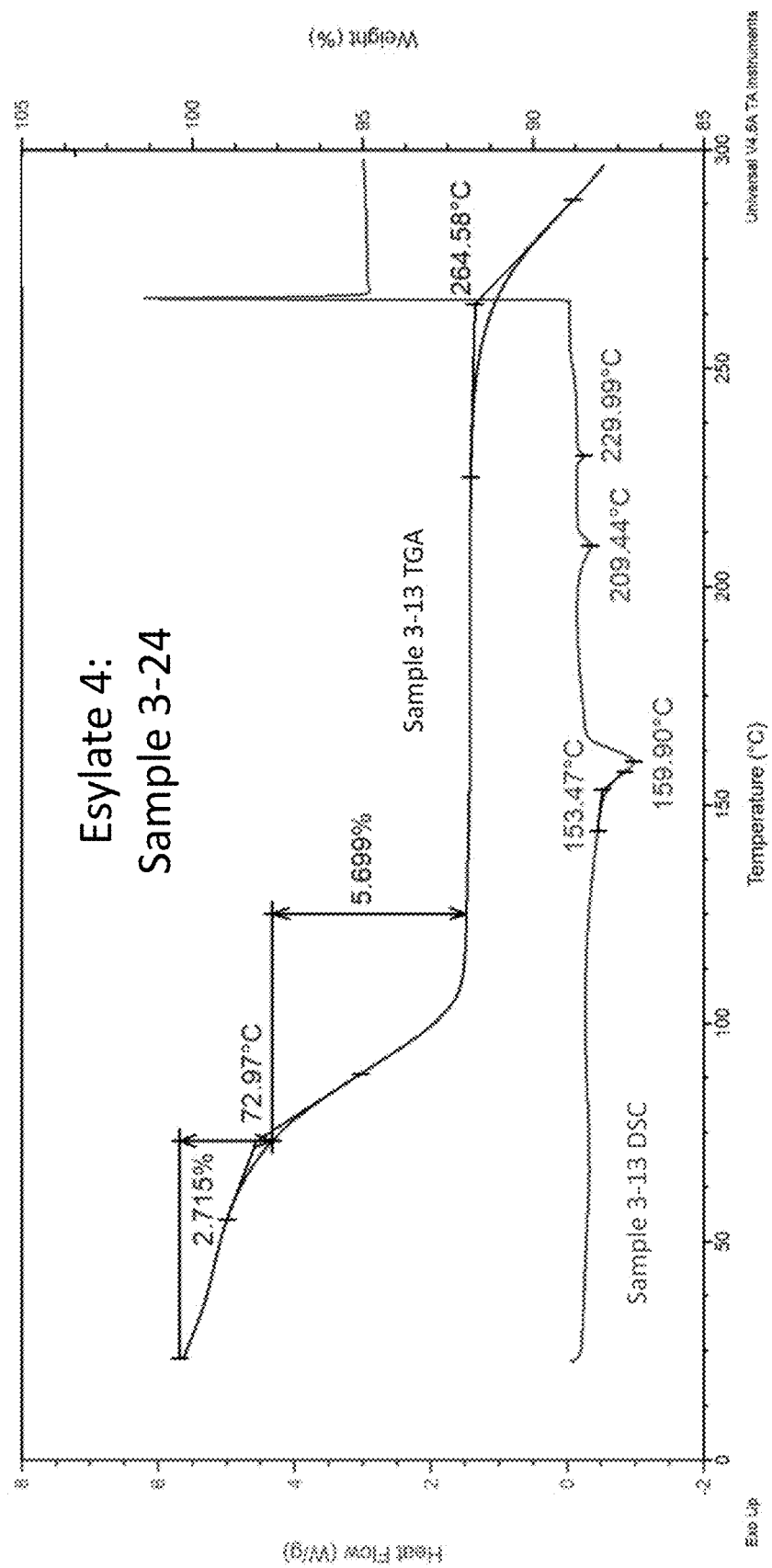
FIG. 27 shows the DSC thermogram of Esylate 4 (Sample 3-24) and the TGA thermogram of Esylate 4 (Sample 3-24).

In one embodiment, the crystalline form Esylate 4 of a linsitinib esylate salt is characterized by a DSC thermogram substantially resembling that of FIG. 27.

In one embodiment, the crystalline form Esylate 4 of a linsitinib esylate salt is characterized by a TGA signal substantially resembling that of FIG. 27.

In one embodiment, provided is a crystalline form Esylate 4 of a linsitinib esylate salt according as characterized by any aspect of the present invention, which is present as a material comprising at least about 95% or more by weight of crystalline form Esylate 4 based of the total amount of linsitinib esylate salt in the material. In one embodiment, the crystalline form Esylate 4 comprises at least about 98% or more by weight of crystalline form Esylate 4 based of the total amount of linsitinib esylate salt in the material. In one embodiment, the crystalline form Esylate 4 comprises at least about 99% or more by weight of crystalline form Esylate 4 based of the total amount of linsitinib esylate salt in the material. In one embodiment, the crystalline form Esylate 4 comprises at least about 99.5% or more by weight of crystalline form Esylate 4 based of the total amount of linsitinib esylate salt in the material.

Esylate 5

In one embodiment, provided is a crystalline linsitinib esylate salt comprising crystalline form Esylate 5. In one embodiment, the crystalline form Esylate 5 of a linsitinib esylate salt is characterized by a powder x-ray diffraction (PXRD) pattern substantially resembling that of FIG. 4, as determined on a diffractometer using Cu-Kα radiation.

Figure 29:
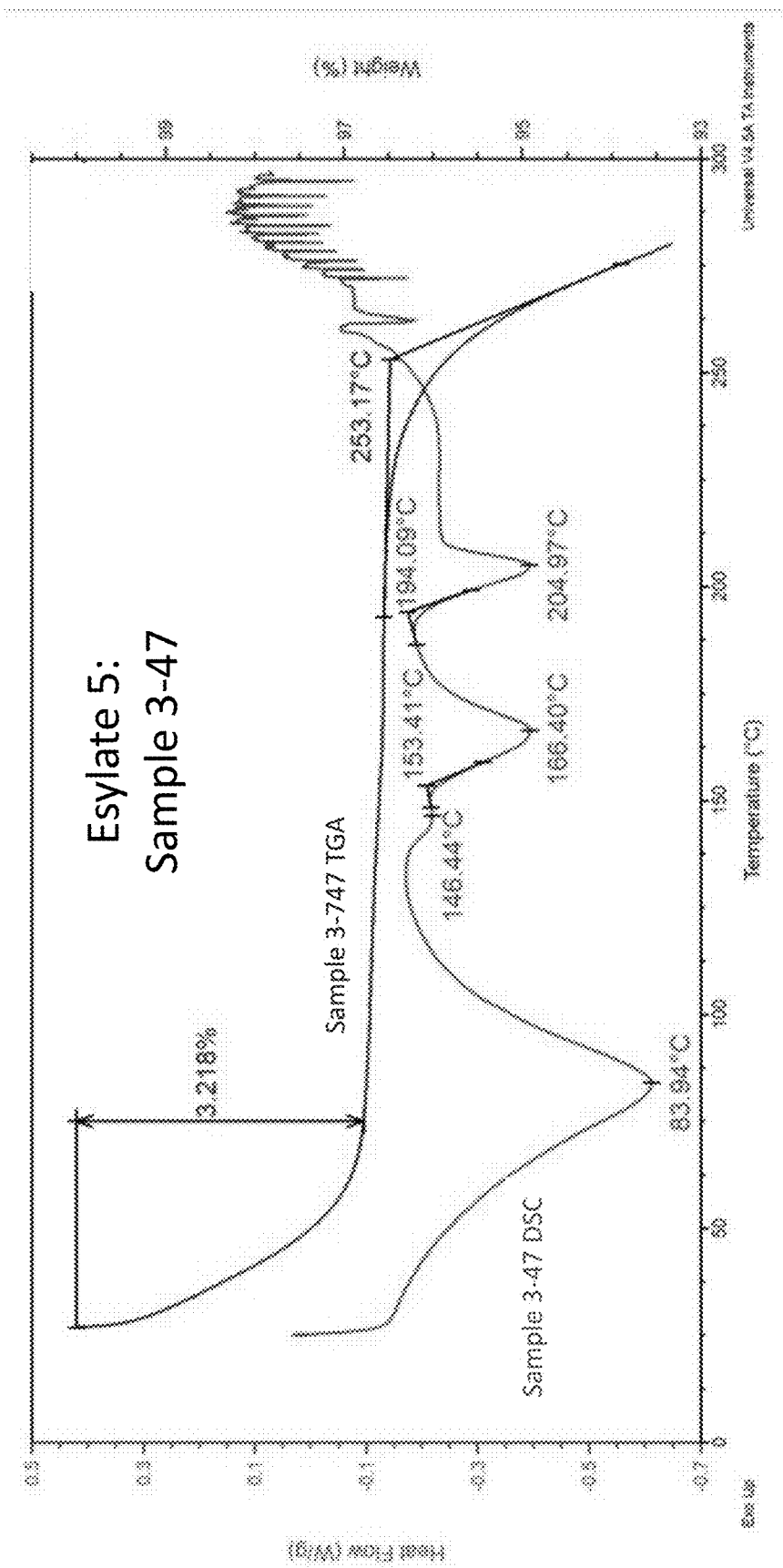
FIG. 29 shows the DSC thermogram of Esylate 5 (Sample 3-47) and the TGA thermogram of Esylate 5 (Sample 3-47).

In one embodiment, the crystalline form Esylate 5 of a linsitinib esylate salt is characterized by a DSC thermogram substantially resembling that of FIG. 29.

In one embodiment, the crystalline form Esylate 5 of a linsitinib esylate salt is characterized by a TGA signal substantially resembling that of FIG. 29.

In one embodiment, provided is a crystalline form Esylate 5 of a linsitinib esylate salt according as characterized by any aspect of the present invention, which is present as a material comprising at least about 95% or more by weight of crystalline form Esylate 5 based of the total amount of linsitinib esylate salt in the material. In one embodiment, the crystalline form Esylate 5 comprises at least about 98% or more by weight of crystalline form Esylate 5 based of the total amount of linsitinib esylate salt in the material. In one embodiment, the crystalline form Esylate 5 comprises at least about 99% or more by weight of crystalline form Esylate 5 based of the total amount of linsitinib esylate salt in the material. In one embodiment, the crystalline form Esylate 5 comprises at least about 99.5% or more by weight of crystalline form Esylate 5 based of the total amount of linsitinib esylate salt in the material.

Di-Esylate 1

In one embodiment, provided is a crystalline linsitinib esylate salt comprising crystalline form Di-Esylate 1. In one embodiment, the crystalline form Di-Esylate 1 of a linsitinib esylate salt is characterized by a DSC thermogram substantially resembling that of FIG. 32. In one embodiment, the crystalline form Di-Esylate 1 of a linsitinib esylate salt is characterized by a TGA signal substantially resembling that of FIG. 32.

In one embodiment, provided is a crystalline form Di-Esylate 1 of a linsitinib esylate salt according as characterized by any aspect of the present invention, which is present as a material comprising at least about 95% or more by weight of crystalline form Di-Esylate 1 based of the total amount of linsitinib esylate salt in the material. In one embodiment, the crystalline form Di-Esylate 1 comprises at least about 98% or more by weight of crystalline form Di-Esylate 1 based of the total amount of linsitinib esylate salt in the material. In one embodiment, the crystalline form Di-Esylate 1 comprises at least about 99% or more by weight of crystalline form Di-Esylate 1 based of the total amount of linsitinib esylate salt in the material. In one embodiment, the crystalline form Di-Esylate 1 comprises at least about 99.5% or more by weight of crystalline form Di-Esylate 1 based of the total amount of linsitinib esylate salt in the material.

L-Malate Salt

In one embodiment, the invention provides an L-malic acid salt of a compound of Formula I:

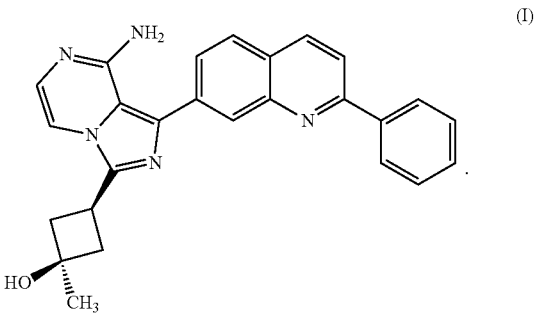 [SMILES: C[C@]1(O)C[C@@H](c2nc(-c3ccc4ccc(-c5ccccc5)nc4c3)c3c(N)nccn32)C1]

(I)

As described above, Formula I corresponds to Linsitinib. (S)-hydroxybutane dioic acid is also referred to by synonyms including (S)-2-hydroxysuccinic acid and L-malic acid. L-malic acid is a diprotic acid with conjugate bases including (S)-3-carboxy-2-hydroxypropanoate, (S)-3-carboxy-3-hydroxypropanoate, and (S)-hydroxysuccinate. As used herein, "L-malic acid salt" or "L-malate salt" refers to a salt containing at least one (S)-3-carboxy-2-hydroxypropanoate or (S)-3-carboxy-3-hydroxypropanoate anion, or at least one (S)-hydroxysuccinate anion. In certain embodiments, the (L)-malate salt of Linsitinib is a salt according to Formula III:

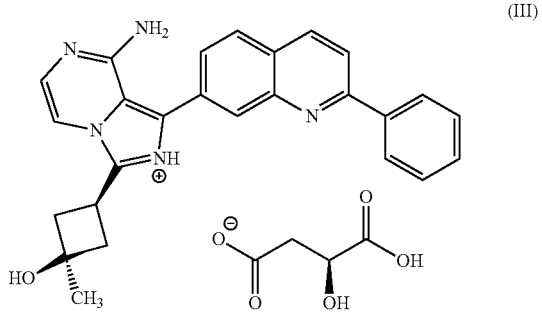

In one aspect, the invention provides a crystalline form of an (L)-malate salt of a compound of Formula I:

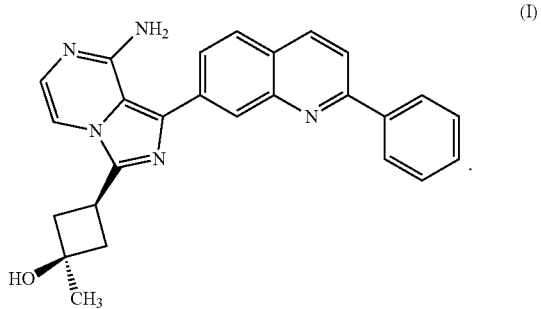 [SMILES: C[C@]1(O)C[C@@H](c2nc(-c3ccc4ccc(-c5ccccc5)nc4c3)c3c(N)nccn32)C1]

L-Malate 1

In one embodiment, provided is a crystalline linsitinib L-malate salt comprising crystalline form L-Malate 1. In some embodiments, crystalline form L-Malate 1 is characterized by an X-ray powder diffraction (XRPD) pattern including at least three peaks selected from the group consisting of 5.42, 8.68, 11.88, 12.40, 16.24, 17.36, 17.96, 18.22, 19.20, 20.88, 22.08, 22.58, 22.90, 23.86, 24.44, 24.92, 25.66, 26.1, 28.58, or 29.44±0.2 02θ, as determined on a diffractometer using Cu-Kα radiation. In one embodiment, the crystalline form L-Malate 1 is characterized by a powder x-ray diffraction (PXRD) pattern substantially resembling that of FIG. 33, as determined on a diffractometer using Cu Kα radiation.

Figure 32:
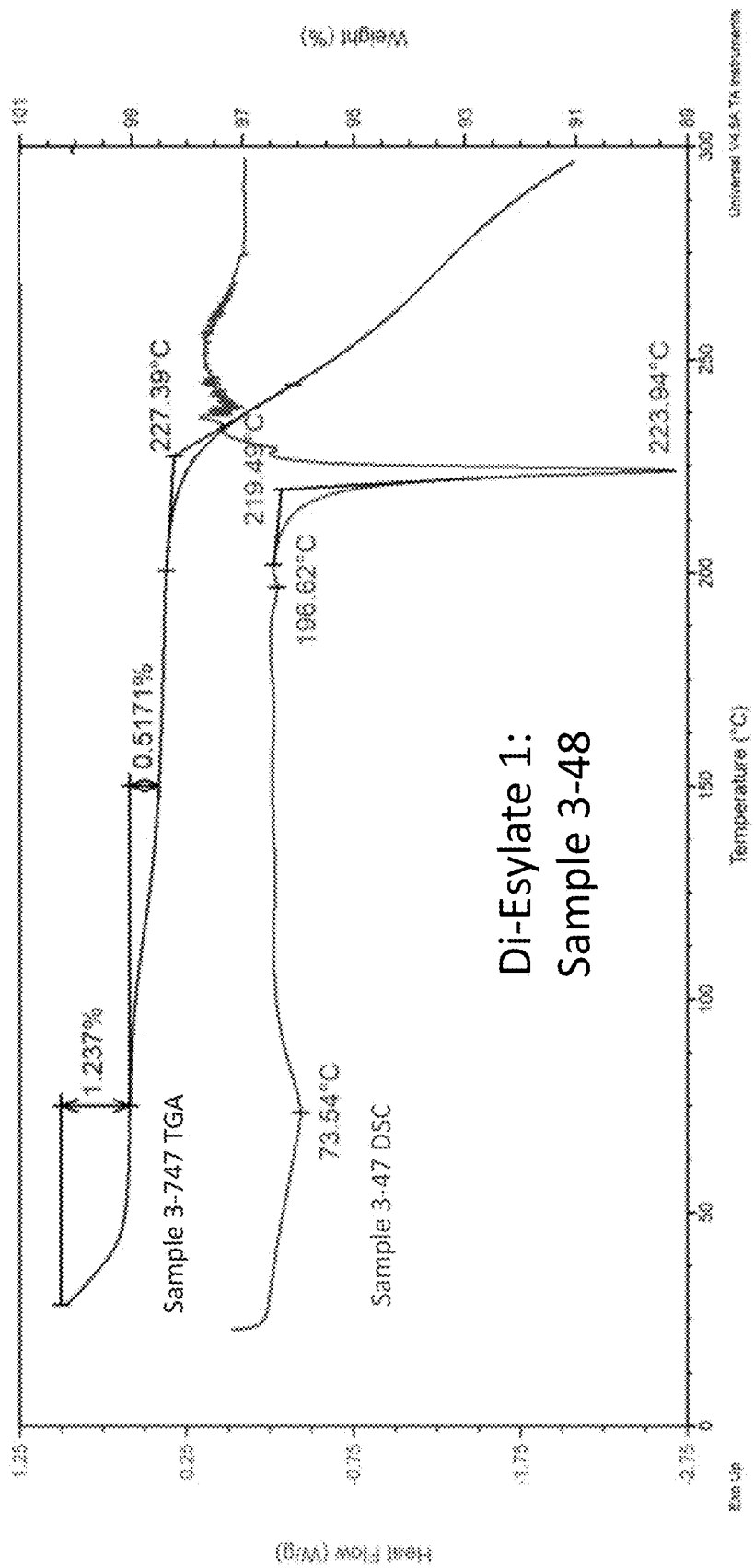
FIG. 32 shows the DSC thermogram of Esylate 5 (Sample 3-24) and the TGA thermogram of Esylate 5 (Sample 3-24).

In one embodiment, the crystalline form L-Malate 1 of a linsitinib L-malate salt is characterized by a DSC thermogram substantially resembling that of FIG. 32.

In one embodiment, the crystalline form L-Malate 1 of a linsitinib L-malate salt is characterized by a TGA signal substantially resembling that of FIG. 32.

In one embodiment, provided is a crystalline form L-Malate 1 of a linsitinib L-malate salt as characterized by any aspect of the present invention, which is present as a material comprising at least about 95% or more by weight of crystalline form L-Malate 1 based of the total amount of linsitinib L-malate salt in the material. In one embodiment, the crystalline form L-Malate 1 comprises at least about 98% or more by weight of crystalline form L-Malate 1 based of the total amount of linsitinib L-malate salt in the material. In one embodiment, the crystalline form L-Malate 1 comprises at least about 99% or more by weight of crystalline form L-Malate 1 based of the total amount of linsitinib L-malate salt in the material. In one embodiment, the crystalline form L-Malate 1 comprises at least about 99.5% or more by weight of crystalline form L-Malate 1 based of the total amount of linsitinib L-malate salt in the material L-Malate 2

In one embodiment, provided is a crystalline linsitinib L-malate salt comprising crystalline form L-Malate 2. In one embodiment, the crystalline form L-Malate 2 of a linsitinib L-malate salt is characterized by a powder x-ray diffraction (PXRD) pattern substantially resembling that of FIG. 36, as determined on a diffractometer using Cu-Kα radiation.

In one embodiment, provided is a crystalline form L-Malate 2 of a linsitinib L-malate salt as characterized by any aspect of the present invention, which is present as a material comprising at least about 95% or more by weight of crystalline form L-Malate 2 based of the total amount of linsitinib L-malate salt in the material. In one embodiment, the crystalline form L-Malate 2 comprises at least about 98% or more by weight of crystalline form L-Malate 2 based of the total amount of linsitinib L-malate salt in the material. In one embodiment, the crystalline form L-Malate 2 comprises at least about 99% or more by weight of crystalline form L-Malate 2 based of the total amount of linsitinib L-malate salt in the material. In one embodiment, the crystalline form L-Malate 2 comprises at least about 99.5% or more by weight of crystalline form L-Malate 2 based of the total amount of linsitinib L-malate salt in the material.

L-Malate 3

In one embodiment, provided is a crystalline linsitinib L-malate salt comprising crystalline form L-Malate 3. In one embodiment, the crystalline form L-Malate 3 of a linsitinib L-malate salt is characterized by a powder x-ray diffraction (PXRD) pattern substantially resembling that of FIG. 36, as determined on a diffractometer using Cu-Kα radiation.

Figure 39:
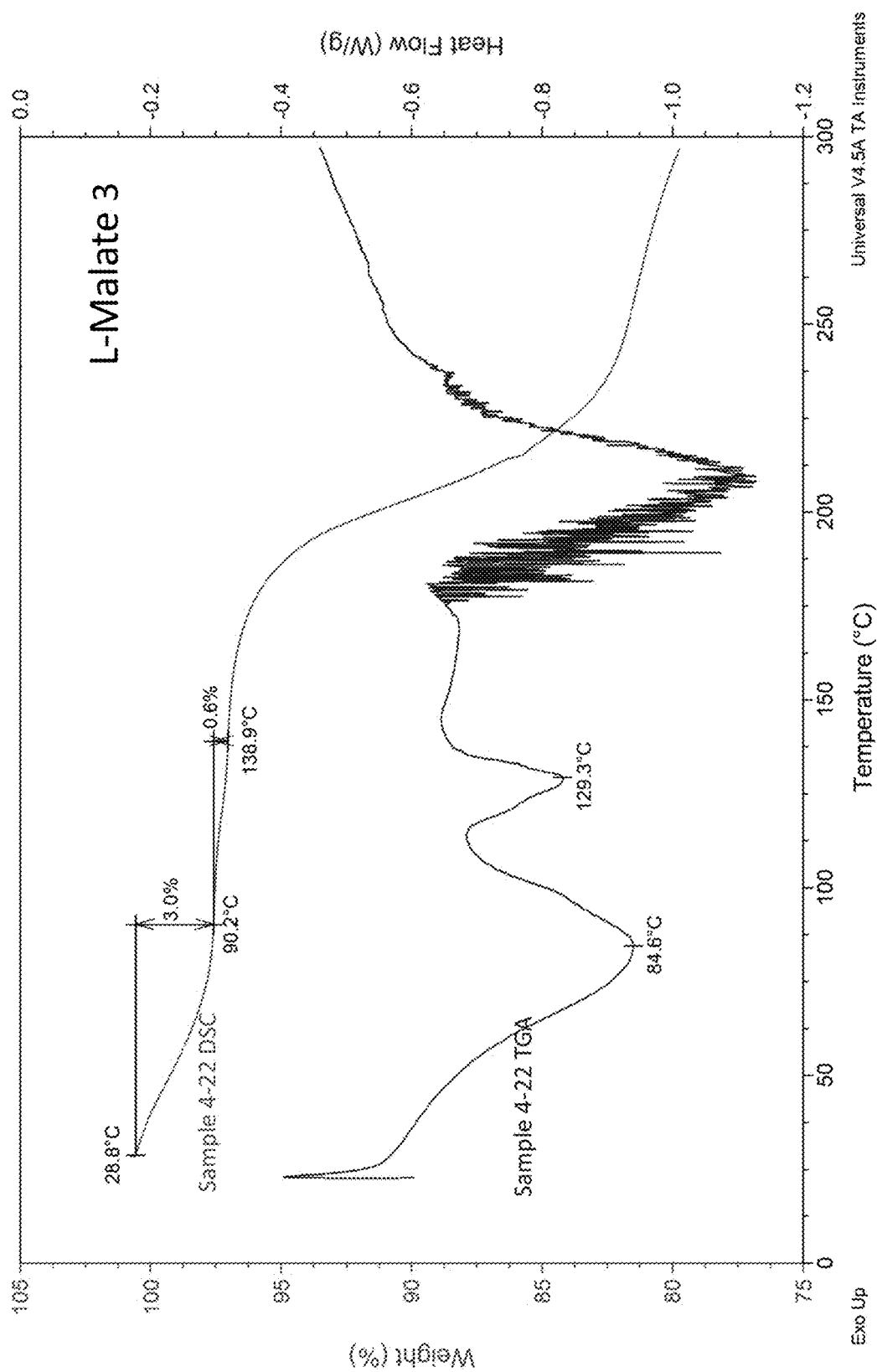
FIG. 39 shows the DSC thermogram of L-Malate 3 (Sample 4-22) and the TGA thermogram of L-Malate 3 (Sample 4-22).

In one embodiment, the crystalline form L-Malate 3 of a linsitinib L-malate salt is characterized by a DSC thermogram substantially resembling that of FIG. 39.

In one embodiment, the crystalline form L-Malate 3 of a linsitinib L-malate salt is characterized by a TGA signal substantially resembling that of FIG. 39.

In one embodiment, provided is a crystalline form L-Malate 3 of a linsitinib L-malate salt as characterized by any aspect of the present invention, which is present as a material comprising at least about 95% or more by weight of crystalline form L-Malate 3 based of the total amount of linsitinib L-malate salt in the material. In one embodiment, the crystalline form L-Malate 3 comprises at least about 98% or more by weight of crystalline form L-Malate 3 based of the total amount of linsitinib L-malate salt in the material. In one embodiment, the crystalline form L-Malate 3 comprises at least about 99% or more by weight of crystalline form L-Malate 3 based of the total amount of linsitinib L-malate salt in the material. In one embodiment, the crystalline form L-Malate 3 comprises at least about 99.5% or more by weight of crystalline form L-Malate 3 based of the total amount of linsitinib L-malate salt in the material.

L-Malate 4

In one embodiment, provided is a crystalline linsitinib L-malate salt comprising crystalline form L-Malate 4. In one embodiment, the crystalline form L-Malate 4 of a linsitinib L-malate salt is characterized by a powder x-ray diffraction (PXRD) pattern substantially resembling that of FIG. 36, as determined on a diffractometer using Cu-Kα radiation.

Figure 41:
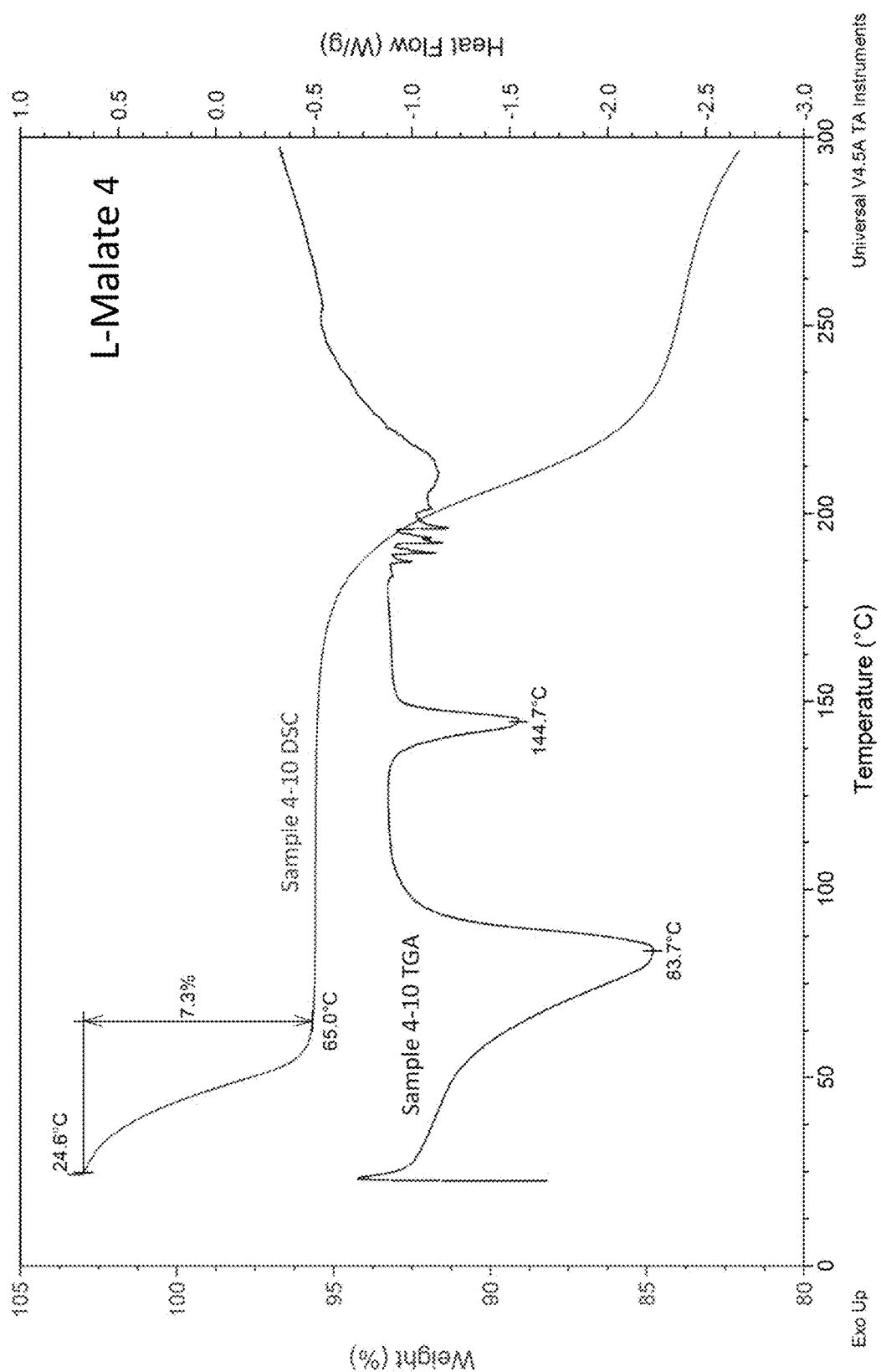
FIG. 41 shows the DSC thermogram of L-Malate 4 (Sample 4-10) and the TGA thermogram of L-Malate 4 (Sample 4-10).

In one embodiment, the crystalline form L-Malate 4 of a linsitinib L-malate salt is characterized by a DSC thermogram substantially resembling that of FIG. 41.

In one embodiment, the crystalline form L-Malate 4 of a linsitinib L-malate salt is characterized by a TGA signal substantially resembling that of FIG. 41.

In one embodiment, provided is a crystalline form L-Malate 4 of a linsitinib L-malate salt as characterized by any aspect of the present invention, which is present as a material comprising at least about 95% or more by weight of crystalline form L-Malate 4 based of the total amount of linsitinib L-malate salt in the material. In one embodiment, the crystalline form L-Malate 4 comprises at least about 98% or more by weight of crystalline form L-Malate 4 based of the total amount of linsitinib L-malate salt in the material. In one embodiment, the crystalline form L-Malate 4 comprises at least about 99% or more by weight of crystalline form L-Malate 4 based of the total amount of linsitinib L-malate salt in the material. In one embodiment, the crystalline form L-Malate 4 comprises at least about 99.5% or more by weight of crystalline form L-Malate 4 based of the total amount of linsitinib L-malate salt in the material.

L-Malate 5

In one embodiment, provided is a crystalline linsitinib L-malate salt comprising crystalline form L-Malate 5. In one embodiment, the crystalline form L-Malate 5 of a linsitinib L-malate salt is characterized by a powder x-ray diffraction (PXRD) pattern substantially resembling that of FIG. 36, as determined on a diffractometer using Cu-Kα radiation.

Figure 43:
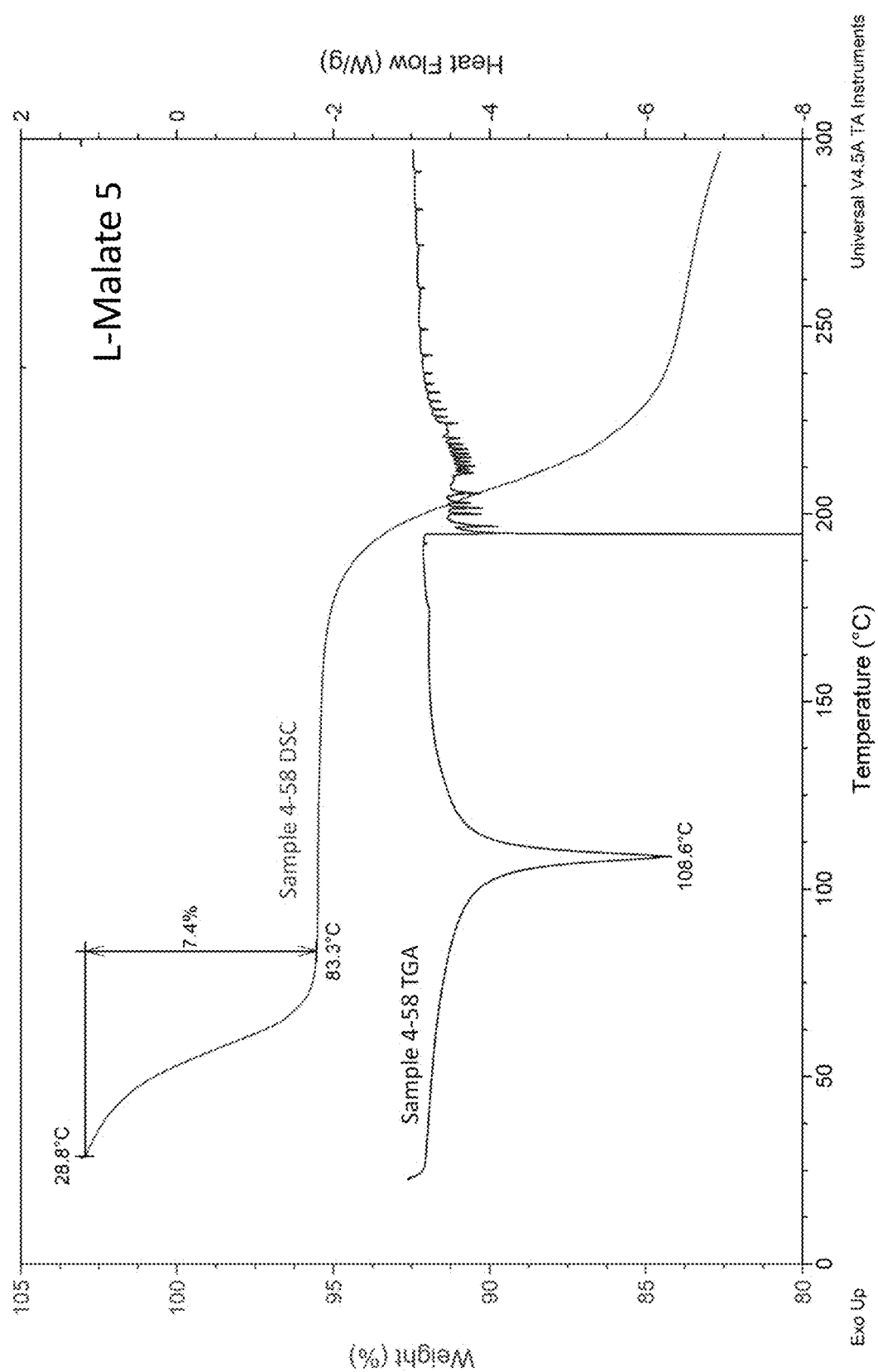
FIG. 43 shows the DSC thermogram of L-Malate 5 (Sample 4-58) and the TGA thermogram of L-Malate 5 (Sample 4-58).

In one embodiment, the crystalline form L-Malate 5 of a linsitinib L-malate salt is characterized by a DSC thermogram substantially resembling that of FIG. 43.

In one embodiment, the crystalline form L-Malate 5 of a linsitinib L-malate salt is characterized by a TGA signal substantially resembling that of FIG. 43.

In one embodiment, provided is a crystalline form L-Malate 5 of a linsitinib L-malate salt as characterized by any aspect of the present invention, which is present as a material comprising at least about 95% or more by weight of crystalline form L-Malate 5 based of the total amount of linsitinib L-malate salt in the material. In one embodiment, the crystalline form L-Malate 5 comprises at least about 98% or more by weight of crystalline form L-Malate 5 based of the total amount of linsitinib L-malate salt in the material. In one embodiment, the crystalline form L-Malate 5 comprises at least about 99% or more by weight of crystalline form L-Malate 5 based of the total amount of linsitinib L-malate salt in the material. In one embodiment, the crystalline form L-Malate 5 comprises at least about 99.5% or more by weight of crystalline form L-Malate 5 based of the total amount of linsitinib L-malate salt in the material.

L-Malate 6

In one embodiment, provided is a crystalline linsitinib L-malate salt comprising crystalline form L-Malate 6. In one embodiment, the crystalline form L-Malate 6 of a linsitinib L-malate salt is characterized by a powder x-ray diffraction (PXRD) pattern substantially resembling that of FIG. 36, as determined on a diffractometer using Cu-Kα radiation.

Figure 45:
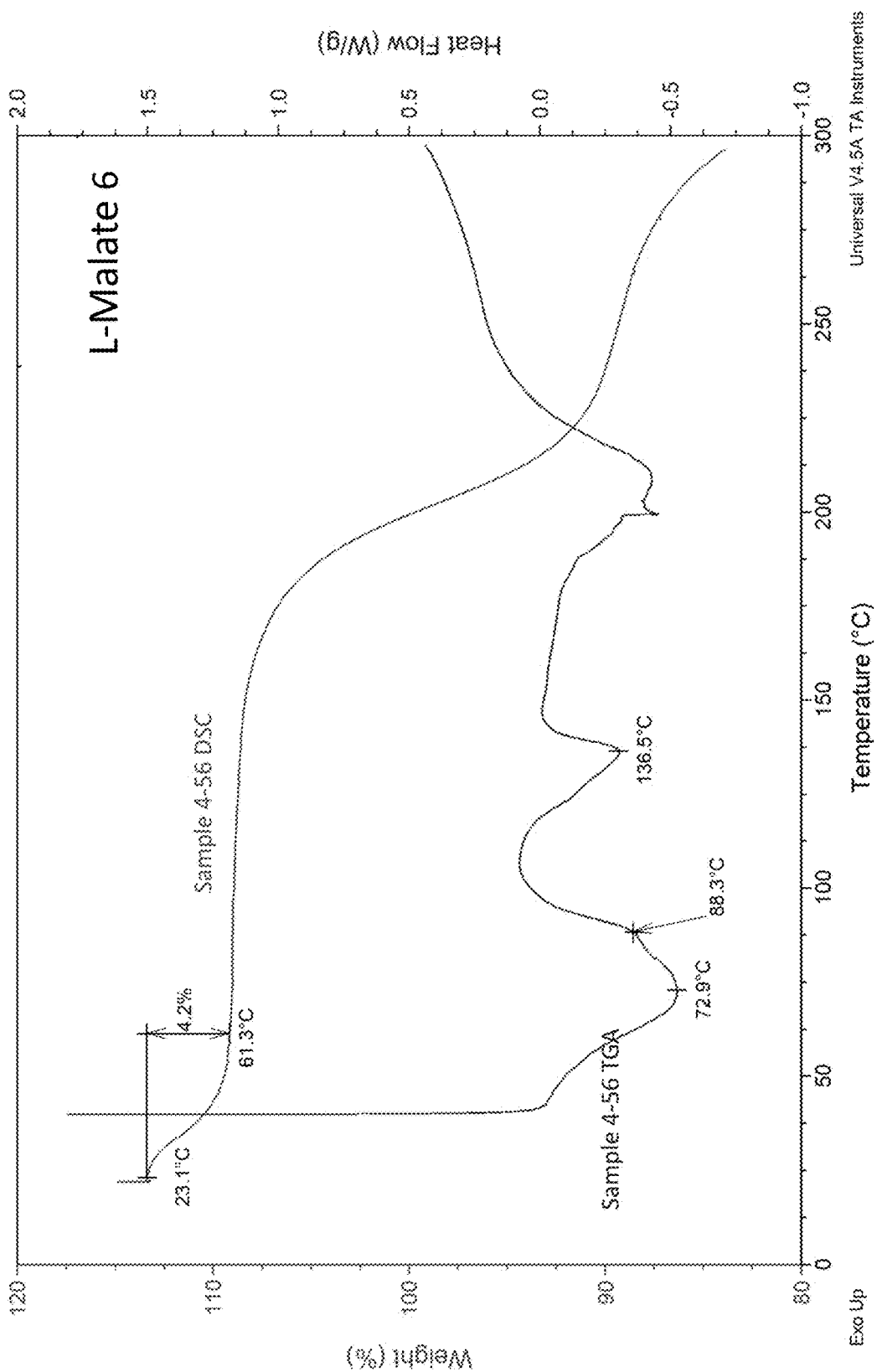
FIG. 45 shows the DSC thermogram of L-Malate 6 (Sample 4-56) and the TGA thermogram of L-Malate 6 (Sample 4-56).

In one embodiment, the crystalline form L-Malate 6 of a linsitinib L-malate salt is characterized by a DSC thermogram substantially resembling that of FIG. 45.

In one embodiment, the crystalline form L-Malate 6 of a linsitinib L-malate salt is characterized by a TGA signal substantially resembling that of FIG. 45.

In one embodiment, provided is a crystalline form L-Malate 6 of a linsitinib L-malate salt as characterized by any aspect of the present invention, which is present as a material comprising at least about 95% or more by weight of crystalline form L-Malate 6 based of the total amount of linsitinib L-malate salt in the material. In one embodiment, the crystalline form L-Malate 6 comprises at least about 98% or more by weight of crystalline form L-Malate 6 based of the total amount of linsitinib L-malate salt in the material. In one embodiment, the crystalline form L-Malate 6 comprises at least about 99% or more by weight of crystalline form L-Malate 6 based of the total amount of linsitinib L-malate salt in the material. In one embodiment, the crystalline form L-Malate 6 comprises at least about 99.5% or more by weight of crystalline form L-Malate 6 based of the total amount of linsitinib L-malate salt in the material.

L-Malate 7

In one embodiment, provided is a crystalline linsitinib L-malate salt comprising crystalline form L-Malate 7. In one embodiment, the crystalline form L-Malate 7 of a linsitinib L-malate salt is characterized by a powder x-ray diffraction (PXRD) pattern substantially resembling that of FIG. 36, as determined on a diffractometer using Cu-Kα radiation.

In one embodiment, provided is a crystalline form L-Malate 7 of a linsitinib L-malate salt as characterized by any aspect of the present invention, which is present as a material comprising at least about 95% or more by weight of crystalline form L-Malate 7 based of the total amount of linsitinib L-malate salt in the material. In one embodiment, the crystalline form L-Malate 7 comprises at least about 98% or more by weight of crystalline form L-Malate 7 based of the total amount of linsitinib L-malate salt in the material. In one embodiment, the crystalline form L-Malate 7 comprises at least about 99% or more by weight of crystalline form L-Malate 7 based of the total amount of linsitinib L-malate salt in the material. In one embodiment, the crystalline form L-Malate 7 comprises at least about 99.5% or more by weight of crystalline form L-Malate 7 based of the total amount of linsitinib L-malate salt in the material.

L-Malate 8

In one embodiment, provided is a crystalline linsitinib L-malate salt comprising crystalline form L-Malate 8. In one embodiment, the crystalline form L-Malate 8 of a linsitinib L-malate salt is characterized by a powder x-ray diffraction (PXRD) pattern substantially resembling that of FIG. 36, as determined on a diffractometer using Cu-Kα radiation.

In one embodiment, provided is a crystalline form L-Malate 8 of a linsitinib L-malate salt as characterized by any aspect of the present invention, which is present as a material comprising at least about 95% or more by weight of crystalline form L-Malate 8 based of the total amount of linsitinib L-malate salt in the material. In one embodiment, the crystalline form L-Malate 8 comprises at least about 98% or more by weight of crystalline form L-Malate 8 based of the total amount of linsitinib L-malate salt in the material. In one embodiment, the crystalline form L-Malate 8 comprises at least about 99% or more by weight of crystalline form L-Malate 8 based of the total amount of linsitinib L-malate salt in the material. In one embodiment, the crystalline form L-Malate 8 comprises at least about 99.5% or more by weight of crystalline form L-Malate 8 based of the total amount of linsitinib L-malate salt in the material.

L-Malate 9

In one embodiment, provided is a crystalline linsitinib L-malate salt comprising crystalline form L-Malate 9. In one embodiment, the crystalline form L-Malate 9 of a linsitinib L-malate salt is characterized by a powder x-ray diffraction (PXRD) pattern substantially resembling that of FIG. 36, as determined on a diffractometer using Cu-Kα radiation.

In one embodiment, provided is a crystalline form L-Malate 9 of a linsitinib L-malate salt as characterized by any aspect of the present invention, which is present as a material comprising at least about 95% or more by weight of crystalline form L-Malate 9 based of the total amount of linsitinib L-malate salt in the material. In one embodiment, the crystalline form L-Malate 9 comprises at least about 98% or more by weight of crystalline form L-Malate 9 based of the total amount of linsitinib L-malate salt in the material. In one embodiment, the crystalline form L-Malate 9 comprises at least about 99% or more by weight of crystalline form L-Malate 9 based of the total amount of linsitinib L-malate salt in the material. In one embodiment, the crystalline form L-Malate 9 comprises at least about 99.5% or more by weight of crystalline form L-Malate 9 based of the total amount of linsitinib L-malate salt in the material.

Edisylate Salt

In one embodiment, the invention provides an edisylate salt of a compound of Formula I:

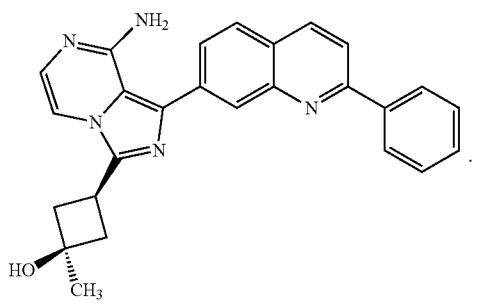

(I)

As described above, Formula I corresponds to Linsitinib. Ethane-1,2-disulfonic acid is a diprotic acid with conjugate bases 2-sulfoethane-1-sulfonate and ethane-1,2-disulfonate, corresponding to each dissociation of the diprotic acid. As used herein, "edisylate" refers to either 2-sulfoethane-1-sulfonate or ethane-1,2-disulfonate. As used herein, "edisylate salt" refers to a salt containing at least one 2-sulfoethane-1-sulfonate or ethane-1,2-disulfonate anion. In certain embodiments, the edisylate salt of Linsitinib is a salt according to Formula IV:

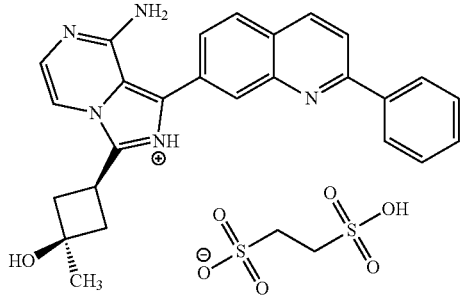

(IV)

In one aspect, the invention provides a crystalline form of an edisylate salt of a compound of Formula I:

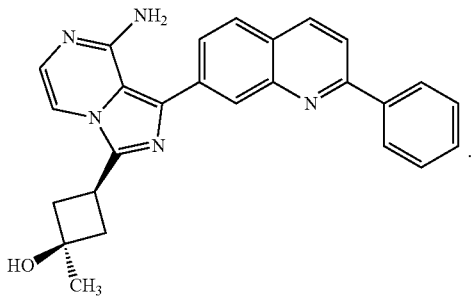

(I)

Edisylate 1

Figure 49:
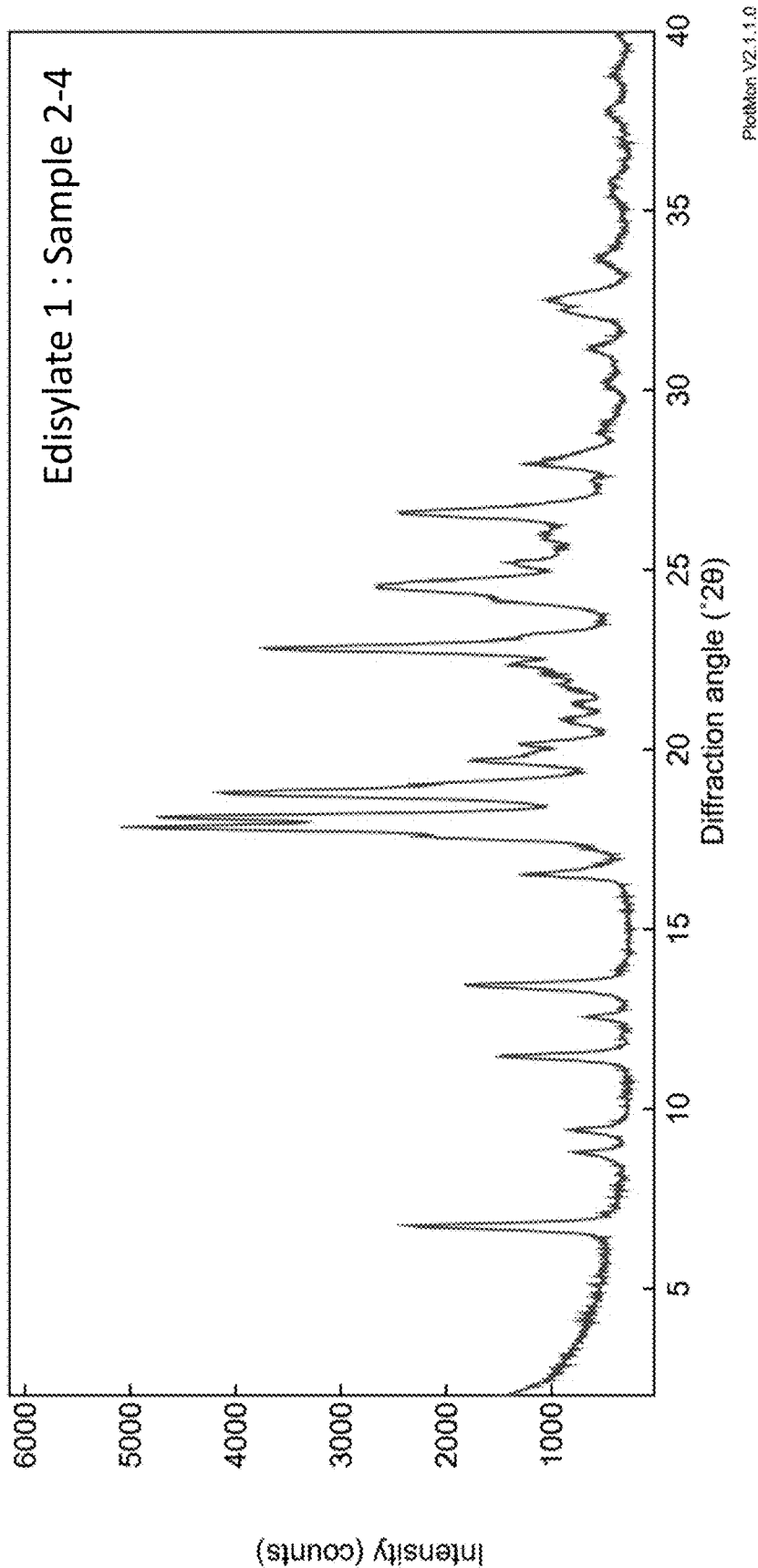
FIG. 49 shows the PXRD of Edisylate 1 (Sample 2-4).

In one embodiment, provided is a crystalline linsitinib edisylate salt comprising crystalline form Edisylate 1. In one embodiment, the crystalline form Edisylate 1 of a linsitinib edisylate salt is characterized by a powder x-ray diffraction (PXRD) pattern substantially resembling that of FIG. 49, as determined on a diffractometer using Cu-Kα radiation.

Figure 52:
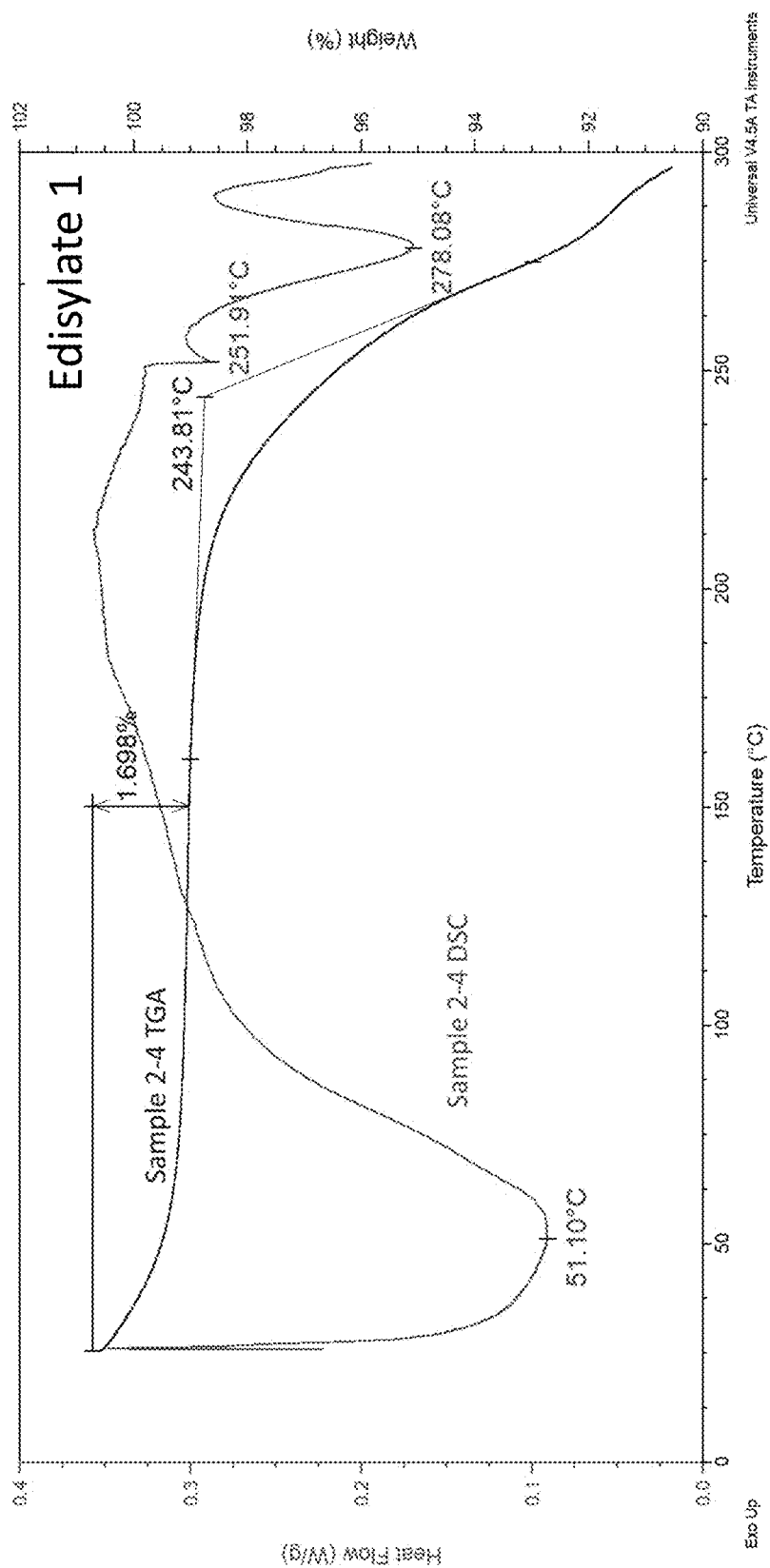
FIG. 52 shows the DSC thermogram of Edisylate 1 (Sample 2-4) and the TGA thermogram of Edisylate 1 (Sample 2-4).

In one embodiment, the crystalline form Edisylate 1 of a linsitinib edisylate salt is characterized by a DSC thermogram substantially resembling that of FIG. 52.

In one embodiment, the crystalline form Edisylate 1 of a linsitinib edisylate salt is characterized by a TGA signal substantially resembling that of FIG. 52.

In one embodiment, provided is a crystalline form Edisylate 1 of a linsitinib edisylate salt as characterized by any aspect of the present invention, which is present as a material comprising at least about 95% or more by weight of crystalline form Edisylate 1 based of the total amount of linsitinib edisylate salt in the material. In one embodiment, the crystalline form Edisylate 1 comprises at least about 98% or more by weight of crystalline form Edisylate 1 based of the total amount of linsitinib edisylate salt in the material. In one embodiment, the crystalline form Edisylate 1 comprises at least about 99% or more by weight of crystalline form Edisylate 1 based of the total amount of linsitinib edisylate salt in the material. In one embodiment, the crystalline form Edisylate 1 comprises at least about 99.5% or more by weight of crystalline form Edisylate 1 based of the total amount of linsitinib edisylate salt in the material.

Maleate Salt

In one embodiment, the invention provides a maleic acid salt of a compound of Formula I:

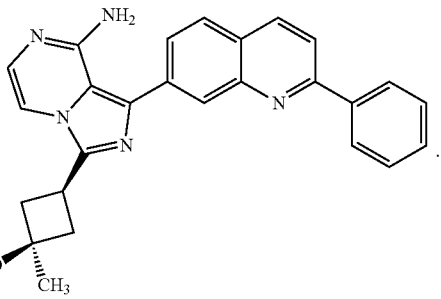

(I)

As described above, Formula I corresponds to Linsitinib. Cis-butenediic acid is a diprotic acid with conjugate bases (Z)-3-carboxyacrylate and maleate, corresponding to each dissociation of the diprotic acid. As used herein, "maleic acid salt" or "maleate salt" refers to a salt containing at least one (Z)-3-carboxyacrylate anion or at least one maleate anion. In certain embodiments, the maleate salt of Linsitinib is a salt according to Formula V:

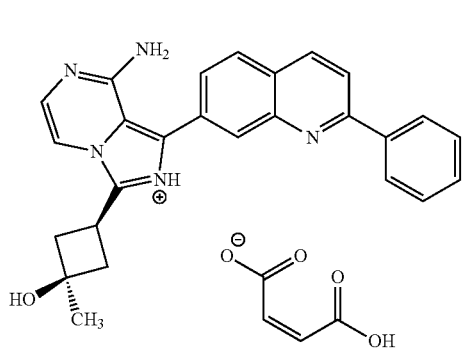

(V)

In one aspect, the invention provides a crystalline of a maleate salt of a compound of Formula I:

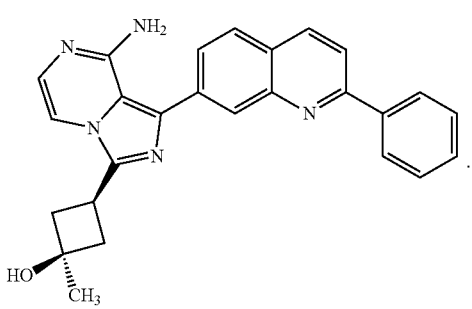

(I)

Maleate 1

In one embodiment, provided is a crystalline linsitinib maleate salt comprising crystalline form Maleate 1. In one embodiment, the crystalline form Maleate 1 of a linsitinib maleate salt is characterized by a powder x-ray diffraction (PXRD) pattern substantially resembling that of FIG. 53, as determined on a diffractometer using Cu-Kα radiation.

Figure 55:
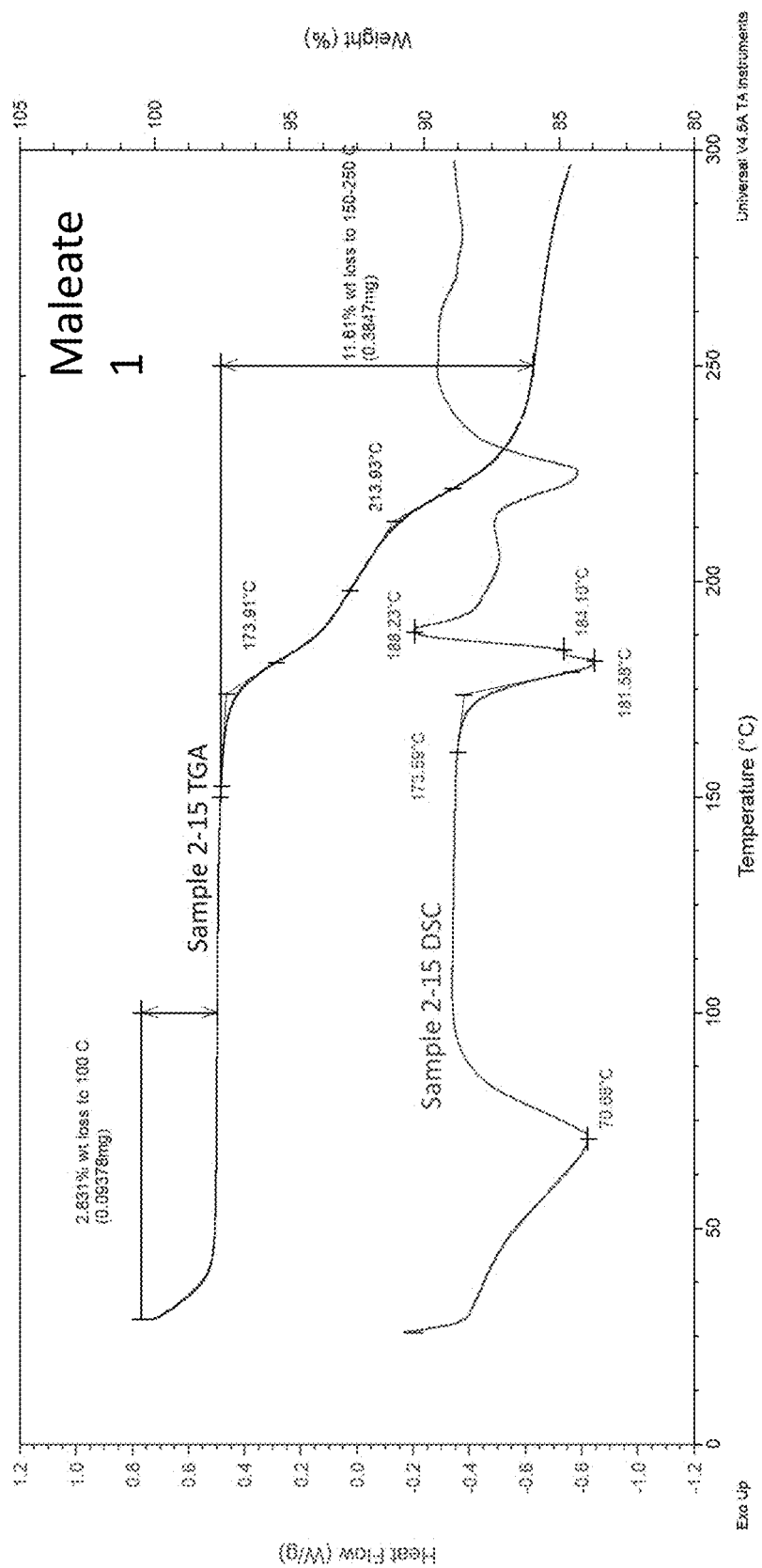
FIG. 55 shows the DSC thermogram of Maleate 1 (Sample 2-15) and the TGA thermogram of Maleate 1 (Sample 2-15).

In one embodiment, the crystalline form Maleate 1 of a linsitinib maleate salt is characterized by a DSC thermogram substantially resembling that of FIG. 55.

In one embodiment, the crystalline form Maleate 1 of a linsitinib maleate salt is characterized by a TGA signal substantially resembling that of FIG. 55.

In one embodiment, provided is a crystalline form Maleate 1 of a linsitinib maleate salt as characterized by any aspect of the present invention, which is present as a material comprising at least about 95% or more by weight of crystalline form Maleate 1 based of the total amount of linsitinib maleate salt in the material. In one embodiment, the crystalline form Maleate 1 comprises at least about 98% or more by weight of crystalline form Maleate 1 based of the total amount of linsitinib maleate salt in the material. In one embodiment, the crystalline form Maleate 1 comprises at least about 99% or more by weight of crystalline form Maleate 1 based of the total amount of linsitinib maleate salt in the material. In one embodiment, the crystalline form Maleate 1 comprises at least about 99.5% or more by weight of crystalline form Maleate 1 based of the total amount of linsitinib maleate salt in the material.

Napsylate Salt

In one embodiment, the invention provides a naphthalene-2-sulfonic acid salt of a compound of Formula I:

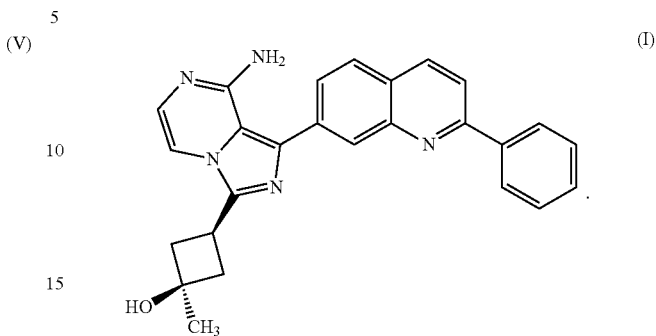

(I)

As described above, Formula I corresponds to Linsitinib. Napthalene-2-sulfonic acid is a monoprotic acid with the conjugate base naphthalene-2-sulfonate. As used herein, "napsylate" refers to a naphthalene-2-sulfonate anion. As used herein, "napsylate salt" refers to a salt containing at least one naphthalene-2-sulfonate anion. In certain embodiments, the napsylate salt of Linsitinib is a salt according to Formula VI:

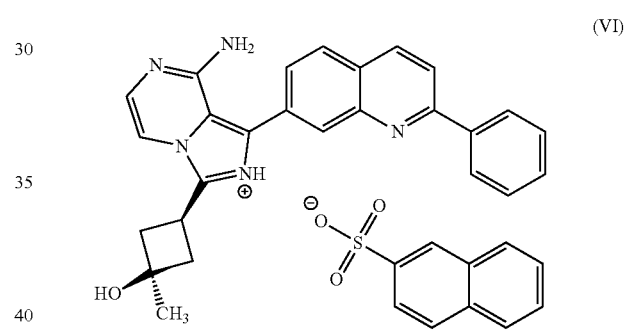

(VI)

In one aspect, the invention provides a crystalline form of a napsylate salt of a compound of Formula I:

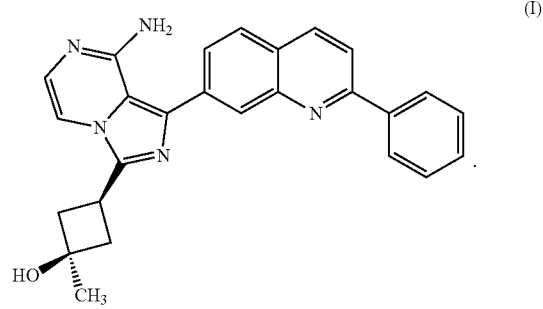 [SMILES: C[C@]1(O)C[C@@H](c2nc(-c3ccc4ccc(-c5ccccc5)nc4c3)c3c(N)nccn32)C1]

(I)

Napsylate 1

In one embodiment, provided is a crystalline linsitinib napsylate salt comprising crystalline form Napsylate 1. In one embodiment, the crystalline form Napsylate 1 of a linsitinib napsylate salt is characterized by a powder x-ray diffraction (PXRD) pattern substantially resembling that of FIG. 56, as determined on a diffractometer using Cu-Kα radiation.

Figure 58:
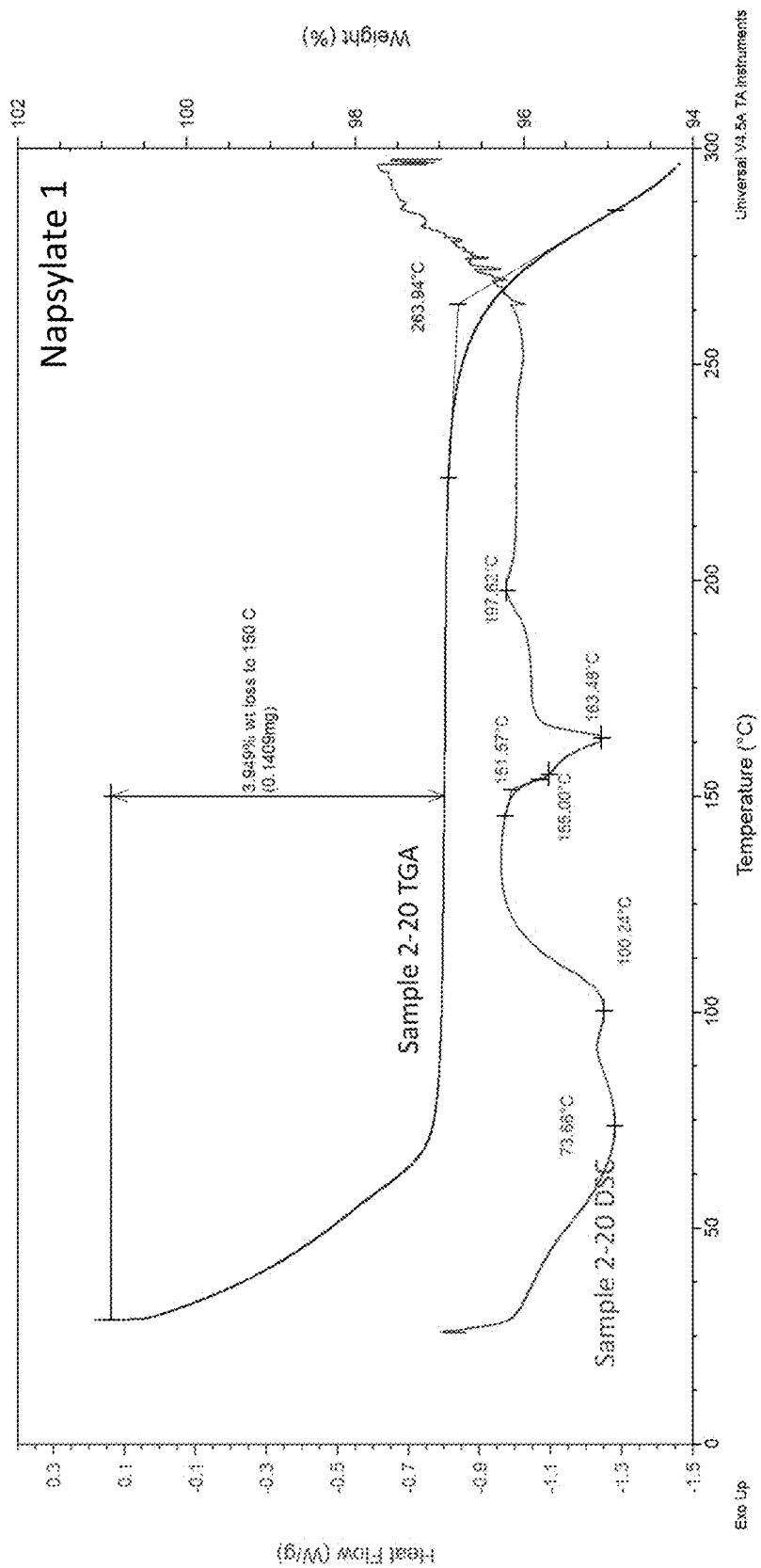
FIG. 58 shows the DSC thermogram of Napsylate 1 (Sample 2-20) and the TGA thermogram of Napsylate 1 (Sample 2-20).

In one embodiment, the crystalline form Napsylate 1 of a linsitinib napsylate salt is characterized by a DSC thermogram substantially resembling that of FIG. 58.

In one embodiment, the crystalline form Napsylate 1 of a linsitinib napsylate salt is characterized by a TGA signal substantially resembling that of FIG. 58.

In one embodiment, provided is a crystalline form Napsylate 1 of a linsitinib napsylate salt as characterized by any aspect of the present invention, which is present as a material comprising at least about 95% or more by weight of crystalline form Napsylate 1 based of the total amount of linsitinib napsylate salt in the material. In one embodiment, the crystalline form Napsylate 1 comprises at least about 98% or more by weight of crystalline form Napsylate 1 based of the total amount of linsitinib napsylate salt in the material. In one embodiment, the crystalline form Napsylate 1 comprises at least about 99% or more by weight of crystalline form Napsylate 1 based of the total amount of linsitinib napsylate salt in the material. In one embodiment, the crystalline form Napsylate 1 comprises at least about 99.5% or more by weight of crystalline form Napsylate 1 based of the total amount of linsitinib napsylate salt in the material.

Phosphate Salt

In one embodiment, the invention provides a phosphoric acid salt of a compound of Formula I:

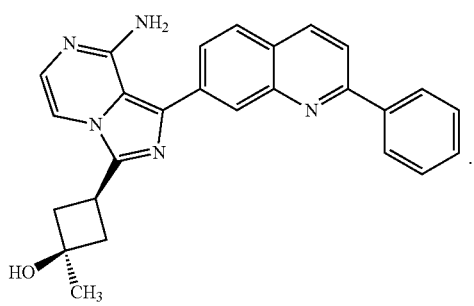

(I)

As described above, Formula I corresponds to Linsitinib. Phosphoric acid is a triprotic acid with conjugate bases including dihydrogen phosphate, hydrogen phosphate, and phosphate. As used herein, "phosphoric acid salt" or "phosphate salt" refers to a salt containing at least one dihydrogen phosphate anion, at least one hydrogen phosphate anion, or at least one phosphate anion. In certain embodiments, the phosphate salt of Linsitinib is a salt according to Formula VII:

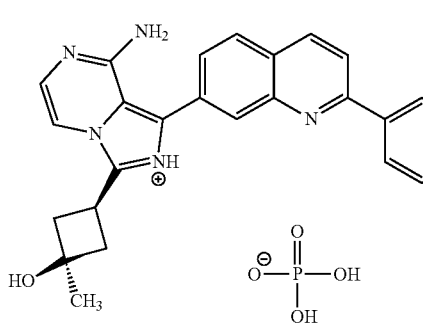

(VII)

In one aspect, the invention provides a crystalline form of a phosphate salt of a compound of Formula I:

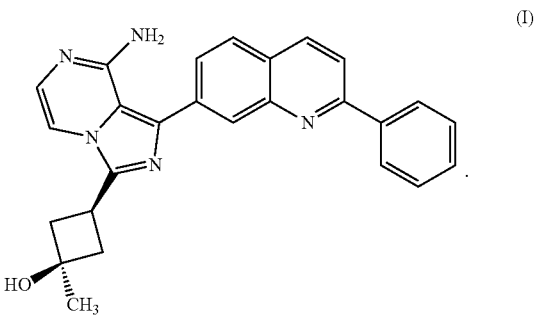 [SMILES: C[C@]1(O)C[C@@H](c2nc(-c3ccc4ccc(-c5ccccc5)nc4c3)c3c(N)nccn32)C1]

(I)

Phosphate 1

In one embodiment, provided is a crystalline linsitinib phosphate salt comprising crystalline form Phosphate 1. In one embodiment, the crystalline form Phosphate 1 of a linsitinib phosphate salt is characterized by a powder x-ray diffraction (PXRD) pattern substantially resembling that of FIG. 59, as determined on a diffractometer using Cu-Kα radiation.

Figure 61:
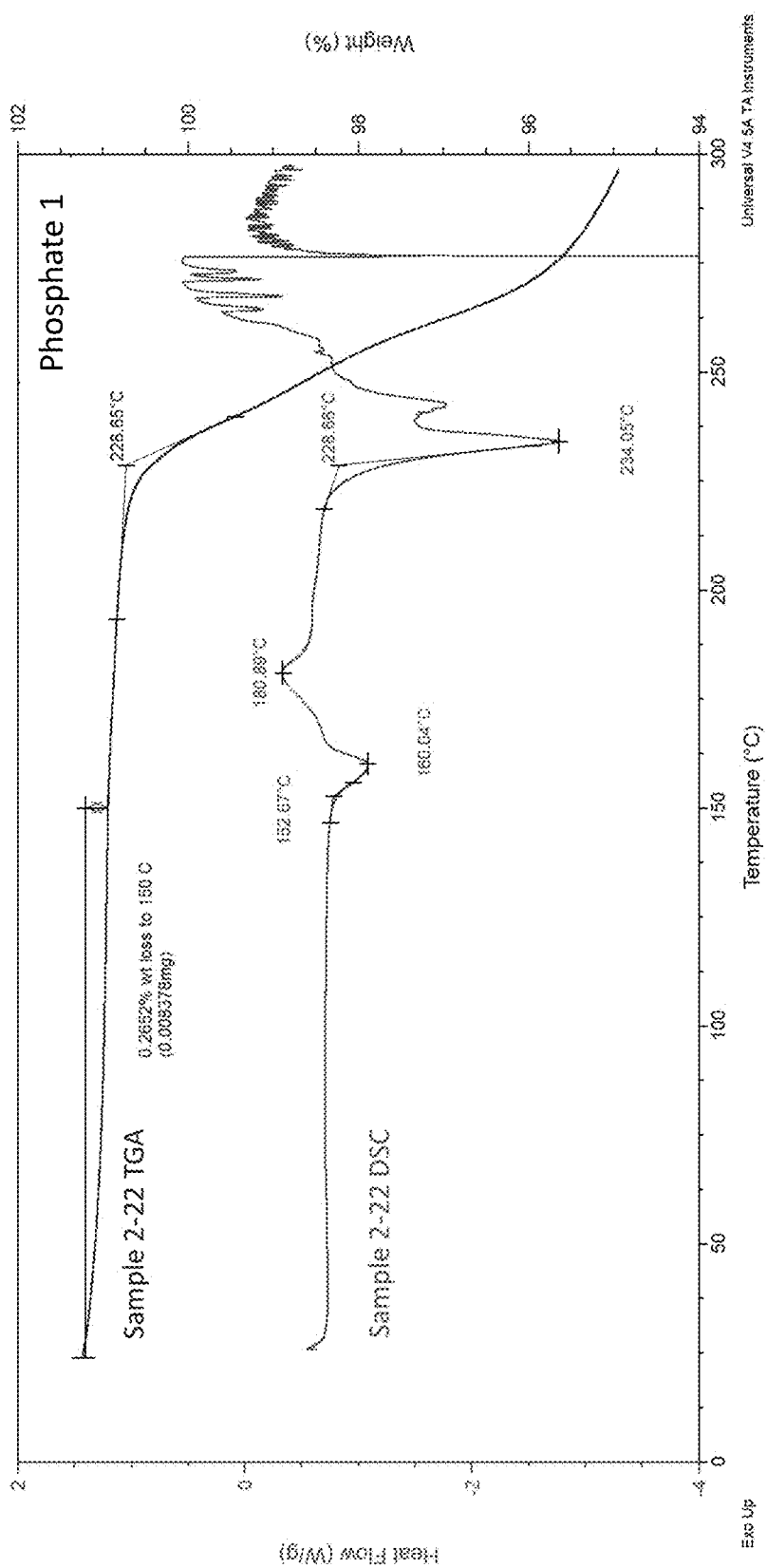
FIG. 61 shows the DSC thermogram of Phosphate 1 (Sample 2-22) and the TGA thermogram of Phosphate 1 (Sample 2-22).

In one embodiment, the crystalline form Phosphate 1 of a linsitinib phosphate salt is characterized by a DSC thermogram substantially resembling that of FIG. 61.

In one embodiment, the crystalline form Phosphate 1 of a linsitinib phosphate salt is characterized by a TGA signal substantially resembling that of FIG. 61.

In one embodiment, provided is a crystalline form Phosphate 1 of a linsitinib phosphate salt as characterized by any aspect of the present invention, which is present as a material comprising at least about 95% or more by weight of crystalline form Phosphate 1 based of the total amount of linsitinib phosphate salt in the material. In one embodiment, the crystalline form Phosphate 1 comprises at least about 98% or more by weight of crystalline form Phosphate 1 based of the total amount of linsitinib phosphate salt in the material. In one embodiment, the crystalline form Phosphate 1 comprises at least about 99% or more by weight of crystalline form Phosphate 1 based of the total amount of linsitinib phosphate salt in the material. In one embodiment, the crystalline form Phosphate 1 comprises at least about 99.5% or more by weight of crystalline form Phosphate 1 based of the total amount of linsitinib phosphate salt in the material.

HCl Salt

In one embodiment, the invention provides a hydrochloric acid salt of a compound of Formula I:

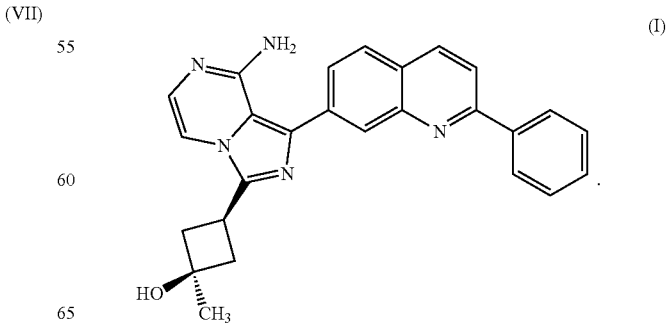

(I)

As described above, Formula I corresponds to Linsitinib. As used herein, "hydrochloric acid salt" or "HCl salt" refers to a salt containing at least one chloride. In certain embodiments, the HCl salt of Linsitinib is a salt according to Formula VIII:

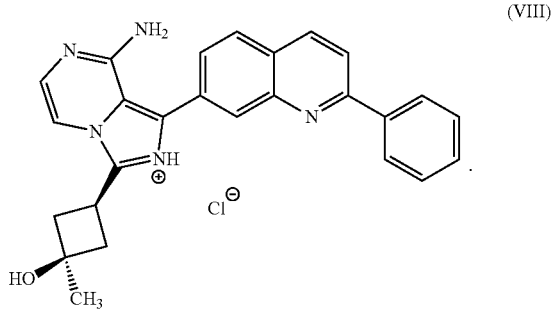 [SMILES: C[C@]1(O)C[C@@H](c2[nH+]c(-c3ccc4ccc(-c5ccccc5)nc4c3)c3c(N)nccn32)C1 ; [Cl-]]
(VIII)

In one aspect, the invention provides a crystalline form of an HCl salt of a compound of Formula I:

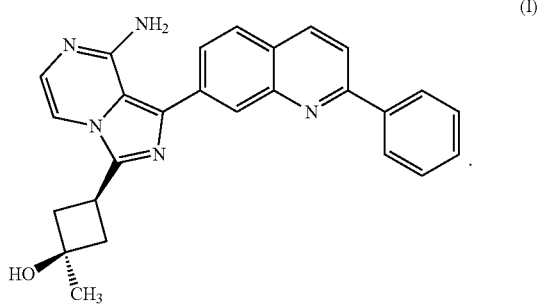 [SMILES: C[C@]1(O)C[C@@H](c2nc(-c3ccc4ccc(-c5ccccc5)nc4c3)c3c(N)nccn32)C1]
(I)

HCl 1

In one embodiment, provided is a crystalline linsitinib HCl salt comprising crystalline form HCl 1. In one embodiment, the crystalline form HCl 1 of a linsitinib HCl salt is characterized by a powder x-ray diffraction (PXRD) pattern substantially resembling that of FIG. 62, as determined on a diffractometer using Cu-Kα radiation.

Figure 65:
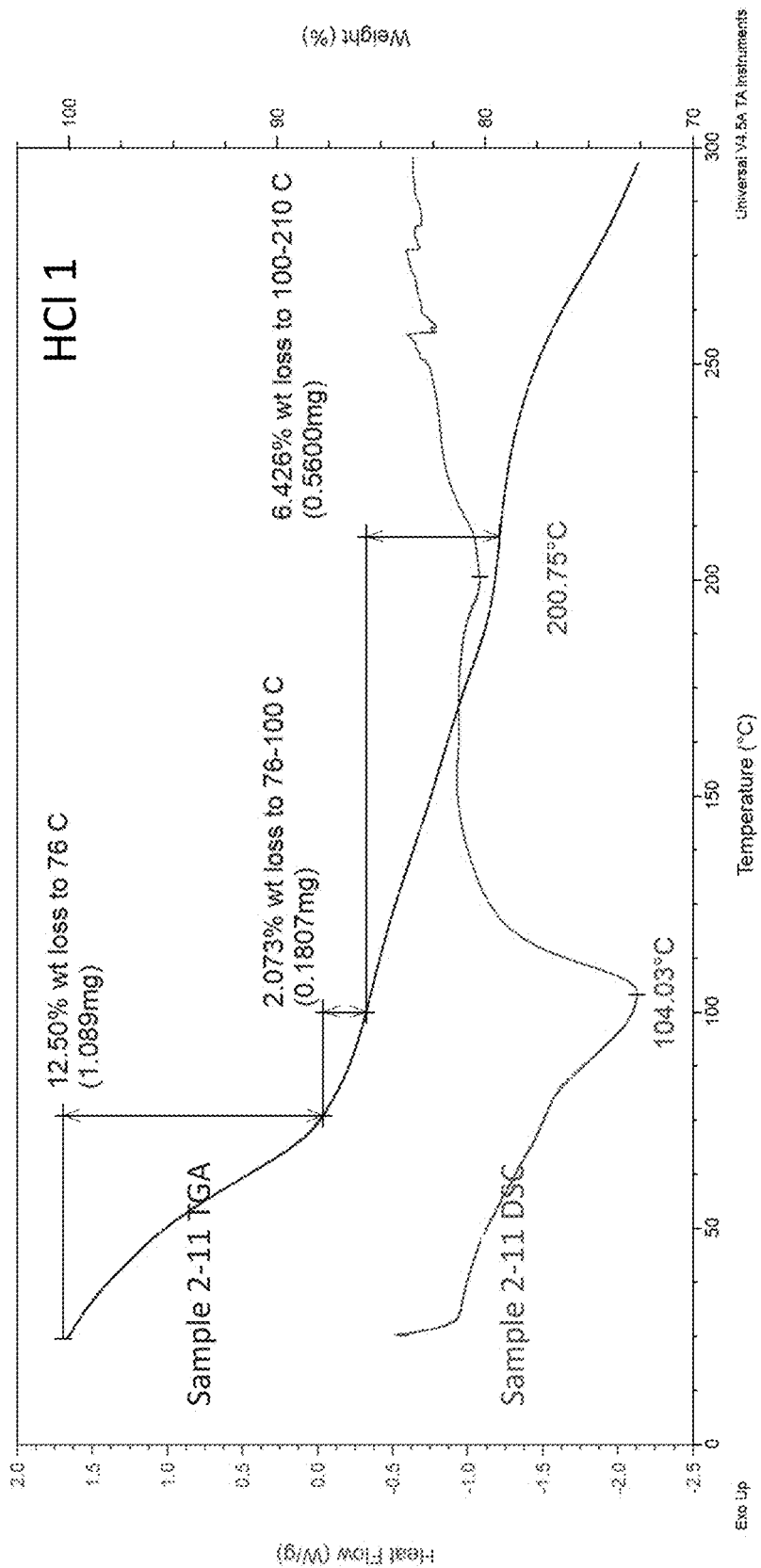
FIG. 65 shows the DSC thermogram of HCl 1 (Sample 2-11) and the TGA thermogram of HCl 1 (Sample 2-11).

In one embodiment, the crystalline form HCl 1 of a linsitinib HCl salt is characterized by a DSC thermogram substantially resembling that of FIG. 65.

In one embodiment, the crystalline form HCl 1 of a linsitinib HCl salt is characterized by a TGA signal substantially resembling that of FIG. 65.

In one embodiment, provided is a crystalline form HCl 1 of a linsitinib HCl salt as characterized by any aspect of the present invention, which is present as a material comprising at least about 95% or more by weight of crystalline form HCl 1 based of the total amount of linsitinib HCl salt in the material. In one embodiment, the crystalline form HCl 1 comprises at least about 98% or more by weight of crystalline form HCl 1 based of the total amount of linsitinib HCl salt in the material. In one embodiment, the crystalline form HCl 1 comprises at least about 99% or more by weight of crystalline form HCl 1 based of the total amount of linsitinib HCl salt in the material. In one embodiment, the crystalline form HCl 1 comprises at least about 99.5% or more by weight of crystalline form HCl 1 based of the total amount of linsitinib HCl salt in the material.

Fumarate Salt

In one embodiment, the invention provides a fumaric acid salt of a compound of Formula I:

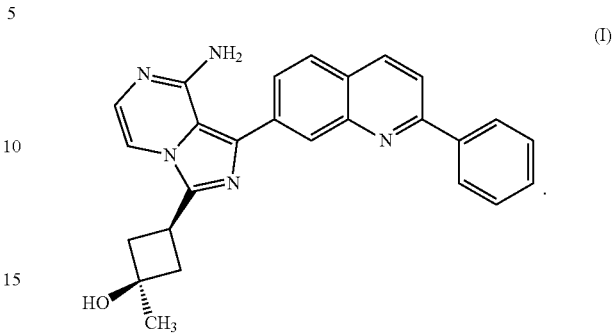
(I)

As described above, Formula I corresponds to Linsitinib. Trans-butenediic acid is a diprotic acid with conjugate bases (E)-3-carboxyacrylate and fumarate, corresponding to each dissociation of the diprotic acid. As used herein, "fumaric acid salt" or "fumarate salt" refers to a salt containing at least one (E)-3-carboxyacrylate anion or at least one fumarate anion. In certain embodiments, the fumarate salt of Linsitinib is a salt according to Formula IX

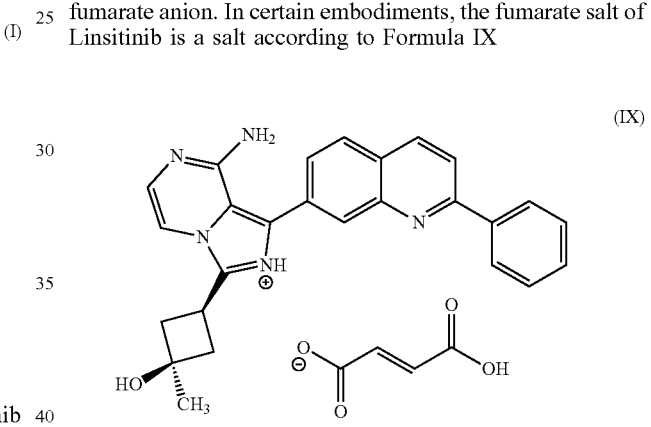
(IX)

In one aspect, the invention provides crystalline form of a fumarate salt of a compound of Formula I:

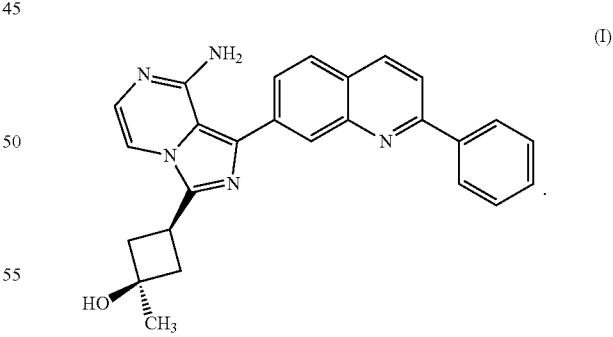
(I)

Fumarate 1

Figure 66:
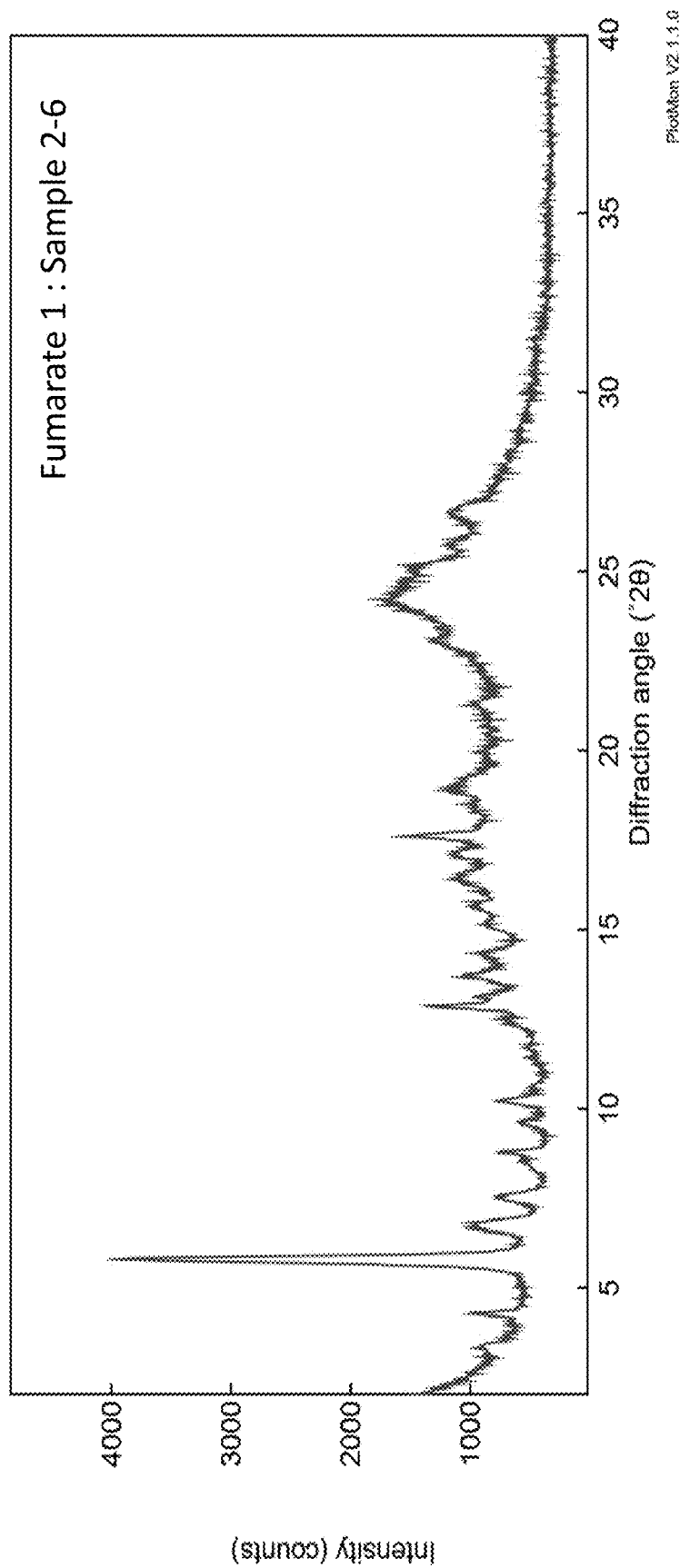
FIG. 66 shows the PXRD of Fumarate 1 (Sample 2-6).

In one embodiment, provided is a crystalline linsitinib fumarate salt comprising crystalline form Fumarate 1. In one embodiment, the crystalline form Fumarate 1 of a linsitinib fumarate salt is characterized by a powder x-ray diffraction (PXRD) pattern substantially resembling that of FIG. 66, as determined on a diffractometer using Cu-Kα radiation.

In one embodiment, provided is a crystalline form Fumarate 1 of a linsitinib fumarate salt as characterized by any aspect of the present invention, which is present as a material comprising at least about 95% or more by weight of crystalline form Fumarate 1 based of the total amount of linsitinib fumarate salt in the material. In one embodiment, the crystalline form Fumarate 1 comprises at least about 98% or more by weight of crystalline form Fumarate 1 based of the total amount of linsitinib fumarate salt in the material. In one embodiment, the crystalline form Fumarate 1 comprises at least about 99% or more by weight of crystalline form Fumarate 1 based of the total amount of linsitinib fumarate salt in the material. In one embodiment, the crystalline form Fumarate 1 comprises at least about 99.5% or more by weight of crystalline form Fumarate 1 based of the total amount of linsitinib fumarate salt in the material.

Linsitinib Cocrystals

One of skill in the art will appreciate that a number of pharmaceutically acceptable coformers can be used to prepare Linsitinib cocrystals. The coformers represent various different hydrogen bond donating and accepting groups that could pair with the donors and acceptors in the structure of linsitinib. The list of coformers included some weaker acids not expected to be strong enough to fully protonate linsitinib but that would likely be able to participate in hydrogen bonding. Pharmaceutically acceptable coformers include, but are not limited to, acesulfame K, adenine, adipic acid, 4-aminosalicylic acid, L-arginine, L-ascorbic acid, benzamide, benzoic acid, betaine HCl, caffeine, cinnamic acid, creatinine, D-fructose, D-gluconic acid, glucosamine HCl, D-glucose, L-glutamine, glutaric acid, glycine, hippuric acid, isonicotinamide, L-lactic acid, lactose, L-leucine, malonic acid, maltol, D-mannitol, methyl paraben, monosodium glutamate, nicotinamide, orotic acid, propyl gallate, saccharin, salicylic acid, sebacic acid, sodium lauryl sulfate, sorbic acid, stearic acid, succinic acid, sucrose, taurine, thiamine chloride HCl, L-threonine, tromethamine HCl, L-tryptophan, urea, L-valine, vanillin, xanthine, xylitol, and the like. In certain embodiments, the Linsitinib cocrystal comprises a cocrystal derived from gluconic acid, orotic acid, or salicylic acid.

Salicylic Cocrystal

In another embodiment, the invention provides salicylic acid cocrystal of a compound of Formula I:

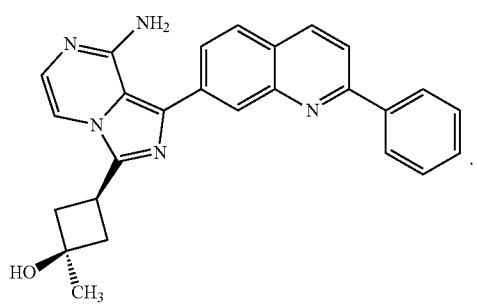

(I)

As described above, Formula I corresponds to Linsitinib. Salicylic acid is a weak acid. As used herein, "salicylic cocrystal" or "salicylic salt" refers to a cocrystal containing at least one salicylic acid. In certain embodiments, the salicylic acid cocrystal of Linsitinib is a cocrystal according to Formula X:

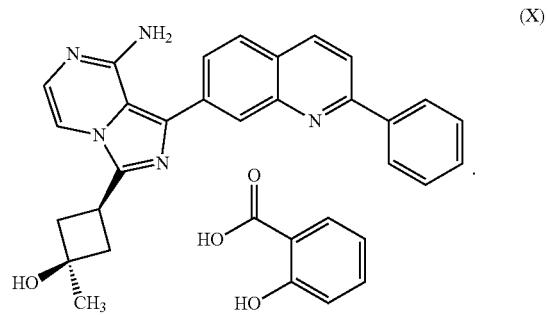

(X)

In one aspect, the invention provides a crystalline form of a salicylic cocrystal of a compound of Formula I:

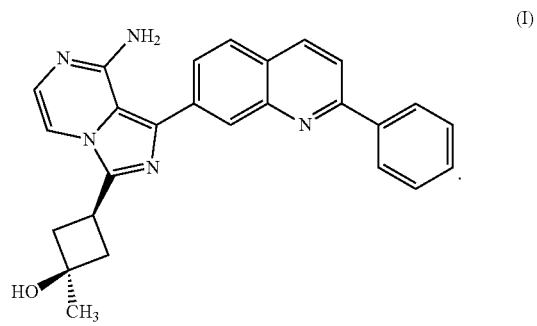 [SMILES: C[C@]1(O)C[C@@H](c2nc(-c3ccc4ccc(-c5ccccc5)nc4c3)c3c(N)nccn32)C1]

(I)

Salicylic 1

Figure 70:
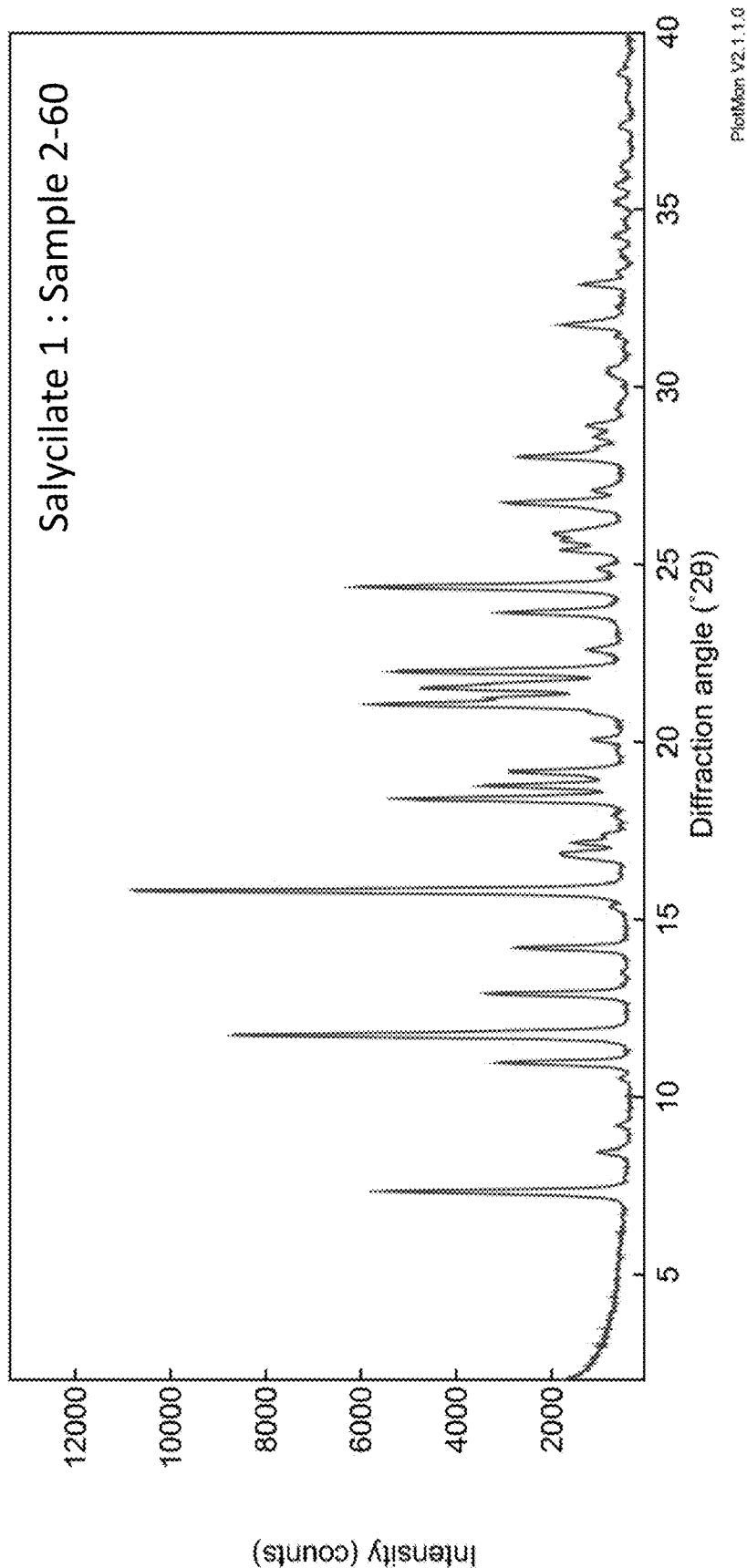
FIG. 70 shows the PXRD of Salicylate 1 and coformer (Sample 2-60).

In one embodiment, provided is a crystalline linsitinib salicylic cocrystal comprising crystalline form Salicylic 1. In one embodiment, the crystalline form Salicylic 1 of a linsitinib salicylic cocrystal is characterized by a powder x-ray diffraction (PXRD) pattern substantially resembling that of FIG. 70, as determined on a diffractometer using Cu-Kα radiation.

In one embodiment, provided is a crystalline form Salicylic 1 of a linsitinib salicylic cocrystal as characterized by any aspect of the present invention, which is present as a material comprising at least about 95% or more by weight of crystalline form Salicylic 1 based of the total amount of linsitinib salicylic cocrystal in the material. In one embodiment, the crystalline form Salicylic 1 comprises at least about 98% or more by weight of crystalline form Salicylic 1 based of the total amount of linsitinib salicylic cocrystal in the material. In one embodiment, the crystalline form Salicylic 1 comprises at least about 99% or more by weight of crystalline form Salicylic 1 based of the total amount of linsitinib salicylic cocrystal in the material. In one embodiment, the crystalline form Salicylic 1 comprises at least about 99.5% or more by weight of crystalline form Salicylic 1 based of the total amount of linsitinib salicylic cocrystal in the material.

Gluconic Cocrystal

In another embodiment, the invention provides a gluconic acid cocrystal of a compound of Formula I:

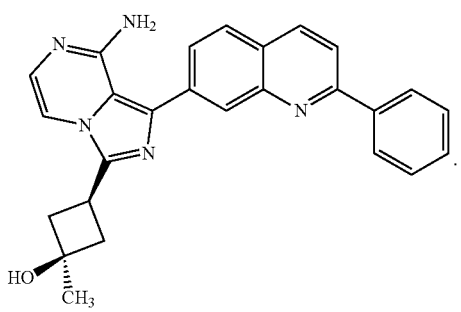

(I)

As described above, Formula I corresponds to Linsitinib. Gluconic acid is a weak acid. As used herein, "gluconic cocrystal" or "gluconic salt" refers to a cocrystal containing at least one gluconic acid. In certain embodiments, the gluconic acid cocrystal of Linsitinib is a cocrystal according to Formula XI:

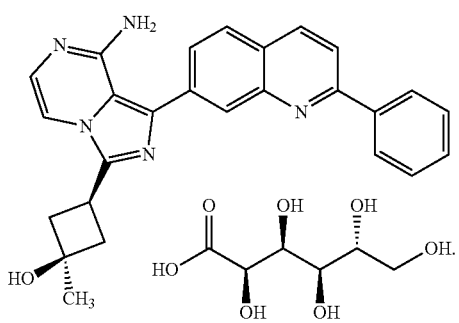

(XI)

In one aspect, the invention provides a crystalline form of a gluconic cocrystal of a compound of Formula I:

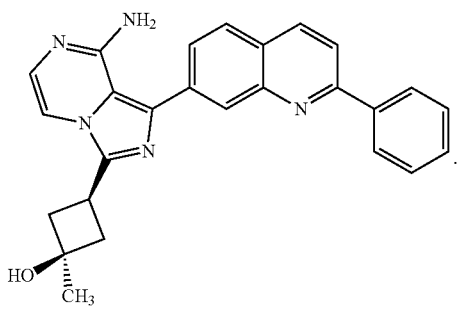

(I)

Gluconic 1

Figure 68:
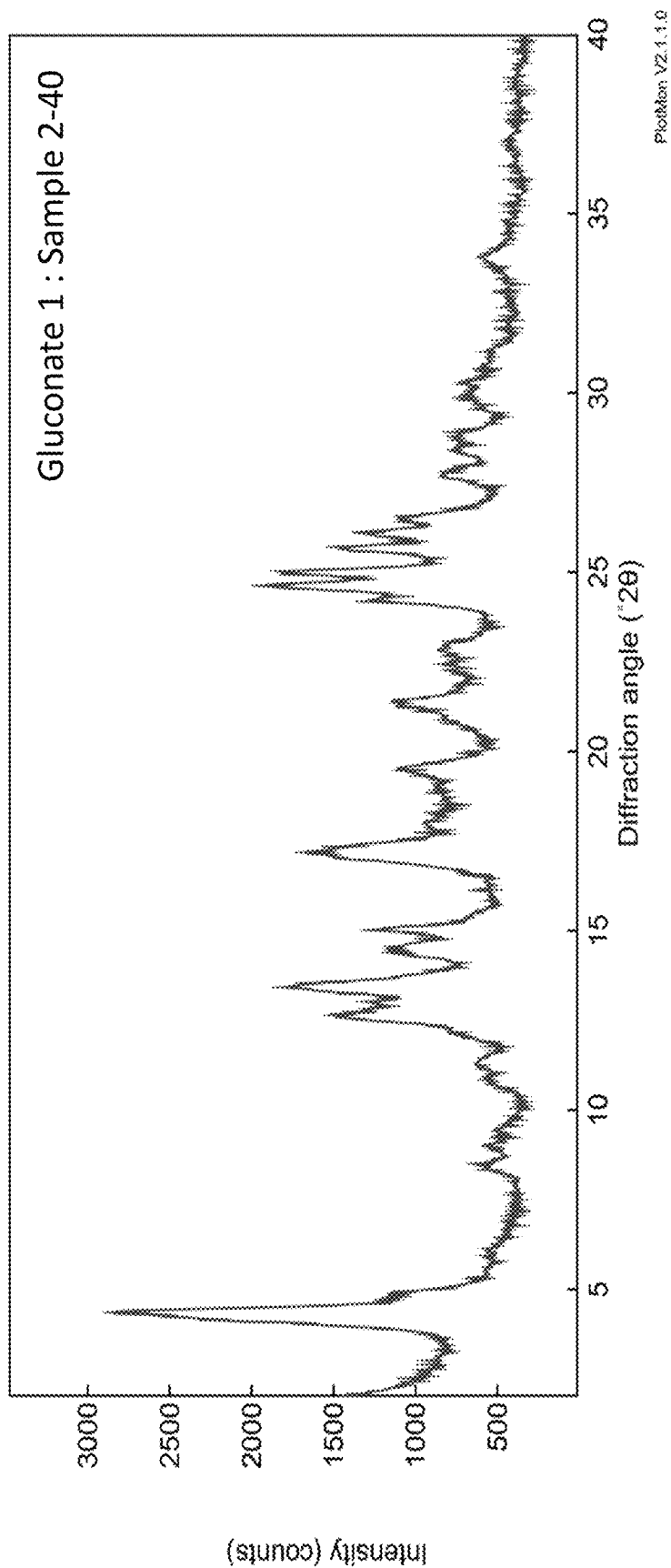
FIG. 68 shows the PXRD of Gluconate 1 (Sample 2-40).

In one embodiment, provided is a crystalline linsitinib gluconic cocrystal comprising crystalline form Gluconic 1. In one embodiment, the crystalline form Gluconic 1 of a linsitinib gluconic cocrystal is characterized by a powder x-ray diffraction (PXRD) pattern substantially resembling that of FIG. 68, as determined on a diffractometer using Cu-Kα radiation.

In one embodiment, provided is a crystalline form Gluconic 1 of a linsitinib gluconic cocrystal as characterized by any aspect of the present invention, which is present as a material comprising at least about 95% or more by weight of crystalline form Gluconic 1 based of the total amount of linsitinib gluconic cocrystal in the material. In one embodiment, the crystalline form Gluconic 1 comprises at least about 98% or more by weight of crystalline form Gluconic 1 based of the total amount of linsitinib gluconic cocrystal in the material. In one embodiment, the crystalline form Gluconic 1 comprises at least about 99% or more by weight of crystalline form Gluconic 1 based of the total amount of linsitinib gluconic cocrystal in the material. In one embodiment, the crystalline form Gluconic 1 comprises at least about 99.5% or more by weight of crystalline form Gluconic 1 based of the total amount of linsitinib gluconic cocrystal in the material.

Orotic Cocrystal

In another embodiment, the invention provides orotic acid cocrystal of a compound of Formula I:

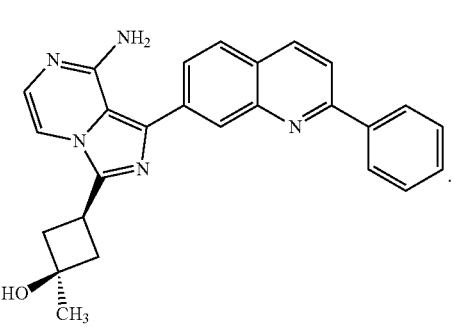

(I)

As described above, Formula I corresponds to Linsitinib. Orotic acid is a weak acid. As used herein, "orotic cocrystal" or "orotic salt" refers to a cocrystal containing at least one orotic acid. In certain embodiments, the orotic acid cocrystal of Linsitinib is a cocrystal according to Formula XII:

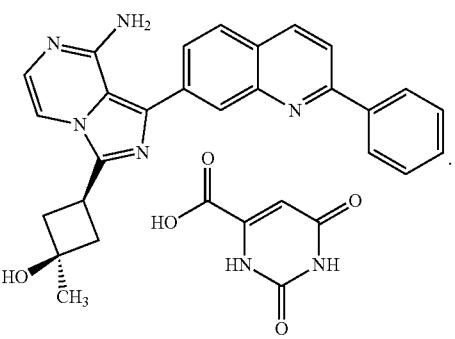

(XII)

In one aspect, the invention provides a crystalline form of an orotic cocrystal of a compound of Formula I:

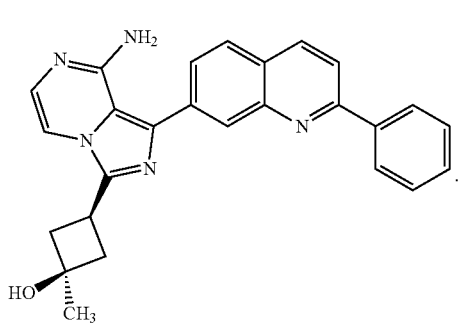

(I)

Orotic 1

Figure 69:
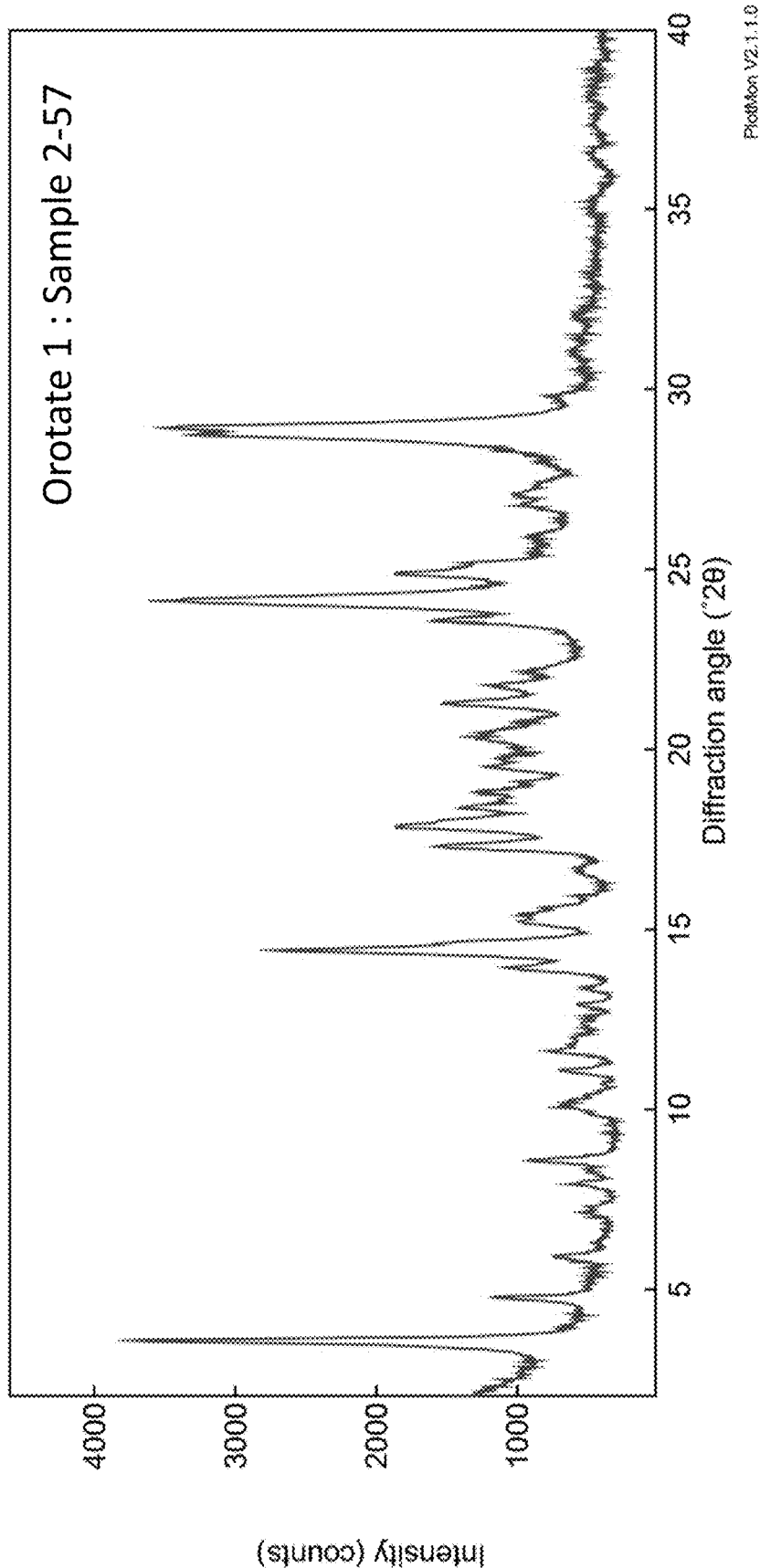
FIG. 69 shows the PXRD of Orotate 1 and coformer (Sample 2-57).

In one embodiment, provided is a crystalline linsitinib orotic cocrystal comprising crystalline form Orotic 1. In one embodiment, the crystalline form Orotic 1 of a linsitinib orotic cocrystal is characterized by a powder x-ray diffraction (PXRD) pattern substantially resembling that of FIG. 69, as determined on a diffractometer using Cu-Kα radiation.

In one embodiment, provided is a crystalline form Orotic 1 of a linsitinib orotic cocrystal as characterized by any aspect of the present invention, which is present as a material comprising at least about 95% or more by weight of crystalline form Orotic 1 based of the total amount of linsitinib orotic cocrystal in the material. In one embodiment, the crystalline form Orotic 1 comprises at least about 98% or more by weight of crystalline form Orotic 1 based of the total amount of linsitinib orotic cocrystal in the material. In one embodiment, the crystalline form Orotic 1 comprises at least about 99% or more by weight of crystalline form Orotic 1 based of the total amount of linsitinib orotic cocrystal in the material. In one embodiment, the crystalline form Orotic 1 comprises at least about 99.5% or more by weight of crystalline form Orotic 1 based of the total amount of linsitinib orotic cocrystal in the material.

Linsitinib Polymorphs

In one embodiment, polymorphic forms of the free base of linsitinib are provided. In one embodiment, a polymorphic form of linsitinib free base is produced by crystallization with a pharmaceutically acceptable salt. In another embodiment, a polymorphic form of linsitinib free base is produced by crystallization with a pharmaceutically acceptable coformer.

Form H

In one aspect, the invention provides crystalline Form H of a compound of Formula I:

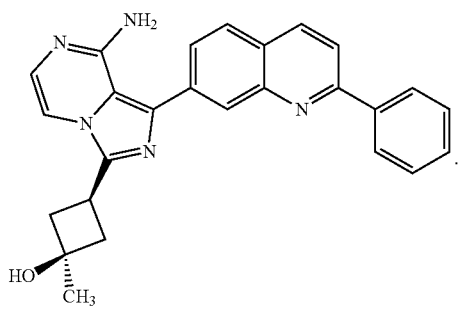

(I)

As described above, Formula I corresponds to linsitinib. As used herein, "linsitinib Form H" or "Form H" refers to a crystalline form of the free base of linsitinib having characteristics of Form H as presented herein.

In one embodiment, provided is a crystalline linsitinib free base comprising crystalline Form H. In one embodiment, the crystalline Form H of a linsitinib free base is characterized by a powder x-ray diffraction (PXRD) pattern substantially resembling that of FIG. 75, as determined on a diffractometer using Cu-Kα radiation.

Figure 77:
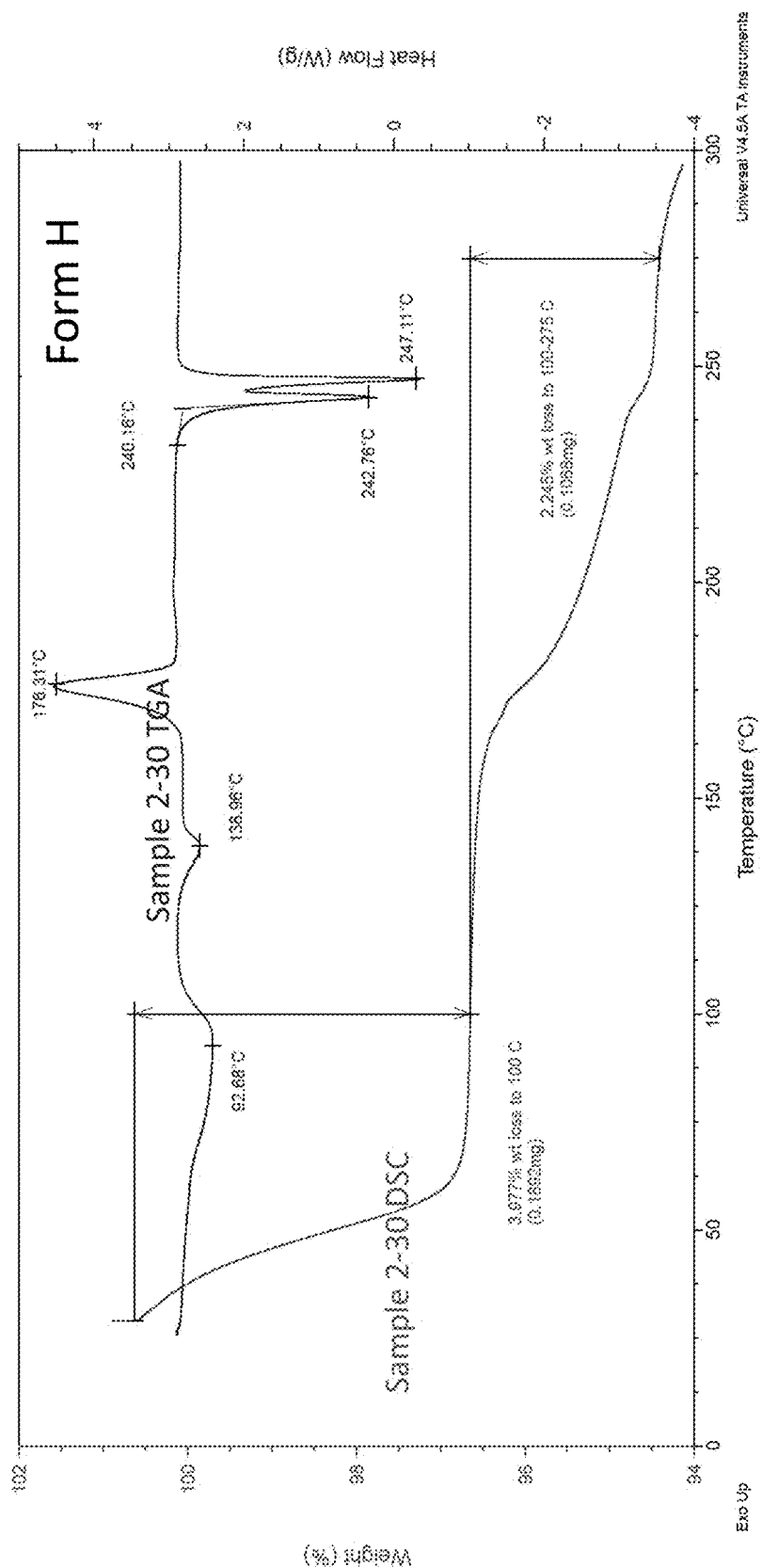
FIG. 77 shows the DSC thermogram of Form H free base from 4-aminosalicylic acid coformer (Sample 2-30) and the TGA thermogram of Form H free base from 4-aminosalicylic acid coformer (Sample 2-30).

In one embodiment, the crystalline Form H of a linsitinib free base is characterized by a DSC thermogram substantially resembling that of FIG. 77.

In one embodiment, the crystalline Form H of a linsitinib free base is characterized by a TGA signal substantially resembling that of FIG. 77.

In one embodiment, provided is a crystalline Form H of a linsitinib free base as characterized by any aspect of the present invention, which is present as a material comprising at least about 95% or more by weight of crystalline Form H based of the total amount of linsitinib free base in the material. In one embodiment, the crystalline Form H comprises at least about 98% or more by weight of crystalline Form H based of the total amount of linsitinib free base in the material. In one embodiment, the crystalline Form H comprises at least about 99% or more by weight of crystalline Form H based of the total amount of linsitinib free base in the material. In one embodiment, the crystalline Form H comprises at least about 99.5% or more by weight of crystalline Form H based of the total amount of linsitinib free base in the material.

Form I

In one aspect, the invention provides crystalline Form I of a compound of Formula I:

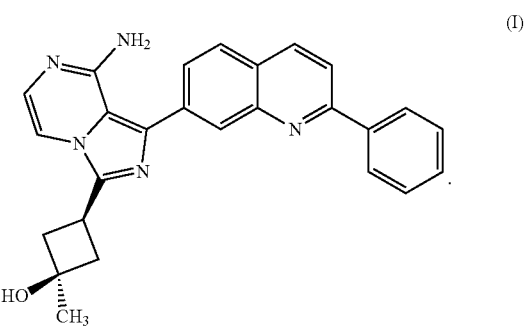 [SMILES: C[C@]1(O)C[C@@H](c2nc(-c3ccc4ccc(-c5ccccc5)nc4c3)c3c(N)nccn32)C1]

(I)

As described above, Formula I corresponds to linsitinib. As used herein, "linsitinib Form I" or "Form I" refers to a crystalline form of the free base of linsitinib having characteristics of Form I as presented herein.

In one embodiment, provided is a crystalline linsitinib free base comprising crystalline Form I. In one embodiment, the crystalline Form I of a linsitinib free base is characterized by a powder x-ray diffraction (PXRD) pattern substantially resembling that of FIG. 78, as determined on a diffractometer using Cu-Kα radiation.

Figure 81:
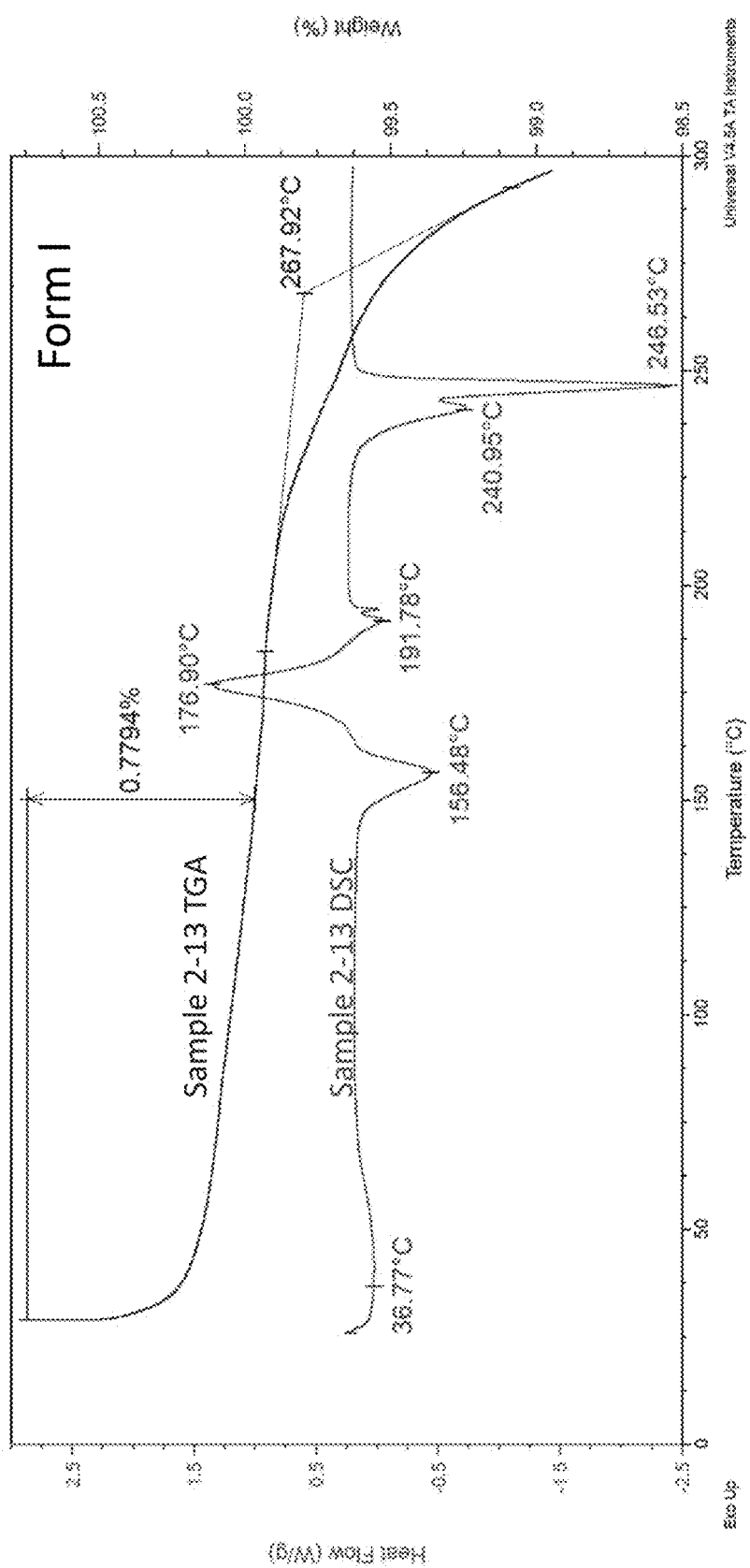
FIG. 81 shows the DSC thermogram of Form I free base from 2-hydroxyethanesulfonic coformer (Sample 2-13) and the TGA thermogram of Form I free base from 2-hydroxyethanesulfonic coformer (Sample 2-13).
Figure 82:
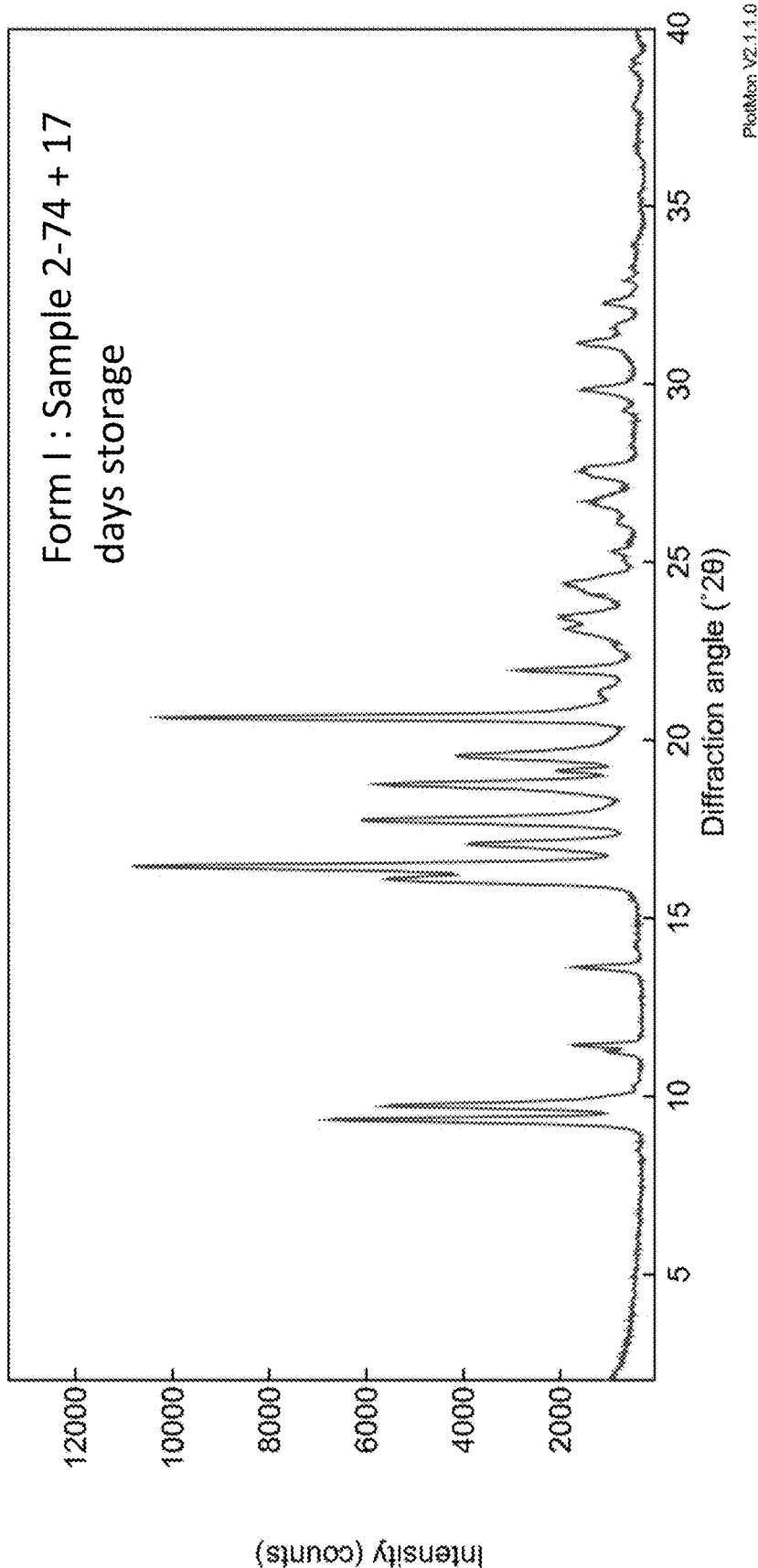
FIG. 82 shows the PXRD of Form I from vanillin (Sample 2-74 after 17 days of storage at RT).

In one embodiment, the crystalline Form I of a linsitinib free base is characterized by a DSC thermogram substantially resembling that of FIG. 81.

In one embodiment, the crystalline Form I of a linsitinib free base is characterized by a TGA signal substantially resembling that of FIG. 81.

In one embodiment, provided is a crystalline Form I of a linsitinib free base as characterized by any aspect of the present invention, which is present as a material comprising at least about 95% or more by weight of crystalline Form I based of the total amount of linsitinib free base in the material. In one embodiment, the crystalline Form I comprises at least about 98% or more by weight of crystalline Form I based of the total amount of linsitinib free base in the material. In one embodiment, the crystalline Form I comprises at least about 99% or more by weight of crystalline Form I based of the total amount of linsitinib free base in the material. In one embodiment, the crystalline Form I comprises at least about 99.5% or more by weight of crystalline Form I based of the total amount of linsitinib free base in the material.

31

Form J

In one aspect, the invention provides crystalline Form J of a compound of Formula I:

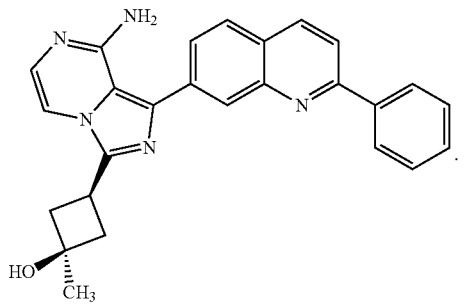

(I)

As described above, Formula I corresponds to linsitinib. As used herein, "linsitinib Form J" or "Form J" refers to a crystalline form of the free base of linsitinib having characteristics of Form J as presented herein.

In one embodiment, provided is a crystalline linsitinib free base comprising crystalline Form J. In one embodiment, the crystalline Form J of a linsitinib free base is characterized by a powder x-ray diffraction (PXRD) pattern substantially resembling that of FIG. 85, as determined on a diffractometer using Cu-Kα radiation.

In one embodiment, provided is a crystalline Form J of a linsitinib free base as characterized by any aspect of the present invention, which is present as a material comprising at least about 95% or more by weight of crystalline Form J based of the total amount of linsitinib free base in the material. In one embodiment, the crystalline Form J comprises at least about 98% or more by weight of crystalline Form J based of the total amount of linsitinib free base in the material. In one embodiment, the crystalline Form J comprises at least about 99% or more by weight of crystalline Form J based of the total amount of linsitinib free base in the material. In one embodiment, the crystalline Form J comprises at least about 99.5% or more by weight of crystalline Form J based of the total amount of linsitinib free base in the material.

Form K

In one aspect, the invention provides crystalline Form K of a compound of Formula I:

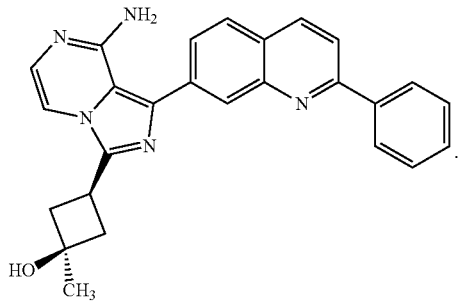

(I)

As described above, Formula I corresponds to linsitinib. As used herein, "linsitinib Form K" or "Form K" refers to a crystalline form of the free base of linsitinib having characteristics of Form K as presented herein.

32

Figure 86:
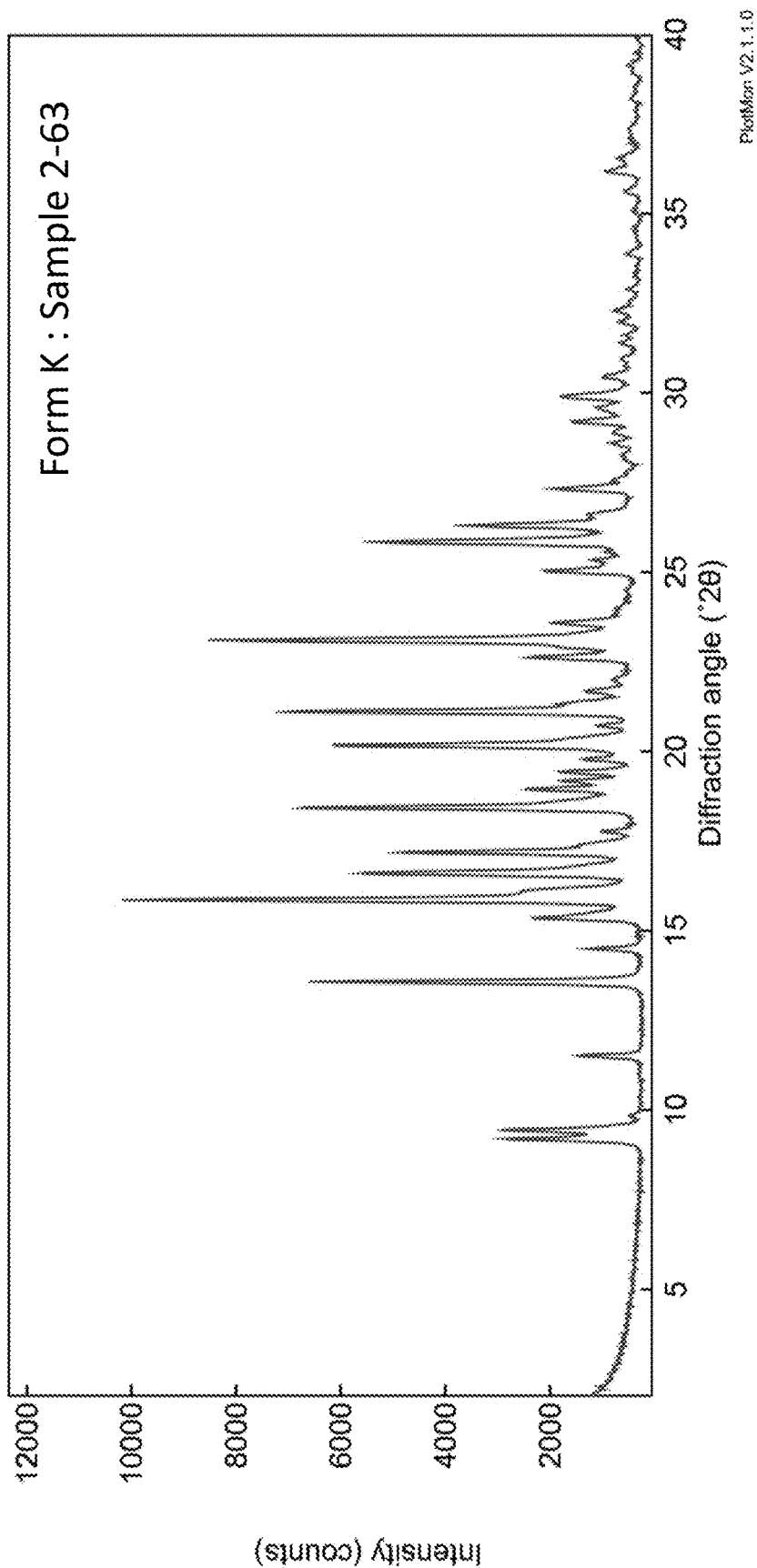
FIG. 86 shows the PXRD of Form K from sorbic acid (Sample 2-63).

In one embodiment, provided is a crystalline linsitinib free base comprising crystalline Form K. In one embodiment, the crystalline Form K of a linsitinib free base is characterized by a powder x-ray diffraction (PXRD) pattern substantially resembling that of FIG. 86, as determined on a diffractometer using Cu-Kα radiation.

Figure 88:
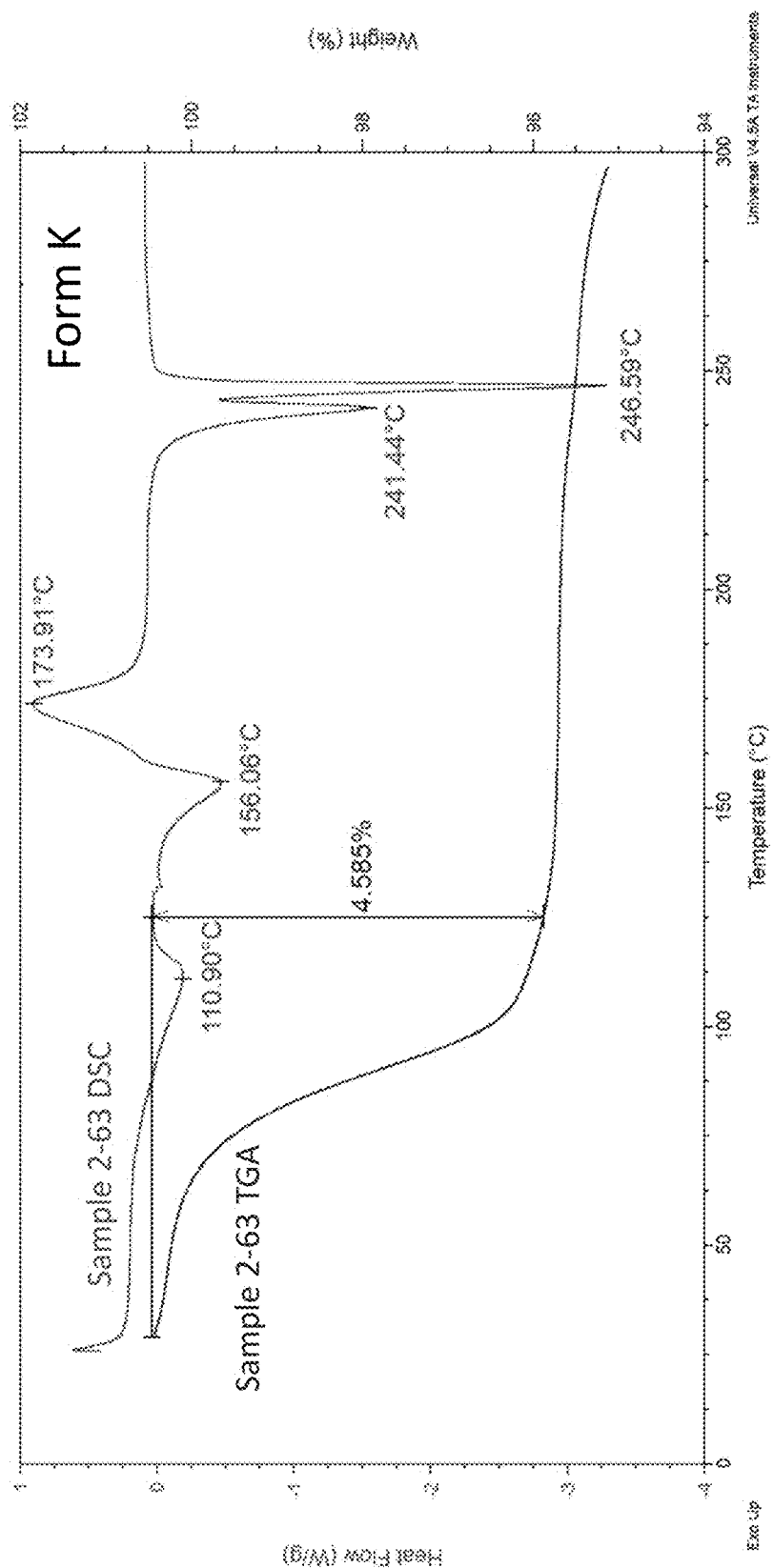
FIG. 88 shows the DSC thermogram of Form K free base from sorbic acid (Sample 2-63) and the TGA thermogram of Form K free base from sorbic acid (Sample 2-63).

In one embodiment, the crystalline Form K of a linsitinib free base is characterized by a DSC thermogram substantially resembling that of FIG. 88.

In one embodiment, the crystalline Form K of a linsitinib free base is characterized by a TGA signal substantially resembling that of FIG. 88.

In one embodiment, provided is a crystalline Form K of a linsitinib free base as characterized by any aspect of the present invention, which is present as a material comprising at least about 95% or more by weight of crystalline Form K based of the total amount of linsitinib free base in the material. In one embodiment, the crystalline Form K comprises at least about 98% or more by weight of crystalline Form K based of the total amount of linsitinib free base in the material. In one embodiment, the crystalline Form K comprises at least about 99% or more by weight of crystalline Form K based of the total amount of linsitinib free base in the material. In one embodiment, the crystalline Form K comprises at least about 99.5% or more by weight of crystalline Form K based of the total amount of linsitinib free base in the material.

Pharmaceutical Compositions

In a related aspect, the invention provides pharmaceutical compositions for the administration of the salts and crystalline forms described herein. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Aqueous suspensions contain the active materials in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing the salts and crystalline forms described herein can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

The salts and crystalline forms described herein can also be administered topically as a solution, ointment, cream, gel, suspension, mouth washes, eye-drops, and the like. Still further, transdermal delivery of the salts and crystalline forms can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, a salt or crystalline form described herein is administered via intraperitoneal injection. In some embodiments, the salt or crystalline form is administered orally. In some embodiments, the salt or crystalline form is administered intravenously.

The pharmaceutical compositions of the invention can also include micronized Linsitinib or a micronized Linsitinib salt or a micronized crystalline form of a Linsitinib salt. In general, compositions containing micronized Linsitinib contain particles consisting essentially of Linsitinib with average diameters below 50 µm. The average diameter of the Linsitinib particles can be, for example, below 45 µm, below 40 µm, below 35 µm, below 30 µm, below 25 µm, or below 20 µm. The average diameter of the Linsitinib particles can be from about 10 µm to about 49 µm, or from about 10 µm to about 45 µm, or from about 15 µm to about 40 µm, or from about 20 µm to about 35 µm, or from about 25 µm to about 30 µm. The average diameter of the Linsitinib particles can be about 15, 16, 17, 18, 19, 20, 21, 22, 23, 24, or about 25 µm. In some embodiments, the particles consist essentially of micronized Linsitinib in its free-base form. In some embodiments, the particles consist essentially of a micronized Linsitinib salt, as described herein, in amorphous or crystalline form.

Methods of Treatment

IGF1R signaling has been found to be dysregulated in a number of diseases. Inhibition of IGF1R signaling has been explored as a potential approach to modulate immune response in a number of diseases.

Thyroid eye disease (TED), also known as Graves' ophthalmopathy, is an autoimmune condition characterized by inflammation and swelling of the tissues surrounding the eyes. It is commonly associated with hyperthyroidism, which is an overactive thyroid gland. TED primarily affects individuals with Graves' disease, an autoimmune disorder characterized by the production of antibodies that stimulate the thyroid gland, leading to excessive thyroid hormone production.

IGF1R signaling has been found to be dysregulated in TED. The exact mechanisms are not fully understood, but it is believed that the antibodies associated with Graves' disease can bind to and activate IGF1R, leading to the release of pro-inflammatory cytokines and the recruitment of immune cells to the orbital tissues. This inflammatory response results in the characteristic features of TED, including eyelid retraction, bulging eyes (proptosis), double vision (diplopia), and eye pain. Inhibition of IGF1R signaling has been explored as a potential approach to modulate the immune response and reduce inflammation in TED.

In one embodiment, provided is a method of inhibiting IGF1R signaling comprising administering to a subject a pharmaceutically acceptable salt of the compound according to Formula (I). In some embodiments, the salt is an edisylate salt. In some embodiments, the salt is an esylate salt. In some embodiments, the salt is a maleate salt. In some embodiments, the salt is an L-malate salt. In some embodiments, the salt is a napsylate salt. In some embodiments, the salt is a phosphate salt. In some embodiments, the salt is an HCl salt. In some embodiments, the salt is a fumarate salt. In some such embodiments, the invention includes administering a salt of linsitinib or a crystalline form of a salt of linsitinib, as described herein.

In one embodiment is provided a method of inhibiting IGF1R signaling comprising administering to a subject a pharmaceutically acceptable salt of the compound according to Formula (X):

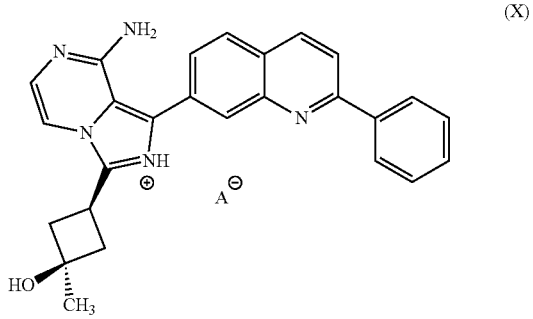

wherein A⁻ is an anion comprising an edisylate anion, an esylate anion, a maleate anion, an L-malate anion, a napsylate anion, a phosphate anion, an HCl anion, or a fumarate ion. In one embodiment, the pharmaceutically acceptable crystalline salt form according to Formula (X) is Esylate 1, Esylate 2, Esylate 3, Esylate 4, Esylate 5, Di-Esylate 1, L-Malate 1, L-Malate 2, L-Malate 3, L-Malate 4, L-Malate 5, L-Malate 6, L-Malate 7, L-Malate 8, L-Malate 9, Edisylate 1, Maleate 1, Napsylate 1, Phosphate 1, HCl 1, or Fumarate 1. In one embodiment, the pharmaceutically acceptable crystalline salt form according to Formula (X) is Esylate 1. In one embodiment, the pharmaceutically acceptable crystalline salt form according to Formula (X) is Esylate 2. In one embodiment, the pharmaceutically acceptable crystalline salt form according to Formula (X) is Esylate 3. In one embodiment, the pharmaceutically acceptable crystalline salt form according to Formula (X) is Esylate 4. In one embodiment, the pharmaceutically acceptable crystalline salt form according to Formula (X) is Esylate 5. In one embodiment, the pharmaceutically acceptable crystalline salt form according to Formula (X) is Di-Esylate 1. In another embodiment, the pharmaceutically acceptable crystalline salt form according to Formula (X) is L-Malate 1. In another embodiment, the pharmaceutically acceptable crystalline salt form according to Formula (X) is L-Malate 2. In another embodiment, the pharmaceutically acceptable crystalline salt form according to Formula (X) is L-Malate 3. In another embodiment, the pharmaceutically acceptable crystalline salt form according to Formula (X) is L-Malate 4. In another embodiment, the pharmaceutically acceptable crystalline salt form according to Formula (X) is L-Malate 5. In another embodiment, the pharmaceutically acceptable crystalline salt form according to Formula (X) is L-Malate 6. In another embodiment, the pharmaceutically acceptable crystalline salt form according to Formula (X) is L-Malate 7. In another embodiment, the pharmaceutically acceptable crystalline salt form according to Formula (X) is L-Malate 8. In another embodiment, the pharmaceutically acceptable crystalline salt form according to Formula (X) is L-Malate 9. In another embodiment, the pharmaceutically acceptable crystalline salt form according to Formula (X) is Edisylate 1. In another embodiment, the pharmaceutically acceptable crystalline salt form according to Formula (X) is Maleate 1. In another embodiment, the pharmaceutically acceptable crystalline salt form according to Formula (X) is Napsylate 1. In another embodiment, the pharmaceutically acceptable crystalline salt form according to Formula (X) is Phosphate 1. In another embodiment, the pharmaceutically acceptable crystalline salt form according to Formula (X) is HCl 1. In another embodiment, the pharmaceutically acceptable crystalline salt form according to Formula (X) is Fumarate 1.

In one embodiment, provided is a method of inhibiting IGF1R signaling comprising administering to a subject a cocrystal of the compound according to Formula (I). In some embodiments, the cocrystal is a salicylic-linsitinib cocrystal. In some embodiments, the cocrystal is a gluconic-linsitinib cocrystal. In some embodiments, the cocrystal is an orotic-linsitinib cocrystal. In one embodiment, the cocrystal is Salicylic 1. In another embodiment, the cocrystal is Gluconic 1. In another embodiment, the cocrystal is Orotic 1. In some embodiments, the invention includes administering a cocrystal of linsitinib, as described herein.

In one embodiment, provided is a method of inhibiting IGF1R signaling comprising administering to a subject a crystalline form of the free base of the compound according to Formula (I). In some embodiments, the crystalline form of the free base is Form H. In some embodiments, the crystalline form of the free base is Form I. In some embodiments, the crystalline form of the free base is Form J. In some embodiments, the crystalline form of the free base is Form K. In some embodiment, the invention includes administering a crystalline form of the linsitinib free base, as described herein.

In one embodiment is provided a method of treating thyroid eye disease comprising administering to a subject a pharmaceutically acceptable salt of the compound according to Formula I. In some embodiments, the salt is an edisylate salt. In some embodiments, the salt is an esylate salt. In some embodiments, the salt is a maleate salt. In some embodiments, the salt is an L-malate salt. In some embodiments, the salt is a napsylate salt. In some embodiments, the salt is a phosphate salt. In some embodiments, the salt is an HCl salt. In some embodiments, the salt is a fumarate salt. In some such embodiments, the invention includes administering a salt or crystalline form of Linsitinib as described herein.

In one embodiment is provided a method of treating thyroid eye disease comprising administering to a subject in need thereof a therapeutically effective amount of a pharmaceutically acceptable crystalline salt form according to Formula (X):

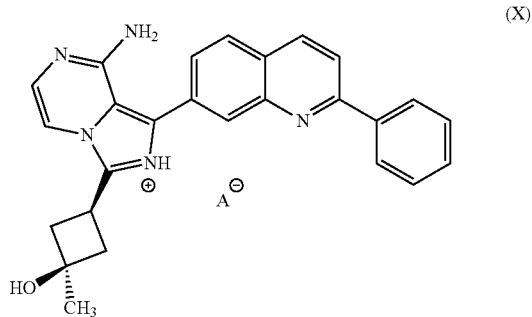

wherein A⁻ is an anion comprising an edisylate anion, an esylate anion, a maleate anion, an L-malate anion, a napsylate anion, a phosphate anion, an HCl anion, or a fumarate ion. In one embodiment, the pharmaceutically acceptable crystalline salt form according to Formula (X) is Esylate 1, Esylate 2, Esylate 3, Esylate 4, Esylate 5, Di-Esylate 1, L-Malate 1, L-Malate 2, L-Malate 3, L-Malate 4, L-Malate 5, L-Malate 6, L-Malate 7, L-Malate 8, L-Malate 9, Edisylate 1, Maleate 1, Napsylate 1, Phosphate 1, HCl 1, or Fumarate 1. In one embodiment, the pharmaceutically acceptable crystalline salt form according to Formula (X) is Esylate 1. In one embodiment, the pharmaceutically acceptable crystalline salt form according to Formula (X) is Esylate 2. In one embodiment, the pharmaceutically acceptable crystalline salt form according to Formula (X) is Esylate 3. In one embodiment, the pharmaceutically acceptable crystalline salt form according to Formula (X) is Esylate 4. In one embodiment, the pharmaceutically acceptable crystalline salt form according to Formula (X) is Esylate 5. In one embodiment, the pharmaceutically acceptable crystalline salt form according to Formula (X) is Di-Esylate 1. In another embodiment, the pharmaceutically acceptable crystalline salt form according to Formula (X) is L-Malate 1. In another embodiment, the pharmaceutically acceptable crystalline salt form according to Formula (X) is L-Malate 2. In another embodiment, the pharmaceutically acceptable crystalline salt form according to Formula (X) is L-Malate 3. In another embodiment, the pharmaceutically acceptable crystalline salt form according to Formula (X) is L-Malate 4. In another embodiment, the pharmaceutically acceptable crystalline salt form according to Formula (X) is L-Malate 5. In another embodiment, the pharmaceutically acceptable crystalline salt form according to Formula (X) is L-Malate 6. In another embodiment, the pharmaceutically acceptable crystalline salt form according to Formula (X) is L-Malate 7. In another embodiment, the pharmaceutically acceptable crystalline salt form according to Formula (X) is L-Malate 8. In another embodiment, the pharmaceutically acceptable crystalline salt form according to Formula (X) is L-Malate 9. In another embodiment, the pharmaceutically acceptable crystalline salt form according to Formula (X) is Edisylate 1. In another embodiment, the pharmaceutically acceptable crystalline salt form according to Formula (X) is Maleate 1. In another embodiment, the pharmaceutically acceptable crystalline salt form according to Formula (X) is Napsylate 1. In another embodiment, the pharmaceutically acceptable crystalline salt form according to Formula (X) is Phosphate 1. In another embodiment, the pharmaceutically acceptable crystalline salt form according to Formula (X) is HCl 1. In another embodiment, the pharmaceutically acceptable crystalline salt form according to Formula (X) is Fumarate 1.

In one embodiment is provided a method of treating thyroid eye disease comprising administering to a subject in need thereof a therapeutically effective amount of a cocrystal of a compound according to Formula (I):

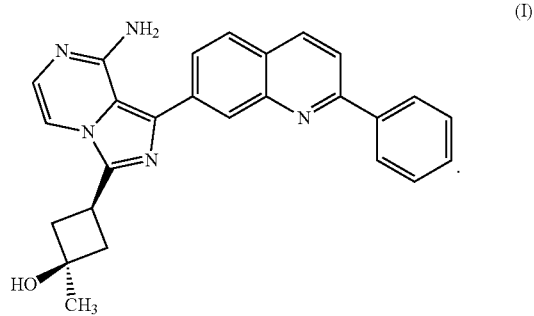 [SMILES: C[C@]1(O)C[C@@H](c2nc(-c3ccc4ccc(-c5ccccc5)nc4c3)c3c(N)nccn32)C1]
(I)

In some embodiments, the cocrystal is a salicylic-linsitinib cocrystal. In some embodiments, the cocrystal is a gluconic-linsitinib cocrystal. In some embodiments, the cocrystal is an orotic-linsitinib cocrystal. In one embodiment, the cocrystal is Salicylic 1. In another embodiment, the cocrystal is Gluconic 1. In another embodiment, the cocrystal is Orotic 1.

In one embodiment is provided a method of treating thyroid eye disease comprising administering to a subject in need thereof a therapeutically effective amount of a crystalline form of a compound according to Formula (I):

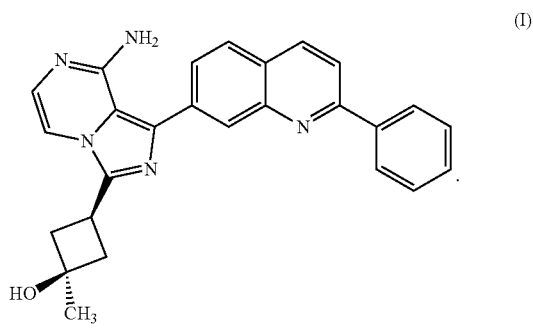 [SMILES: C[C@]1(O)C[C@@H](c2nc(-c3ccc4ccc(-c5ccccc5)nc4c3)c3c(N)nccn32)C1]
(I)

wherein the crystalline form is Form H, Form I, Form J, or Form K. In one embodiment, the crystalline form is Form H. In one embodiment, the crystalline form is Form I. In one embodiment, the crystalline form is Form J. In one embodiment, the crystalline form is Form K.

The salts and crystalline forms described herein can be administered at any suitable dose in the methods of the invention. In general, a salt or crystalline form is administered at a dose ranging from about 0.01 milligrams to about 1000 milligrams per kilogram of a subject's body weight (i.e., about 0.01-1000 mg/kg). The dose of the salt or crystalline form can be, for example, about 0.01-1000 mg/kg, or about 0.1-500 mg/kg, or about –0.5-250 mg/kg, or about 1-200 mg/kg, or about 2-150 mg/kg. The dose of the salt or crystalline form can be about 0.1, 0.5, 1, 1.5, 2, 2.5, 3, 3.5, 4, 4.5, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950, or 1000 mg/kg. The dose of the salt or crystalline form can be administered at a dose below about 0.1, below about 0.5, below about 1, below about 1.5, below about 2, below about 2.5, below about 3, below about 3.5, below about 4, below about 4.5, below about 5, below about 10, below about 15, below about 20, below about 25, below about 30, below about 35, below about 40, below about 45, below about 50, below about 55, below about 60, below about 65, below about 70, below about 75, below about 85, below about 90, below about 95, below about 100, below about 150, below about 200, below about 250, below about 300, below about 350, below about 400, below about 450, below about 500, below about 550, below about 600, below about 650, below about 700, below about 750, below about 800, below about 850, below about 900, below about 950, or below about 1000 mg/kg. In some embodiments, the salt or crystalline form is administered at a dose below 200 mg of compound per kg of the subject's body weight (200 mg/kg). In some embodiments, the salt or crystalline form is administered at a dose below 150 mg/kg. In some embodiments, the salt or crystalline form is administered at a dose below 100 mg/kg. In some embodiments, the salt or crystalline form is administered at a dose below 50 mg/kg. In some embodiments, the salt or crystalline form is administered at a dose below 20 mg/kg. In some embodiments, the salt or crystalline form is administered at a dose below 15 mg/kg. In some embodiments, the salt or crystalline form is administered at a dose below 10 mg/kg. In some embodiments, the salt or crystalline form is administered at a dose below 5 mg/kg. In some embodiments, the salt or crystalline form is administered at a dose below 4 mg/kg. In some embodiments, the salt or crystalline form is administered at a dose below 3 mg/kg. In some embodiments, the salt or crystalline form is administered at a dose below 2 mg/kg. In some embodiments, the salt or crystalline form is administered at a dose below 1 mg/kg. In some embodiments, the salt or crystalline form is administered at a dose below 0.5 mg/kg. In some embodiments, the salt or crystalline form is administered at a dose below 0.1 mg/kg.

Combination Therapy

Linsitinib can be used in combination with at least one other drug. In one embodiment, a pharmaceutically acceptable salt of linsitinib can be used in combination with at least one other drug. In a further embodiment, the pharmaceutically acceptable salt of linsitinib is an esylate salt, an L-malate salt, and edisylate salt, a maleate salt, a napsylate salt, a phosphate salt, an HCl salt, or a fumarate salt. In another embodiment, a pharmaceutically acceptable crystalline salt form of linsitinib can be used in combination with at least one other drug. In a further embodiment, the pharmaceutically acceptable crystalline salt form of linsitinib is Esylate 1, Esylate 2, Esylate 3, Esylate 4, Esylate 5, Di-Esylate 1, L-Malate 1, L-Malate 2, L-Malate 3, L-Malate 4, L-Malate 5, L-Malate 6, L-Malate 7, L-Malate 8, L-Malate 9, Edisylate 1, Maleate 1, Napsylate 1, Phosphate 1, HCl 1, or Fumarate 1. In one embodiment, the pharmaceutically acceptable crystalline salt form of linsitinib is Esylate 1. In one embodiment, the pharmaceutically acceptable crystalline salt form of linsitinib is Esylate 2. In one embodiment, the pharmaceutically acceptable crystalline salt form of linsitinib is Esylate 3. In one embodiment, the pharmaceutically acceptable crystalline salt form of linsitinib is Esylate 4. In one embodiment, the pharmaceutically acceptable crystalline salt form of linsitinib is Esylate 5. In one embodiment, the pharmaceutically acceptable crystalline salt form of linsitinib is Di-Esylate 1. In another embodiment, the pharmaceutically acceptable crystalline salt form of linsitinib is L-Malate 1. In another embodiment, the pharmaceutically acceptable crystalline salt form of linsitinib is L-Malate 2. In another embodiment, the pharmaceutically acceptable crystalline salt form of linsitinib is L-Malate 3. In another embodiment, the pharmaceutically acceptable crystalline salt form of linsitinib is L-Malate 4. In another embodiment, the pharmaceutically acceptable crystalline salt form of linsitinib is L-Malate 5. In another embodiment, the pharmaceutically acceptable crystalline salt form of linsitinib is L-Malate 6. In another embodiment, the pharmaceutically acceptable crystalline salt form of linsitinib is L-Malate 7. In another embodiment, the pharmaceutically acceptable crystalline salt form of linsitinib is L-Malate 8. In another embodiment, the pharmaceutically acceptable crystalline salt form of linsitinib is L-Malate 9. In another embodiment, the pharmaceutically acceptable crystalline salt form of linsitinib is Edisylate 1. In another embodiment, the pharmaceutically acceptable crystalline salt form of linsitinib is Maleate 1. In another embodiment, the pharmaceutically acceptable crystalline salt form of linsitinib is Napsylate 1. In another embodiment, the pharmaceutically acceptable crystalline salt form of linsitinib is Phosphate 1. In another embodiment, the pharmaceutically acceptable crystalline salt form of linsitinib is HCl 1. In another embodiment, the pharmaceutically acceptable crystalline salt form of linsitinib is Fumarate 1.

In one embodiment, a cocrystal of linsitinib can be used in combination with at least one other drug. In some embodiments, the cocrystal is a salicylic-linsitinib cocrystal. In some embodiments, the cocrystal is a gluconic-linsitinib cocrystal. In some embodiments, the cocrystal is an orotic-linsitinib cocrystal. In one embodiment, the cocrystal is Salicylic 1. In another embodiment, the cocrystal is Gluconic 1. In another embodiment, the cocrystal is Orotic 1.

In one embodiment, a crystalline form of the linsitinib free base can be used in combination with at least one other drug. In some embodiments, the crystalline form of the free base is Form H. In some embodiments, the crystalline form of the free base is Form I. In some embodiments, the crystalline form of the free base is Form J. In some embodiments, the crystalline form of the free base is Form K.

In one embodiment, at least one other drug for use in a combination therapy includes, but is not limited to, a thyroid stimulating hormone receptor (TSHR) inhibitor.

EXAMPLES

Instrumental Techniques

The following instrumental techniques were used to characterize the salt forms or crystalline salt forms of Linsitinib presented in the examples below.

Differential Scanning Calorimetry (DSC)

DSC analysis was carried out using a TA Instruments Q2500 Discovery Series instrument. The instrument temperature calibrations were performed using indium. The DSC cell was kept under a nitrogen purge of ~50 mL per minute during the analysis. The sample was placed in a standard, crimped aluminum pan and heated from approximately 25° C. to 300° C. at a rate of 10° C. per minute $^1$H Nuclear Magnetic Resonance (NMR)

$^1$H NMR spectra were acquired on a Bruker Avance NEO 400 spectrometer. Samples were prepared by dissolving material in DMSO-$d_6$. The solutions were placed into individual 5-mm NMR tubes for subsequent spectral acquisition. The temperature controlled (298K)$^1$H NMR spectra acquired on the Avance NEO 400 utilized a 5-mm cryoprobe operating at an observing frequency of 400.18 MHz. Each spectrum was processed using TopSpin version 4.1.4 and referenced to the chemical shift of the residual DMSO-$d_6$ (2.5 ppm) peak.

Powder X-ray Diffraction (PXRD)

A Rigaku SmartLab X-Ray Diffractometer was configured in Bragg-Brentano reflection geometry equipped with a beam stop and knife edge to reduce incident beam and air scatter. Data collection parameters are shown in Table 2.

TABLE 2

PXRD Data Collection Parameters

| Parameter | Value |
| --- | --- |
| Geometry | Bragg-Brentano |
| Tube Anode | Cu |
| Tube Type | Long Fine Focus |
| Tube Voltage (kV) | 40 |

TABLE 2-continued

PXRD Data Collection Parameters

| Parameter | Value |
|---|---|
| Tube Current (mA) | 44 |
| Detector | D/teX Ultra 250 (XR1 or XR3) HyPix-3000 (XR4) |
| Monochromator | Ni foil Cu Kβ Filter |
| Incident Slit (°) | 1/3 |
| Receiving Slit 1 (mm) | 18 |
| Receiving Slit 2 (mm) | open |
| Start Angle 2θ (°) | 2 |
| End Angle 2θ (°) | 40 |
| Step Size (°) | 0.02 |
| Scan Speed (°/min) | 6 |
| Spinning (rpm) | 11 |
| Sample Holder | Low-background Si |

Thermogravimetric Analysis (TGA)

The TG analysis was carried out using a TA Instruments Q5500 Discovery Series instrument. The instrument balance was calibrated using class M weights and the temperature calibration was performed using alumel. The nitrogen purge was ~10 mL per minute at the balance and ~25 mL per minute at the furnace. The sample was placed into a pre-tared platinum pan and heated from approximately 25° C. to 300° C. at a rate of 10° C. per minute.

Example 1: Prior Characterization

Linsitinib is in clinical development for TED and currently progressing as an anhydrous/non-solvated free base form that is non-hygroscopic with a high melting point (onset of endotherm at 246° C., maximum at 249° C. in differential scanning calorimetry (DSC)). Previous polymorph screening was conducted and suggested a complicated solid form landscape including one anhydrous form (Form A), four hydrated forms (Forms B, C, D, and E) and two solvated forms (Form F—IPA solvate and Form G—nitromethane solvate). Form A, the anhydrous form, was selected as the target form for development. The compound has good solubility under acidic conditions as well as good permeability suggesting that maintaining supersaturation and avoiding precipitation in the upper intestines are important factors in the levels of exposure obtained and consequently the dose needed.

Figure 2:
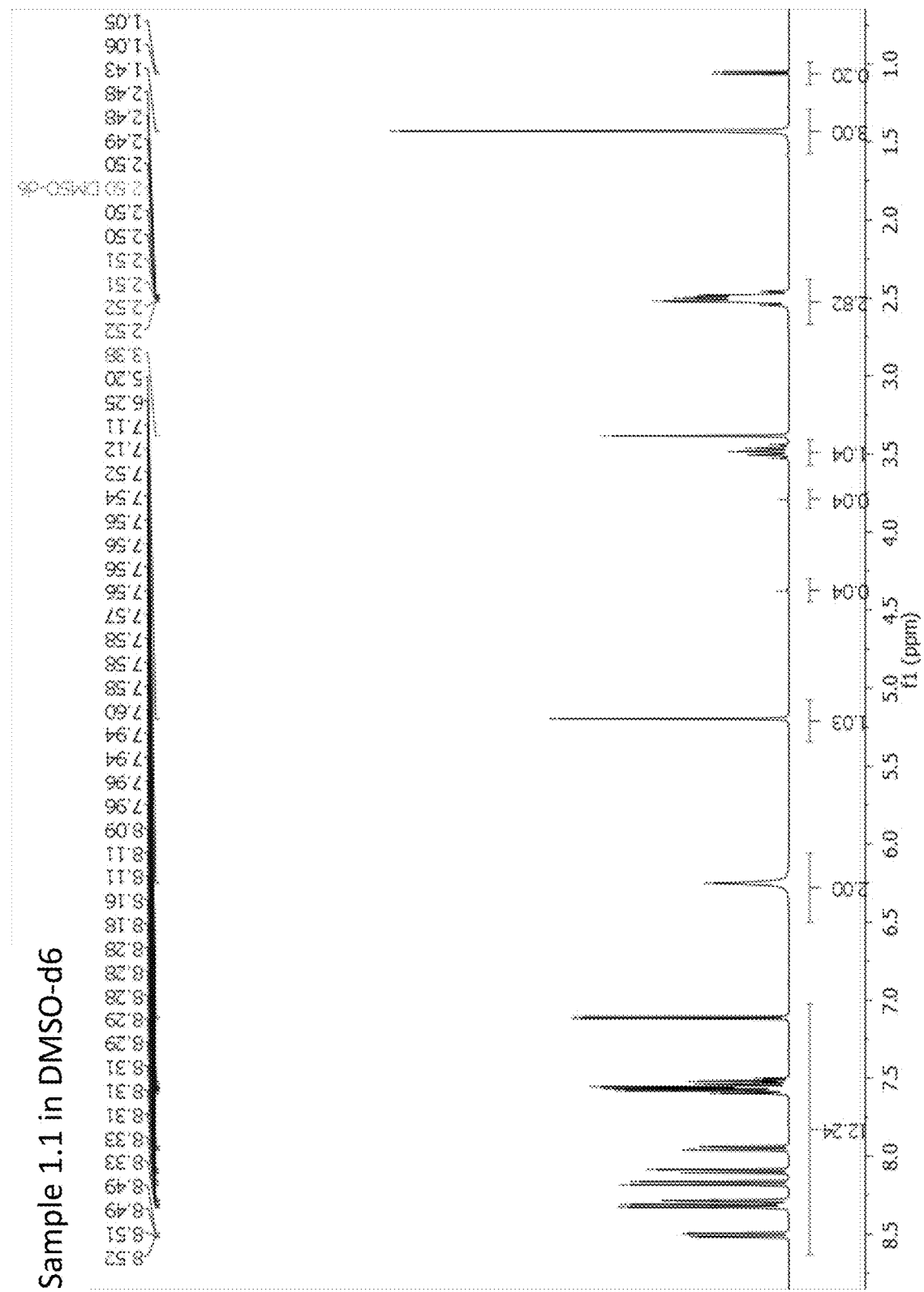
FIG. 2 shows the $^1$H NMR of Sample 1.1 (starting material).

Samples of linsitinib were used in the polymorph and salt screen. Initial characterization of the linsitinib starting material (Table 3) by powder X-ray diffraction (PXRD) and $^1$H nuclear magnetic resonance (NMR) spectroscopy was conducted to have for comparison with samples generated during the screen. The initial Linsitinib lot was found to be crystalline and was visually consistent with Form A (FIG. 1). Proton NMR spectroscopy analysis of the lot was generally consistent with the chemical structure of linsitinib with minor additional unidentified peaks present (FIG. 2).

TABLE 3

Characterization of Starting Material

| Sample | Technique | Result | FIG. |
|---|---|---|---|
| Linsitinib Sample 1A | PXRD | Crystalline; Visually consistent with Form A | FIG. 1 |
| Sample 1A.1 (Subsample of Sample 1A) | NMR in DMSO-$d_6$ | Generally consistent with chemical structure of linsitinib; water and residual isopropyl alcohol signals are present. | FIG. 2 |
| Linsitinib Sample 1B | — | — | — |

PXRD = powder X-ray diffraction; NMR = nuclear magnetic resonance

Example 2: Salt and Cocrystal Screens

Salt and cocrystal screening of linsitinib was conducted in an attempt to find novel solid forms of linsitinib with physical properties suitable for development.

Salt Screen

Counterions for the salt screen were selected based on structural diversity as well as their pKa values relative to the pKa of linsitinib. The acids selected were on the GRAS list or designated as Class I or II by Stahl and Wermuth. The pKa of linsitinib is estimated to be between 5.0 and 5.51. Based on the structure of the molecule, pKa values of 6.5 (pyrazine nitrogen) and 2.8 (quinoline nitrogen) were predicted.

An equimolar ratio of linsitinib and acid was used in the experiments. Various solvent systems were examined in an attempt to utilize a diverse set of conditions. Similarly, different crystallization techniques, including slurry, cooling, and evaporation were incorporated into the screen. A single attempt was conducted with each acid. Samples generated and analyzed are listed in Table 4. Unique crystalline patterns of each potential linsitinib salt were given a unique designation that included the name of the acid (i.e., Fumarate 1, Maleate 1, etc.).

TABLE 4

Salt Screening Experiments

Figure 50:
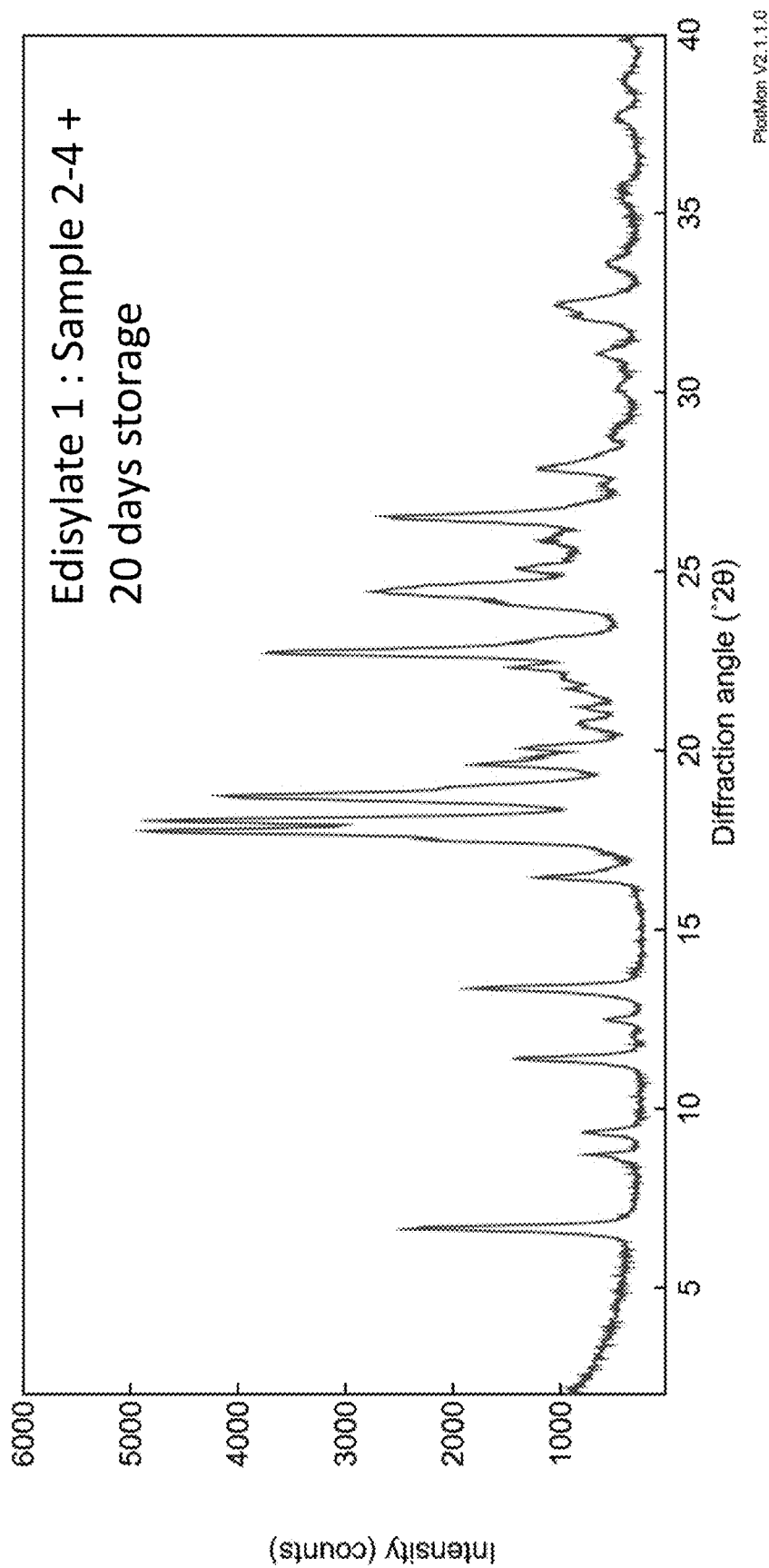
FIG. 50 shows the PXRD of Edisylate 1 (Sample 2-4 after 20 days of storage at RT).

| Sample No. | Acid | Conditions [a] | Result [b] | PXRD FIG. |
|---|---|---|---|---|
| 2-1 | L-Aspartic | Slurry in water at ET | Form A | |
| 2-2 | Benzenesulfonic | Dissolve in MeOH; SE at RT | NC | |
| 2-3 | Citric | Slurry at ET overnight in MEK; cooled to RT | NC | |
| 2-4 | 1,2-Ethanedisulfonic | Slurry in dioxane | Edisylate 1 | FIG. 49 |
| | | Sample reanalyzed after 20 days of storage at RT. | Edisylate 1 | FIG. 50 |
| 2-5 | Ethanesulfonic | Slurry at ET in IPA | Esylate 1 | FIG. 5 |
| 2-6 | Fumaric | Slurry at RT in IPA | Fumarate 1 (LC) | FIG. 66 |

TABLE 4-continued

Salt Screening Experiments

Figure 33:
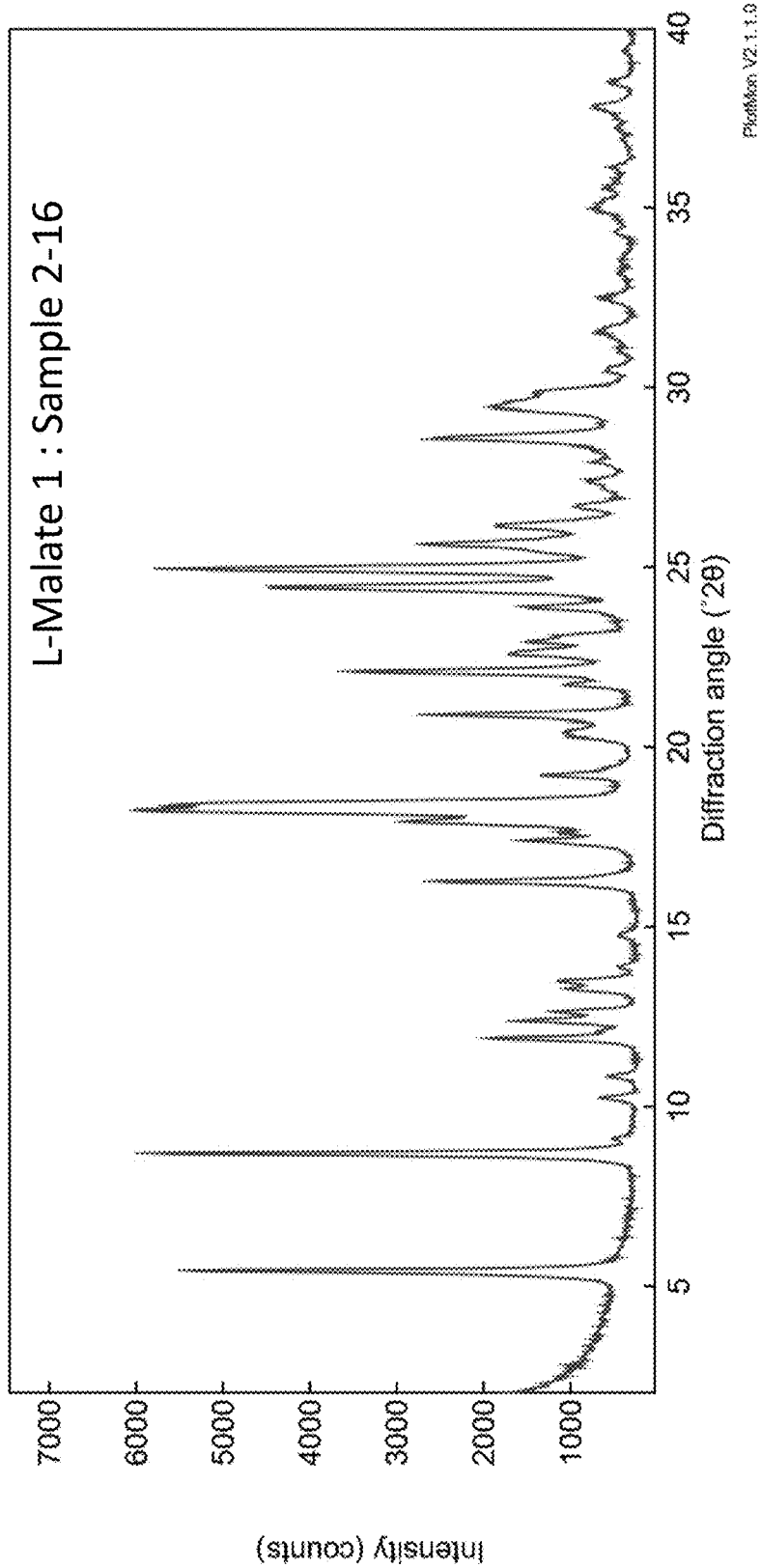
FIG. 33 shows PXRD of L-Malate 1 (Sample 2-16).
Figure 53:
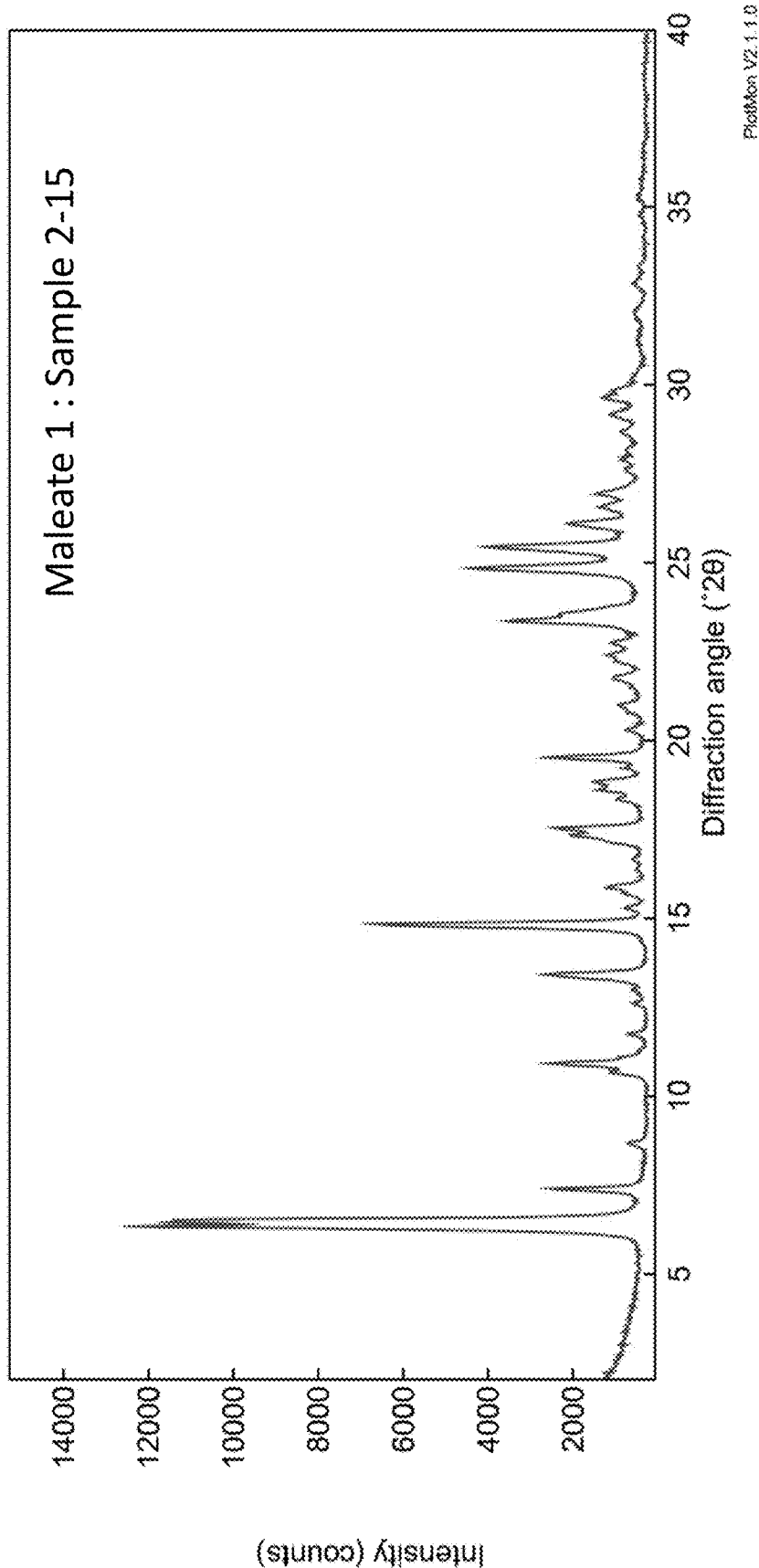
FIG. 53 shows the PXRD of Maleate 1 (Sample 2-15).
Figure 56:
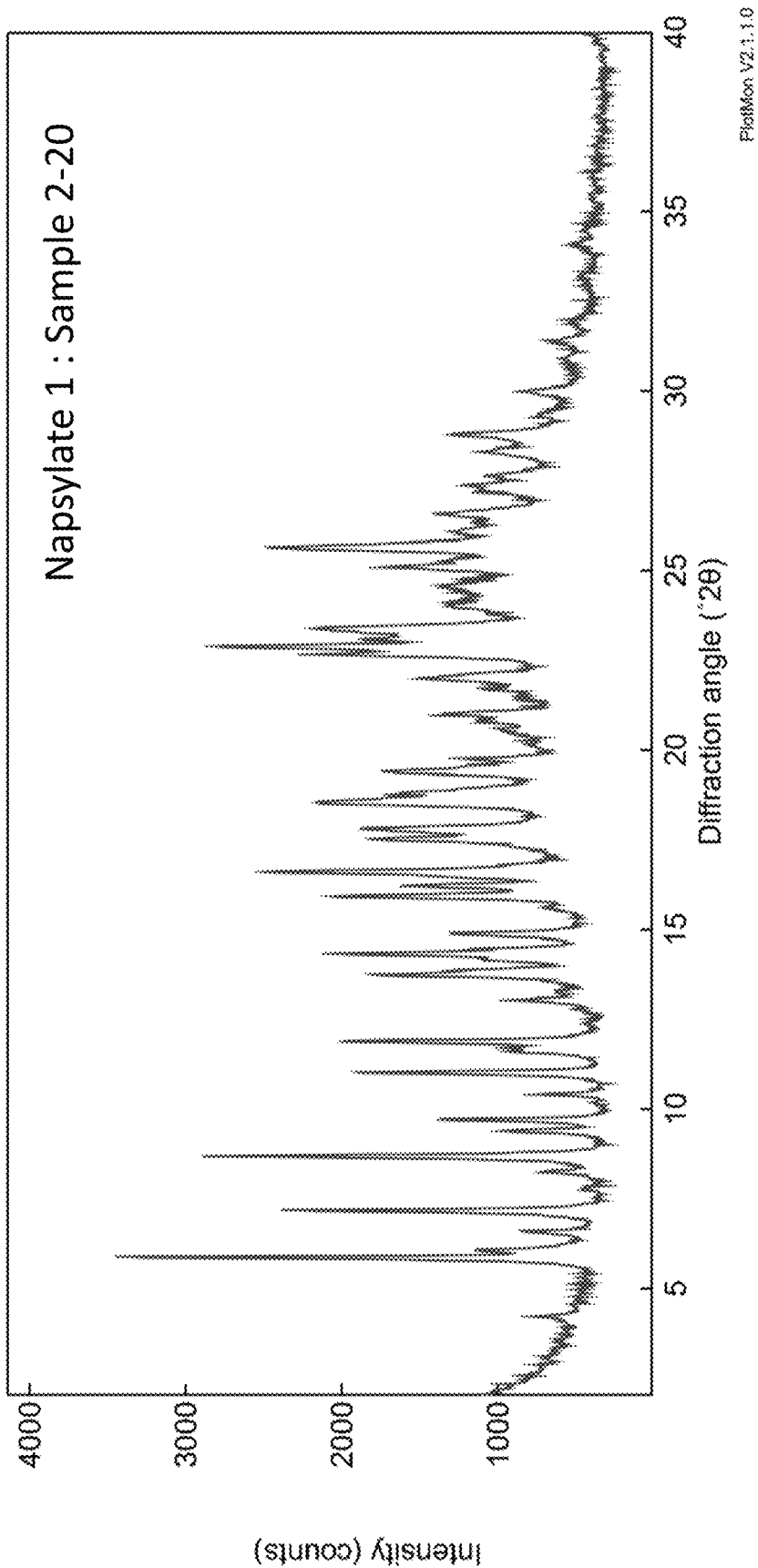
FIG. 56 shows the PXRD of Napsylate 1 (Sample 2-20).
Figure 59:
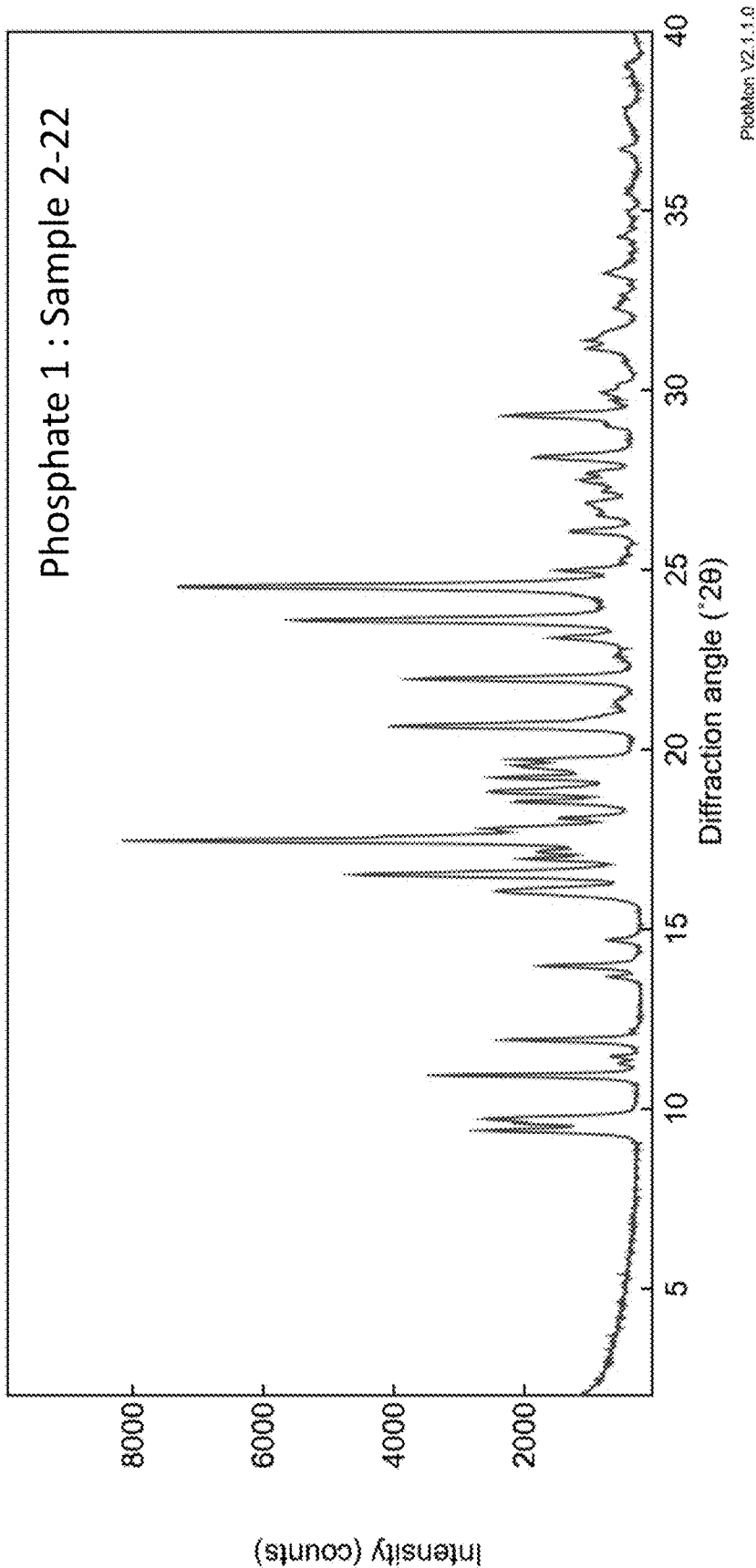
FIG. 59 shows the PXRD of Phosphate 1 (Sample 2-22).
Figure 62:
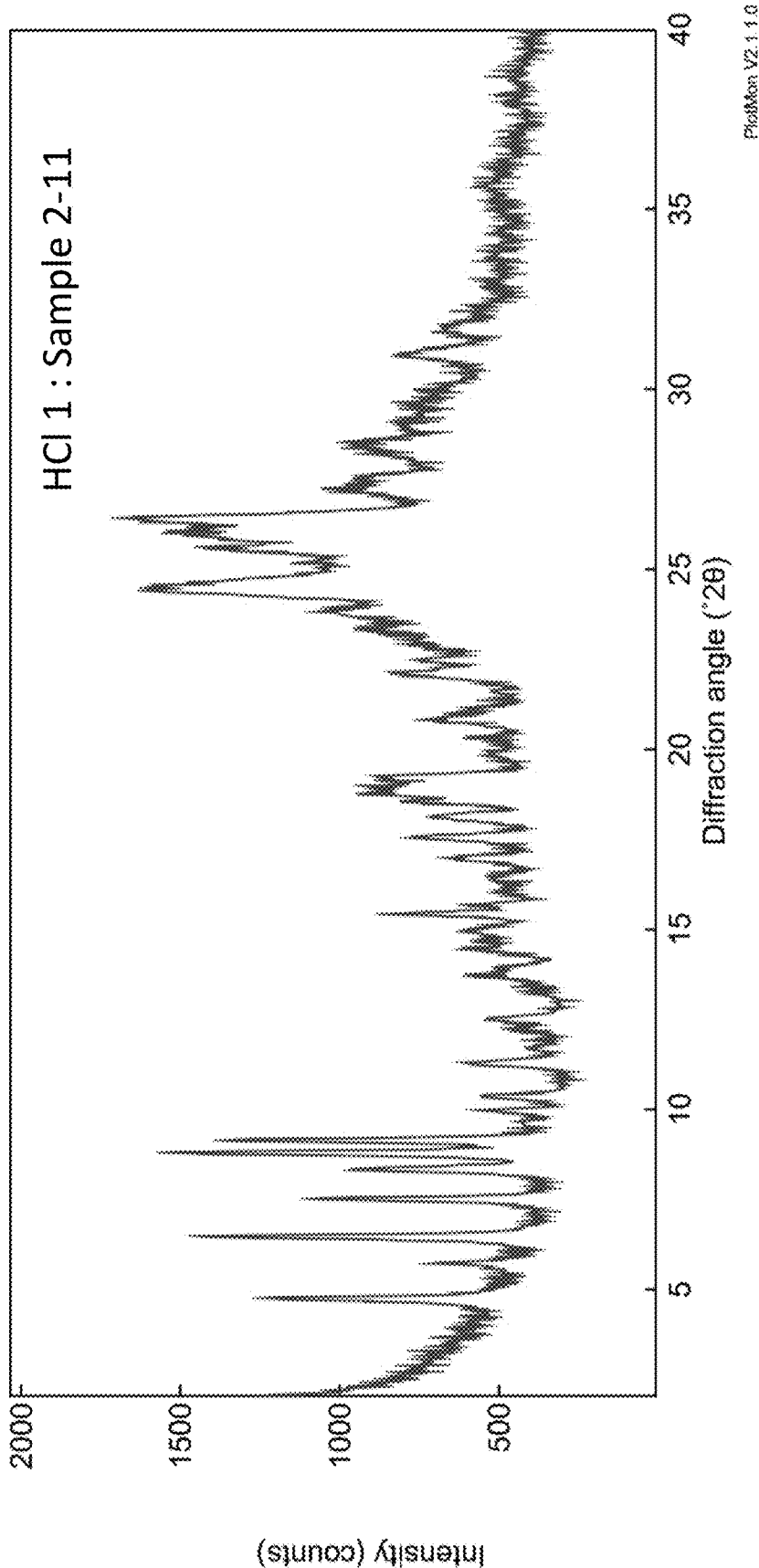
FIG. 62 shows the PXRD of HCl 1 (Sample 2-11).
Figure 63:
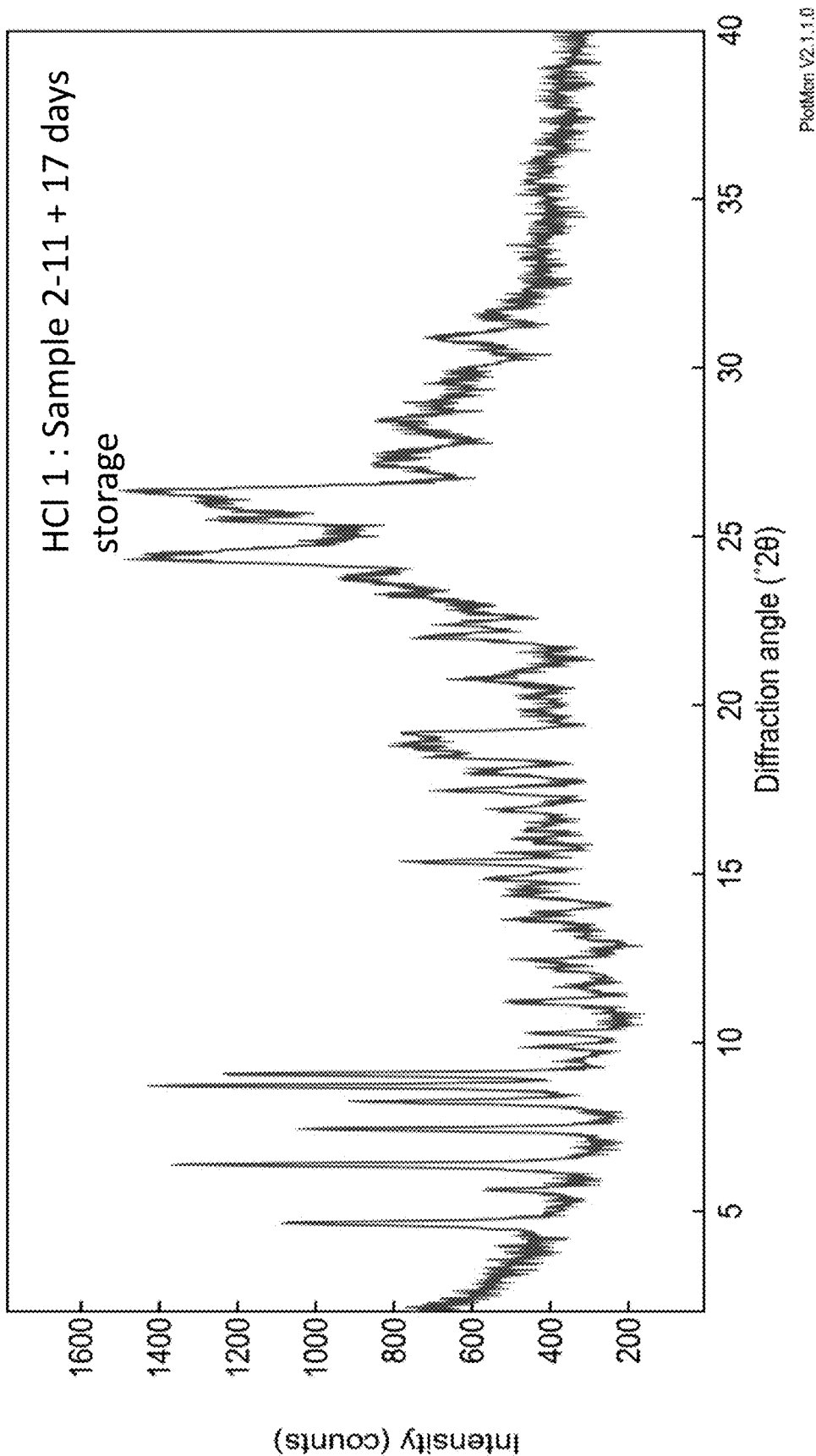
FIG. 63 shows the PXRD of HCl 1 (Sample 2-11 after 17 days of storage at RT).
Figure 78:
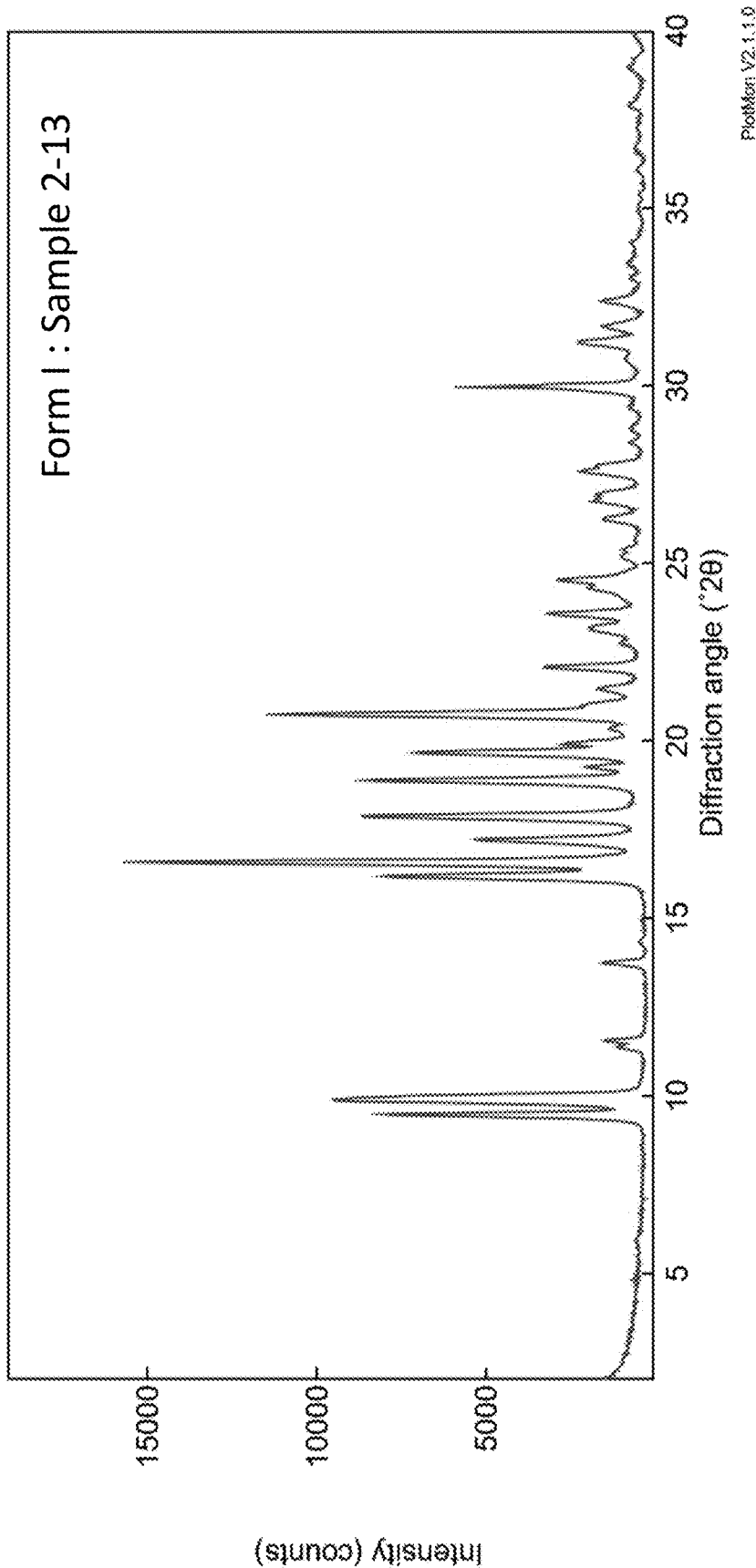
FIG. 78 shows the PXRD of Form I from 2-hydroxyethanesulfonic acid (Sample 2-13).
Figure 79:
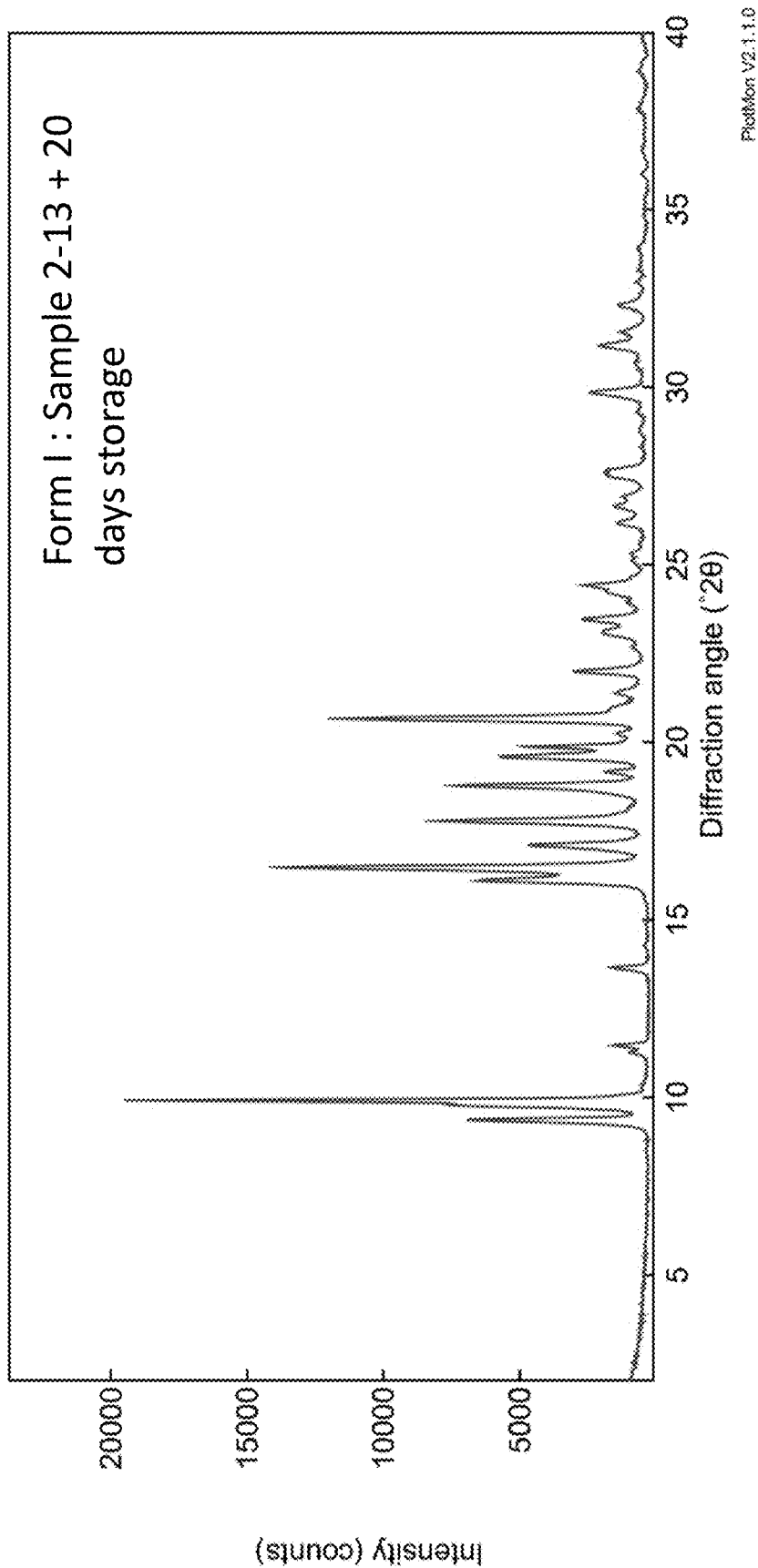
FIG. 79 shows the PXRD of Form I from 2-hydroxyethanesulfonic acid (Sample 2-13 after 20 days of storage at RT).
Figure 80:
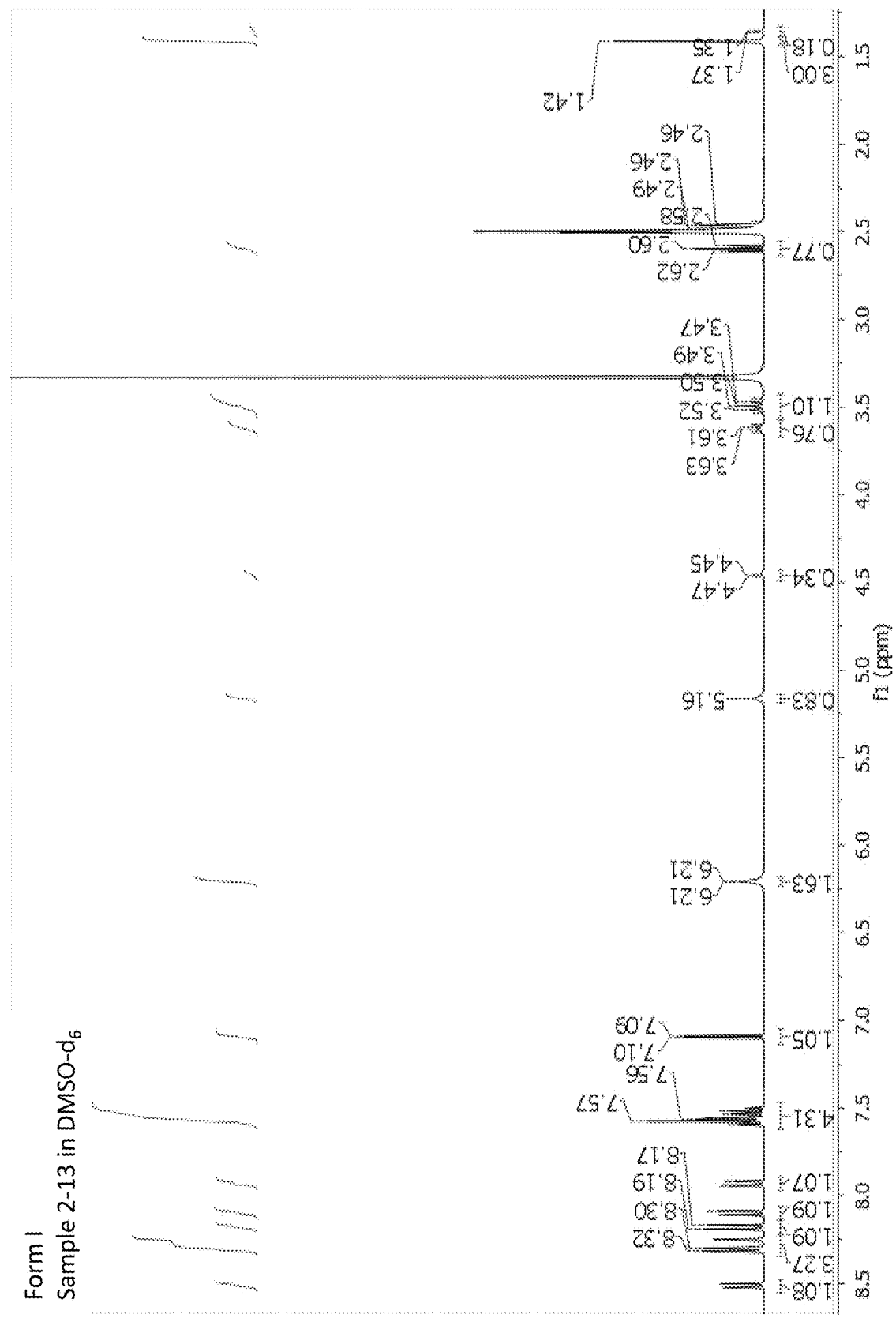
FIG. 80 shows the $^1$H NMR in DMSO-$d_6$ of Form I free base from 2-hydroxyethanesulfonic coformer (Sample 2-13).

| Sample No. | Acid | Conditions [a] | Result [b] | PXRD FIG. |
|---|---|---|---|---|
| 2-7 | Gentisic | Slurry at RT in IPA | Potential salt + Form A (LC) | |
| 2-8 | D-Glucuronic | Slurry in 5% aqueous ACN at ET | NC | |
| 2-9 | Glutamic | Slurry in water at RT | Form A | |
| 2-10 | Glycolic | Slurry in ACN at RT | Form A | |
| 2-11 | Hydrochloric | SE in THF | HCl 1 | FIG. 62 |
| | | Sample reanalyzed after 17 days of storage at RT. | HCl 1 | FIG. 63 |
| 2-12 | 1-Hydroxy-2-naphthoic | Slurry in IPA | Potential CI + peaks (LC) | |
| 2-13 | 2-Hydroxyethanesulfonic | Slurry in ACN | Form I | FIG. 78 |
| | | Sample reanalyzed after 20 days of storage at RT | Form I | FIG. 79 |
| 2-14 | α-Ketoglutaric | Slurry in 5% aqueous IPA at RT | Form A + peaks (LC) | |
| 2-15 | Maleic | Slurry in IPA at RT | Maleate 1 | FIG. 53 |
| 2-16 | L-Malic | Slurry in ACN at RT | L-Malate 1 | FIG. 33 |
| 2-17 | Methanesulfonic | Slurry in acetone at RT | NC | |
| 2-18 | Mucic | Slurry in 5% aqueous IPA | Form B + CI | |
| 2-19 | 1,5-Naphthalenedisulfonic | Slurry in dioxane | CI | |
| 2-20 | 2-Naphthalenesulfonic | Slurry in ACN at ET | Napsylate 1 | FIG. 56 |
| 2-21 | Oxalic | Slurry in ACN at RT | Form A (LC) | |
| 2-22 | Phosphoric | Slurry in ACN at RT | Phosphate 1 | FIG. 59 |
| 2-23 | L-Pyroglutamic acid | Dissolved in THF; precipitated with heptane | NC | |
| 2-24 | Sulfuric | Slow evaporation in THF | Form A (LC) | |
| 2-25 | L-Tartaric | Slurry in MEK at ET | Form A | |
| 2-26 | p-Toluenesulfonic | Dissolved in EtOH; SE | NO | |

Figure 3:
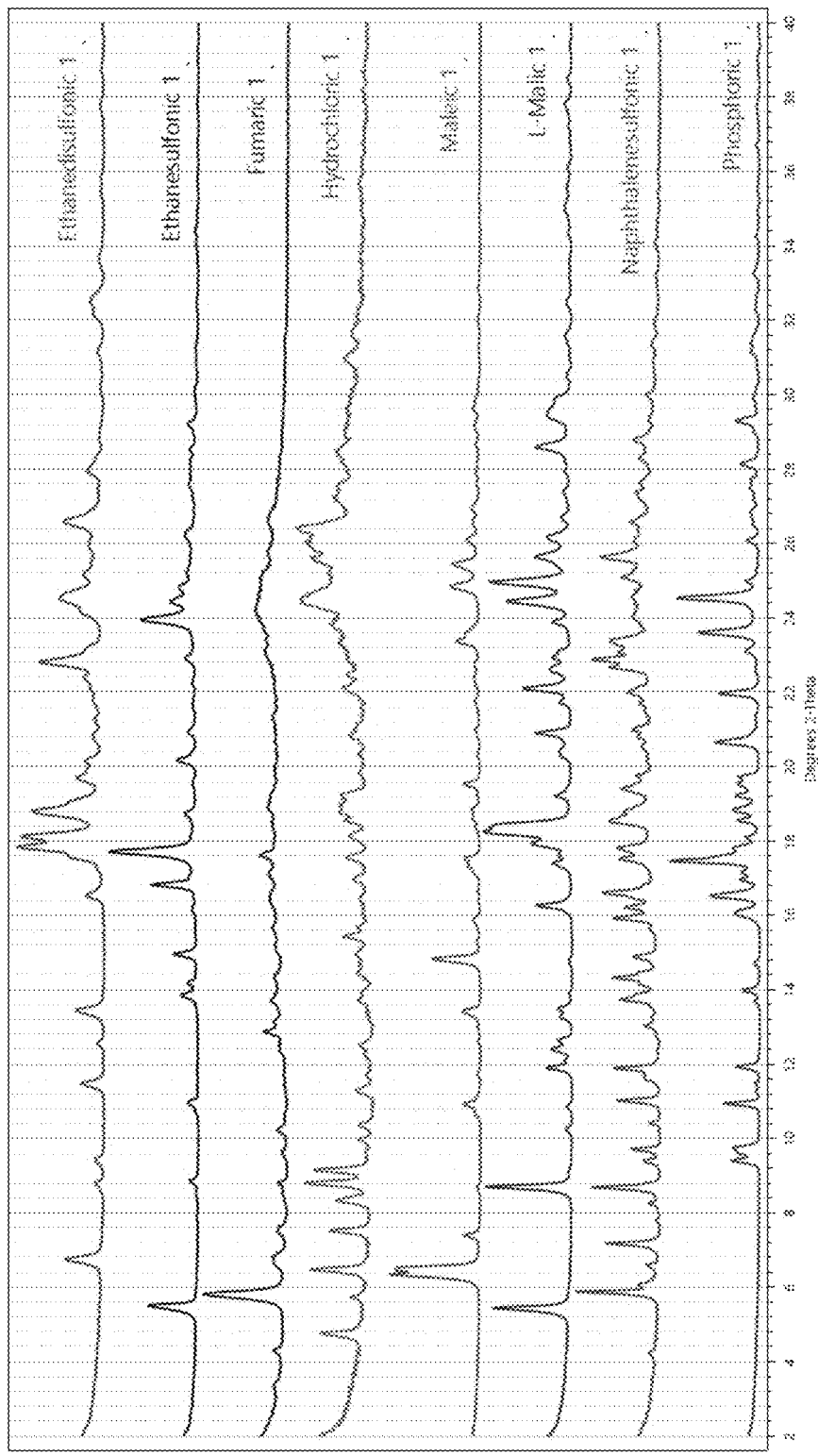
FIG. 3 shows the PXRD comparison of crystalline salt forms identified in salt screen.

[a] SE = slow evaporation, MeOH = methanol, RT = room temperature, ET = elevated temperature, ACN = acetonitrile, MEK = methyl ethyl ketone, IPA = isopropanol; EtOH = ethanol; THF = tetrahydrofuran
[b] CI = counterion (acid); LC = low crystallinity, Form A = free base Form A, Form I = free base Form I; NC = non-crystalline Materials having unique crystalline PXRD patterns were obtained from experiments involving several acids including 1,2-ethanedisulfonic, ethanesulfonic, fumaric, hydrochloric, maleic, L-malic, 2-naphthalenesulfonic, and phosphoric acid (FIG. 3).

Cocrystal Screen

A variety of different coformers were selected for inclusion in the cocrystal screen of linsitinib. The coformers represent various different hydrogen bond donating and accepting groups that could pair with the donors and acceptors in the structure of linsitinib. The list of coformers included some weaker acids not expected to be strong enough to fully protonate linsitinib but that would likely be able to participate in hydrogen bonding. Some coformers such as sorbic acid were included due to their surfactant-like structures with the hope to potentially impact the solubility/dissolution profile compared to linsitinib free base. Generally, the coformers screened were on the GRAS list or were considered Class I or II by Stahl and Wermuth.

The majority of the cocrystal screening experiments were conducted using an equimolar ratio of linsitinib and the coformer. Selected experiments were conducted using a 5× or 10× excess of the coformer in an effort to lower the solubility of the cocrystal and generate conditions that would promote crystallization of the cocrystal. A single attempt was made with each conformer. Initial conditions focused on a wide variety of solvent systems and crystallization methods including the use of solvent-mediated grinding experiments. Samples generated and analyzed during the cocrystal screen are listed in Table 4. Unique crystalline patterns of each potential linsitinib cocrystal were given a unique designation that included the name of the acid (i.e., Orotate 1, Salicylate 1, etc.).

Figure 18:
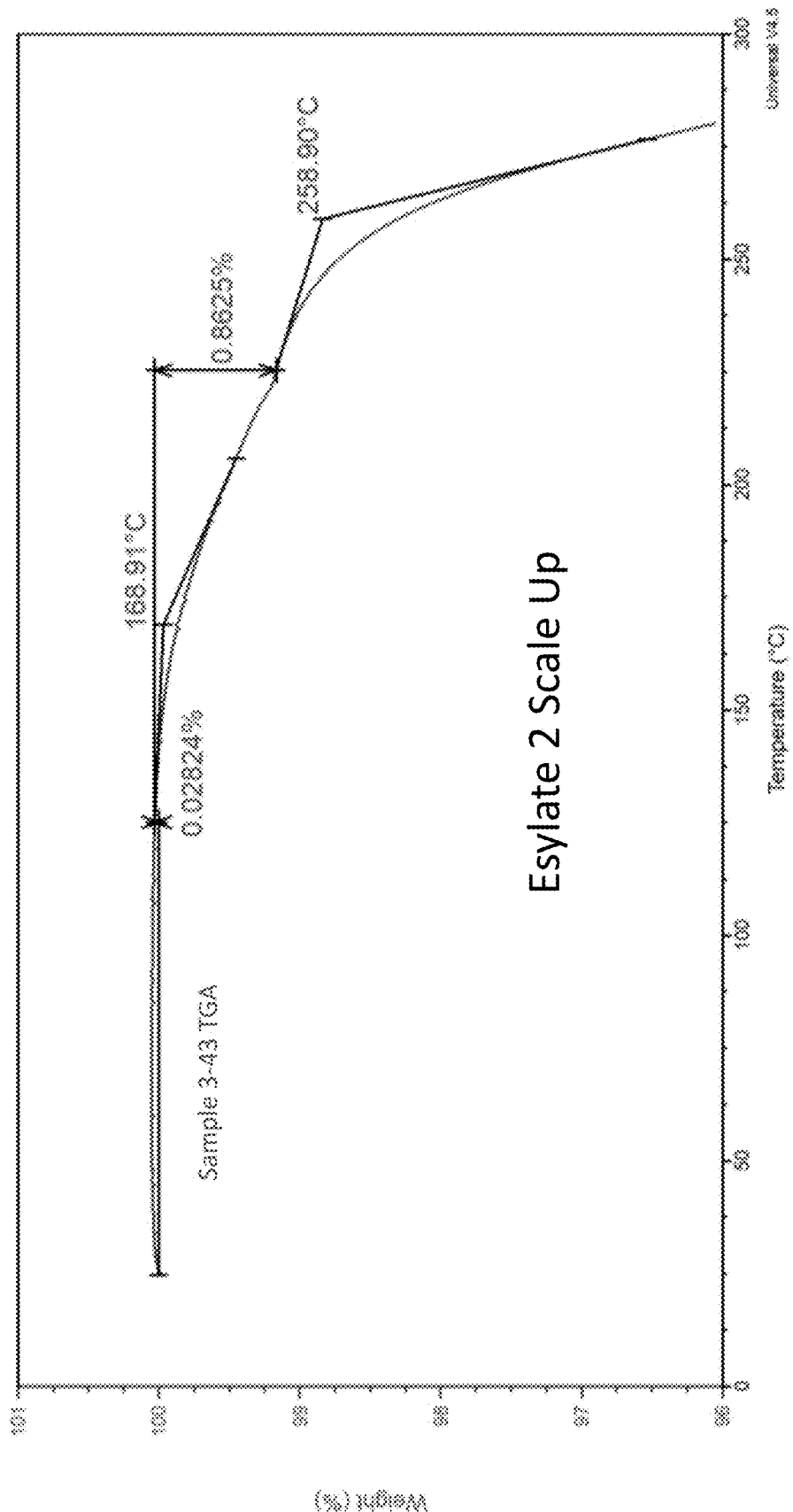
FIG. 18 shows the TGA thermogram of Esylate 2 Scale Up (Sample 3-43).

Materials having unique crystalline PXRD patterns were observed from experiments with gluconic acid, orotic acid, and salicylic acid (FIG. 18). Each of these phases was found to be either poorly crystalline or was isolated as a mixture with the starting material(s).

TABLE 5

Cocrystal Screening Experiments

Figure 71:
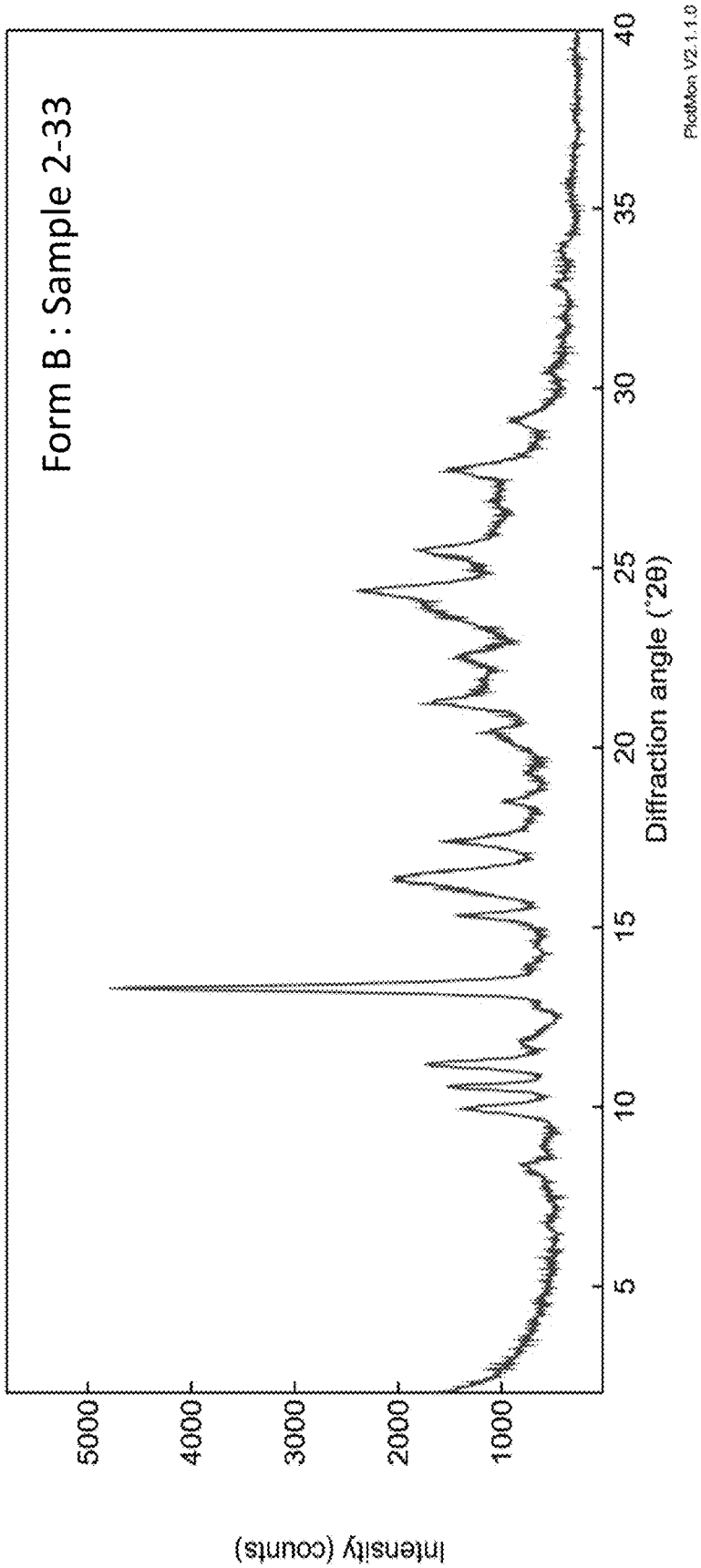
FIG. 71 shows the PXRD of Form B free base from benzamide coformer (Sample 2-33).
Figure 72:
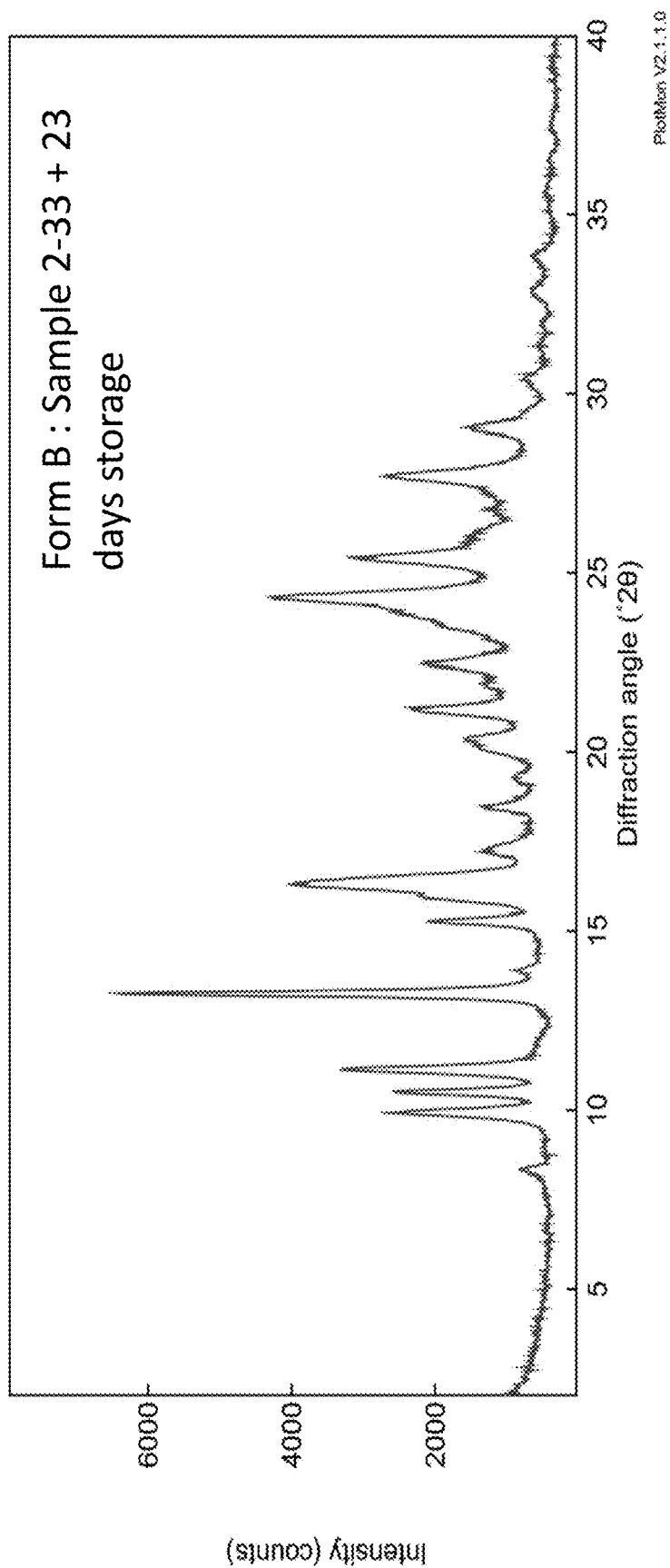
FIG. 72 shows the PXRD of Form B free base from benzamide coformer (Sample 2-33 after 3 days of storage at RT).
Figure 75:
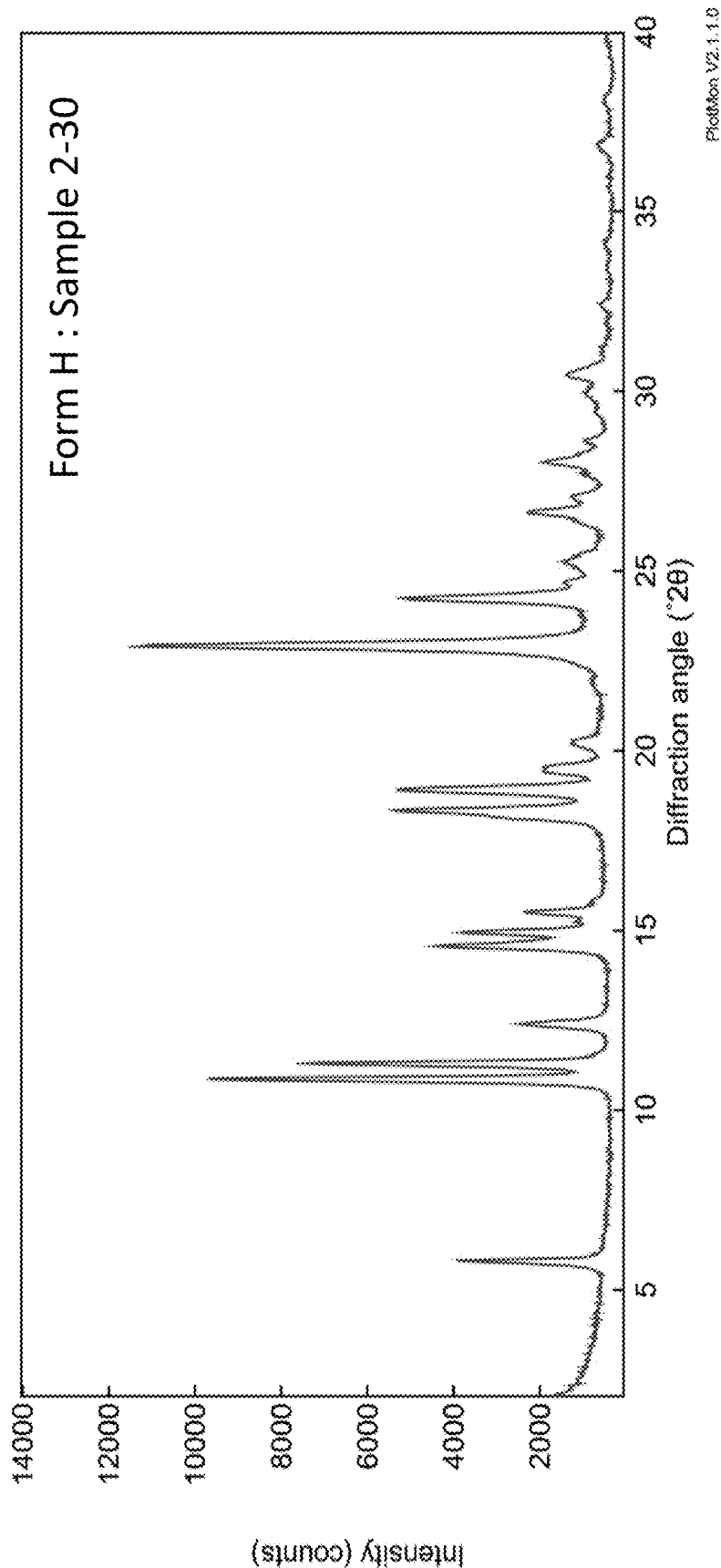
FIG. 75 shows the PXRD of Form H free base from 4-aminosalicylic acid coformer (Sample 2-30).

| Sample No. | Coformer | Conditions [a] | Result [b] | PXRD FIG. |
|---|---|---|---|---|
| 2-27 | Acesulfame K | Grind in MEK | Form A + CF | |
| 2-28 | Adenine | Slurry in MeOH | Form H + CF | |
| 2-29 | Adipic acid | Slurry in MEK at ET | Form A | |
| 2-30 | 4-Aminosalicylic acid | Slurry in MeOH | Form H | FIG. 75 |
| 2-31 | L-Arginine | Slurry in MeOH | Form H + CF | |
| 2-32 | L-Ascorbic acid | Grind in IPE | Form A + CF | |
| 2-33 | Benzamide | Slurry in EtOH | Form B (LC) | FIG. 71 |
| | | Sample reanalyzed after 23 days of storage at RT | Form B (LC) | FIG. 72 |
| 2-34 | Benzoic acid | Slurry in THF, 10 Eq. CF | Form A + NC | |
| 2-35 | Betaine HCl | Grind in EtOH | Potential cocrystal + Form A + CF | |
| 2-36 | Caffeine | Slurry in chloroform, 5 Eq. CF | Form A + CF | |
| 2-37 | Cinnamic acid | Precipitation from DMSO using DEE | Form A | |
| 2-38 | Creatinine | Grind in acetone | Form A + Form J + CF + Peaks | |
| 2-39 | D-Fructose | Grind in EtOAc | Form A + CF | |
| 2-40 | D-Gluconic acid | Grind in acetone | Gluconate 1 (LC) | FIG. 68 |
| 2-41 | Glucosamine HCl | Grind in EtOH | Form A + CF + Peaks (LC) | |
| 2-42 | D-Glucose | Grind in MEK | Form A + CF | |
| 2-43 | L-Glutamine | Grind in EtOAc | Form A + CF | |
| 2-44 | Glutaric acid | Slow evaporation in THF | NC | |
| 2-45 | Glycine | Grind with EtOAc | Form A + CF | |
| 2-46 | Hippuric acid | Slow evaporation in THF | NC | |
| 2-47 | Isonicotinamide | Slurry in chloroform | Form A + CF | |
| 2-48 | L-Lactic acid | Slurry in MEK at ET | Form A | |
| 2-49 | Lactose | Grind with acetone | Form A + Form I + CF | |
| 2-50 | L-Leucine | Grind in IPE | Form A + CF | |
| 2-51 | Malonic acid | Slow evaporation in THF | NC | |
| 2-52 | Maltol | Slurry in IPE | Form A + CF | |
| 2-53 | D-Mannitol | Grind in EtOAc | Form A + CF | |
| 2-54 | Methyl paraben | Slurry in EtOAc | Form A | |
| 2-55 | Monosodium glutamate | Grind in MEK | Form A + CF | |
| 2-56 | Nicotinamide | Grind in MTBE | Form A + CF | |
| 2-57 | Orotic acid | Slurry in chloroform | Orotate 1 + CF | FIG. 69 |
| 2-58 | Propyl gallate | Slurry in MEK at ET | Form A | |
| 2-59 | Saccharin | Slow evaporation in chloroform | NC | |
| 2-60 | Salicylic acid | Slurry in MeOH with excess coformer | Salicylate 1 + CF | FIG. 70 |
| 2-61 | Sebacic acid | Slurry in dioxane | Form A | |
| 2-62 | Sodium lauryl sulfate | Grind in EtOH | Form A + CF | |
| 2-63 | Sorbic acid | Slurry in acetone | Form K | FIG. 86 |
| 2-64 | Stearic acid | Precipitation from DMSO using DEE | Form A | |
| 2-65 | Succinic acid | Slurry in EtOH at ET | Form A | |
| 2-66 | Sucrose | Grind with EtOAc | Form A + CF | |
| 2-67 | Taurine | Grind in MEK | Form A + CF | |
| 2-68 | Thiamine chloride HCl | Slurry in chloroform, 5 Eq. CF | Form A + CF | |
| 2-69 | L-Threonine | Slurry in MeOH | Form H + CF | |
| 2-70 | Tromethamine HCl | Grind in EtOH | Peaks + CF + Form A (LC) | |
| 2-71 | L-Tryptophan | Grind in MTBE | Form A + CF | |
| 2-72 | Urea | Grind with acetone | Form A + CF | |
| 2-73 | L-Valine | Grind MTBE | Form A + CF | |
| 2-74 | Vanillin | Slurry in acetone | Form J | |
| | | Sample reanalyzed after 17 days of storage at RT | Form I | |

TABLE 5-continued

Cocrystal Screening Experiments

| Sample No. | Coformer | Conditions [a] | Result [b] | PXRD FIG. |
|---|---|---|---|---|
| 2-75 | Xanthine | Slurry in MEK at ET | Form A + CF | |
| 2-76 | Xylitol | Grind in acetone | Form A + Form J + CF | |

[a] DEE = diethyl ether, DMSO = dimethyl sulfoxide, ET = elevated temperature, EtOAc = ethyl acetate, EtOH = ethanol, IPE = isopropyl ether, MeOH = methanol, MEK = methyl ethyl ketone, MTBE = methyl tert-butyl ether, THF = tetrahydrofuran; RT = room temperature; Eq. = equivalent(s); CF = coformer;
[b] CF = coformer; LC = low crystallinity; Form A = free base Form A, Form J = free base Form J, Form I = free base Form I Characterization of Selected Solid Forms Each of the materials was further characterized by $^1$H NMR spectroscopy, DSC, and thermogravimetric analysis (TGA) except Fumarate 1 which was poorly crystalline compared to the other materials (Table 6). These analyses were conducted to confirm the chemical structure, determine stoichiometry if possible, and evaluate the nature of the materials generated (anhydrous, solvated, hydrated, etc.). Some characterization results are discussed in further detail in the Examples below.

TABLE 6

Characterization of Selected Samples

Figure 6:
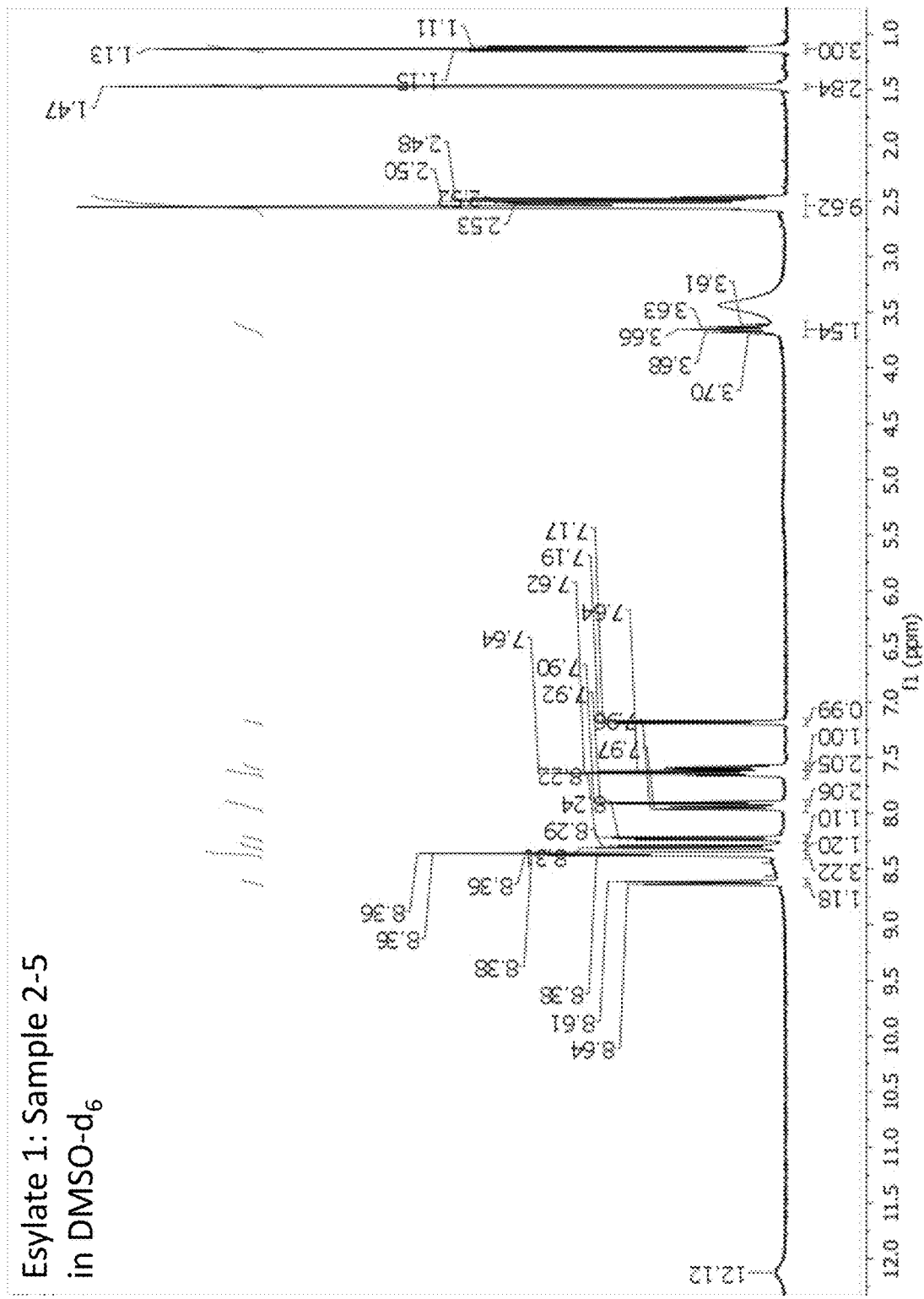
FIG. 6 shows the $^1$H NMR in DMSO-$d_6$ of Esylate 1 (Sample 2-5).
Figure 34:
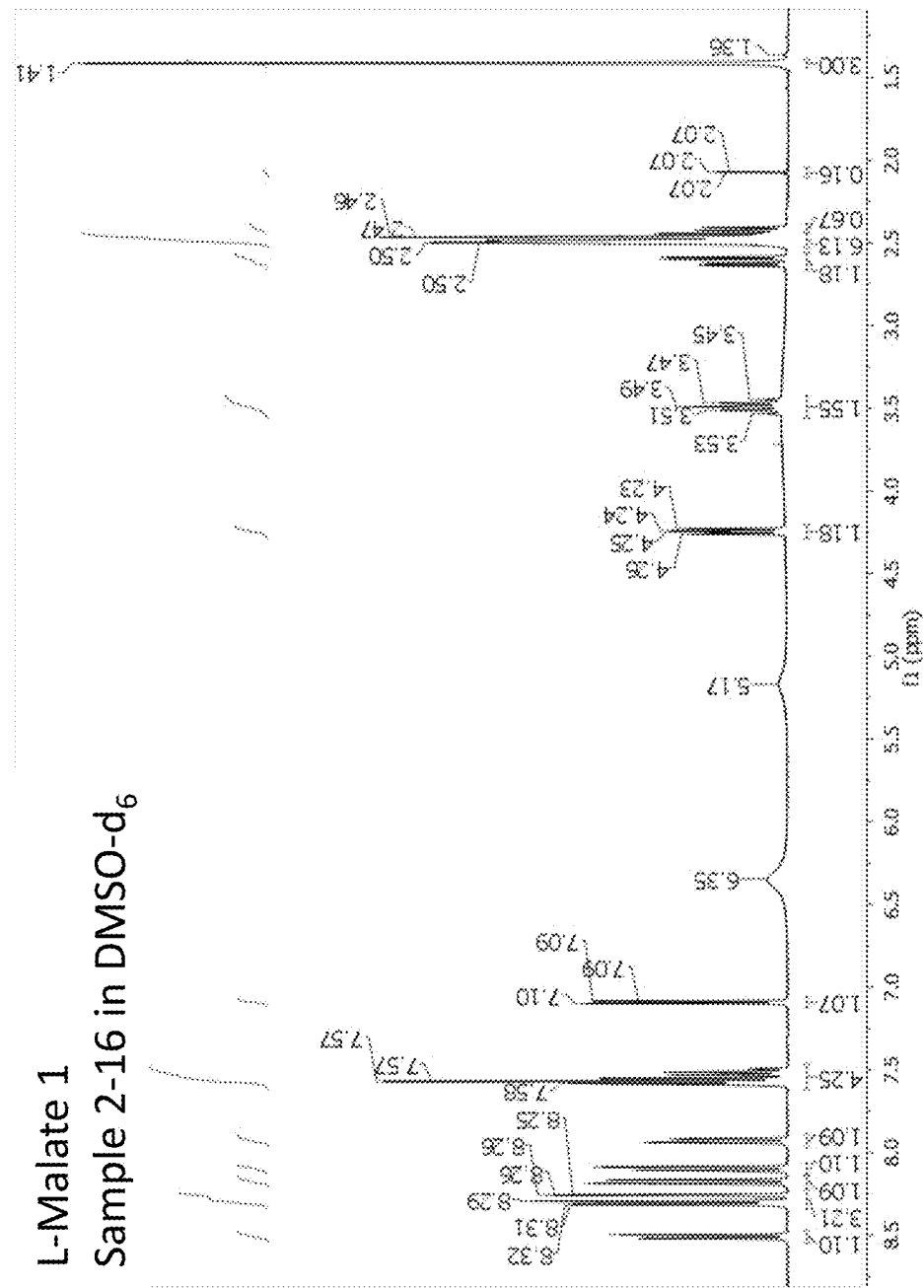
FIG. 34 shows the $^1$H NMR in DMSO-$d_6$ of L-Malate 1 (Sample 2-16).
Figure 67:
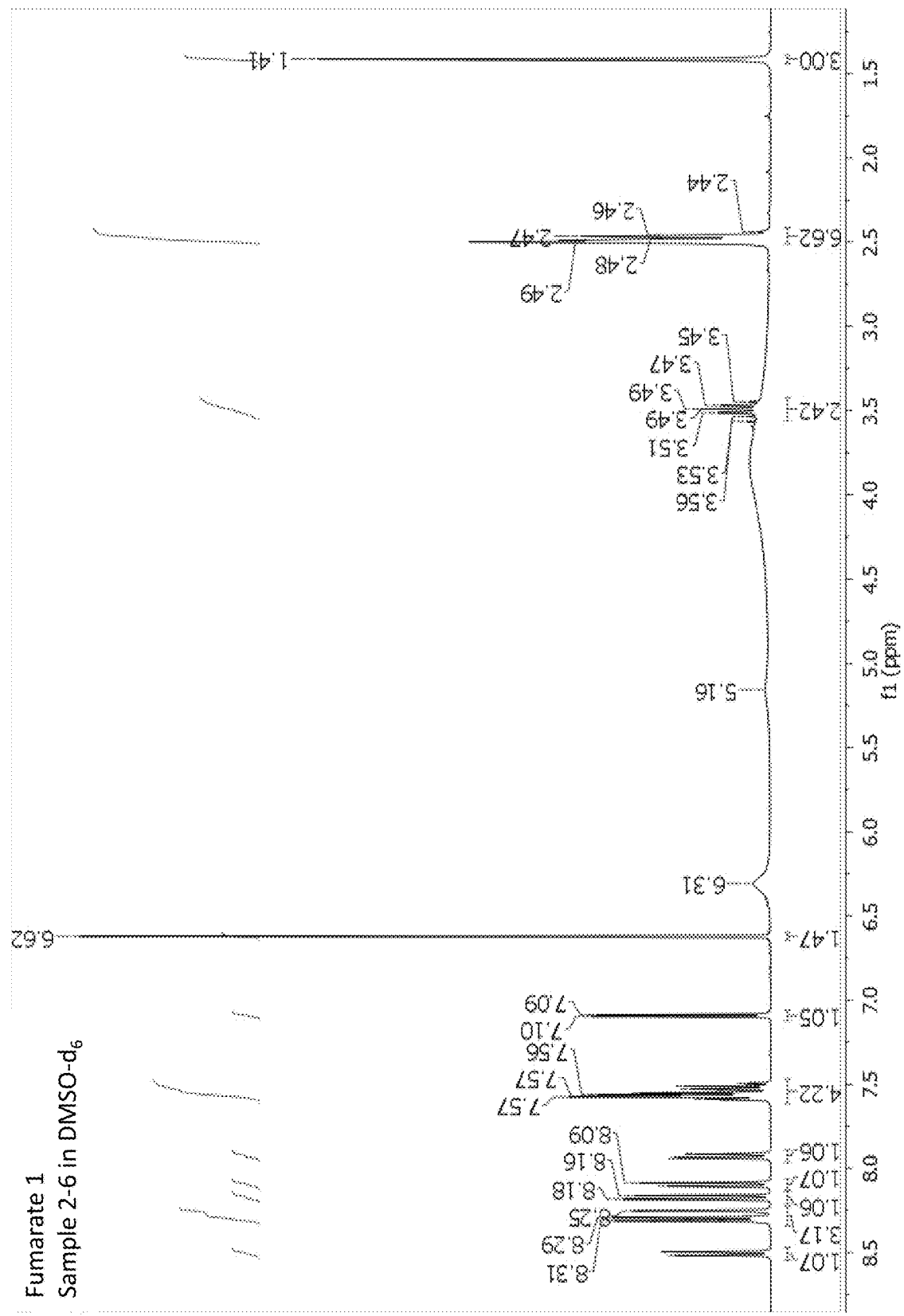
FIG. 67 shows the $^1$H NMR in DMSO-$d_6$ of Fumarate 1 (Sample 2-6)

| Sample (ID) | Analytical Technique [a] | Results [b] | FIG. |
|---|---|---|---|
| Esylate 1 Sample 2-5 | NMR in DMSO-d$_6$ | 1:1 API:CI | FIG. 6 |
| | DSC | Broad endo at 79° C.; Overlapping broad endo-exo-endo at 175-198-212° C. | FIG. 7 |
| | TGA | 4.1% wt loss to 150° C.; Onset of apparent degradation at 265° C. | |
| L-Malate 1 Sample 2-16 | NMR in DMSO-d$_6$ | 1:1 API:CI, residual acetonitrile | FIG. 34 |
| | DSC | Major endo with an onset at 179° C. and peak at 181° C. | FIG. 35 |
| | TGA | 0.4% wt loss to 150° C.; Onset of apparent degradation at 190° C. | |
| Edisylate 1 Sample 2-4 | NMR in DMSO-d$_6$ | 1:1 API:CI (based on CI peak at 2.7) | FIG. 51 |
| | DSC | Major broad endo at 51° C.; Endo at 252° C. and 278° C. | FIG. 52 |
| | TGA | 1.7% weight loss to 150° C., Onset of apparent degradation at 244° C. | |
| Maleate 1 Sample 2-15 | NMR in DMSO-d$_6$ | 1:1 API:CI | FIG. 54 |
| | DSC | Broad endo at 71° C.; Overlapping endos at 182 and 184° C. overlapped with exo at 188° C. | FIG. 55 |
| | TGA | 2.8% weight loss to 100° C.; Onset apparent degradation at 174° C. | |
| Napsylate 1 Sample 2-20 | NMR in DMSO-d$_6$ | 1:1 API:CI | FIG. 57 |
| | DSC | Broad overlapping endos at 74 and 100° C.; Broad endo at 163° C. and shoulder at 155° C. Exo at 198° C. | FIG. 58 |
| | TGA | 3.9% wt loss to 150° C.; Onset of apparent degradation at 264° C. | |
| Phosphate 1 Sample 2-22 | NMR in DMSO-d$_6$ | Minor peak shifting suggestive of potential salt formation, residual acetonitrile; no major water peak | FIG. 60 |
| | DSC | Broad overlapped endo-exo at 160 and 181° C.; Major endotherm with onset at 229° C. | FIG. 61 |
| | TGA | 0.3% wt loss to 150° C.; Onset of apparent decomposition at 229° C. | |
| HCl 1 Sample 2-11 | NMR in DMSO-d$_6$ | Peaks shifted which is consistent with salt formation | FIG. 64 |
| | DSC | Major broad endo at 104° C.; Minor endo at 201° C. | FIG. 65 |
| | TGA | 12.5% weight loss to 76° C.; 2.1% weight loss 76-100° C.; 6.4% weight loss 100-210° C. | |
| Fumarate 1 Sample 2-6 | NMR in DMSO-d$_6$ | 1:0.7 API:CI | FIG. 67 |
| Form B | NMR in | linsitinib free base | 73 |

TABLE 6-continued

Characterization of Selected Samples

Figure 74:
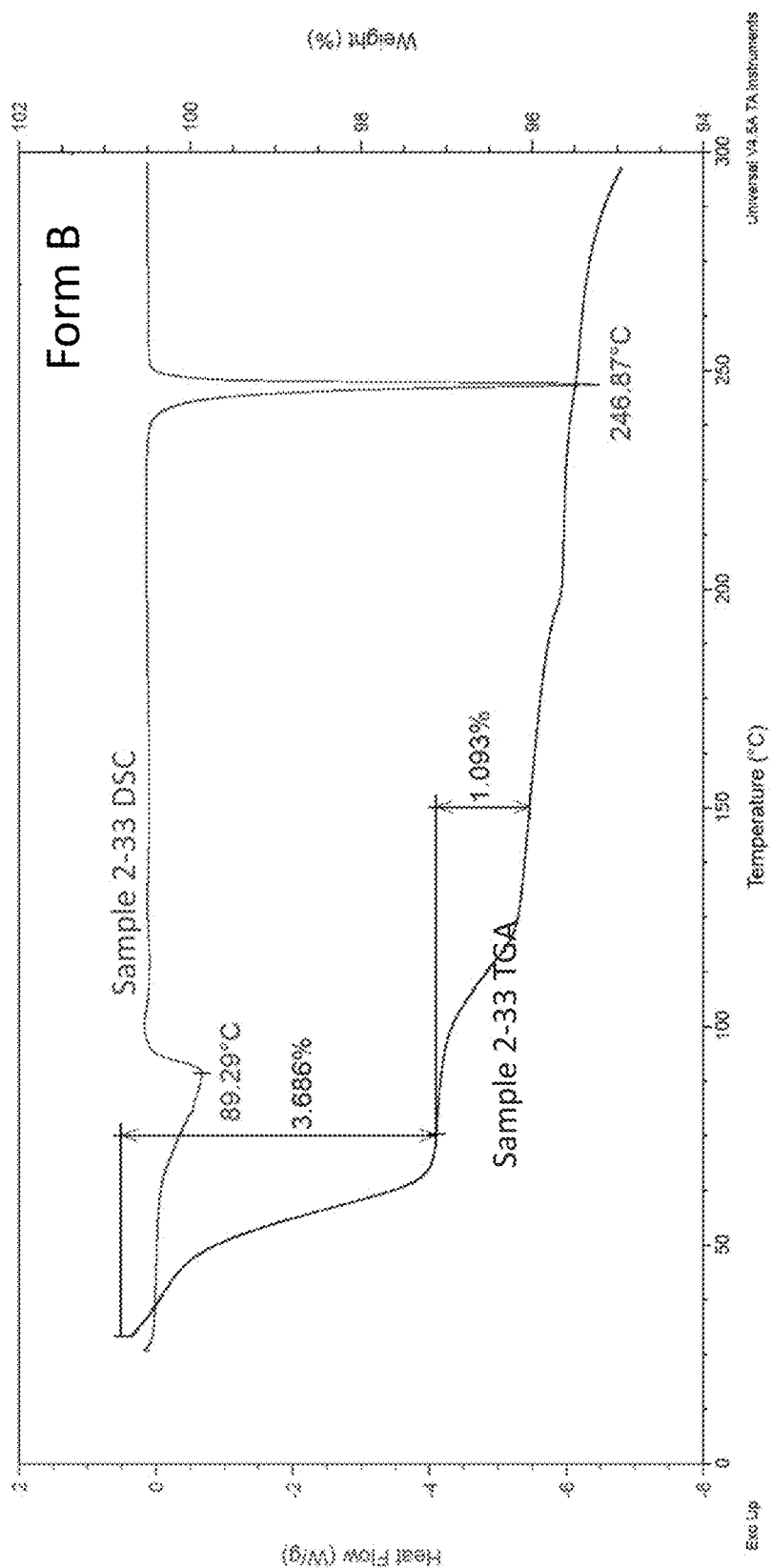
FIG. 74 shows the DSC thermogram of Form B free base from benzamide coformer (Sample 2-33) and the TGA thermogram of Form B free base from benzamide coformer (Sample 2-33).
Figure 76:
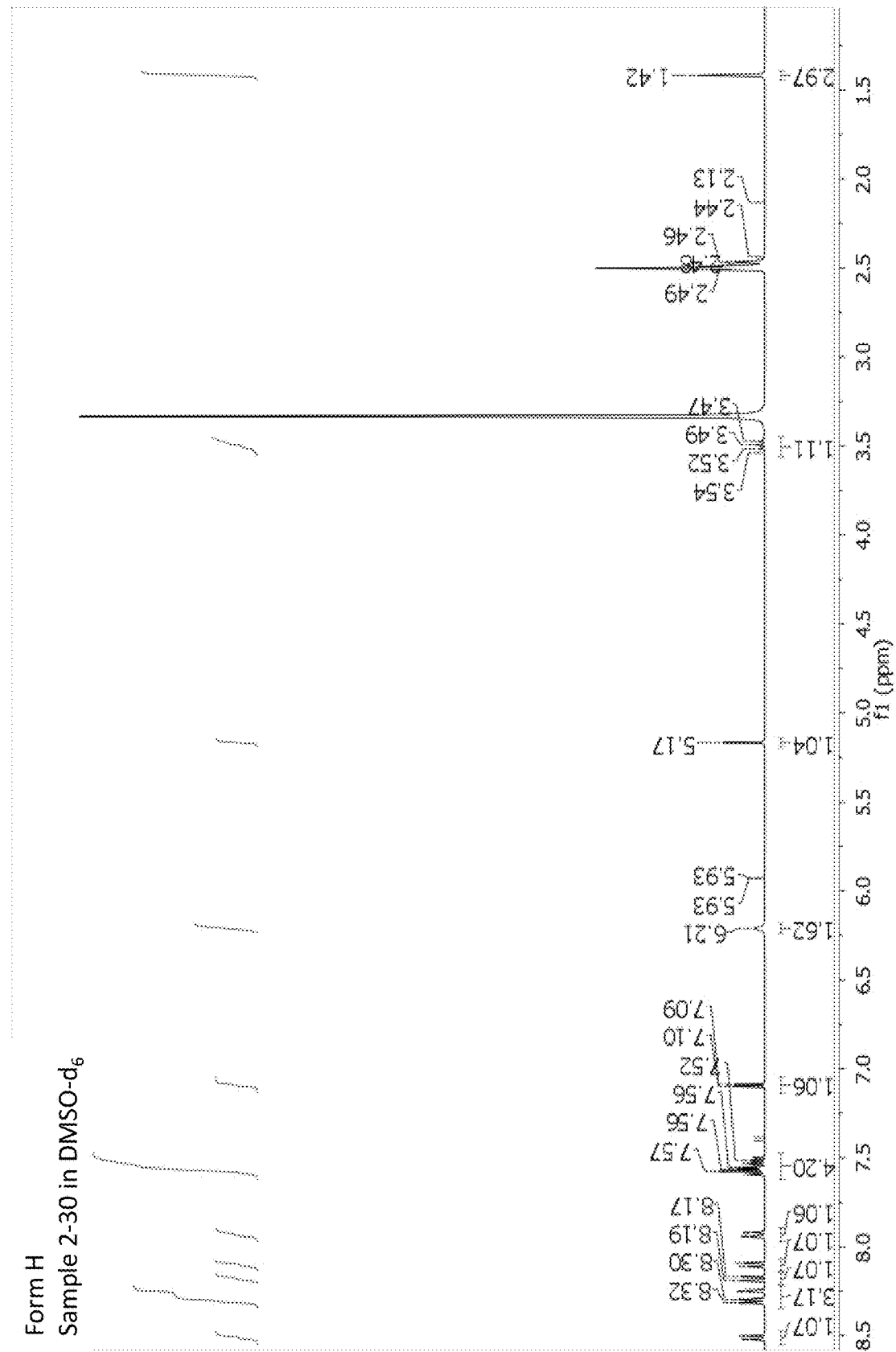
FIG. 76 shows the $^1$H NMR in DMSO-$d_6$ of Form H free base from 4-aminosalicylic acid coformer (Sample 2-30).
Figure 83:
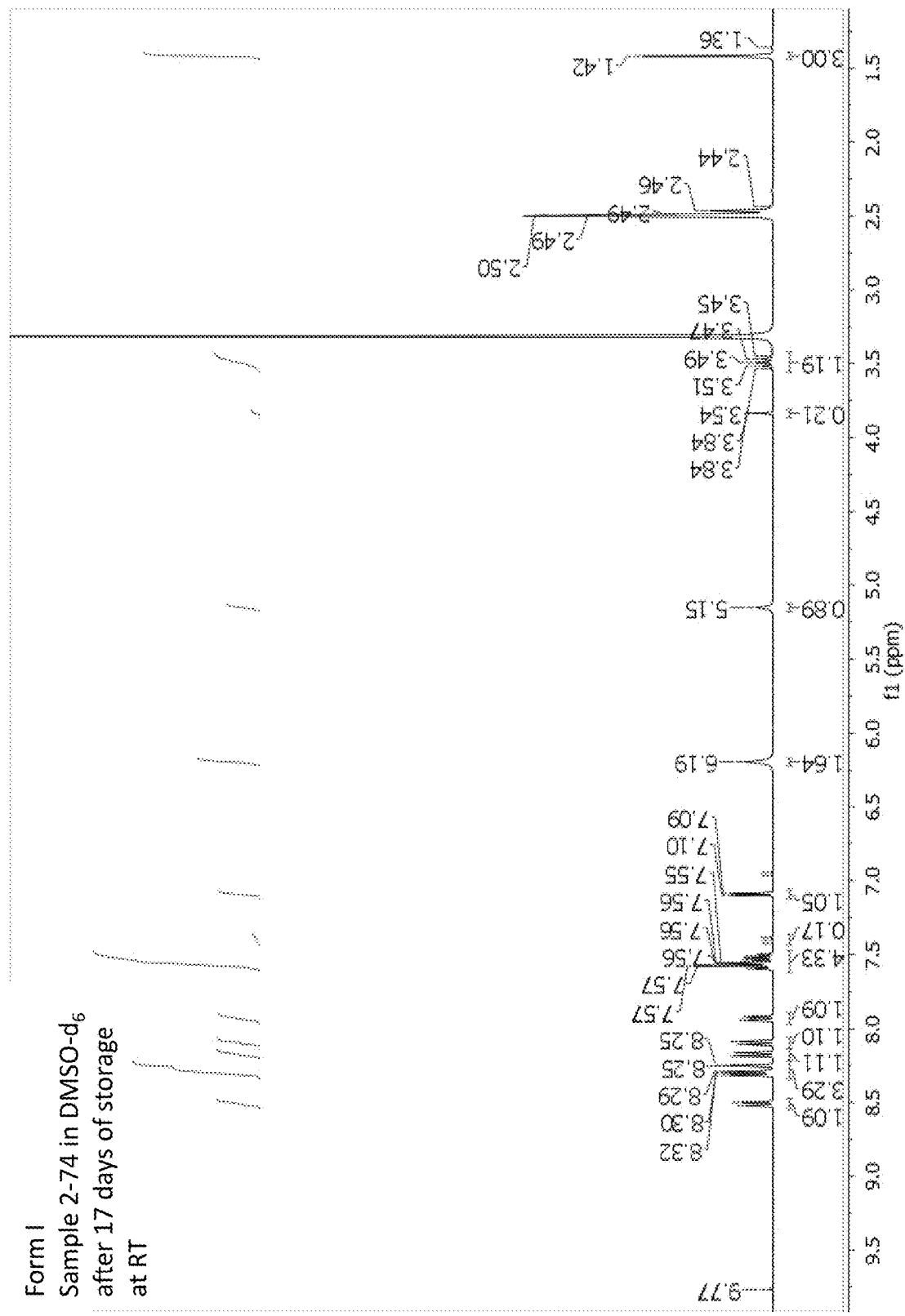
FIG. 83 shows the $^1$H NMR in DMSO-$d_6$ of Form I free base from vanillin (Sample 2-74 after 17 days of storage at RT).
Figure 84:
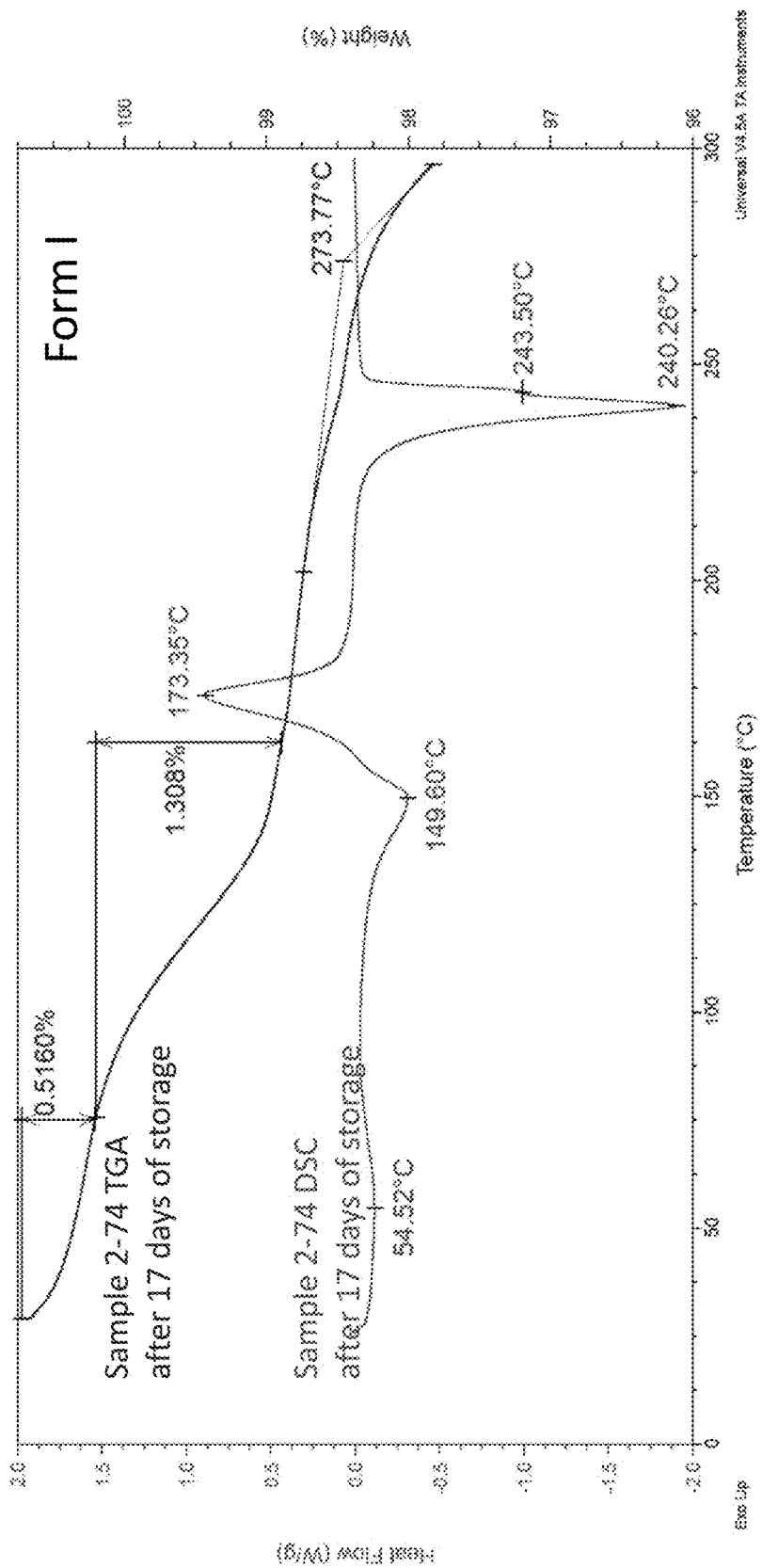
FIG. 84 shows the DSC thermogram of Form I free base from vanillin (Sample 2-74 after 17 days of storage at RT) and the TGA thermogram of Form I free base from vanillin (Sample 2-74 after 17 days of storage at RT).

| Sample (ID) | Analytical Technique [a] | Results [b] | FIG. |
|---|---|---|---|
| Sample 2-33 | DMSO-d$_6$ | | |
| | DSC | Broad endo at 89° C.; Major endo at 247° C. | FIG. 74 |
| | TGA | 3.7% weight loss to 75° C.; Further 1.1% weight loss to 150° C. | |
| Form H + Adenine (1247-34-1) | DSC | Broad shallow overlapping endos at 77 and 91° C.; Endotherm at 142, exotherm at 177, and overlapping endos at 239 and 244° C. | |
| | TGA | 3.1% weight loss to 100° C.; Onset of apparent decomposition 262° C. | |
| Form H Sample 2-30 | NMR in DMSO-d$_6$ | linsitinib free base | FIG. 76 |
| | DSC | Broad shallow endo at 93° C.; Endotherm at 139, exotherm at 176, and overlapping endos at 243 and 247° C. | FIG. 77 |
| | DSC | Broad shallow endo at 90° C.; Endotherm at 139, exotherm at 177, and overlapping endos at 241 and 246° C. | |
| | TGA | 4.0% wt loss to 100° C.; 2.2% wt loss 100-275° C. | FIG. 77 |
| | TGA | 4.0% wt loss to 100° C.; 2.5% wt loss 100-275° C. | |
| Form I Sample 2-13 | NMR in DMSO-d$_6$ | 1:0.3 API:2-hydroxyethanesulfonic acid (based on acid peak at 2.6) | FIG. 75 |
| | DSC | Minor broad endo at 37° C.; Endo-exo-endo at 156, 177 & 192° C.; Overlapping endos at 241 & 247° C. | FIG. 81 |
| | TGA | 0.8% weight loss to 150° C., Onset of apparent degradation at 268° C. | |
| Form I Sample 2-74 | NMR in DMSO-d$_6$ | 1:0.08 API:CF (vanillin) | FIG. 83 |
| | DSC | Minor broad endo at 55° C.; Overlapping endo-exo at 150 & 173° C.; Overlapping endos at 240 & 244° C. | FIG. 84 |
| | TGA | 0.5% weight loss to 75° C.; Further 1.3% weight loss to 163° C.; Onset of apparent degradation at 274° C. | |
| Form K Sample 2-63) | NMR in DMSO-d$_6$ | Consistent with API, 0.4 mol acetone/mol API | FIG. 87 |
| | DSC | Broad endotherm at 111° C.; Overlapping endo-exo at 156 & 174° C.; Overlapping endos at 241 & 247° C. | FIG. 88 |
| | TGA | 4.6% weight loss to 125° C. corresponds to 0.4 Eq Acetone | |

[a] NMR = nuclear magnetic resonance, DSC = differential scanning calorimetry, TGA = thermogravimetric analysis
[b] CI = counterion; API = active pharmaceutical ingredient (linsitinib); DSC temperatures are for peak maximum unless otherwise noted; exo = exotherm; endo = endotherm; wt = weight; eq = equivalent(s); water peak observed in NMR spectra unless otherwise noted. CF = coformer

Example 3: Crystalline Salt Forms of Linsitinib Esylate

Esylate 1 was prepared from a 70° C. slurry of linsitinib and ethanesulfonic acid in isopropanol (IPA). Specifically, 25.5 mg of linsitinib was added to 0.5 mL of isopropanol and heated to 70° C. 5.2 µL of ethanesulfonic acid was added producing finely turbid suspension. After 4 days of equilibration, a yellow-orange suspension was produced. The sample was filtered producing an orange filtrate and yellow solids. The solids were dried overnight under ambient conditions prior to analysis.

The preparation of Esylate 1 was later scaled up. 4.0193 g of linsitinib suspended in 70 ml isopropanol and reacted with 0.82 ml (1 Eq) ethanesulfonic acid at room temperature. This slurry was seeded with Esylate 1 and set to stir overnight at 75° C. Isolating, drying and characterizing the resulting yellow solids revealed successful crystallization of Esylate 1 (FIG. 5), which was then used as the starting material for the rest of this study.

Esylate Salt Polymorph Screen

Various crystallization experiments were conducted in an attempt to utilize a diverse set of conditions in an attempt to identify additional polymorphs of linsitinib esylate salt. Unique crystalline patterns of each linsitinib esylate crystalline salt were given a unique designation that included the name of the acid. Different crystalline forms of the linsitinib esylate salt were prepared and identified by PXRD: Esylate 1, Esylate 2, Esylate 3, Esylate 4, Esylate 5, Di-Esylate 1, etc. Different crystallization techniques, including slurry, cooling, and evaporation were incorporated into the screen.

The polymorph screen of linsitinib esylate was initiated with a focus on slurries at room temperature (RT), sub-ambient temperature (ST) and elevated temperature (ET) in-order to determine the stable form at different conditions early on. Water was incorporated into certain slurries to investigate the presence potential hydrates. Two anhydrous/unsolvated forms of linsitinib esylate, designated Esylate 2 (Green, FIG. 3) and Esylate 3 (Blue, FIG. 3) were observed from the slurry experiments. Esylate 3 was recovered primarily from solvent systems containing alcohols while Esylate 2 was recovered from a wider variety of conditions including the majority of the slurries conducted at room temperature. These forms are discussed in more detail in Section 3.1.1 and 3.1.2 respectively. Esylate 1, used as the starting material for the screen, was recovered from only a single slurry, suggesting Esylate 1 may be metastable.

Additional samples generated and analyzed are listed in Table 7 with corresponding crystallization conditions:

TABLE 7

Rapid Kinetic Crystallizations using Esylate 1

| Sample No. | Method | Solvent | Conditions | PXRD Result | FIG. No. |
|---|---|---|---|---|---|
| 3-1 | Cooling | DOX | ~50 mg dissolved in 0.50 mL solvent with heating, does not ppt upon cooling to 4° C. Vial frozen at −18° C, thawing produces clear orange solution which spontaneously precipitates solids | Esylate 3 | |
| 3-2 | Recrystallization | ACN | ~50 mg almost completely dissolved in 2.00 mL solvent, precipitates crystalline chunks after few hours. | Esylate 2 | |
| 3-3 | Recrystallization | AE | ~50 mg almost completely dissolved in 3.00 mL solvent, precipitates crystalline chunks after few hours. | Esylate 2 | FIG. 8 |
| 3-4 | Recrystallization | NME | ~50 mg almost completely dissolved in 0.75 mL solvent, spontaneously precipitates off-white solids. | Esylate 2 | |

A representative PXRD pattern for Esylate 2 is provided for Sample 3-3, Figure XX. The representative peak positions and intensity for Esylate 2 from Sample 3-3 is provided in Table 8, below.

TABLE 8

Representative Esylate 2 PXRD Peaks

| 2θ Position | d-value | Height | Relative Intensity |
|---|---|---|---|
| 6.7400 | 13.1142 | 12649.3682 | 100.0000 |
| 8.9200 | 9.9134 | 4789.0864 | 37.8603 |
| 10.2600 | 8.6215 | 3906.8389 | 30.8856 |
| 11.0400 | 8.0141 | 3855.5923 | 30.4805 |
| 12.5800 | 7.0363 | 1693.2736 | 13.3862 |
| 12.8000 | 6.9158 | 2020.6283 | 15.9741 |
| 13.5400 | 6.5395 | 1019.3627 | 8.0586 |
| 14.3200 | 6.1850 | 1754.0468 | 13.8667 |
| 14.7600 | 6.0016 | 5073.9492 | 40.1123 |
| 15.5000 | 5.7167 | 827.0829 | 6.5385 |
| 15.6200 | 5.6730 | 1364.8450 | 10.7898 |
| 16.1400 | 5.4914 | 1556.9310 | 12.3084 |
| 16.8000 | 5.2771 | 4146.9639 | 32.7840 |
| 17.6000 | 5.0390 | 10849.2773 | 85.7693 |
| 17.9000 | 4.9552 | 5957.5483 | 47.0976 |
| 18.5600 | 4.7805 | 11324.1348 | 89.5233 |
| 19.2000 | 4.6226 | 418.6443 | 3.3096 |
| 19.7200 | 4.5018 | 2041.6976 | 16.1407 |
| 20.2400 | 4.3873 | 4359.0215 | 34.4604 |
| 20.5600 | 4.3198 | 7568.0684 | 59.8296 |
| 20.7400 | 4.2827 | 3529.9824 | 27.9064 |
| 21.2000 | 4.1908 | 2230.6340 | 17.6344 |
| 21.4600 | 4.1406 | 1379.6281 | 10.9067 |
| 22.1400 | 4.0149 | 489.9688 | 3.8735 |
| 23.4800 | 3.7887 | 2309.3740 | 18.2568 |
| 23.7400 | 3.7478 | 1820.7926 | 14.3943 |
| 23.9000 | 3.7231 | 770.9970 | 6.0951 |
| 24.1600 | 3.6836 | 1456.9354 | 11.5179 |
| 24.5800 | 3.6216 | 5287.1294 | 41.7976 |
| 25.2800 | 3.5229 | 474.6046 | 3.7520 |
| 25.8000 | 3.4531 | 3070.7500 | 24.2759 |
| 26.1200 | 3.4115 | 2326.2798 | 18.3905 |
| 26.9400 | 3.3095 | 760.1328 | 6.0093 |
| 27.1200 | 3.2879 | 1265.5188 | 10.0046 |
| 27.3400 | 3.2620 | 2027.1040 | 16.0253 |
| 27.4400 | 3.2503 | 1579.8429 | 12.4895 |
| 27.7000 | 3.2204 | 457.8565 | 3.6196 |
| 28.1800 | 3.1666 | 1172.2533 | 9.2673 |
| 28.5200 | 3.1296 | 762.1695 | 6.0254 |
| 28.8600 | 3.0935 | 989.5453 | 7.8229 |
| 29.1000 | 3.0686 | 1135.2419 | 8.9747 |
| 29.6400 | 3.0139 | 814.3291 | 6.4377 |
| 29.9400 | 2.9844 | 544.7113 | 4.3062 |
| 30.0200 | 2.9766 | 416.9756 | 3.2964 |
| 30.2000 | 2.9593 | 1240.3318 | 9.8055 |
| 30.5600 | 2.9252 | 578.3536 | 4.5722 |
| 30.8800 | 2.8956 | 441.4384 | 3.4898 |
| 31.0600 | 2.8793 | 626.7237 | 4.9546 |
| 31.2800 | 2.8595 | 1161.0465 | 9.1787 |
| 31.5000 | 2.8400 | 486.3415 | 3.8448 |
| 32.6200 | 2.7450 | 419.8454 | 3.3191 |
| 33.2800 | 2.6921 | 591.7639 | 4.6782 |
| 33.4800 | 2.6765 | 817.3016 | 6.4612 |
| 33.7800 | 2.6534 | 316.6649 | 2.5034 |
| 34.1000 | 2.6292 | 1055.4093 | 8.3436 |
| 34.4400 | 2.6040 | 277.1772 | 2.1912 |
| 35.1600 | 2.5523 | 444.5155 | 3.5141 |
| 36.2200 | 2.4800 | 430.6686 | 3.4047 |
| 37.1800 | 2.4182 | 295.2324 | 2.3340 |
| 37.6400 | 2.3897 | 748.0143 | 5.9135 |
| 38.6600 | 2.3289 | 424.6900 | 3.3574 |
| 39.4400 | 2.2847 | 436.0428 | 3.4472 |

Kinetic screening experiments also identified additional forms of linsitinib esylate. A salt formation attempt from IPA with 1 equivalent (Eq) ESA at RT resulted in a solvate designated as Esylate 4 (Black, FIG. 4). Drying this same sample of Esylate 4 resulted in a de-solvated solvate designated as Esylate 5 (Red, FIG. 4). These same patterns for Esylate 4 and 5 were also observed from other solvent systems including ST slurries at 4° C. in 95:5 IPA:H2O and chloroform respectively (Blue and green respectively, FIG. 4). This pointed to Esylate 4 being an isostructural solvate, capable of forming a solvate with different crystallization solvents.

TABLE 9

Slow Thermodynamic Crystallizations using Esylate 1

| Sample No. | Method | Solvent | Conditions | PXRD Result | FIG. No. |
|---|---|---|---|---|---|
| 3-5 | Slow Evaporation | H2O | ~50 mg dissolved in 0.50 mL solvent, filtered and placed in fume hood with cap slightly loose. Orange glass. | Amorphous | |
| 3-6 | Slow Evaporation | MeOH | ~50 mg dissolved in 0.50 mL solvent, filtered and placed in fume hood with cap slightly loose. Orange chunks. | Esylate 3 | |
| 3-7 | Slow Evaporation | HFIPA | ~50 mg dissolved in 0.25 mL solvent, filtered and placed in fume hood with cap slightly loose. Yellow plates. | Amorphous | |
| 3-8 | Vapor Diffusion | DCM into DMF | ~50 mg dissolved in 0.25 mL DMF, filtered into a vial which is placed into a larger vial filled with DCM. Clear colorless needles | Esylate 2 | |
| 3-9 | Vapor Diffusion | IPE into MeOH | ~50 mg dissolved in 1.50 mL MeOH with heating, filtered into a vial which is placed into a larger vial filled with IPE. Yellow residue upon agitation | Esylate 3 | |
| 3-10 | Organic Slurry | AE | ~50 mg suspended in 1.50 mL solvent and stirred at RT for 14 days. White residue. | Esylate 2 | |
| 3-11 | Organic Slurry | CLF | ~50 mg suspended in 0.75 mL solvent and stirred at ST at 4° C. for 14 days. Off-white residue. | Esylate 4 Esylate 5 | |
| 3-12 | Organic Slurry | EtOAc | ~50 mg suspended in 1.50 mL solvent and stirred at RT for 14 days. White residue. | Esylate 2 | |
| 3-13 | Organic Slurry | 1:1 EtOH:HEP | ~50 mg suspended in 0.75 mL solvent and stirred at ST at 4° C. for 14 days. White residue. | Esylate 3 | FIG. 22 |
| 3-14 | Organic Slurry | IPA | ~50 mg suspended in 0.75 mL solvent and stirred at ET at 60° C. for 14 days. White residue. | Esylate 4 Esylate 5 | |
| 3-15 | Organic Slurry | IPAE | ~50 mg suspended in 1.00 mL solvent (Reversible conversion to yellow color on heating) and stirred at RT for 1 Day. Light-yellow residue. | Esylate 2 | |
| 3-16 | Organic Slurry | IPE | ~50 mg suspended in 1.50 mL solvent and stirred at RT for 14 days. White residue. | Esylate 2 | |
| 3-17 | Organic Slurry | 9:1 MCH:MeOH | ~50 mg suspended in 0.75 mL solvent and binary phase slurry stirred at RT for 1 Day. Light-yellow residue. | Esylate 3 | |
| 3-18 | Organic Slurry | MEK | ~50 mg suspended in 3.00 mL solvent and stirred at RT for 14 days. Off-white residue. | Esylate 2 | |
| 3-19 | Organic Slurry | MIBK | ~50 mg suspended in 0.75 mL solvent and stirred at ET at 60° C. for 14 days. Off-white residue. | Esylate 2 | |
| 3-20 | Organic Slurry | MTBE | ~50 mg suspended in 0.75 mL and stirred at RT for 1 Day. Light-yellow residue. | Esylate 1 | |
| 3-21 | Organic Slurry | THF | ~50 mg suspended in 1.50 mL solvent and stirred at RT for 14 days. Off-white residue. | Esylate 2 | |
| 3-22 | Organic Slurry | TOL | ~50 mg suspended in 0.75 mL and stirred at ET at 60° C. for 1 Day. Light-yellow residue. | Esylate 2 | |
| 3-23 | Aqueous slurry | 95:5 IPA:H2O aw = 0.40 | ~50 mg suspended in 0.75 mL and stirred at ST at 4° C. for 14 days. Off-white residue. | Esylate 4 Esylate 5 | |

TABLE 10

Salt Formation Attempts using Linsitinib Free Base

Figure 25:
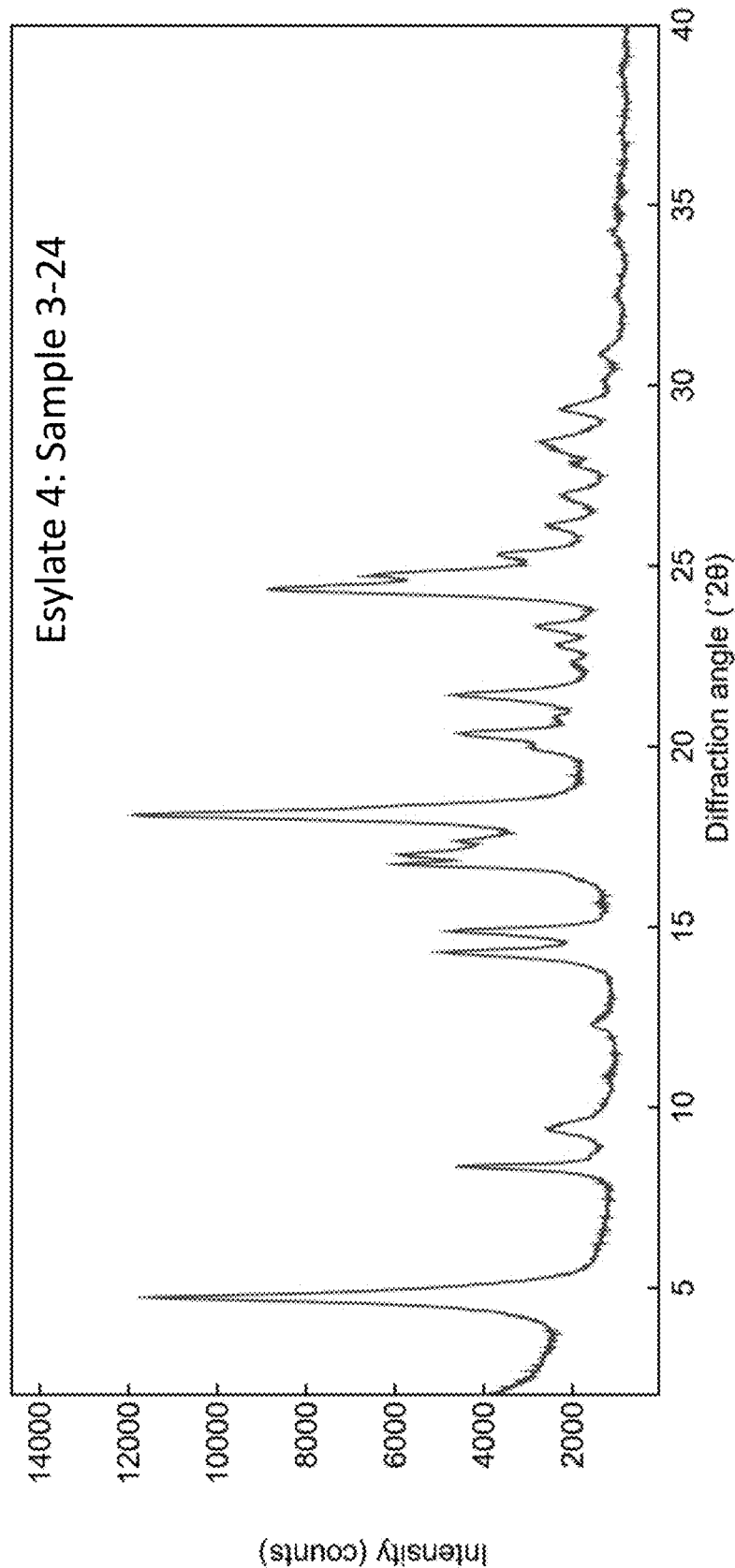
FIG. 25 shows the PXRD of Esylate 4 (Sample 3-24).

| Sample No. | Solvent | Conditions | PXRD Result | FIG. No. |
|---|---|---|---|---|
| 3-24 | IPA | 50.5 mg Linsitinib is suspended in 1.00 mL solvent, to which 1 Eq ESA (10.4 μL) is added and the slurry stirred overnight at RT. | Esylate 4 | FIG. 25 |

TABLE 10-continued

Salt Formation Attempts using Linsitinib Free Base

Figure 30:
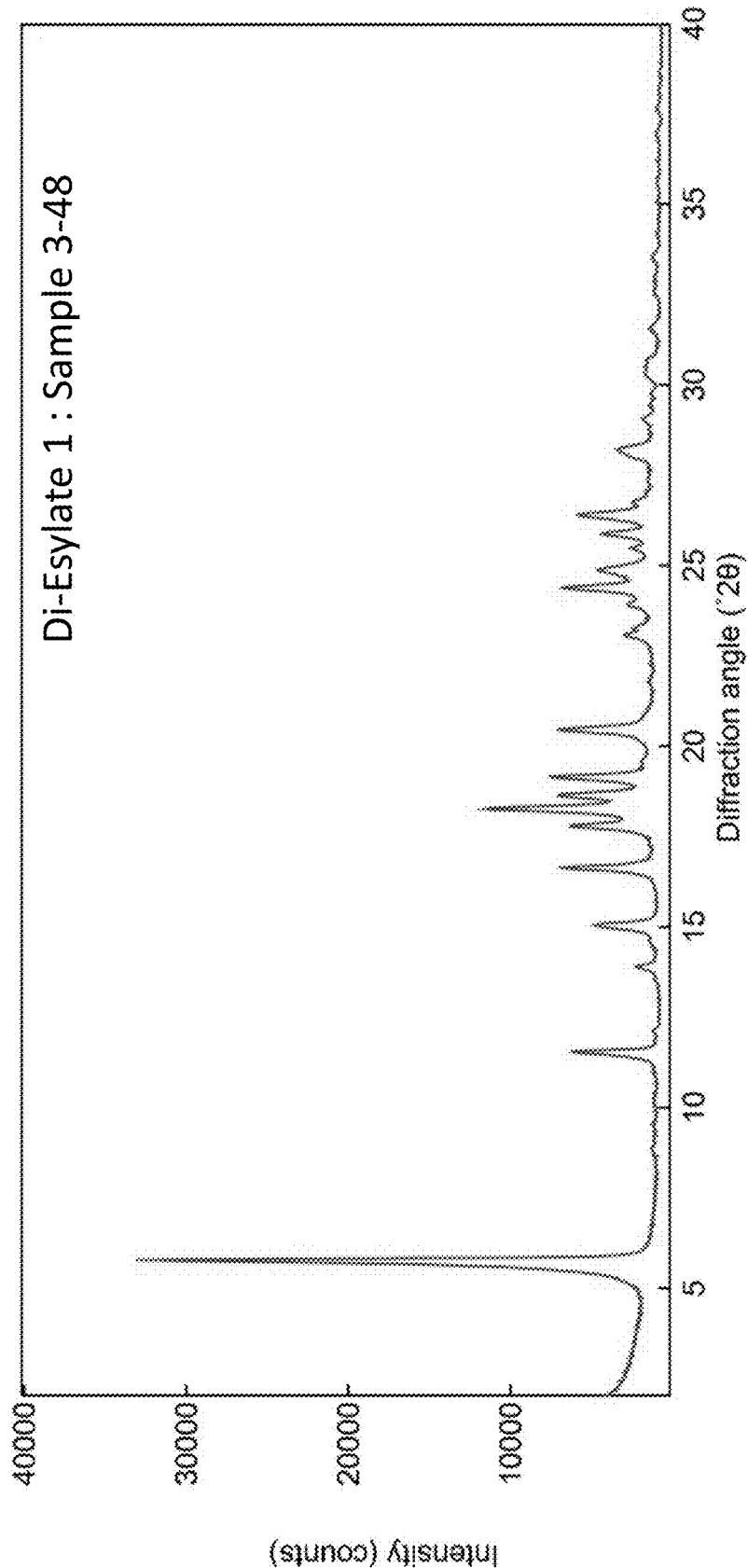
FIG. 30 shows the PXRD of Di-Esylate 1 (Sample 3-24).

| Sample No. | Solvent | Conditions | PXRD Result | FIG. No. |
|---|---|---|---|---|
| 3-25 | IPA | 50.5 mg Linsitinib is suspended in 1.00 mL solvent, to which 2 Eq ESA (20.8 µL) is added and the slurry stirred overnight at RT. | Di-Esylate 1 | FIG. 30 |
| 3-26 | IPA | 50.4 mg Linsitinib is suspended in 1.00 mL solvent, to which 1 Eq ESA (10.4 µL) is added and the slurry stirred overnight at ST at 4° C. | Esylate 4 + Peaks at 3.5, 5.7 2θ | |
| 3-27 | IPA | 50.2 mg Linsitinib is suspended in 0.75 mL solvent, to which 3 Eq ESA (31.2 µL) is added and clear solution stirred overnight at RT. | Di-Esylate 1 + Peaks | |
| 3-28 | ACN | 50.5 mg Linsitinib is suspended in 0.75 mL solvent, to which 1 Eq ESA (10.4 µL) is added and the slurry stirred overnight at RT. | Esylate 2 | |
| 3-29 | AE | 50.4 mg Linsitinib is suspended in 0.75 mL solvent, to which 1 Eq ESA (10.4 µL) is added and the slurry stirred overnight at RT. | Esylate 2 | |
| 3-30 | EtOH | 50.4 mg Linsitinib is suspended in 0.75 mL solvent, to which 1 Eq ESA (10.4 µL) is added and the slurry stirred overnight at RT. | Esylate 2 | |
| 3-31 | THF | 50.4 mg Linsitinib is suspended in 0.75 mL solvent, to which 1 Eq ESA (10.4 µL) is added and the slurry stirred overnight at RT. | Esylate 2 | |
| 3-32 | MTBE | 50.3 mg Linsitinib is suspended in 0.75 mL solvent, to which 1 Eq ESA (10.4 µL) is added and seeded with Esylate 1 (1341-9-1-1), and slurry is stirred overnight at RT. | New-1 | |

To find the thermodynamically stable form of the mono-salt, interconversion slurries were set-up at three different temperatures in two different solvent systems between Esylates 1, 2, 3 and Esylate 4+Esylate 5 (Table 11). A sample of Esylate 4+Esylate 5 was included as part of the interconversion slurry in-spite of Esylate 4 being a solvate as Esylate 5 could not be isolated as a separate pure phase until the drying experiment was carried out on Esylate 4 towards the end of the study. Slurries were set-up at 4° C., RT and at 60° C. in MEK and 2:1 EtOH:HEP, resulting in a total of six experiments which were run for a total of 7 days. All slurries unanimously resulted in Esylate 2, pointing to it being the most stable form under the conditions explored between all these forms.

TABLE 11

Interconversion Slurries

| Sample No. | Solvent | Conditions[a] | PXRD Result |
|---|---|---|---|
| 3-33 | 2:1 EtOH:HEP | SL at ET at 60° C. for 7 Days. White residue. | Esylate 2 |
| 3-34 | 2:1 EtOH:HEP | SL at RT for 7 Days. White residue. | Esylate 2 |
| 3-35 | 2:1 EtOH:HEP | SL at ST at 4° C. for 7 Days. White residue. | Esylate 2 |
| 3-36 | MEK | SL at ET at 60° C. for 7 Days. White residue. | Esylate 2 |
| 3-37 | MEK | SL at RT for 7 Days. White residue. | Esylate 2 |
| 3-38 | MEK | SL at ST at 4° C. for 7 Days. White residue. | Esylate 2 |

[a]All slurries utilized~5 mg of Esylate 4 + Esylate 5 (1341-21-8) along with~10 mg each of Esylate 3 (1341-21-14, 16), Esylate 2 (1341-21-2, 3) and Esylate 1 (1341-3-1-1).
b. SL = slurry, ET = elevated temperature, IPA = isopropanol, MIBK = methyl isobutyl ketone, RT = room temperature, AE = acetone, EA = ethyl acetate, HEP = heptanes, EOH = ethanol, IPE = isopropyl ether, THF = tetrahydrofuran, ST = sub-ambient temperature, CLF = chloroform, H₂O = water, WA = water activity, SE = slow evaporation, MOH = methanol, ACN = acetonitrile, CL = cooling, DOX = dioxanes, MEK = methyl ethyl ketone, VD = vapor diffusion, MCH = Methyl cyclohexane, MTBE = Methyl tert-butyl ether, NME = Nitromethane, TOL = Toluene, IPAE = Isopropyl acetate, HFIPA = Hexafluoro isopropanol, DMF = Dimethylformamide, DCM = Dichloromethane Characterization of Linsitinib Esylate Salt Polymorphs Select samples were identified for further characterization for each of the five linsitinib esylate crystalline salt polymorphs. A summary of the results is presented below:

Esylate 2 Water Activity Test

Water activity slurries were set-up with Esylate 2 and seeds of Esylate 1 to explore the presence of a potential hydrate and any associated critical water activity (Table 12). Four slurries were set-up in varying ratios of THF and H2O corresponding to 0.45, 0.63, 0.78 and 0.91 aw respectively. All residues after 17 days of stirring at RT unanimously resulted in Esylate 2 (FIG. 7), revealing no hydrate exists under ambient conditions, and any critical water activity, if present, is above aw=0.91. The results confirm that Esylate 1 is metastable under these conditions and could suggest that Esylate 1 may not be hydrated and that the weight loss observed previously may be residual moisture rather than water incorporated within the lattice.

TABLE 12

Water Activity Slurry

| Sample No. | Solvent | Conditions[a] | PXRD Result |
|---|---|---|---|
| 3-39 | 97.6% THF in H₂O, a$_w$ = 0.45. | 50.0 mg Esylate 2 was SL in 1.00 mL solvent | Esylate 2 |
| 3-40 | 96.2% THF in H₂O, a$_w$ = 0.63. | 51.3 mg Esylate 2 was SL in 1.00 mL solvent | Esylate 2 |
| 3-41 | 94.7% THF in H₂O, a$_w$ = 0.78. | 102.5 Esylate 2 was SL in 1.00 mL solvent | Esylate 2 |
| 3-42 | 93.1% THF in H₂O, a$_w$ = 0.91. | 101.5 mg Esylate 2 was SL in 1.00 mL solvent | Esylate 2 |

[a]All slurries started with Esylate 2, were seeded with Esylate 1 and stirred for a total of 10 days at RT.

Esylate 2 Scale-Up, Relative Humidity Stress Test, and Mechanical Stress Test

A scale-up attempt for Esylate 2 was carried out towards the relative humidity stress test and the mechanical stress test. A long term 75% RH stress for 24 days at RT revealed no weight gain by TGA and no form change by PXRD analysis of the stressed sample (FIG. 10). Mechanical stress of Esylate 2 by neat grinding for 30 minutes resulted in a poorly crystalline Esylate 2 along with amorphous residue, suggesting excess mechanical stress is best avoided.

Figure 19:
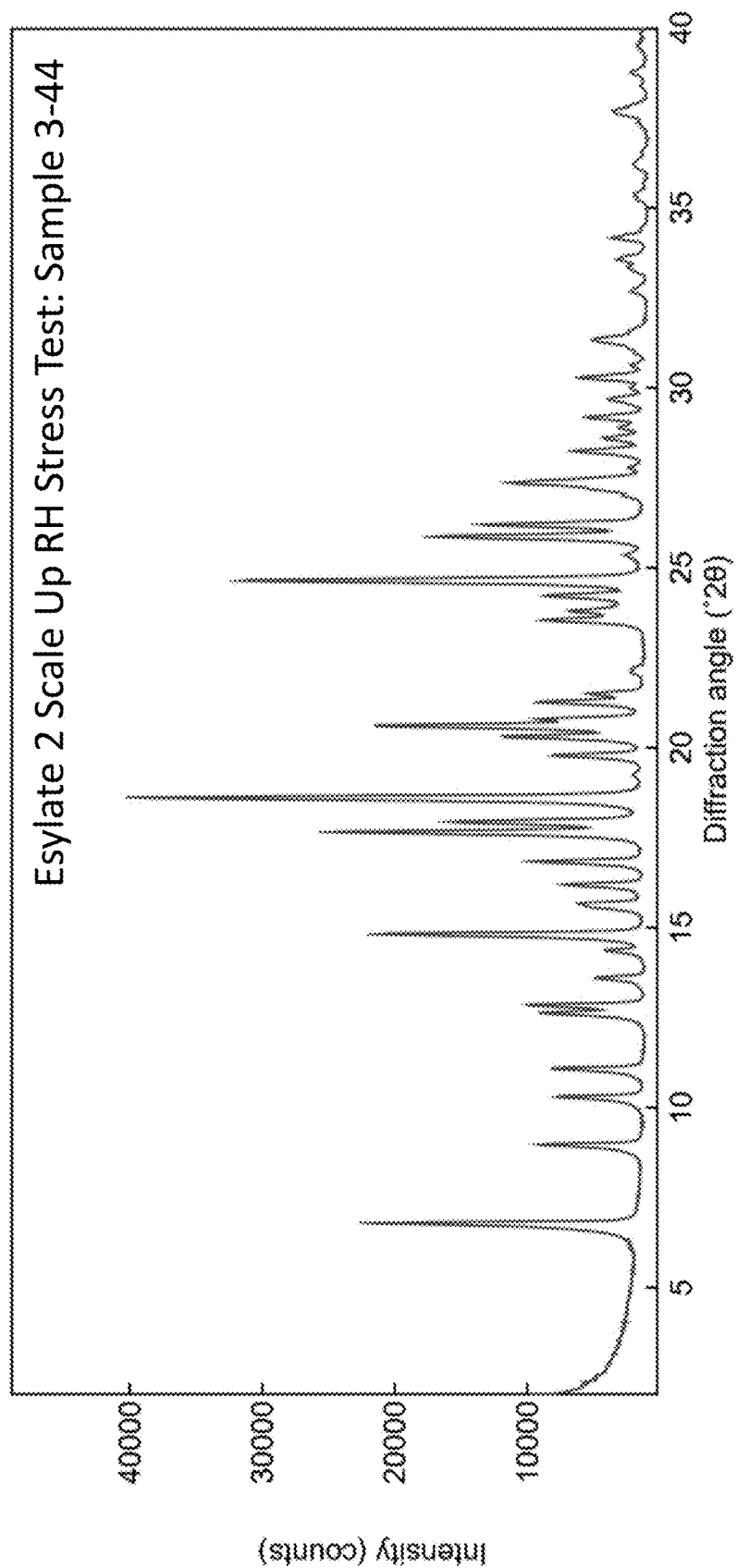
FIG. 19 shows the PXRD of Esylate 2 Scale Up after 24 Day 75% RH stress of Sample 3-43 at room temperature (Sample 3-44).
Figure 20:
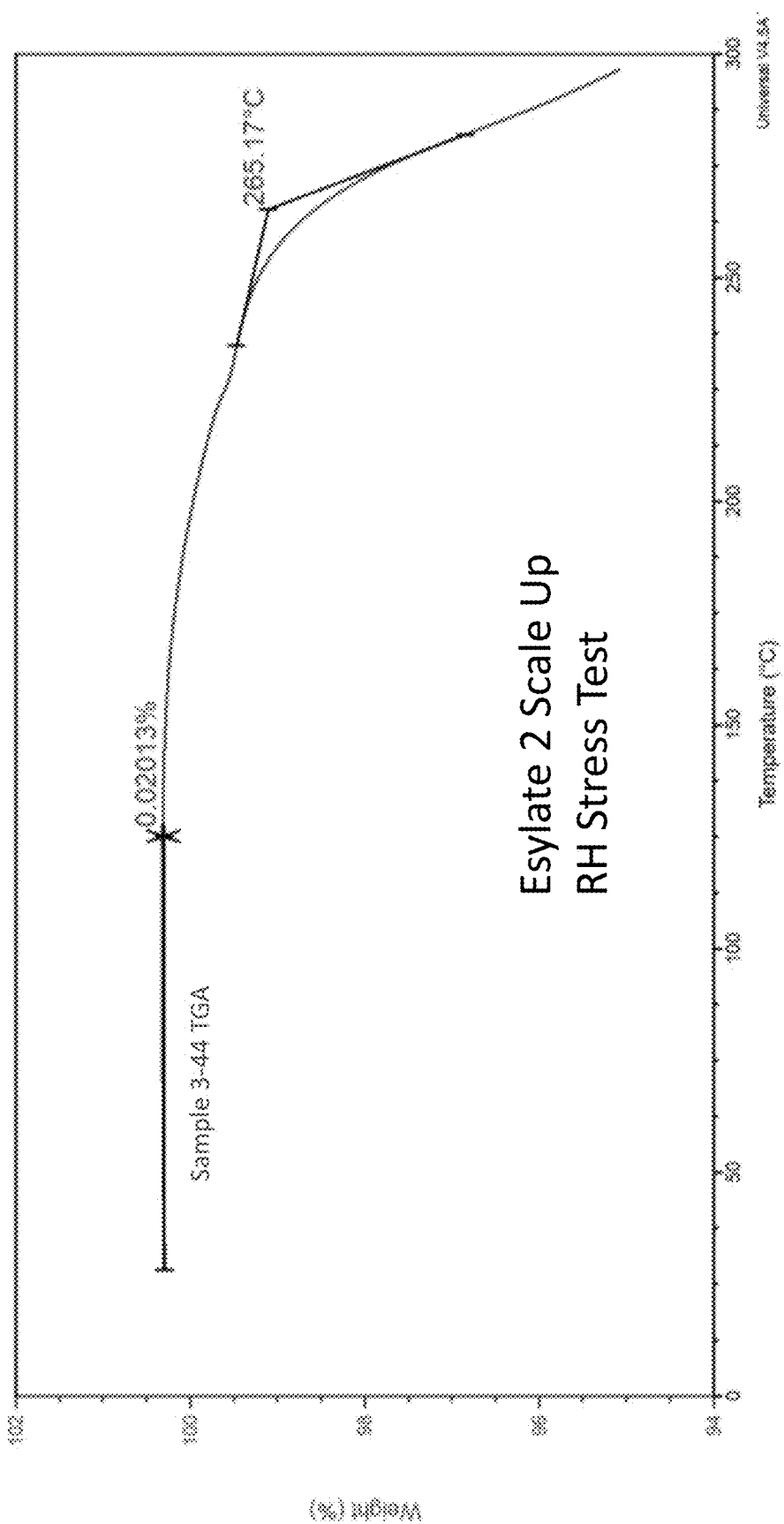
FIG. 20 shows the TGA thermogram of Esylate 2 Scale Up after 24 Day 75% RH stress of Sample 3-43 at room temperature (Sample 3-44).
Figure 21:
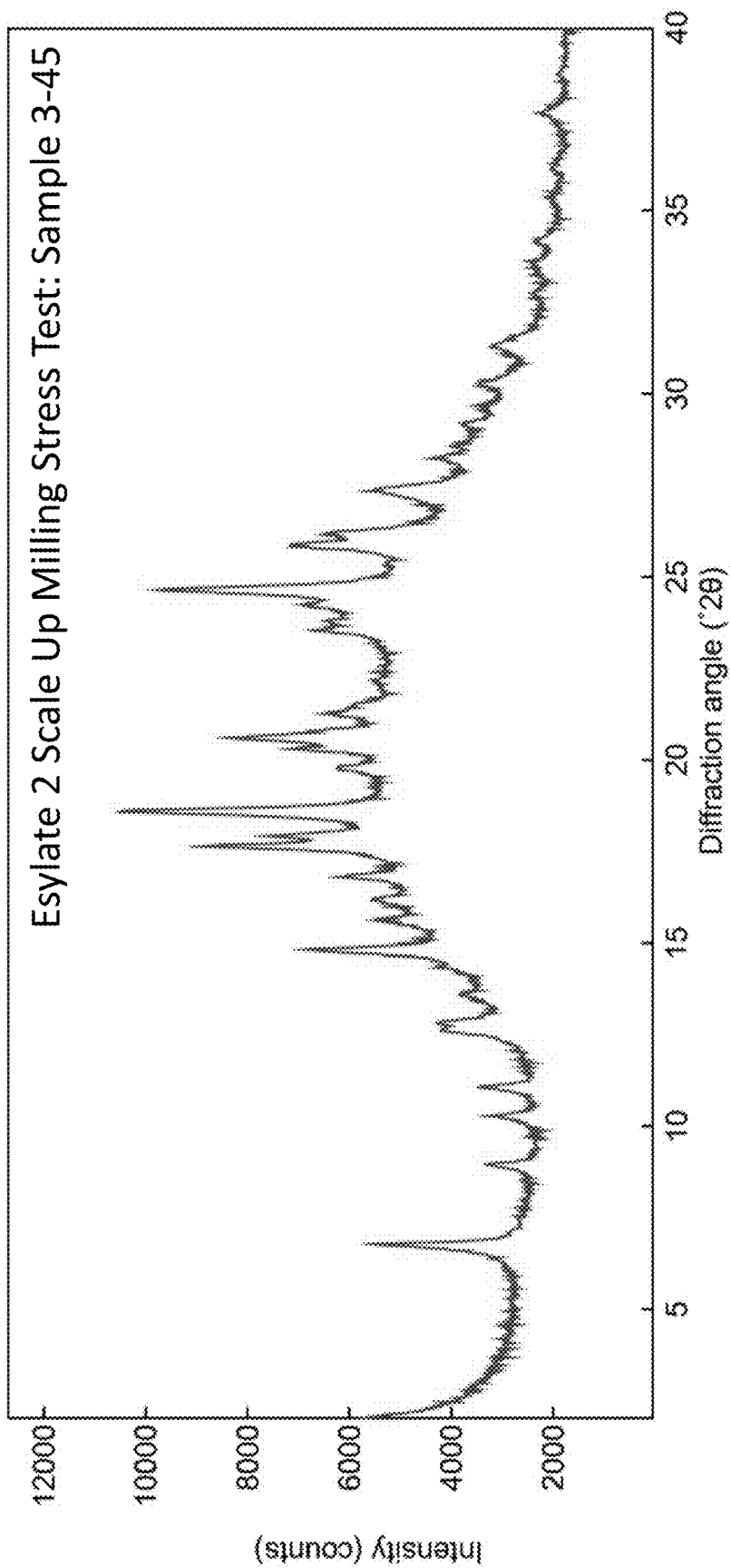
FIG. 21 shows the PXRD of Esylate 2 Scale Up after 30 minutes of milling at max power of Sample 3-43 (Sample 3-45).

| Sample No. | Experiment | Conditions | Analytical Technique | Result | FIG. No. |
|---|---|---|---|---|---|
| 3-43 | Scale up. RT SL. | ~1 g of Esylate 1 (1341-9-1-1) is suspended in 15 mL MEK at RT and SD w 1341-21-12. SL for 3 Days (Reaction complete in 1 Day) and filtered. Off-white residue. | PXRD | Esylate 2 | FIG. 16 |
| 3-44 | 75% RH stress | ~50 mg of Esylate 2 (1341-49-1) is transferred into a vial and placed uncapped into a vacuum oven and dried at 50° C. for 18 hours. | PXRD | Esylate 2 | FIG. 19 |
| 3-44 | 75% RH stress | ~50 mg of Esylate 2 (1341-49-1) is transferred into a vial and placed uncapped into a vacuum oven and dried at 50° C. for 18 hours. | TGA | No weight loss till 125° C. | FIG. 20 |
| 3-45 | Grinding | ~30 mg of Esylate 2 (1341-49-1) is milled neat at max power for 30 minutes. Orange powder. | PXRD | Esylate 2 (LC) + Amorphous | FIG. 21 |

Esylate 2 Characterization

Figure 8:
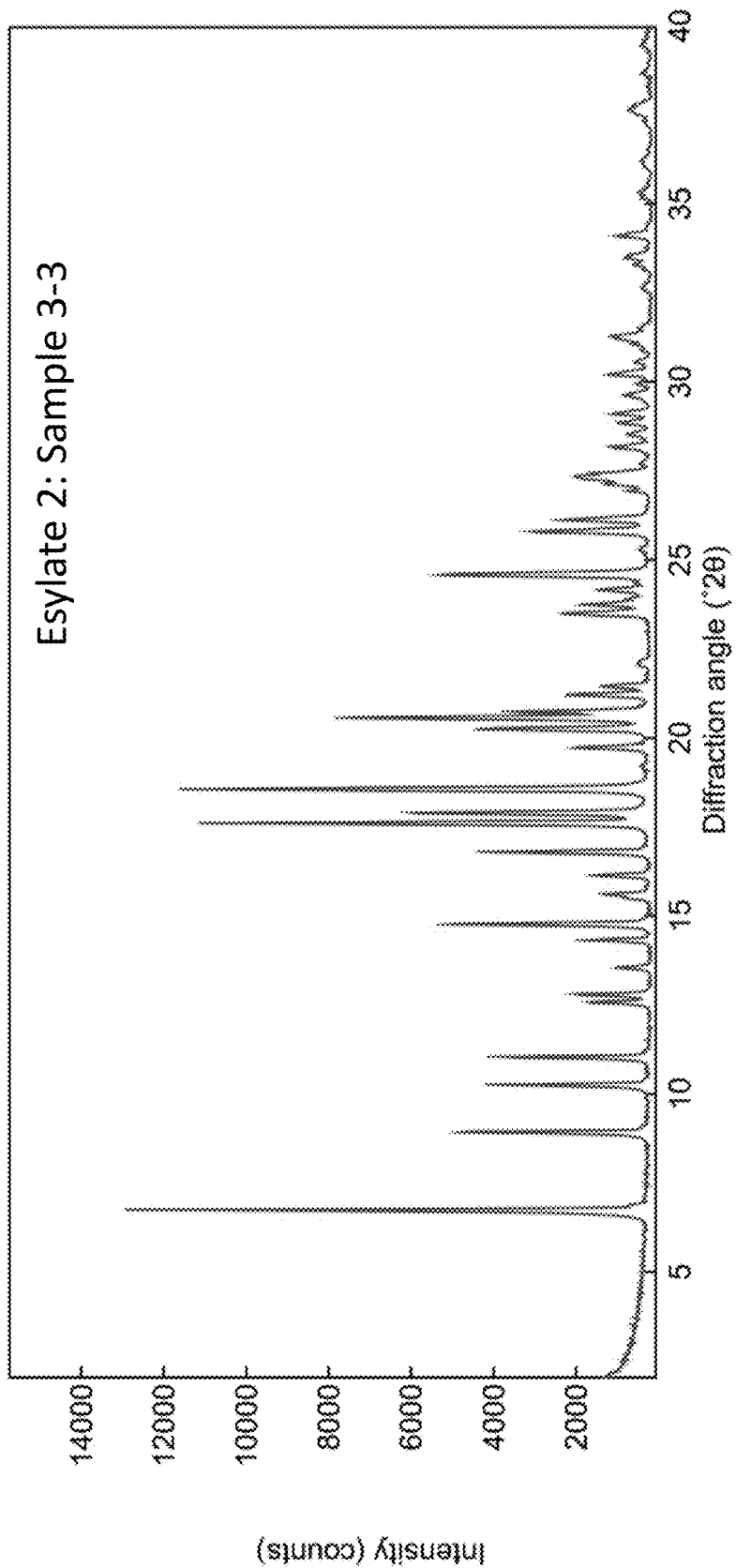
FIG. 8 shows the PXRD of Esylate 2 (Sample 3-3).
Figure 9:
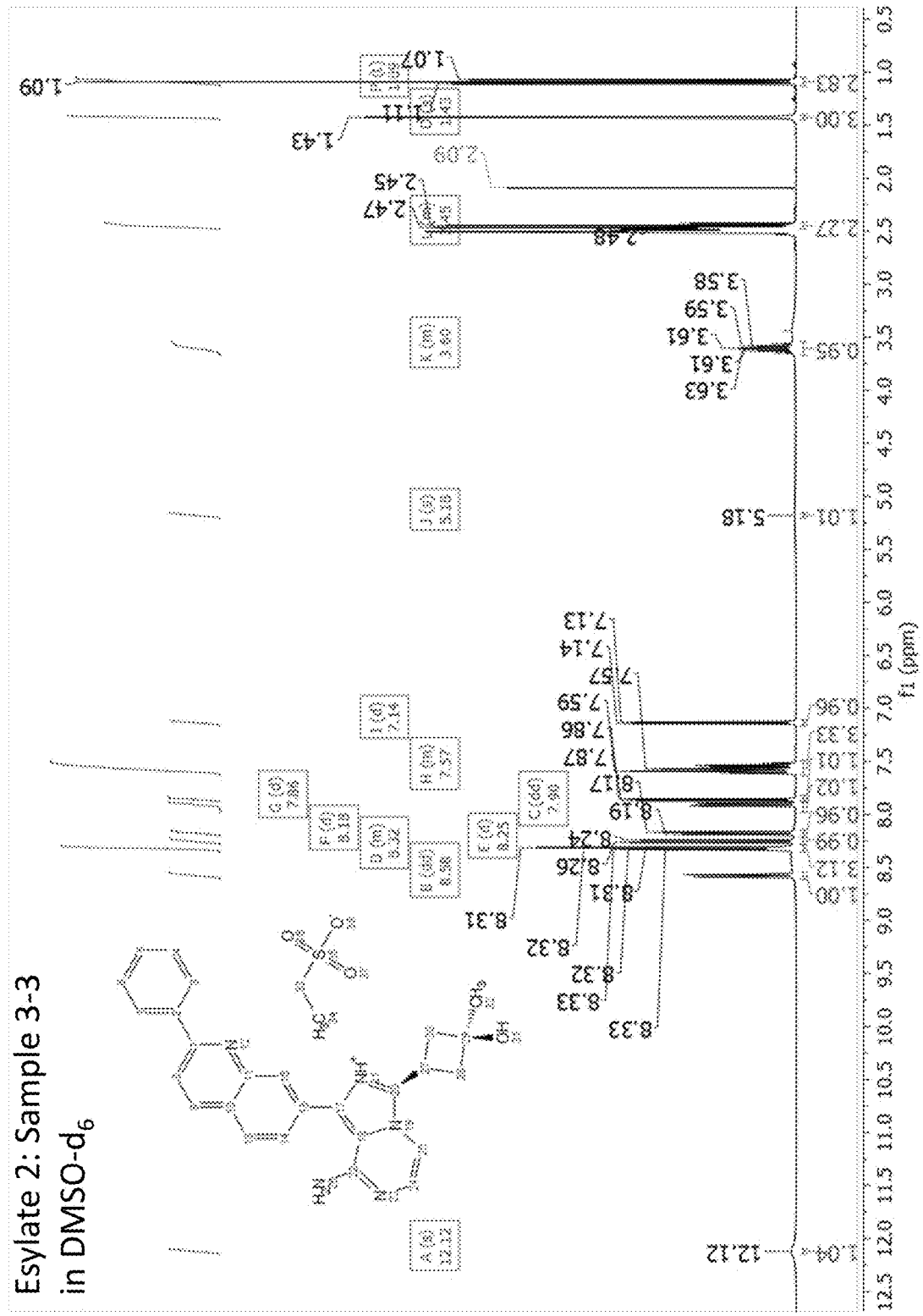
FIG. 9 shows the $^1$H NMR in DMSO-$d_6$ of Esylate 2 (Sample 3-3).

Esylate 2 appears to be a stable polymorph of the esylate salt of linsitinib. Esylate 2 was isolated from a wide range of techniques, solvents and temperatures, and a few samples were characterized further (Table 13). NMR analysis confirmed it to be a 1:1 linsitinib esylate salt. DSC analysis revealed a major endotherm at 225° C. potentially due to melting, while TGA analysis pointed towards an anhydrous/non-solvated form (FIG. 8). This was further supported by successful indexing of its PXRD pattern, whose calculated unit cell volume pointed to a 1:1 salt (Section 0). A single crystal grown by vapor diffusion of DCM into DMF was successfully characterized by SCXRD to be Esylate 2, which confirmed its anhydrous/non-solvated nature.2 DVS analysis revealed Esylate 2 to be slightly hygroscopic, with 1% weight gain and loss during the sorption and desorption cycles respectively, but no net weight change was observed after the analysis (FIG. 9). The majority of the water up-take (~0.8%) was observed above 85% RH, suggesting that exposure to very high RH should be avoided.

TABLE 13

Characterization of Esylate 2

Figure 17:
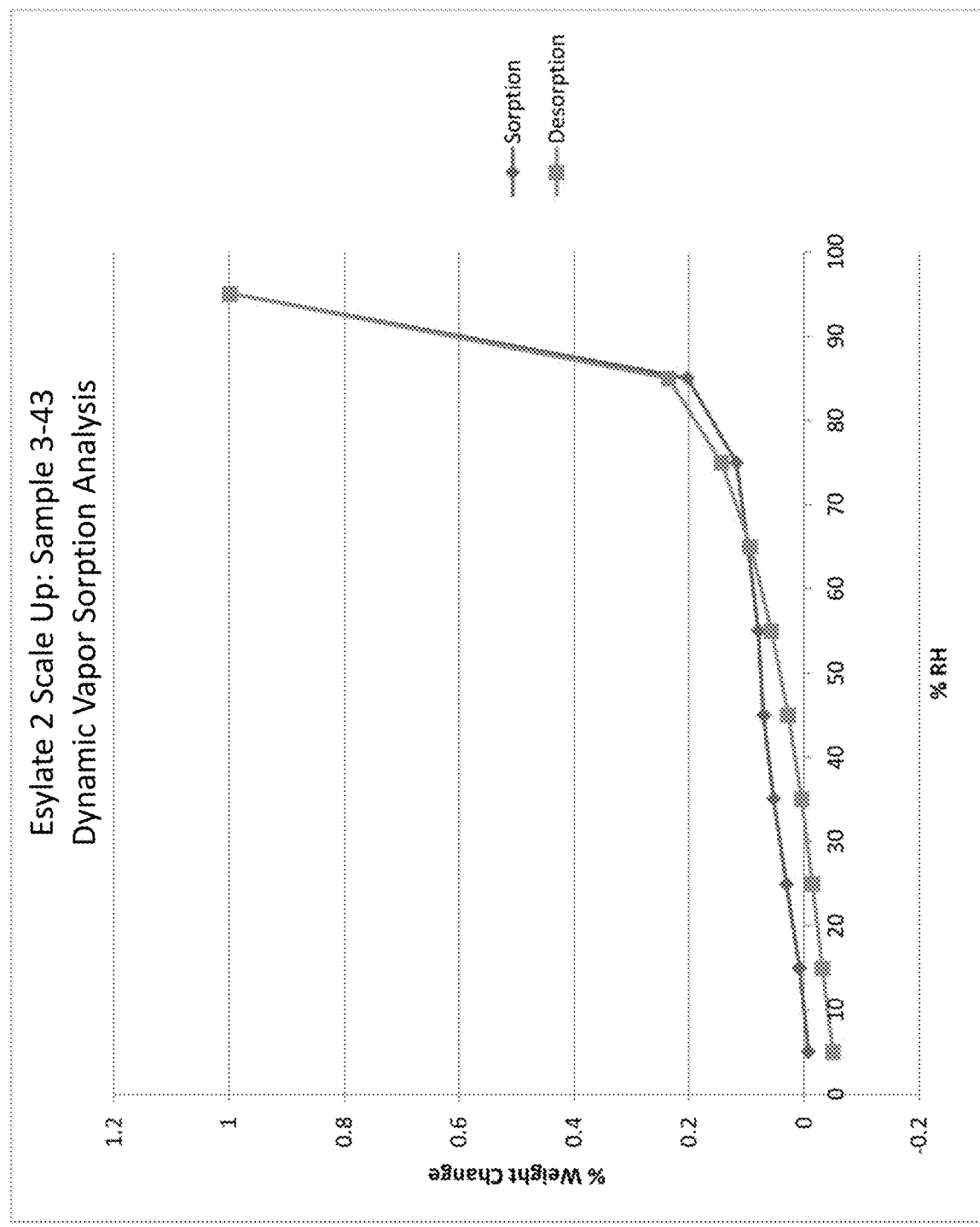
FIG. 17 shows the DVS thermogram of Esylate 2 Scale Up (Sample 3-43).

| Form (Sample) | Analytical Technique | Results | FIG. |
|---|---|---|---|
| Esylate 2 (Sample No. 3-3) | NMR | Consistent with a 1:1 salt | FIG. 9 |
| | DSC | Major endotherm at 230° C. | FIG. 10 |
| | TGA | No weight loss before major endotherm | FIG. 10 |
| | Indexing | Suggests an unsolvated 1:1 salt | |
| Esylate 2 | DVS | Sorption: | FIG. 17 |

TABLE 13-continued

Characterization of Esylate 2

| Form (Sample) | Analytical Technique | Results | FIG. |
|---|---|---|---|
| (Scale Up Sample No. 3-43) | | 5-95% RH: Total 33.1% weight gain<br>35-75% RH: 12.0% weight gain<br>75-95% RH: 16.9% weight gain<br>Desorption:<br>95-5% RH: Total 33.1% weight loss | |

TABLE 13-continued

Characterization of Esylate 2

| Form (Sample) | Analytical Technique | Results | FIG. |
|---|---|---|---|
| | | 95-75% RH: 14.2% weight loss<br>75-35% RH: 12.3% weight loss<br>Net weight change:<br>−0.04% weight loss | |
| | TGA | No weight loss before onset of decomposition | FIG. 18 |

Esylate 2 Solubility

A second scale-up attempt for Esylate 2 was carried out towards the solubility study. Linsitinib was slurried with 1 Eq Ethanesulfonic acid at RT in ethanol for 3 days with seeding. PXRD analysis of the product after drying revealed successful synthesis of Esylate 2 with a 94% yield at 4-gram scale. The results of the solubility study are presented in Example 16.

Esylate 2 Single Crystal Structure

The crystal structure of linsitinib esylate Form 2 (Esylate 2) was solved (FIG. 1) according to the following procedures. The structure was confirmed to be anhydrous/unsolvated. The compound crystallized in a chiral space group; however, the cation contains a molecular mirror plane such that no chiral centers were observed.

Linsitinib free base was used to prepare linsitinib esylate Form 1. 50.1 mg of linsitinib esylate Form 1 was dissolved in 0.25 mL of DMF. The resulting solution was filtered using a 0.2 µm PTFE syringe filter into a new clean vial. The vial was placed uncapped in a larger vial containing dichloromethane. The larger vial was capped and held at room temperature to allow vapor diffusion to occur. The experiment produced clear plates of sufficient size and quality for single crystal analysis.

A colorless plate shaped crystal with formula $C_{26}H_{24}N_5O \cdot C_2H_5O_3S$ having approximate dimensions of 0.05×0.20×0.41 mm was mounted on a Mitegen micromesh mount in a random orientation. Data were collected from a shock-cooled single crystal at 150(2) K on a Bruker AXS D8 Quest four circle diffractometer with an I-mu-S microsource X-ray tube using a laterally graded multilayer (Goebel) mirror as monochromator and a PhotonIII_C14 charge-integrating and photon counting pixel array detector. The diffractometer used CuKα radiation (λ=1.54178 Å). All data were integrated with SAINT V8.40B and a multi-scan absorption correction using SADABS 2016/2 was applied. The structure was solved by dual methods with SHELXT and refined by full-matrix least-squares methods against $F^2$ using SHELXL-2018/3. All non-hydrogen atoms were refined with anisotropic displacement parameters. Carbon bound hydrogen atoms were refined isotropically on calculated positions using a riding model. Methyl $CH_3$ were allowed to rotate but not to tip to best fit the experimental electron density. Positions of amine and alcohol H atoms and water H atoms were refined isotropically. $U_{iso}$ values were constrained to 1.5 times the $U_{eq}$ of their pivot atoms for methyl and hydroxyl groups and 1.2 times for all other hydrogen atoms.

The Flack X parameter was determined using 1989 quotients [(I+)−(I−)]/[(I+)+(I−)] using Parson's method and refined to 0.003(7). No chiral centers are present in the anion and cation (the cation possesses a molecular mirror plane).

Crystal data and structure refinement data is summarized in Table 14.

TABLE 14

Crystal data and structure refinement of linsitinib esylate Form 2

| | |
|---|---|
| Empirical formula | $C_{28}H_{29}N_5O_4S$ |
| Moiety formula | $C_{26}H_{24}N_5O \cdot C_2H_5O_3S$ |
| Formula weight | 531.62 |
| Temperature [K] | 150(2) |
| Crystal system | orthorhombic |
| Space group (number) | $P2_12_12_1$ (19) |
| a [Å] | 7.4100(8) |
| b [Å] | 17.4900(17) |
| c [Å] | 19.769(2) |
| α [°] | 90 |
| β [°] | 90 |
| γ [°] | 90 |
| Volume [Å$^3$] | 2562.0(5) |
| Z | 4 |
| $\rho_{calc}$ [gcm$^{-3}$] | 1.378 |
| µ [mm$^{-1}$] | 1.497 |
| F (000) | 1120 |
| Crystal size [mm$^3$] | 0.050 × 0.200 × 0.410 |
| Crystal color | colorless |
| Crystal shape | plate |
| Radiation | CuKα (λ = 1.54178 Å) |
| 2θ range [°] | 6.75 to 161.42 (0.78 Å) |
| Index ranges | −6 ≤ h ≤ 9 |
| | −22 ≤ k ≤ 21 |
| | −25 ≤ l ≤ 22 |
| Reflections collected | 17917 |
| Independent reflections | 5353 |
| | $R_{int}$ = 0.0434 |
| | $R_{sigma}$ = 0.0469 |

TABLE 14-continued

Crystal data and structure refinement of linsitinib esylate Form 2

| | |
|---|---|
| Completeness to θ = 67.679° | 99.9% |
| Data/Restraints/Parameters | 5353/0/357 |
| Goodness-of-fit on F2 | 1.111 |
| Final R indexes [I ≥ 2σ(I)] | $R_1$ = 0.0352 |
| | $wR_2$ = 0.0934 |
| Final R indexes [all data] | $R_1$ = 0.0377 |
| | $wR_2$ = 0.0954 |
| Largest peak/hole [eÅ$^{-3}$] | 0.23/−0.39 |
| Flack X parameter | 0.003(7) |

An XRPD pattern calculated from the single-crystal data is overlaid with the reference XRPD pattern of linsitinib Esylate 2. The patterns overlay well, indicating that they represent the same crystalline phase. The observed peak shifting is due to the temperature difference at which the single crystal and X-ray powder diffraction data were collected.

Esylate 3 Characterization

Figure 16:
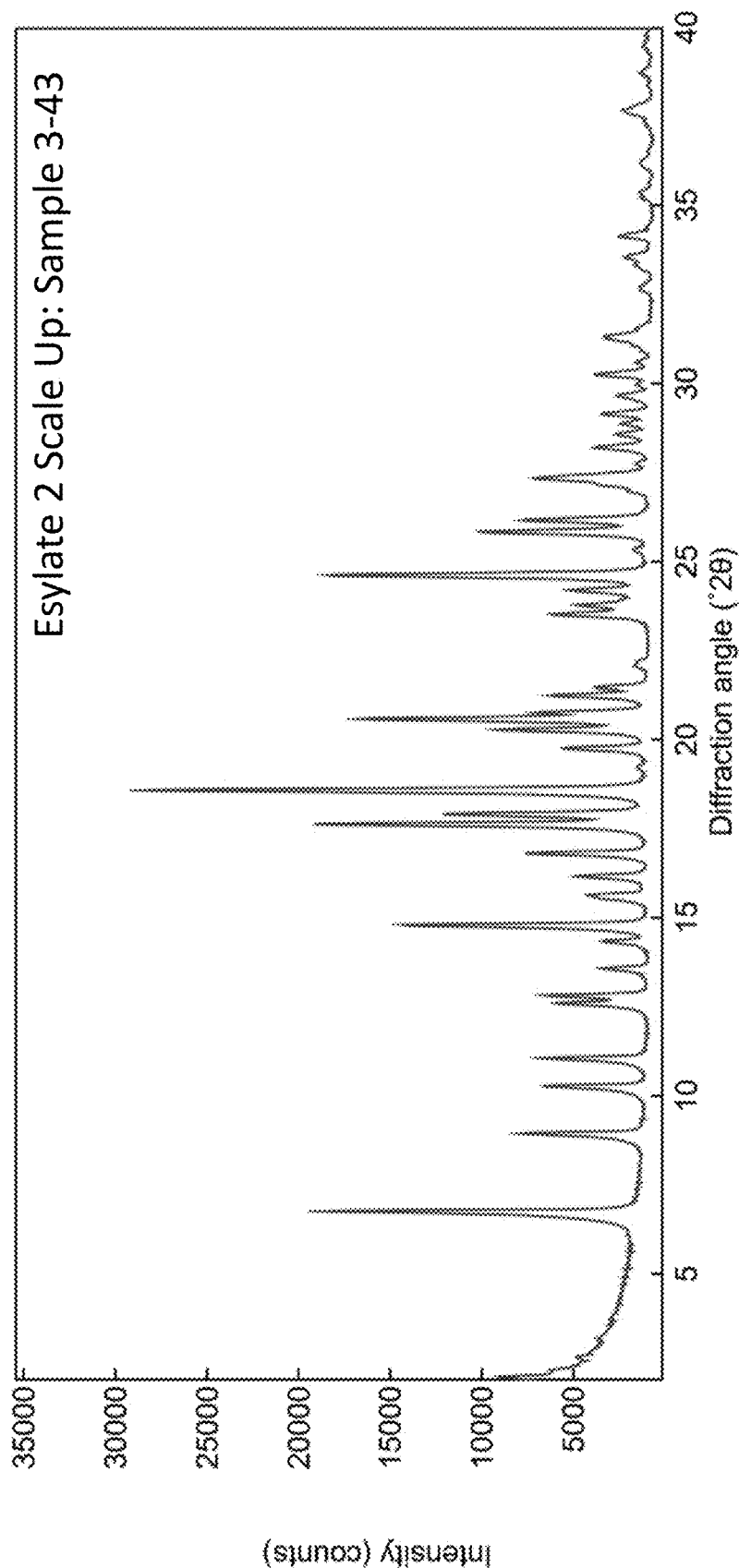
FIG. 16 shows the PXRD of Esylate 2 Scale Up (Sample 3-43).

Esylate 3 was isolated primarily from experiments containing alcohols, in addition to a cooling attempt from dioxane which also resulted in Esylate 3. Esylate 3 was characterized using multiple techniques (Table 15). NMR analysis on this form revealed a 1:1 linsitinib esylate salt. DSC analysis revealed a major broad possible melt endotherm at 194° C. (FIG. 16). This was coupled with a minor endotherm at 231° C., which is similar to that observed in Esylate 2, suggesting it could originate from a trace amount of Esylate 2 either present originally or that crystallized after potential melt of Esylate 3. TGA analysis revealed no weight loss prior to the major endotherm, suggesting an anhydrous/non-solvated form. This was further con-firmed by successful indexing of its PXRD pattern (Section 0), which calculated a unit cell volume that could accommodate a 1:1 salt. This unit cell volume was also slightly larger than that for Esylate 2, indicating it is less dense suggesting it may be metastable to Esylate 2.

TABLE 15

Characterization of Esylate 3

Figure 23:
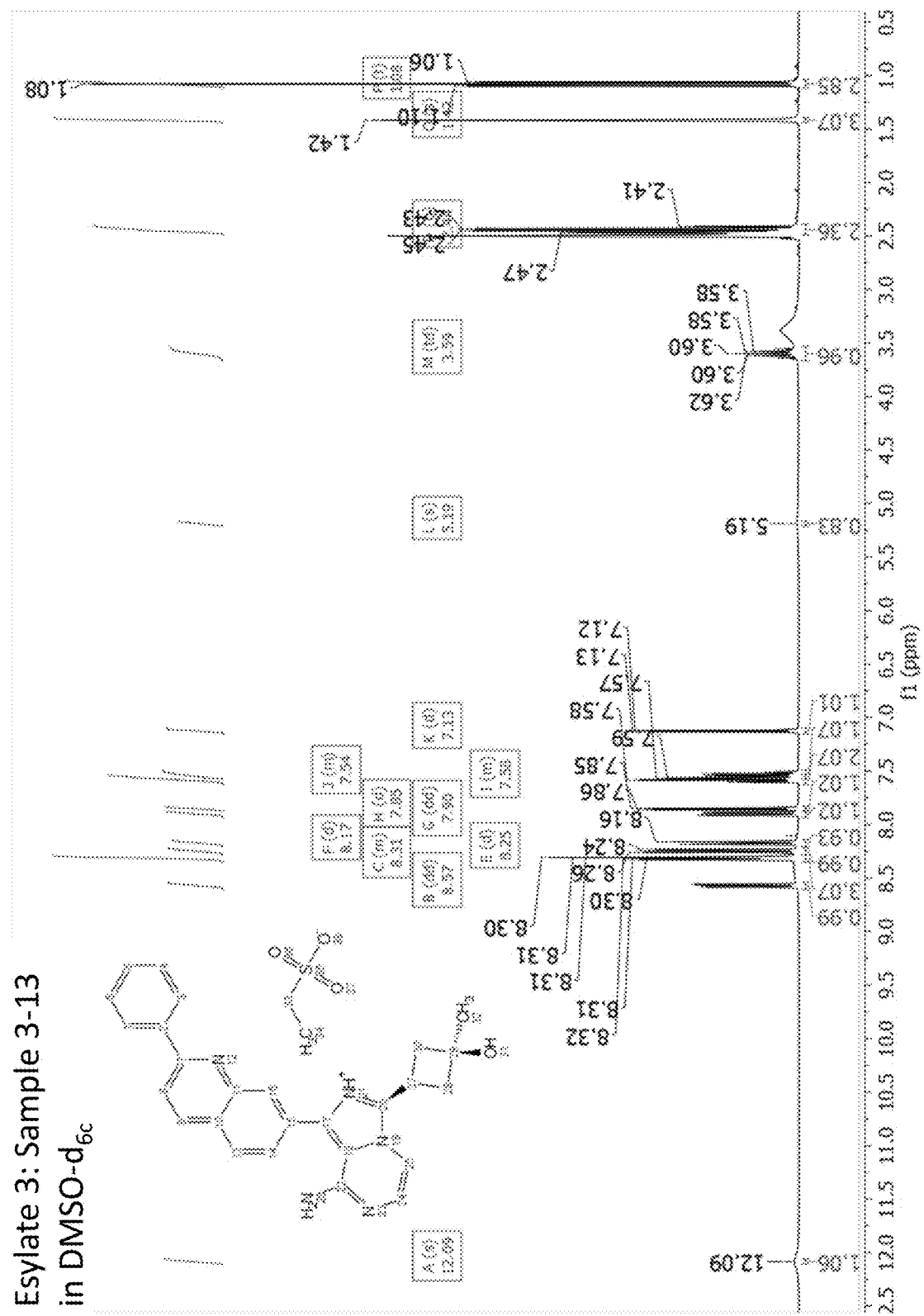
FIG. 23 shows the $^1$H NMR in DMSO-$d_6$ of Esylate 3 (Sample 3-13).

| Form (Sample) | Analytical Technique | Results | FIG. |
|---|---|---|---|
| Esylate 3 (Sample No. 3-13) | NMR | Consistent with a 1:1 salt | FIG. 23 |
| | DSC | Major broad endotherm at 194° C., minor endotherm at 231° C. | FIG. 24 |
| | TGA | No weight loss before major and minor endotherm | FIG. 24 |
| | Indexing | Suggests an unsolvated 1:1 salt | |

Esylate 4 Characterization

Esylate 4 was obtained from salt formation experiments using 1 Eq ESA at RT and ST in IPA and was further characterized using multiple techniques (Table 16). NMR analysis revealed it to be a 1:1 linsitinib esylate salt with 0.6 moles of IPA present. TGA analysis revealed a 2.7% weight loss by 73° C., probably originating from surface solvent or moisture. An additional 5.7% weight loss was observed upon further heating till 125° C., which corresponds to ~0.6 moles of IPA, suggesting that Esylate 4 is an IPA solvate. A drying study on an Esylate 4 sample by heating it to 60° C. under vacuum for 18 hours revealed a form change into Esylate 5 (Table 17).

Esylate 4 and 5 were obtained from several other slurries (FIG. 4) in different solvent systems. This suggests that Esylate 4 is capable of forming a solvate with different crystallization solvents, suggesting that it is an isostructural solvate system, which may be capable of de-solvating into Esylate 5. Esylate 4 was not obtained from any of the interconversion slurries, indicating it is metastable under the conditions investigated. (Table 18).

TABLE 16

Characterization of Esylate 4

Figure 26:
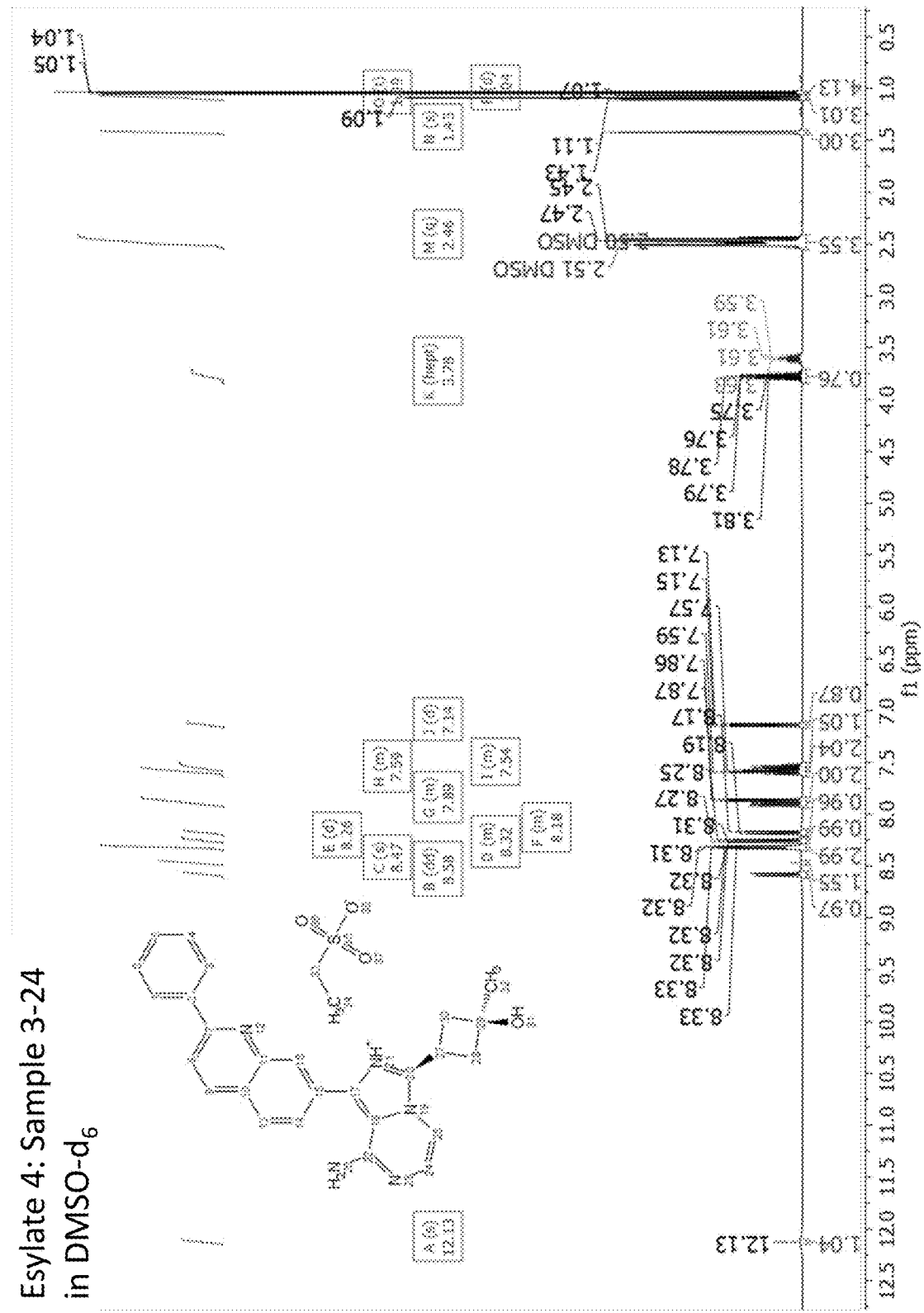
FIG. 26 shows the $^1$H NMR in DMSO-$d_6$DMSO-$d_6$ of Esylate 4 (Sample 3-24).

| Form (Sample) | Analytical Technique | Results | FIG. |
|---|---|---|---|
| Esylate 4 (Sample No. 3-24) | NMR | Consistent with a 1:1 salt, with~0.6 moles IPA present | FIG. 26 |
| | DSC | Major broad endotherm starting at 153° C., followed by two minor endotherms with peaks at 209° C. & 230° C. | FIG. 27 |
| | TGA | 2.7% weight loss by 73° C., additional 5.7% weight loss (~0.6 moles IPA) by 125° C. Onset of decomposition at 265° C. | FIG. 27 |

TABLE 17

Physical stability testing of Esylate 4

Figure 28:
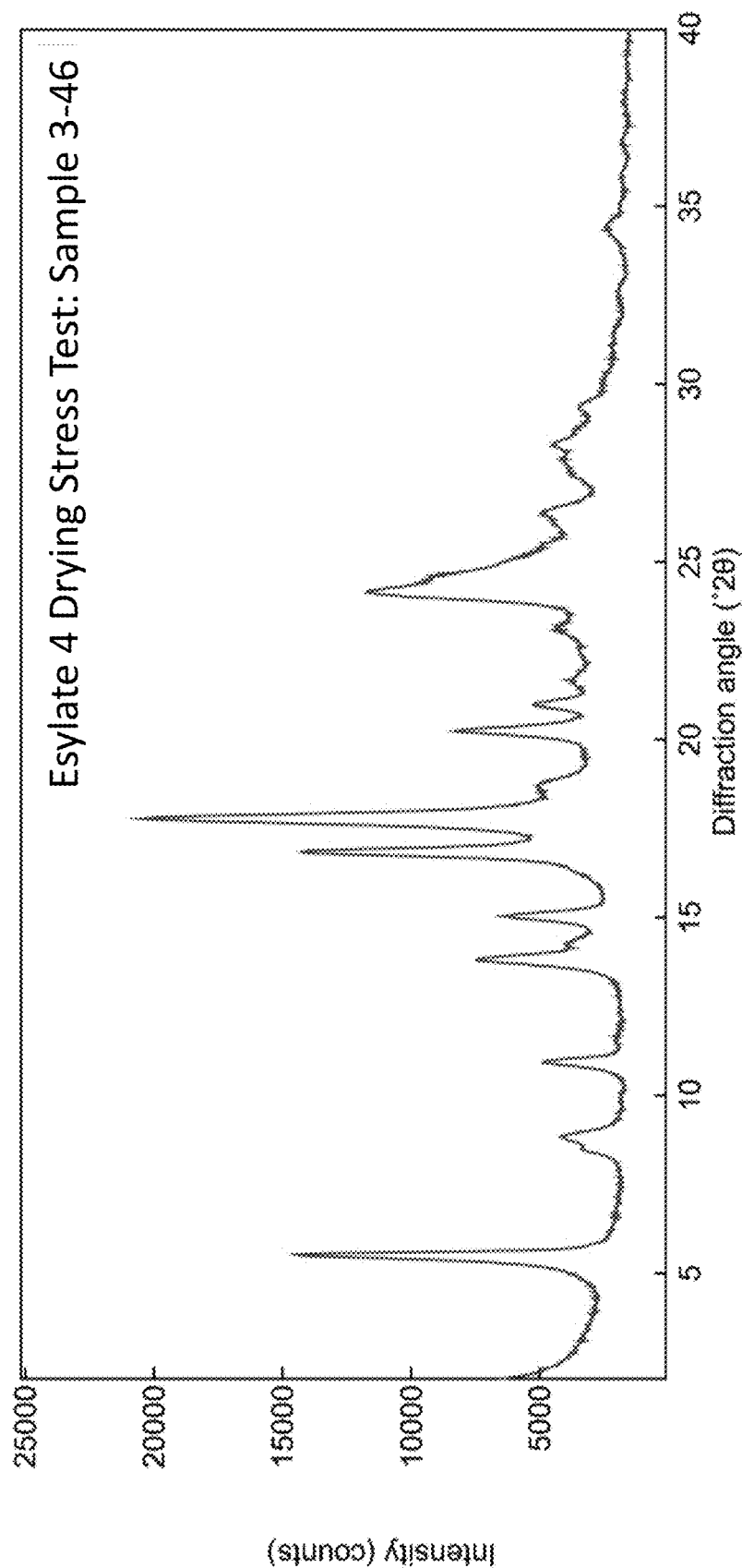
FIG. 28 shows the PXRD or Sample 3-26 after being uncapped and placed into vacuum oven and dried at 60° C. for 18 hours. (Sample 3-46).

| Experiment | Conditions | Sample No. | Analytical technique | Result | FIG. No. |
|---|---|---|---|---|---|
| ET Vacuum drying | Sample 3-26 is uncapped and placed into vacuum oven and dried at 60° C. for 18 hours. | 3-46 | PXRD | Esylate 5 | FIG. 28 |

Esylate 5 Characterization

Figure 4:
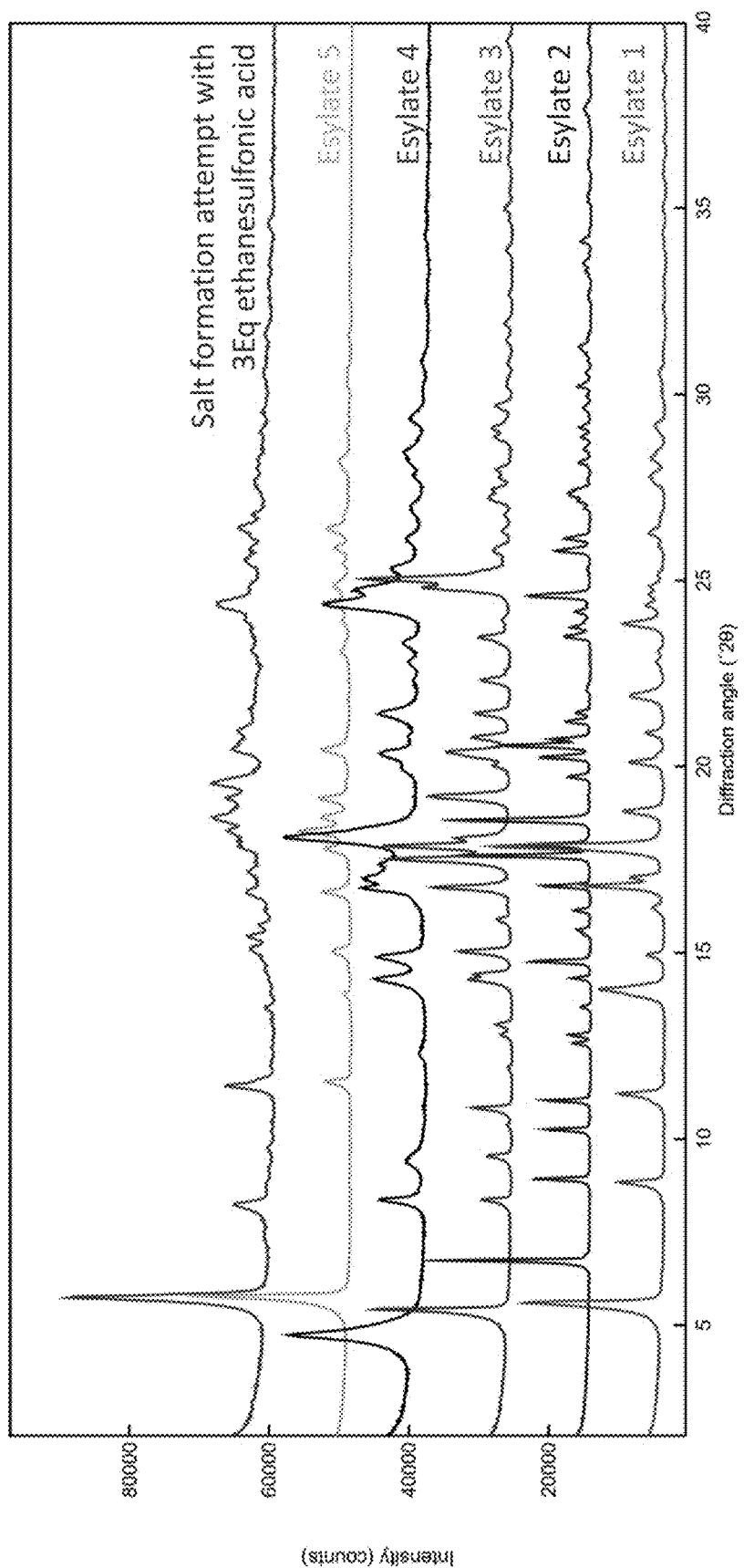
FIG. 4 shows the PXRD of Esylates 1-5.

Esylate 5 was initially only obtained in-tandem with Esylate 4 from slurries in several different solvent systems (FIG. 4). Vacuum drying a sample of Esylate 4 at 60° C. for 18 hours resulted in a form change to Esylate 5. Thermal analysis revealed a rapid 3.3% weight loss by 75° C. by TGA, coupled with a major broad endotherm with a peak at 84° C. by DSC. Due to the fact that the sample had been generated via drying at elevated temperature, the weight loss observed upon heating is likely due to surface or channel water absorbed during exposure to ambient conditions. The high temperature (>80° C.) weight loss previously observed for the Esylate 4 solvate was not observed this time, suggesting that Esylate 5 is a de-solvated solvate of Esylate 4. Esylate 5 was not obtained from any of the interconversion slurries, indicating it is metastable under the conditions investigated (Table 18).

TABLE 18

Characterization of Esylate 5

| Sample | Analytical Technique | Results | FIG. No. |
|---|---|---|---|
| Esylate 5 (Sample 47, Vacuum drying Esylate 4 at 60° C. for 18 hours) | DSC | Major broad endotherm with peak at 84° C., followed by a minor endotherm with peak at 146° C., and endotherms at 153° C. and 194° C. | FIG. 29 |
| Esylate 5 (Sample 47, Vacuum drying Esylate 4 at 60° C. for 18 hours) | TGA | 3.2% weight loss by 75° C. Onset of decomposition at 253° C. | FIG. 29 |

Di-Esylate 1 Characterization

Di-Esylate f was obtained from a salt formation attempt between linsitinib and 2 Eq ESA at RT in IPA. NMR analysis revealed it to be a 1:2 linsitinib Di-esylate salt, along with trace amounts of IPA. DSC analysis revealed a broad minor endotherm with a peak at 74° C. coupled with a 1.2% weight loss by 75° C. in its TGA spectrum, possibly from evaporation of surface solvent. Upon additional heating, a continuous minor weight loss was observed. The DSC also showed a shoulder peak at 197° C. and a major endotherm associated with a potential melt at 219° C. A similar salt formation attempt, this time using 3 Eq ESA also resulted in Di-Esylate 1, with several additional peaks (1341-49-2, Table 19, FIG. 5, red pattern).

TABLE 19

Characterization of Di-Esylate 1

| Sample | Analytical Technique | Results | FIG. No. |
|---|---|---|---|
| Di-Esylate 1 (Sample 3-48, RT SL | DSC | Minor very broad endotherm with a peak at 74° C., followed by a shoulder peak at 197° C. and a major | FIG. 32 |

TABLE 19-continued

Characterization of Di-Esylate 1

Figure 31:
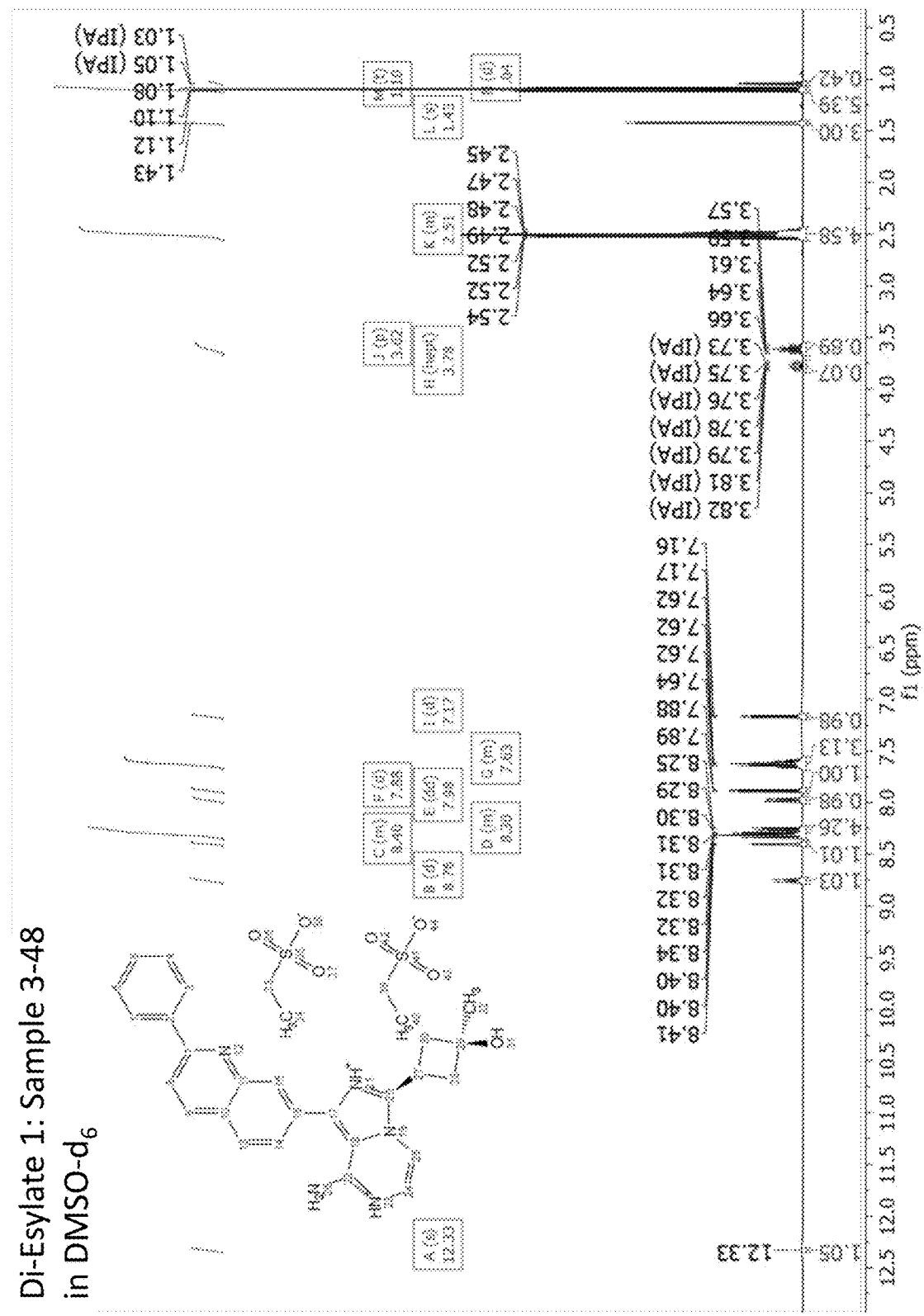
FIG. 31 shows the $^1$H NMR in DMSO-$d_6$ of Esylate 5 (Sample 3-24).

| Sample | Analytical Technique | Results | FIG. No. |
|---|---|---|---|
| in IPA, 2 Eq ESA) | | endotherm at 219° C. | |
| Di-Esylate 1 (1341-43-2, RT SL in IPA, 2 Eq ESA) | TGA | 1.2% weight loss by 75° C., additional 0.5% weight loss by 200° C. Onset of de-composition at 227° C. | FIG. 32 |
| Di-Esylate 1 (1341-43-2, RT SL in IPA, 2 Eq ESA) | Indexing | Suggests an unsolvated 1:2 linsitinib ethanesulfonic acid salt, with additional peaks | |
| 1341-47-2 (1341-43-2 dis-solved in DMSO-$d_6$) | NMR | Consistent with 1:2 linsitinib ethanesulfonic acid salt. Trace (0.07 moles) IPA present. | FIG. 31 |

Example 5: Crystalline Salt Forms of Linsintinib L-Malate

L-Malate 1

An equimolar slurry of L-malic acid and linsitinib in acetonitrile at room temperature produced a unique phase that was designated as L-Malate 1. Specifically, 24.8 mg of linsitinib was combined with 7.9 mg of L-malic acid and 0.5 mL of acetonitrile. The sample was allowed to stir overnight at room temperature producing a thick white paste. 0.5 mL of additional isopropanol was added to the sample to produce a mobile suspension. The suspension was left to stir an additional 6 days producing a white slurry. White solids were produced upon filtration and overnight drying at ambient conditions.

Figure 35:
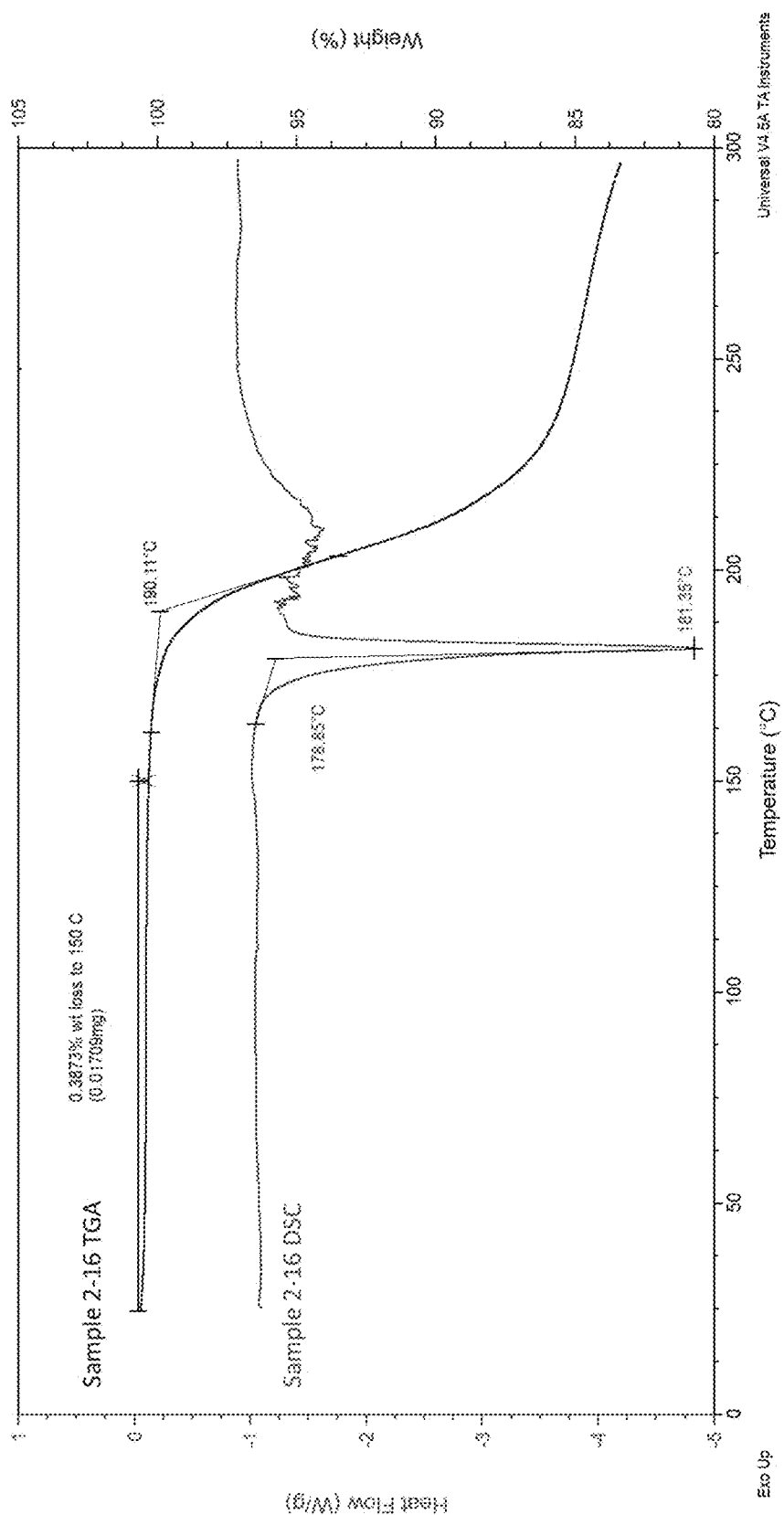
FIG. 35 shows the DSC thermogram of L-Malate 1 (Sample 2-16) and the TGA thermogram of L-Malate 1 (Sample 2-16).

The sample was analyzed by $^1$H NMR spectroscopy and the spectrum was consistent with a 1:1 malic acid:linsitinib salt with residual acetonitrile present. Thermal analysis of the sample was consistent with an anhydrous/unsolvated form with an apparent melting point of 179° C. (FIG. 35).

In a scale up of L-Malate, L-malic acid (1 equiv.) was added to suspended linsitinib free base (2.0 g) in ACN (37 mL) at RT, resulting in a thick suspension. Additional solvent was added, preparing a slurry at RT for 5 days. Solids were isolated via VF and dried under vacuum at RT for 2 days. The sample was analyzed by PXRD, having the diffraction pattern as presented in FIG. 33. The representative peak positions and intensity for L-Malate 1 from the scale up sample is provided in Table 20, below.

TABLE 20

Representative L-Malate 1 PXRD Peaks

| 2θ Position | d-value | Height | Relative |
|---|---|---|---|
| 5.42 | 16.30 | 10912 | 79.61 |
| 8.68 | 10.19 | 10439 | 76.16 |
| 9.10 | 9.72 | 1431 | 10.44 |
| 10.22 | 8.66 | 1605 | 11.71 |
| 10.84 | 8.16 | 1590 | 11.60 |
| 11.88 | 7.45 | 4121 | 30.06 |
| 12.40 | 7.14 | 3275 | 23.89 |
| 12.58 | 7.04 | 2507 | 18.29 |
| 13.30 | 6.66 | 2445 | 17.84 |
| 13.44 | 6.59 | 2539 | 18.52 |
| 13.86 | 6.39 | 1226 | 8.94 |
| 14.76 | 6.00 | 1175 | 8.57 |
| 16.24 | 5.46 | 5449 | 39.75 |
| 17.36 | 5.11 | 3298 | 24.06 |
| 17.60 | 5.04 | 2750 | 20.06 |
| 17.96 | 4.94 | 6121 | 44.66 |
| 18.22 | 4.87 | 13707 | 100.00 |
| 19.20 | 4.62 | 2830 | 20.65 |
| 20.32 | 4.37 | 2607 | 19.02 |
| 20.88 | 4.25 | 5379 | 39.24 |
| 21.72 | 4.09 | 2646 | 19.30 |
| 22.08 | 4.03 | 6866 | 50.09 |
| 22.58 | 3.94 | 3888 | 28.37 |
| 22.90 | 3.88 | 3141 | 22.92 |
| 23.06 | 3.86 | 2521 | 18.39 |
| 23.86 | 3.73 | 3206 | 23.39 |
| 24.44 | 3.64 | 7705 | 56.21 |
| 24.92 | 3.57 | 9289 | 67.77 |
| 25.66 | 3.47 | 4888 | 35.66 |
| 26.10 | 3.41 | 3612 | 26.35 |
| 26.66 | 3.34 | 2012 | 14.68 |
| 27.38 | 3.26 | 1782 | 13.00 |
| 27.90 | 3.20 | 1568 | 11.44 |
| 28.58 | 3.12 | 4362 | 31.82 |
| 29.44 | 3.03 | 3617 | 26.39 |
| 30.44 | 2.94 | 1287 | 9.39 |
| 31.52 | 2.84 | 1517 | 11.07 |
| 32.46 | 2.76 | 1358 | 9.91 |
| 33.20 | 2.70 | 975 | 7.11 |
| 33.54 | 2.67 | 999 | 7.29 |
| 34.34 | 2.61 | 1075 | 7.84 |
| 35.04 | 2.56 | 1607 | 11.72 |
| 35.48 | 2.53 | 1201 | 8.76 |
| 36.10 | 2.49 | 1034 | 7.54 |
| 36.86 | 2.44 | 939 | 6.85 |
| 37.24 | 2.41 | 1017 | 7.42 |
| 37.74 | 2.38 | 1619 | 11.81 |
| 38.44 | 2.34 | 1217 | 8.88 |
| 39.36 | 2.29 | 841 | 6.14 |

Polymorph Screen of L-malate Salts

A polymorph screen of linsitinib malate was conducted. Experiments were designed to target thermodynamically stable forms and therefore utilized techniques such as long-term slurry, cooling, anti-solvent addition, and evaporation. Reaction crystallization experiments with linsitinib free base and L-malic acid were also conducted. Additionally, non-crystalline material was used as an alternative starting material as this can provide access to polymorphs that would not be accessible from crystalline starting material.

TABLE 21

Polymorph Screen of Linsitinib Malate

| Method | Sample No. | Solvent | Conditions | PXRD Results | FIG. |
|---|---|---|---|---|---|
| Slurry | 4-1 | acetone/DMF 90/10 | RT | Malate 1 (PO) | |
| | 4-2 | ACN | 50° C. | Malate 1 | |
| | 4-3 | CHCl$_3$ | 50° C. | Malate 1 | |
| | 4-4 | CHCl$_3$/DMF 95/5 | RT | Malate 1 | |
| | 4-5 | EtOAc/DMF 87/13 | RT | Malate 1 + NC (PO) | |
| | 4-6 | EtOH | 50° C. (clear) RT (solids slowly pp'd) | Malate 1 | |
| | 4-7 | MeOH | RT | Malate 1 | |
| | 4-8 | THF | RT | Malate 1 (PO) | |
| | 4-9 | acetone/H$_2$O 15/85 a$_w$ = 0.97 | RT | Malate 4 | |
| | 4-10 | EtOH/H$_2$O 50/50 a$_w$ = 0.89 | RT | Malate 4 | FIG. 36 |
| | 4-11 | EtOH/H$_2$O 70/30 a$_w$ = 0.81 | RT | Malate 1 + pks (4.2°, 6.6°, 14.9°, 19.0°) | |
| | 4-12 | EtOH/H$_2$O 80/20 a$_w$ = 0.70 | RT | Malate 1 | |
| | 4-13 | EtOH/H$_2$O 85/15 a$_w$ = 0.62 | RT | Malate 1 (PO) | |
| | 4-14 | EtOH/H$_2$O 95/5 a$_w$ = 0.3 | RT | Malate 1 (PO) | |
| | 4-15 | IPA/H$_2$O 50/50 a$_w$ = 0.96 | RT | Malate 4 | |
| | 4-16 | H$_2$O a$_w$ = 1.00 | RT | Malate 4 | |
| | 4-17 | wet EtOAc | RT | Malate 1 + Malate 2 | |
| Cooling | 4-18 | ACN/DMF 86/14 | 50° C.→5° C.; NS. E, RT; gel. | — | |
| | 4-19 | CHCl$_3$/MeOH 83/17 | 50° C.→−20° C.; NS. Sonicated w/probe, returned to freezer; NS. E, RT | NC | |
| | 4-20 | dioxane | 50° C.→5° C.; NS. Sonicated w/probe; NS. Added DEE; solids pp'd. | IS | |
| | 4-21 | EtOAc/MeOH 84/16 | 50° C.→−20° C.; NS. Sonicated w/ probe, returned to freezer; NS. E, RT | NC | |
| | 4-22 | EtOH | 50° C.→−20° C.; NS. Sonicated w/probe, returned to freezer; NS. Added DEE, returned to freezer; NS. E, RT | Malate 3; LC | FIG. 36 |
| | 4-23 | H$_2$O | 50° C.→5° C. | Malate 2; LC | |
| | 4-24 | IPA | 50° C.→−20° C.; NS. Sonicated w/probe, returned to freezer; NS. Added heptane, returned to freezer; solids pp'd. | NC | |
| | 4-25 | IPE/DMF 86/14 | 50° C.→−20° C.; NS. Sonicated w/probe, returned to freezer; NS. Added more IPE, returned to freezer; NS. | — | |
| | 4-26 | iPrOAc/DMF 89/11 | 50° C→−20° C.; NS. Sonicated w/probe, returned to freezer; NS. Added DEE, returned to freezer; flocculent solids. Isolated via VF; film. | — | |
| | 4-27 | MEK/MeOH 93/7 | 50° C.→−20° C.; NS. Sonicated w/probe, returned to freezer; NS. E, RT | NC | |
| | 4-28 | MEK/MeOH 99/1 | 50° C→−20° C.; NS. Sonicated w/probe, returned to freezer; NS. Added DEE, returned to freezer; NS. | — | |
| | 4-29 | MeOH | 50° C.→−20° C.; NS. Sonicated w/probe, returned to freezer; NS. Added IPE, returned to freezer; solids pp'd. | NC | |
| | 4-30 | 2-Me THF | 50° C.→−20° C.; NS. Sonicated w/probe, returned to freezer; NS. Added IPE, returned to freezer; solids pp'd. | NC | |

TABLE 21-continued

Polymorph Screen of Linsitinib Malate

| Method | Sample No. | Solvent | Conditions | PXRD Results | FIG. |
|---|---|---|---|---|---|
| | 4-31 | MIBK/DMF 93/7 | 50 C.→−20° C.; NS. Sonicated w/probe, returned to freezer; NS. E, RT; gel. | | |
| | 4-32 | MTBE/MeOH 77/23 | 50° C.→−20° C.; NS. Sonicated w/probe; NS. Added more MTBE; NS. E, RT | NC | |
| | 4-33 | THF | 50° C.→−20° C.; NS. Sonicated w/probe, returned to freezer; NS. Added MTBE; solids pp'd. | NC | |
| | 4-34 | | 50° C.→−20° C.; NS. Sonicated w/probe, returned to freezer; NS. Added hexanes; solids pp'd. | NC | |
| Precipitation | 4-35 | DMF/DEE | RT→−20° C.; film. | — | |
| | 4-36 | DMF/MTBE | RT→−20° C.; solids melted upon isolation at RT | — | |
| | 4-37 | EtOH/cyclohexane | 50° C.→−20° C. | NC | |
| | 4-38 | EtOH/DEE | 50° C.→−20° C.; NS. Added more DEE, returned to freezer; solids melted upon isolation at RT | | |
| | 4-39 | EtOH/heptane | 50° C.→−20° C. | NC | |
| | 4-40 | EtOH/hexanes | 50° C.→−20° C. | NC | |
| | 4-41 | EtOH/IPE | 50° C.→−20° C. | NC | |
| | 4-42 | EtOH/iPrOAc | 50° C.→−20° C.; NS. E, RT | NC | |
| | 4-43 | EtOH/MIBK | 50° C.→−20° C.; NS. E, RT; gel. | — | |
| | 4-44 | EtOH/MTBE | 50° C.→−20° C.; NS. E, RT; gel. | — | |
| | 4-45 | H2O | solubility sample; solids re-precipitated at RT | Malate 2 | FIG. 36 |
| | 4-46 | MeOH/DCE | RT→−20° C.; NS. E, RT | NC | |
| | 4-47 | MeOH/DEE | RT→−20° C. | IS | |
| | 4-48 | MeOH/IPE | RT→−20° C. | NC | |
| | 4-49 | MeOH/iPrOAc | RT→−20° C.; NS. E, RT | NC (weak diffraction) | |
| | 4-50 | MeOH/MTBE | RT→−20° C. NS. E, RT | NC | |
| | 4-51 | MeOH/toluene | RT→−20° C.; NS. E, RT | NC | |
| Lyophilization | 4-52 | dioxane/H2O | −50° C. | NC | |

TABLE 22

Reaction Crystallization Experiments with Linsitinib free base and L-Malic acid

| Sample No. | Solvent | Conditions | XRPD Results | FIG. No. |
|---|---|---|---|---|
| 4-53 | acetone | Slurry, RT. | Malate 1 | |
| 4-54 | CHCl₃ | Slurry; 50° C., 2-3 h (gel)→RT. Stirring, RT, 3 d (gel persisted). | — | |
| 4-55 | EtOAc | Slurry, RT. | FB A + NC | |
| 4-56 | EtOH | P; RT (clear). Stirring, RT→5° C. (solids pp'd). | Malate 6 | FIG. 36 |
| 4-57 | IPA | Slurry; 50° C., 3 d→RT. | FB A + acid + pks | |
| 4-58 | IPA/H₂O 50/50 | P; RT (clear). Stirring, RT (solids pp'd). | Malate 5 (similar to Malate 2) | FIG. 36 |
| 4-59 | iPrOAc | Slurry; 50° C., 3 d (flocculent solids)→RT. | Malate 1 | |
| 4-60 | MEK | Slurry; 50° C., 3 d→RT. | Malate 1 | |
| 4-61 | MTBE | Slurry; 50° C., 3 d→RT. | FB A + NC | |
| 4-62 | THF | P; RT (clear). Stirring, RT (NS). | — | |

TABLE 23

Polymorph Screen Experiments with Non-crystalline Linsitinib L-Malate

Figure 36:
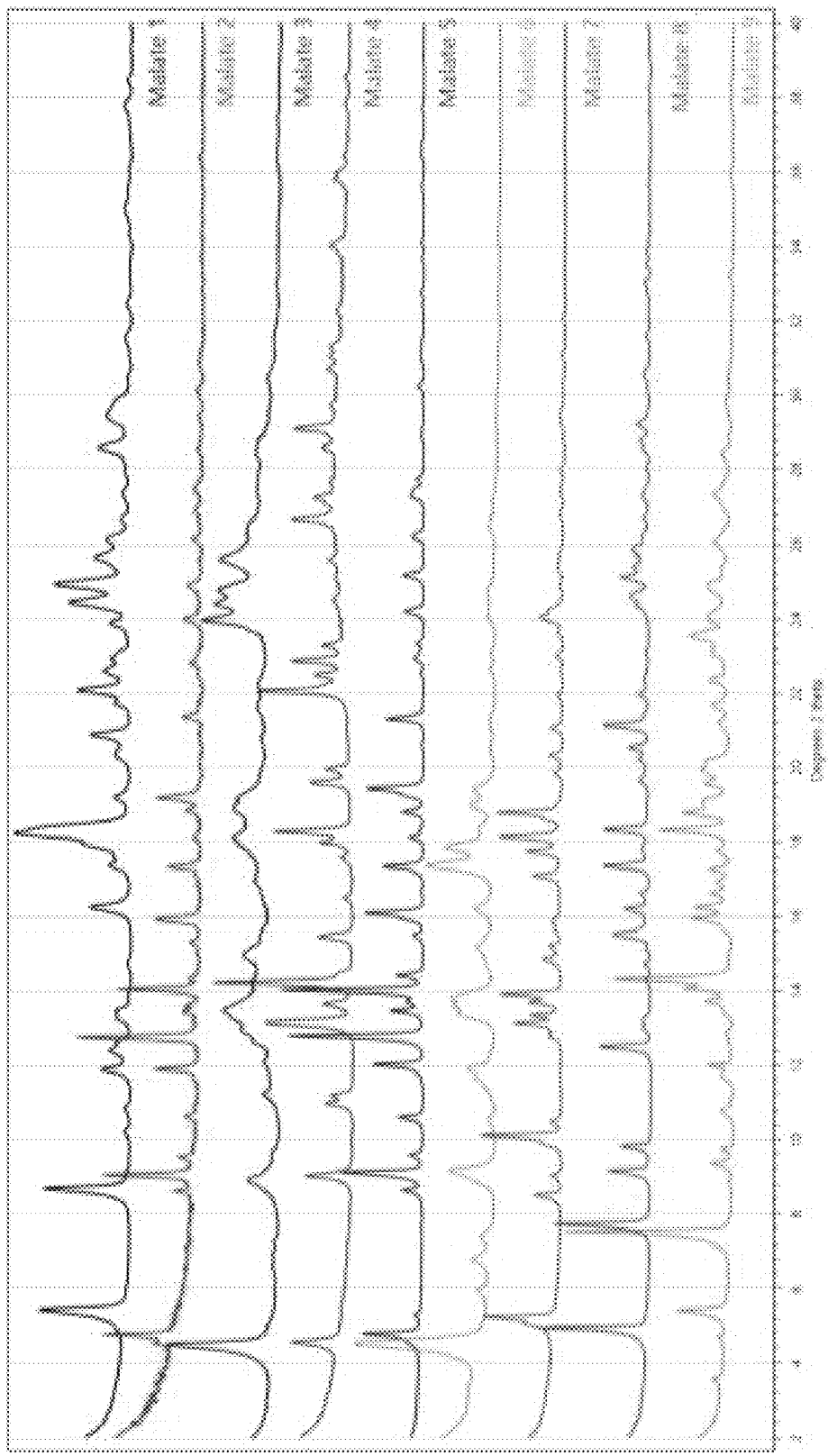
FIG. 36 shows the PXRD of L-Malate 2 (Sample 4-45), L-Malate 3 (Sample 4-22), L-Malate 4 (Sample 4-10), L-Malate 5 (Sample 4-58), L-Malate 6 (Sample 4-56), L-Malate 7 (Sample 4-78), L-Malate 8 (Sample 4-76), and L-Malate 9 (Sample 4-66).

| Technique | Sample No. | Solvent | Conditions | XRPD Results | FIG. No. |
|---|---|---|---|---|---|
| Vapor stress | 4-63 | acetone | RT | NC + pks (likely Malate 1) | |
| | 4-64 | DCM | RT | NC | |
| | 4-65 | EtOAc | RT | NC | |
| | 4-66 | EtOH | RT | Malate 9 | FIG. 36 |
| | 4-67 | H₂O | RT | Malate 4 | |
| Humidity stress | 4-68 | — | 93% RH | Malate 4 + Malate 2 | |
| | 4-69 | — | 75% RH | NC | |
| Slurry | 4-70 | ACN | 50° C. (mostly clear, a few solids remained) RT | Malate 1 | |
| | 4-71 | CHCl₃ | 50° C. (gummy solids) | NC | |
| | 4-72 | EtOAc (wet) | 50° C. (initially solids formed a gel, then solidified at ET) | Malate 1 + Malate 5 | |
| | 4-73 | iPrOAc | 50° C. | Malate 1; LC | |
| | 4-74 | 2-Me THF | 50° C. | NC + 18.0° pk | |
| | 4-75 | MEK | 50° C. (mostly clear, a few solids remained) RT | NC | |
| Precipitation | 4-76 | MeOH | Added minimal solvent at RT (clear). Transferred to fridge. | Malate 8, may contain trace acid | FIG. 36 |
| | 4-77 | THF | Added minimal solvent at RT (clear). Transferred to fridge (NS). | — | |

TABLE 24

Heating Experiments with Selected Samples

| Sample | Source Material | Conditions | XRPD Results | FIG. |
|---|---|---|---|---|
| 4-78 | Malate 4 (Sample 4-10) | 92° C., 15 min | Malate 7 | FIG. 36 |
| 4-79 | Malate 5 (Sample 4-58) | 92° C., 15 min | Malate 7 + pk | |

In addition to Malate 1 (the starting form for the majority of the current screen experiments), eight materials with unique peaks by PXRD (i.e., do not contain peaks of known forms of the free base, the malate salt, or malic acid) were also identified. Those confirmed to be the malate salt by ¹H NMR spectroscopy were designated as Malate 2 through Malate 9.

Malate 2, Malate 4, and Malate 5 were all obtained from high water activity conditions and are suspected to be hydrated forms. Based on the weight loss in the TG thermograms of Malate 4 and Malate 5, they could be di-hydrates. The water activity boundary between Malate 4 and Malate 1 was determined to be approximately 0.9 water activity, or 90% relative humidity. At a water activity of 0.8, Malate 1 was obtained; however, there were additional peaks present by PXRD.

Upon dehydration, Malate 4 and Malate 5 both convert to Malate 7. Malate 7 could be an anhydrous form or a lower hydrate.

Note that Malate 2 and Malate 5 appear quite similar by PXRD, which suggests their crystal structures are closely related and may only differ slightly by a small amount of water.

Malate 3 and Malate 6 were both obtained from experiments using ethanol. While organic solvent is not present by ¹H NMR spectroscopy, there is an observed weight loss in the TG thermograms. The weight loss is equivalent to approximately one mole of water and suggests Malate 3 and Malate 6 could be mono-hydrates.

Malate 8 and Malate 9 were observed from experiments starting with the non-crystalline malate salt. Based on ¹H NMR data, they could be a methanol solvate and ethanol solvate, respectively.

Characterization of Linsitinib L-Malate Salt Polymorphs

Select samples were identified for further characterization for each of the nine linsitinib L-malate crystalline salt polymorphs. The results are presented in Table 25, below:

TABLE 25

Characterization of L-Malate Polymorphs

Figure 37:
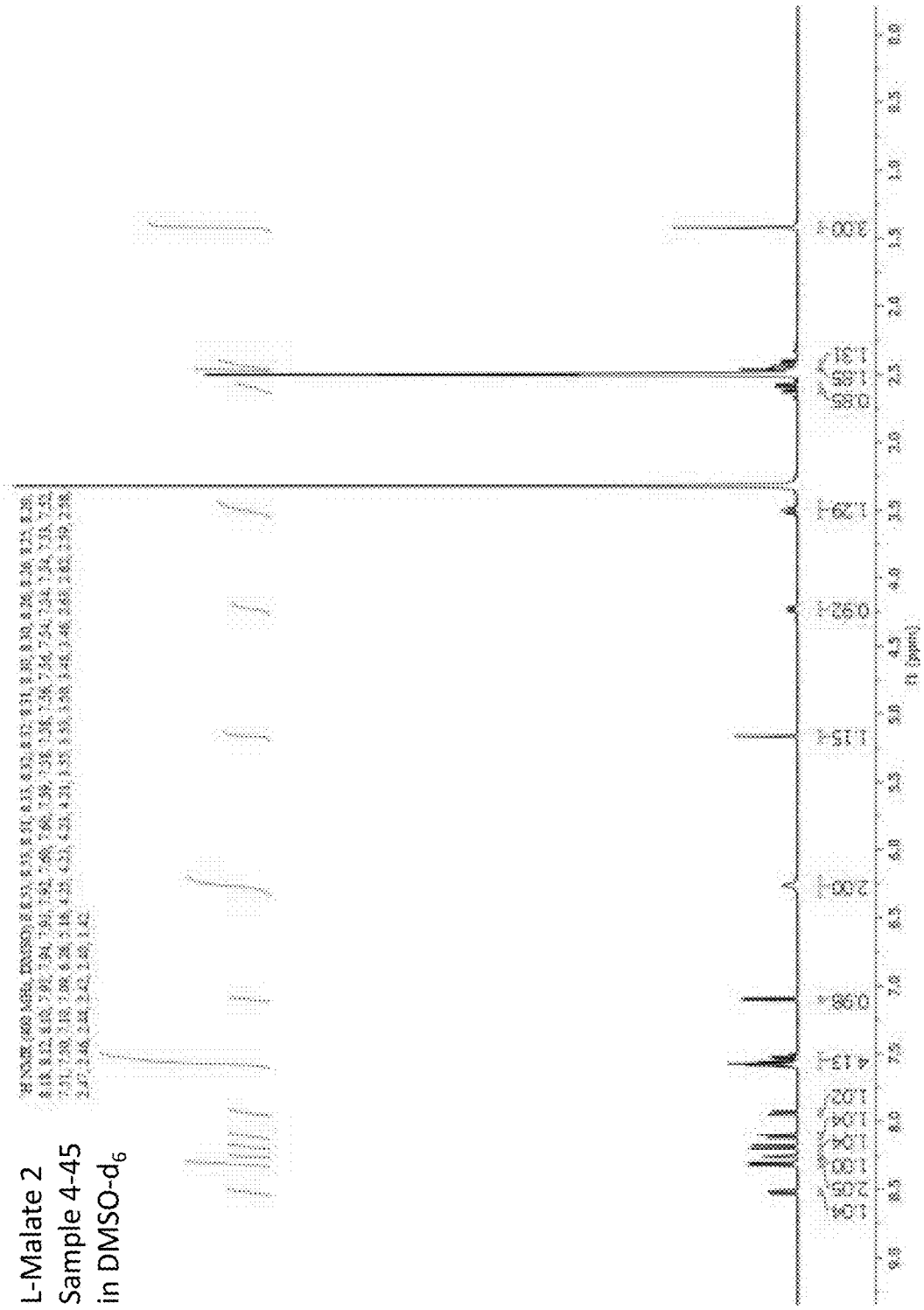
FIG. 37 shows the $^1$H NMR $^1$H NMR in DMSO-$d_6$ of L-Malate 2 (Sample 4-45).
Figure 38:
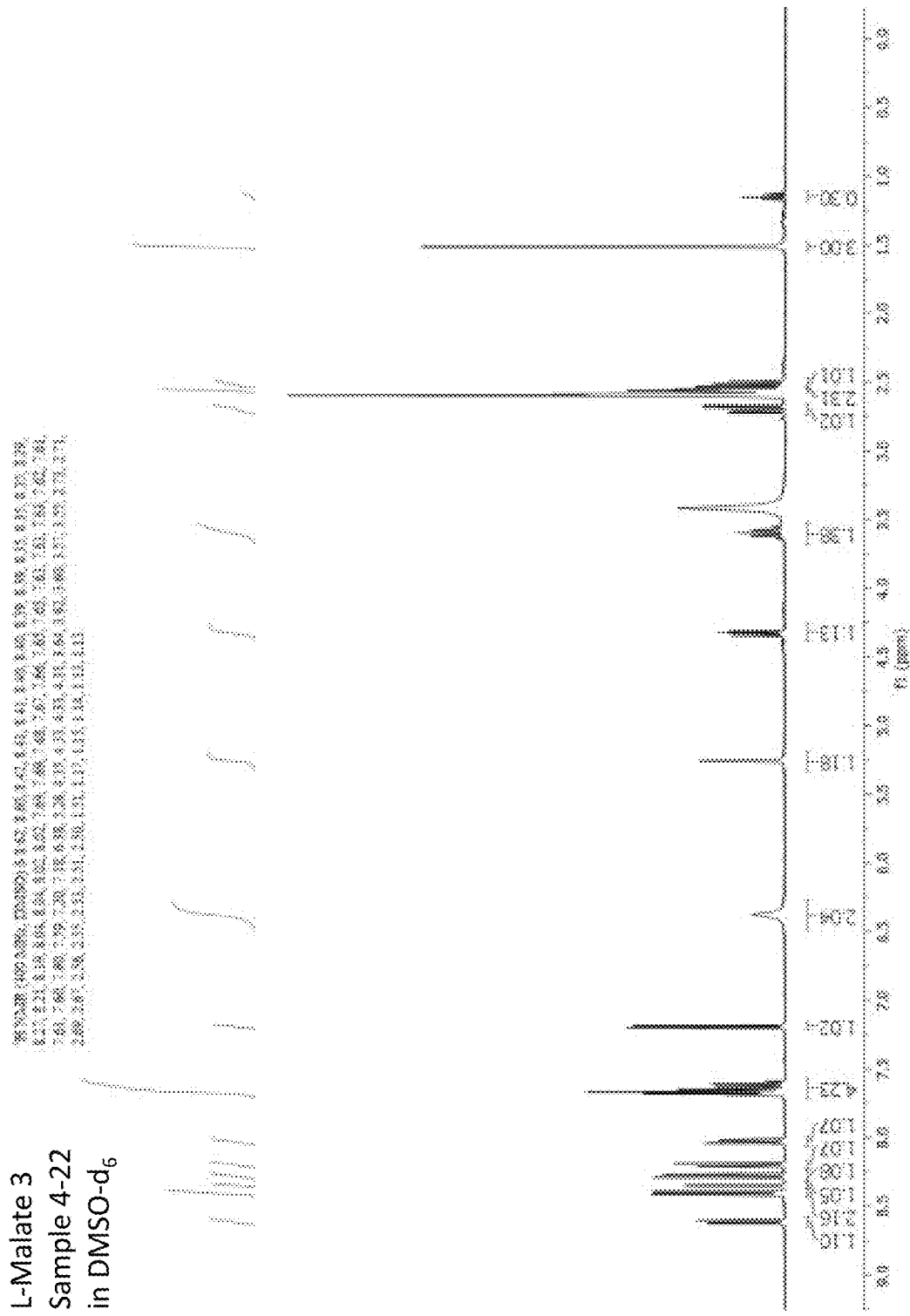
FIG. 38 shows the $^1$H NMR in DMSO-$d_6$ of L-Malate 3 (Sample 4-22).

| Form (Sample) | Analytical Technique | Results | FIG. |
|---|---|---|---|
| Malate 2 (Sample 4-45) | ¹H NMR | Consistent with structure 1:1 linsitinib:malic acid stoichiometry No organic solvents | FIG. 37 |
| Malate 3 (Sample 4-22) | ¹H NMR | Consistent with structure 1:1 linsitinib:malic acid stoichiometry 0.1 moles EtOH or DEE | FIG. 38 |
| | TGA | 3.0%, start to 90° C. 0.6%, 90° C. to 139° C. | FIG. 39 |
| | DSC | Endo: 85° C., 129° C. | FIG. 39 |

TABLE 25-continued

Characterization of L-Malate Polymorphs

Figure 40:
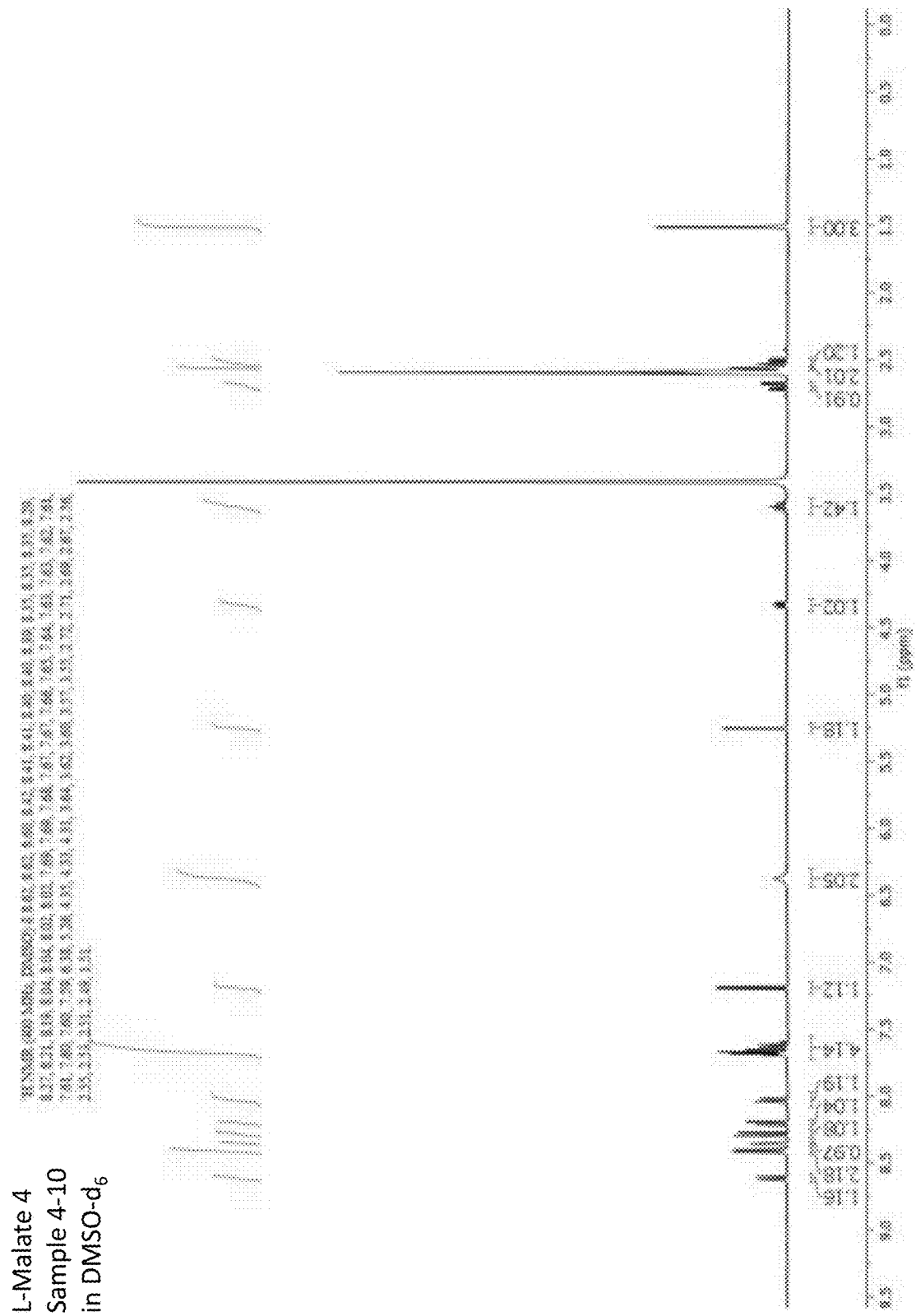
FIG. 40 shows the $^1$H NMR in DMSO-$d_6$ of L-Malate 4 (Sample 4-10).
Figure 42:
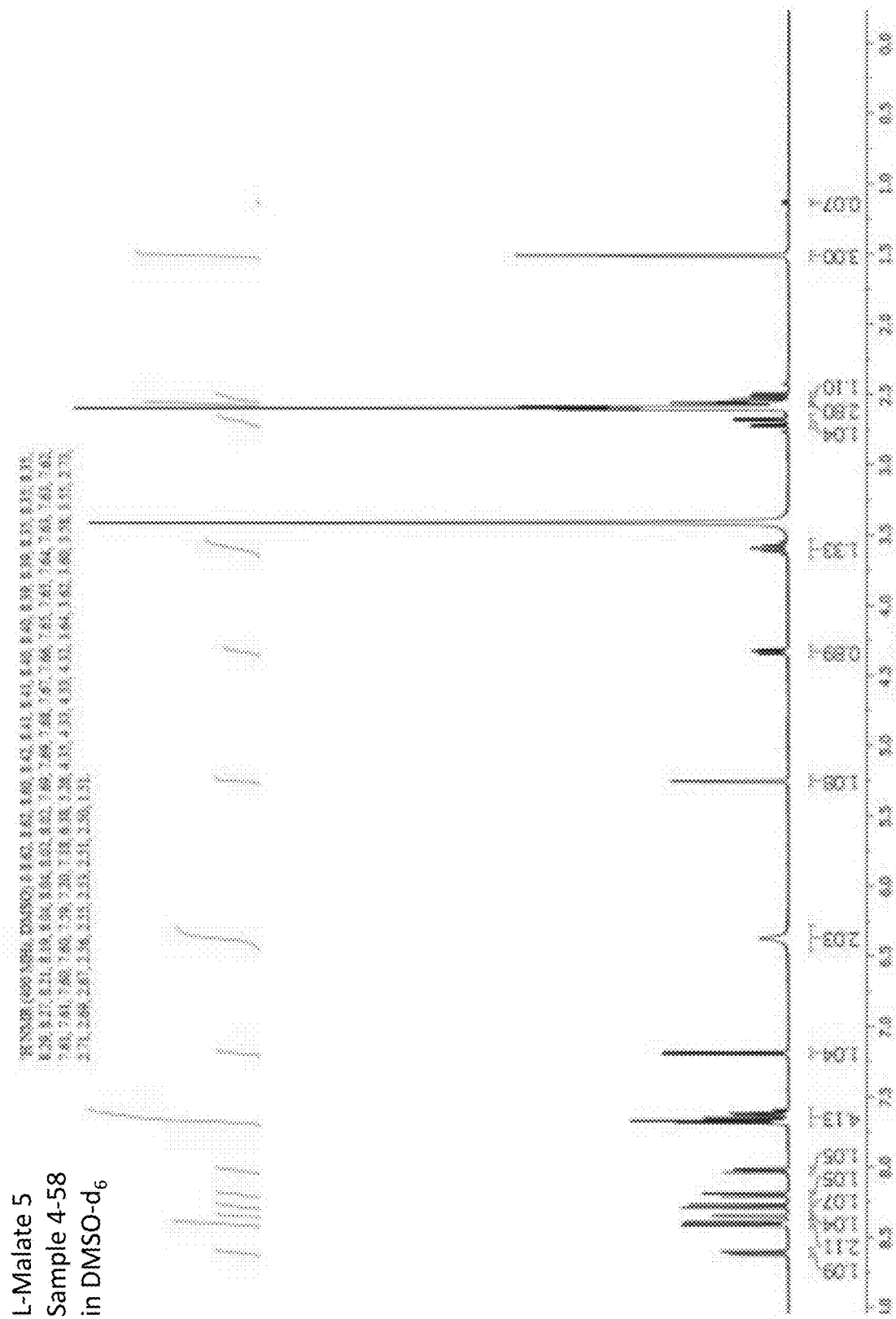
FIG. 42 shows the $^1$H NMR in DMSO-$d_6$ of L-Malate 5 (Sample 4-58).
Figure 44:
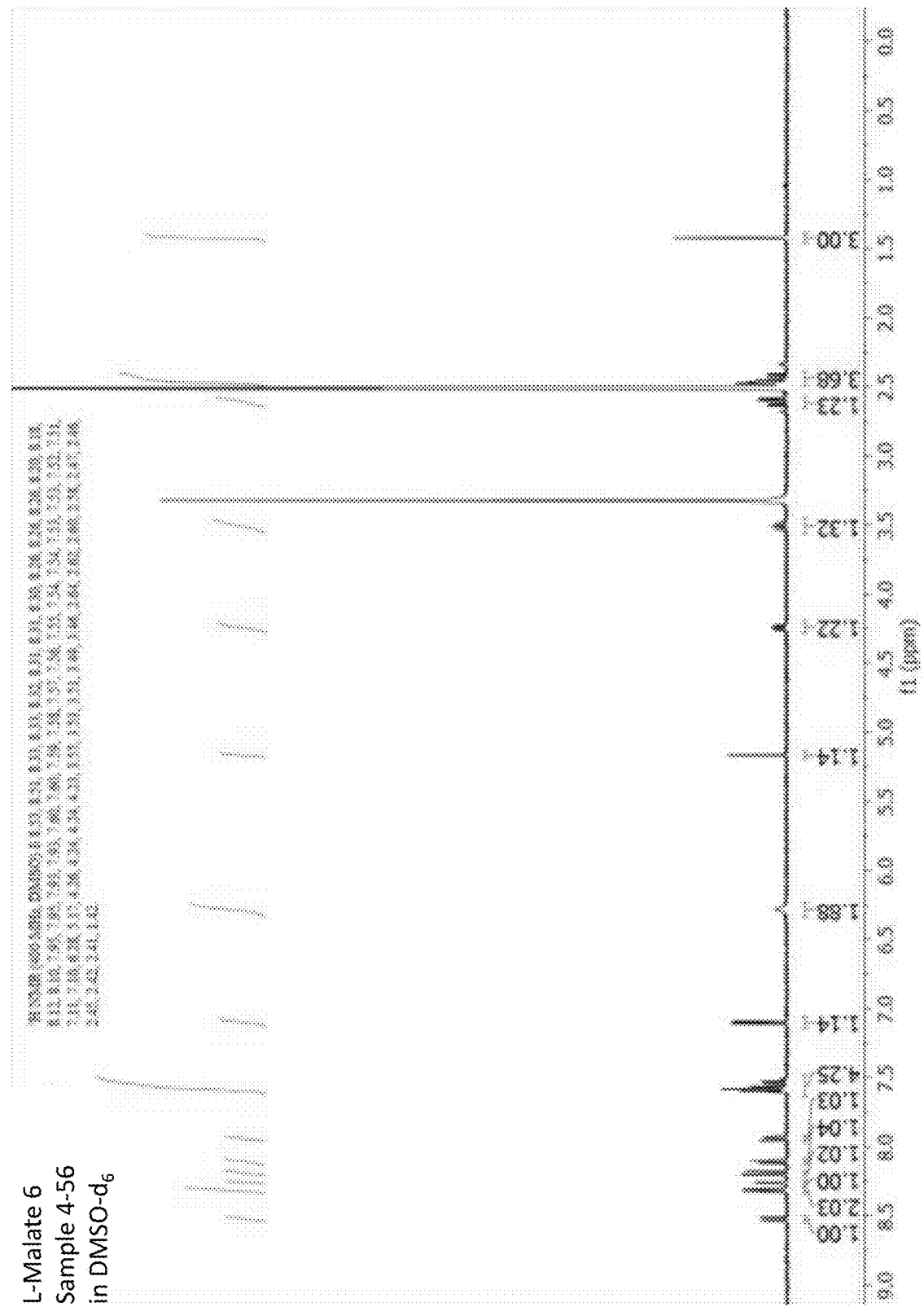
FIG. 44 shows the $^1$H NMR in DMSO-$d_6$ of L-Malate 6 (Sample 4-56).
Figure 46:
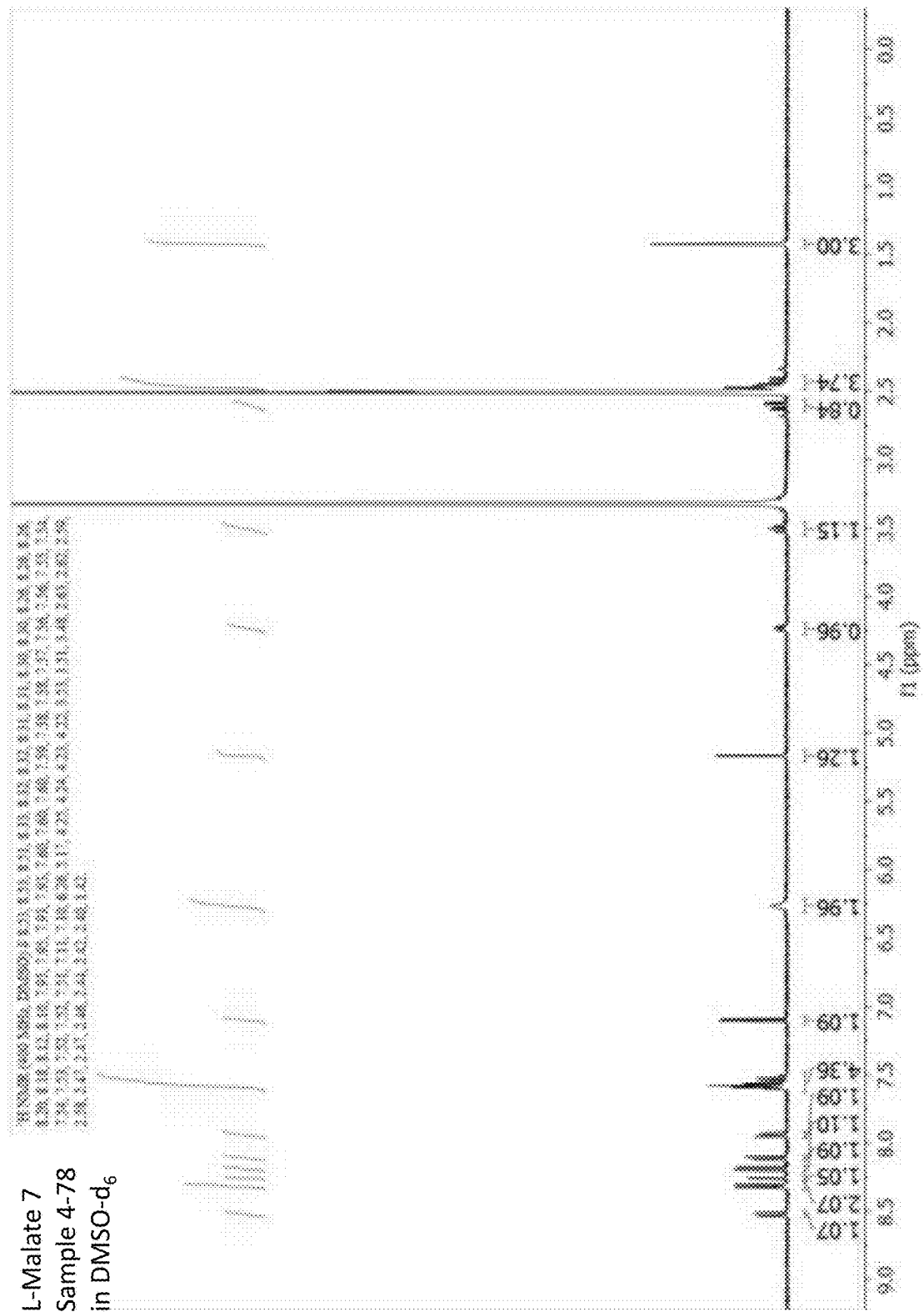
FIG. 46 shows the $^1$H NMR in DMSO-$d_6$ of L-Malate 7 (Sample 4-78).
Figure 47:
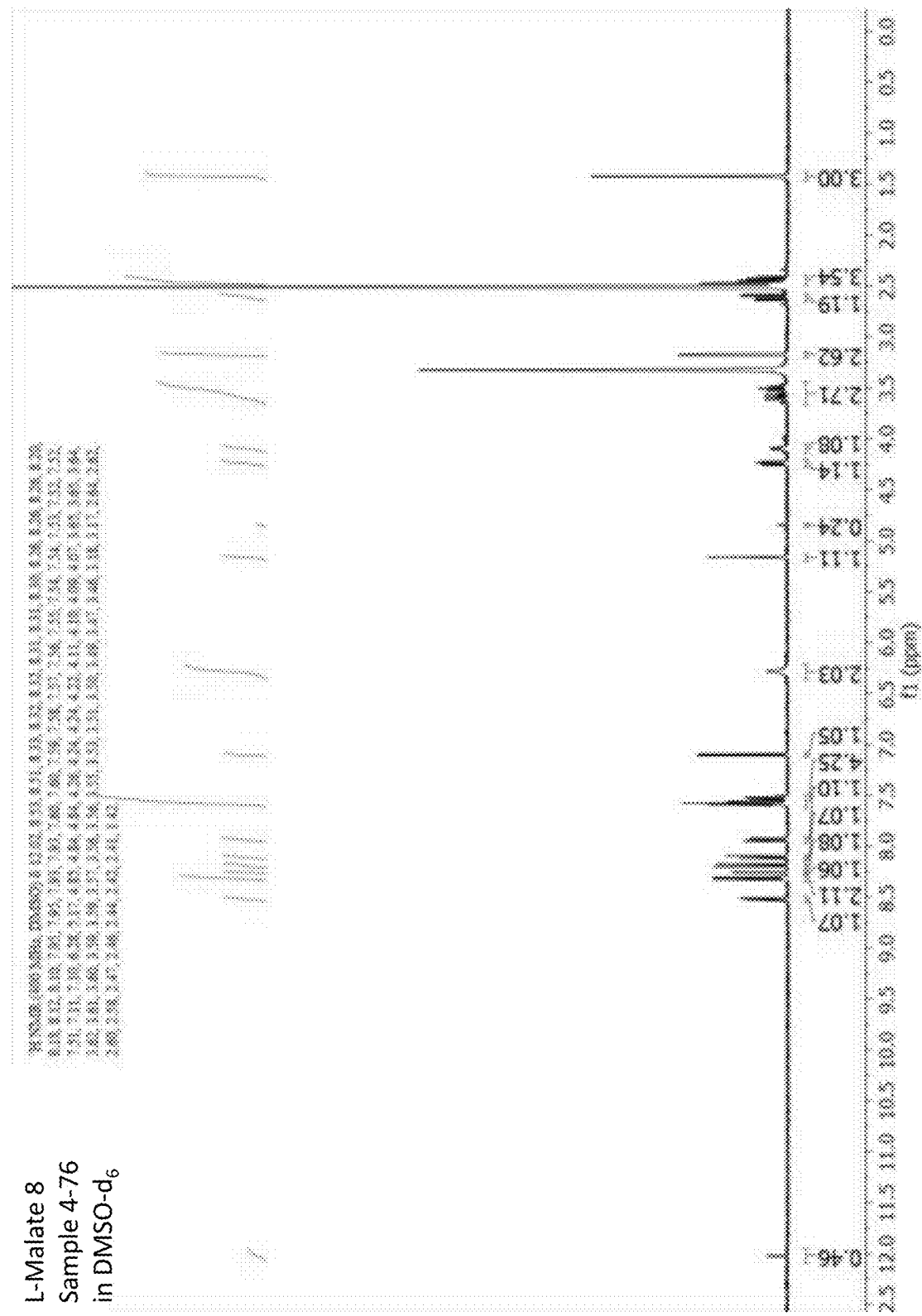
FIG. 47 shows the $^1$H NMR in DMSO-$d_6$ of L-Malate 8 (Sample 4-76).
Figure 48:
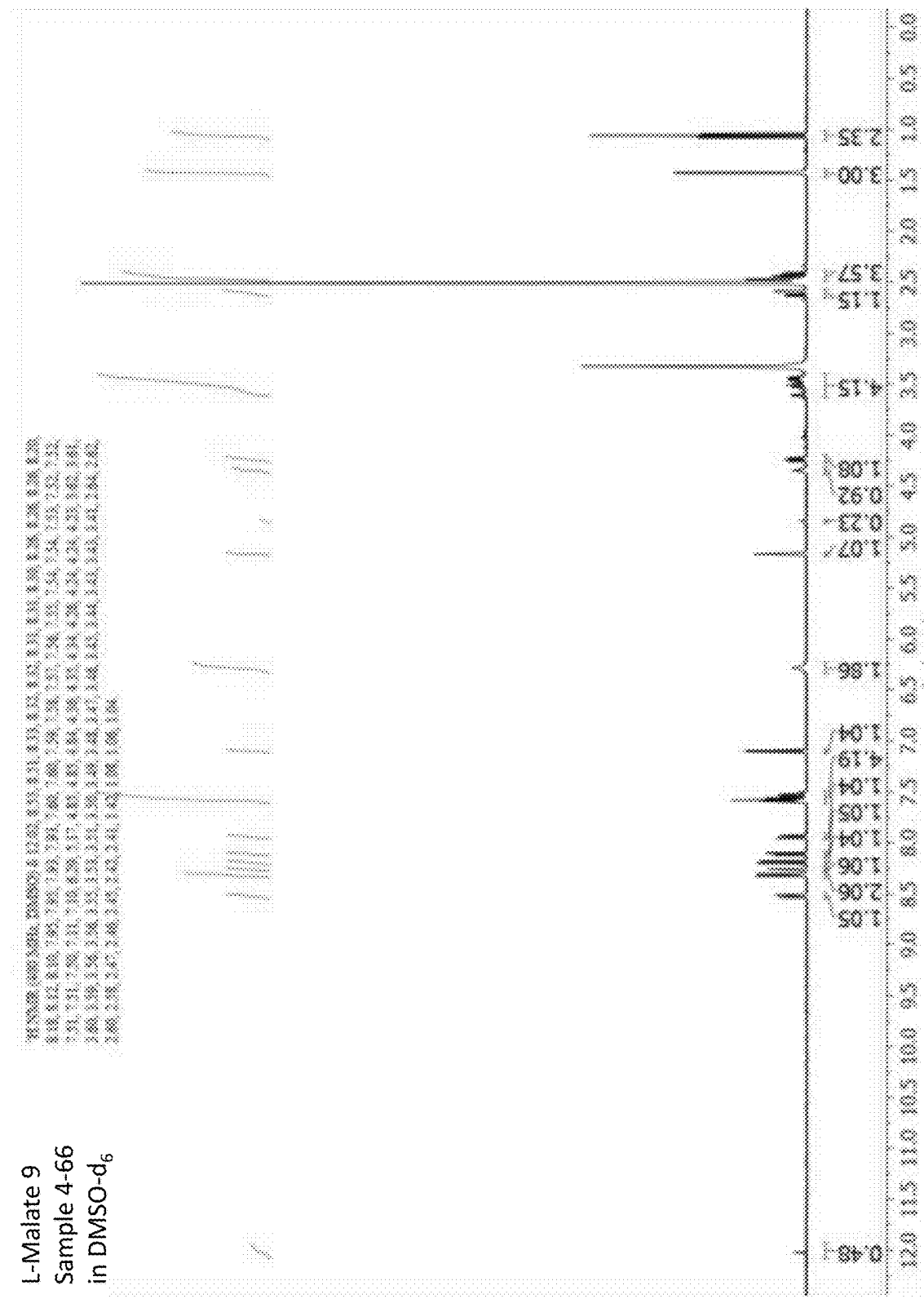
FIG. 48 shows the $^1$H NMR in DMSO-$d_6$ of L-Malate 9 (Sample 4-66).

| Form (Sample) | Analytical Technique | Results | FIG. |
|---|---|---|---|
| Malate 4 (Sample 4-10) | $^1$H NMR | Consistent with structure 1:1 linsitinib:malic acid stoichiometry No organic solvents | FIG. 40 |
| | TGA | 7.3%, start to 65° C. | FIG. 41 |
| | DSC | Endo: 84° C., 145° C. | FIG. 41 |
| Malate 5 (Sample 4-58) | $^1$H NMR | Consistent with structure 1:1 linsitinib:malic acid stoichiometry 0.01 moles IPA | FIG. 42 |
| | TGA | 7.4%, start to 83° C. | FIG. 43 |
| | DSC | Endo: 109° C. | FIG. 43 |
| Malate 6 (Sample 4-56) | $^1$H NMR | Consistent with structure 1:1 linsitinib:malic acid stoichiometry Contains excess acid (0.2 moles) No organic solvents | FIG. 44 |
| | TGA | 4.2%, start to 61° C. | FIG. 45 |
| | DSC | Endo: 73° C., 88° C. (br, overlapping), 137° C. (br) | FIG. 45 |
| Malate 7 (Sample 4-78 | $^1$H NMR | Consistent with structure 1:1 linsitinib:malic acid stoichiometry No organic solvents | FIG. 46 |
| Malate 8 (Sample 4-76) | $^1$H NMR | Consistent with structure 1:1 linsitinib:malic acid stoichiometry 0.9 moles MeOH Small, unidentified peaks at 3.6, 4.2, and 4.8 ppm | FIG. 47 |
| Malate 9 (Sample 4-66) | $^1$H NMR | Consistent with structure 1:1 linsitinib:malic acid stoichiometry 0.8 moles EtOH Small, unidentified peaks at 3.6, 4.6, and 4.8 ppm | FIG. 48 |

Note that the PXRD patterns for several of the new materials appear very similar to each other, indicating that they are likely related. Peak shifts were observed between some of the samples, in particular Malate 2 and Malate 5, which suggests they may have the same crystal lattice but have variable volatile content (FIG. 2).

Malate 3, Malate 4, Malate 5, and Malate 6 were further characterized by TG and DSC. Malate 3 and Malate 6 could be mono-hydrates. Malate 3 contained only a trace amount of organic solvent present in the NMR spectrum but exhibited a 3.6% weight loss in the TG thermogram. The residual solvent would account for ~1% of the loss and the remaining ~2.6% is equivalent to about one mole of water, per mole of salt. Similarly, organic solvent was not observed in the $^1$H NMR spectrum of Malate 6 but a 4.2% weight loss was present in the TG thermogram.

Malate 4 and Malate 5 could be di-hydrates. No organic solvents are present in the NMR spectra, but each material had a 7.3-7.4% weight loss in the TG thermogram. This would be equivalent to ~2.4 moles of water, per mole of salt.

The water activity boundary between Malate 4 and Malate 1 was determined to be approximately 0.9 water activity, or 90% relative humidity. At a water activity of 0.8, Malate 1 was obtained; however, there were additional peaks present by PXRD.

Based on the thermal data, Malate 4 and Malate 5 were heated at ~90° C. for 15 minutes. The solids were re-analyzed by PXRD after heating to investigate any form change upon dehydration. Based on the data, Malate 4 and Malate 5 appear to dehydrate to a new form, designated as Malate 7. While there was an insufficient amount of sample to further characterize Malate 7, based on the conditions upon which it was generated, it could be a lower hydrate or an anhydrous form.

Example 6: Linsitinib Crystalline Salt Form Edisylate 1

Edisylate 1 was prepared from an equimolar slurry in dioxane. 25.0 mg of linsitinib was combined with 13.4 mg of 1,2-ethanedisulfonic acid dihydrate and 1.0 mL of dioxane. The sample was heated to 90° C. producing a turbid white solution with a small yellow sticky residue at the bottom of the vial. The sample was held at 90° C. overnight producing a thick dark yellow slurry. The sample was removed from the heat and allowed to quickly cool to room temperature. The sample was allowed to stir for 5 days at ambient temperature producing a dark yellow slurry. The solids were isolated via filtration and the solids were dried overnight at ambient. Visible shrinking of the sample was observed. The sample was broken up with a spatula to produce yellow powder.

Figure 51:
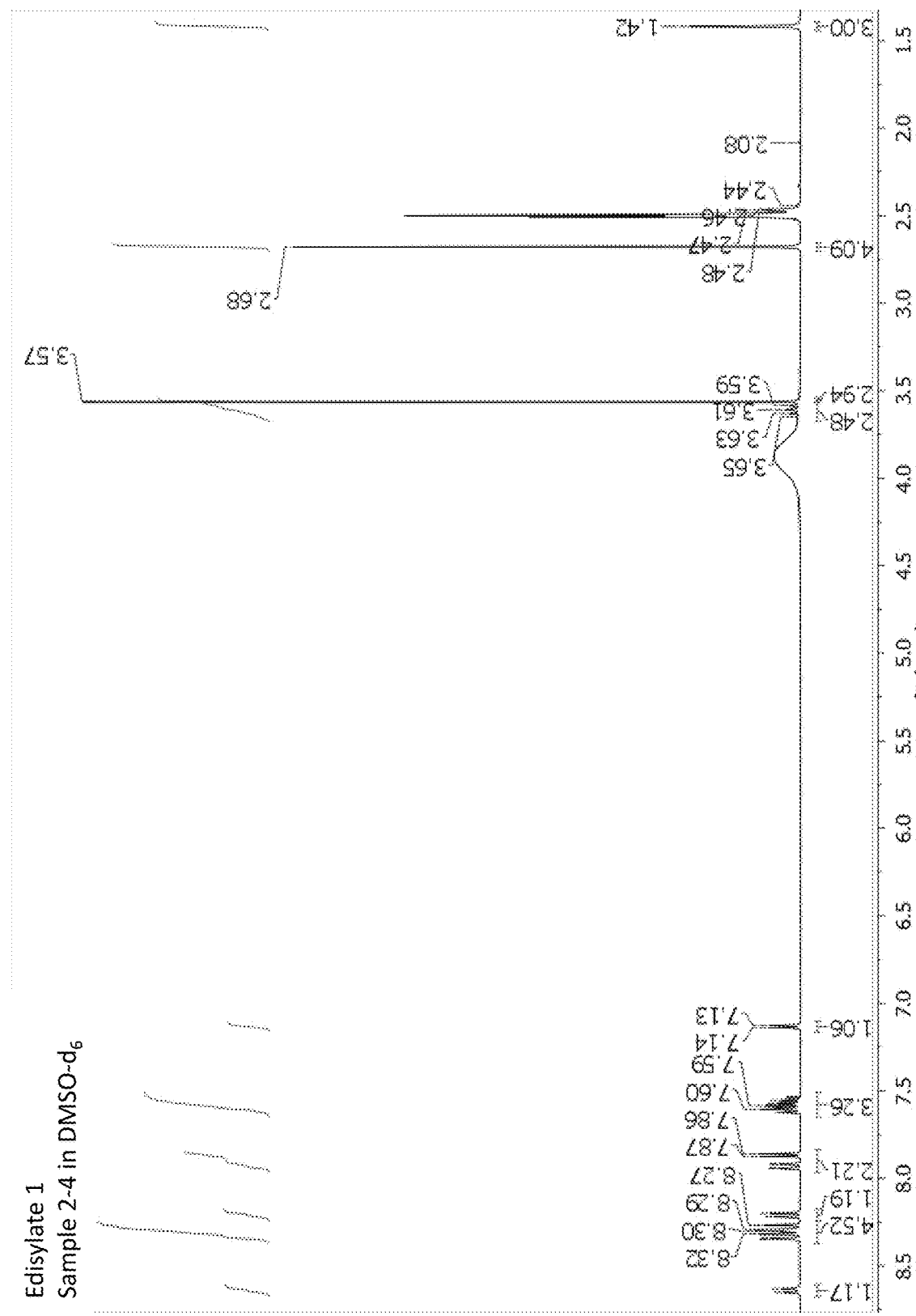
FIG. 51 shows the $^1$H NMR in DMSO-$d_6$ of Edisylate 1 (Sample 2-4).

PXRD analysis of the sample after capped storage at room temperature for 20 days showed no significant changes indicating the sample was physically stable under these conditions. $^1$H NMR analysis of the sample was consistent with a 1:1 molar ratio of linsitinib:acid (FIG. 51). Thermal analysis of the material (FIG. 52) showed a 1.7% weight loss upon heating to 150° C. with an accompanying broad endotherm with a peak maximum of 51° C. in the DSC data. The weight loss is likely associated with water as no significant dioxane or other organic solvents was observed in the NMR spectrum. A theoretical hemi-hydrate for a mono-edisylate salt of linsitinib would contain 1.4% water. Additional endotherms are observed at 252 and 278° C. that are likely due to melt/decomposition based on the corresponding weight loss in the TGA beginning around 244° C. Characterization results indicate that Edisylate 1 is a potential hemi-hydrate mono-salt of linsitinib.

Example 7: Linsitinib Crystalline Salt Form Maleate 1

Maleate 1 was generated from an equimolar slurry of linsitinib and maleic acid in 95/5 IPA/water at room temperature. Specifically, 24.8 mg of linsitinib and 6.8 mg of maleic acid were combined with 0.5 mL of 95-5 v-v isopropanol-water. After overnight stirring at room temperature a thick white paste was observed. An additional 0.5 mL of isopropanol was added to the sample to produce a mobile suspension. After 6 additional days of stirring the sample was observed to a white slurry. The solids were filtered and left to dry at ambient conditions producing light yellow solids.

Figure 54:
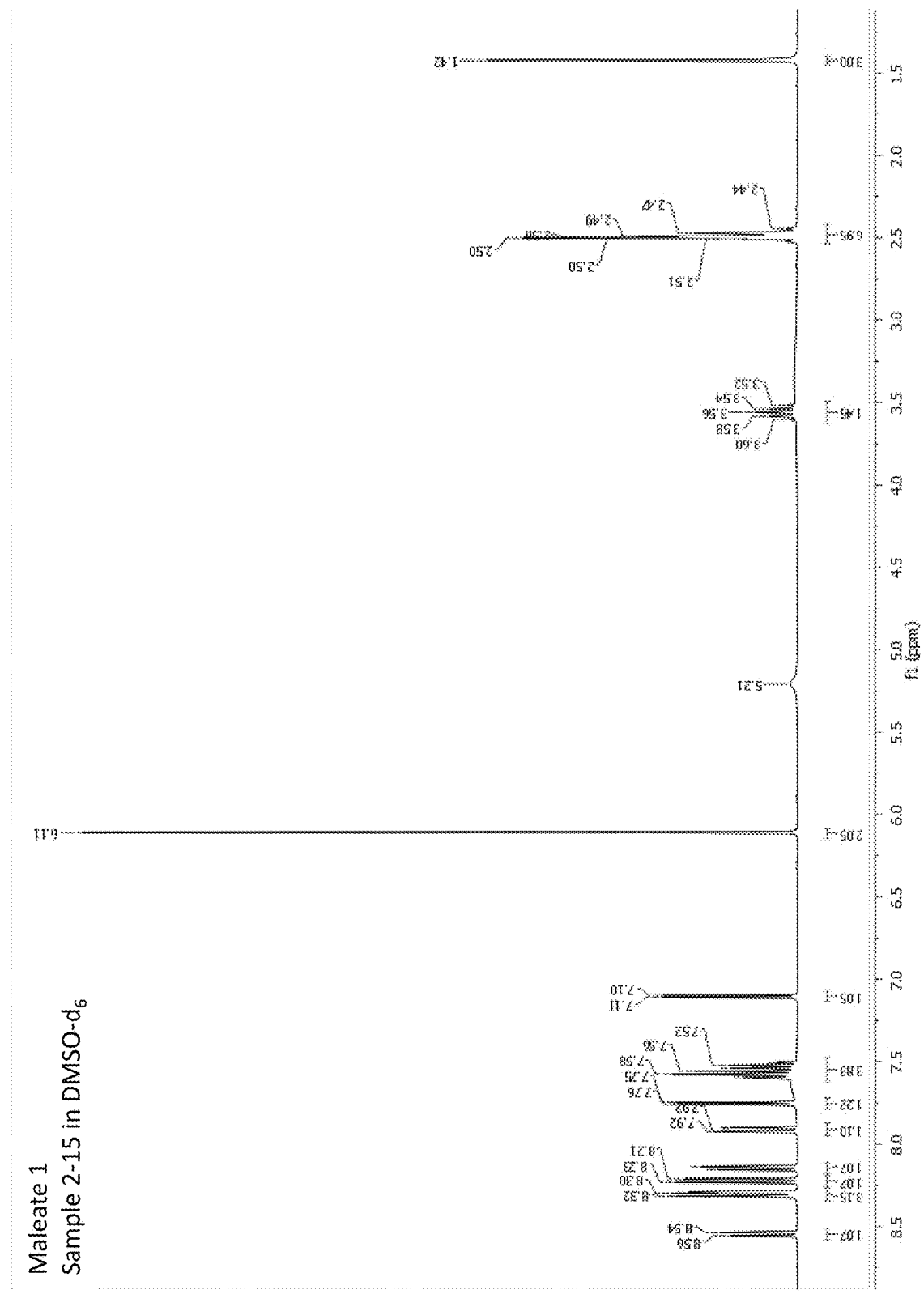
FIG. 54 shows the $^1$H NMR in DMSO-$d_6$ of Maleate 1 (Sample 2-15).

The $^1$H NMR spectrum of the resulting solids showed a 1:1 linsitinib:maleic acid molar ratio with no evidence of organic solvent in the spectrum (FIG. 54). Thermal analysis was consistent with a potentially hydrated form (FIG. 55). The sample shows a step loss of 2.8% to 100° C. with a corresponding broad endotherm at 71° C. in the DSC. The weight loss is expected to be due to water based on the lack of organic solvents observed in the $^1$H NMR spectrum. A mono-hydrated mono-maleate salt of linsitinib would be expected to contain around 3.2% water. Multiple endothermic and exothermic events are observed with a corresponding significant weight loss around 174° C. indicative of a potential melt/decomposition event though additional testing would be needed to confirm. Characterization results indicate that Maleate 1 is a potentially hydrated mono-salt of linsitinib.

Example 8: Linsitinib Crystalline Salt Form Napsylate 1

Napsylate 1 was produced from a 70° C. slurry of linsitinib and 2-napthalenesulfonic acid hydrate in acetonitrile. Specifically, 25.5 mg of linsitinib and 13.7 mg of 2-napthalenesulfonic acid hydrate were combined with 0.5 mL of acetonitrile. The sample was heated to 70° C. producing a turbid yellow suspension after 1 hour. After 4 days of equilibration a white slurry was observed. Solids were isolated via filtration and subsequently dried overnight at ambient conditions.

Figure 57:
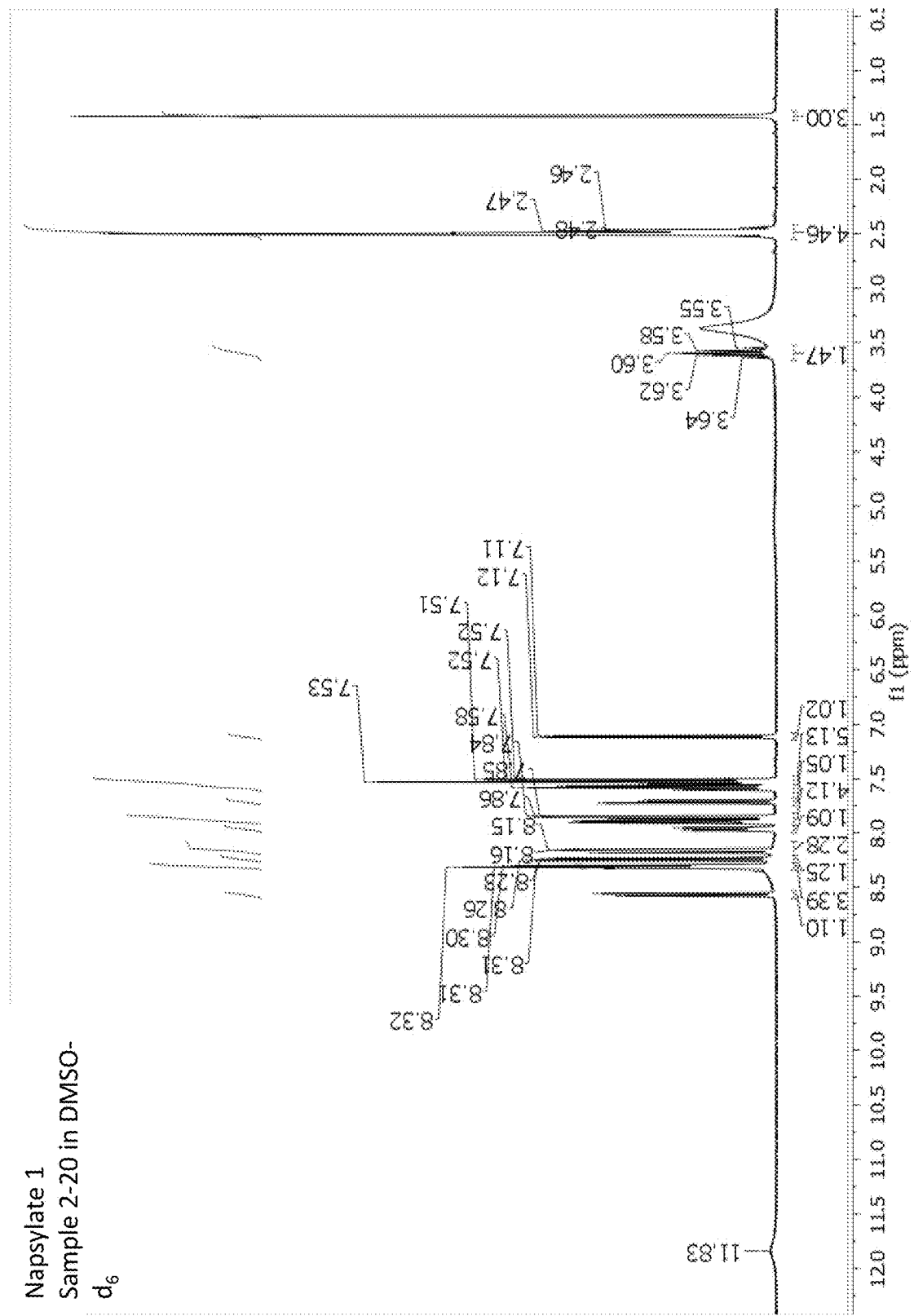
FIG. 57 shows the $^1$H NMR in DMSO-$d_6$ of Napsylate 1 (Sample 2-20).

The $^1$H NMR spectrum was consistent with a mono-salt and no organic solvent was observed in the spectrum. A 3.9% weight loss (FIG. 58) was observed upon heating the sample attributable to water based on the lack of organic solvent in the $^1$H NMR spectrum (FIG. 57). A sesqui-hydrate of a mono-napsylate salt of linsitinib would be expected to have 4.1% water in the sample. Multiple thermal events were observed in the DSC indicating a complicated thermal profile. Additional investigation via hot-stage microscopy would be needed to confirm the nature of these events. Characterization results indicate that Napsylate 1 is a potentially hydrated mono-salt of linsitinib.

Example 9: Linsitinib Crystalline Salt Form Phosphate 1

Slurrying an equimolar amount of linsitinib and phosphoric acid in acetonitrile at 70° C. produced a unique phase designated Phosphate 1. Specifically, 25.0 mg of linsitinib was added to 0.5 mL of acetonitrile. The sample was heated to 70° C. before 4.1 µL of phosphoric acid (85% w/w aqueous solution) was added producing a yellow suspension of chunky solids. After 4 days of equilibration a yellow slurry was produced with a light pink residue above the liquid level on the walls. The suspension was filtered and the solids dried under ambient conditions overnight producing light yellow solids.

Figure 60:
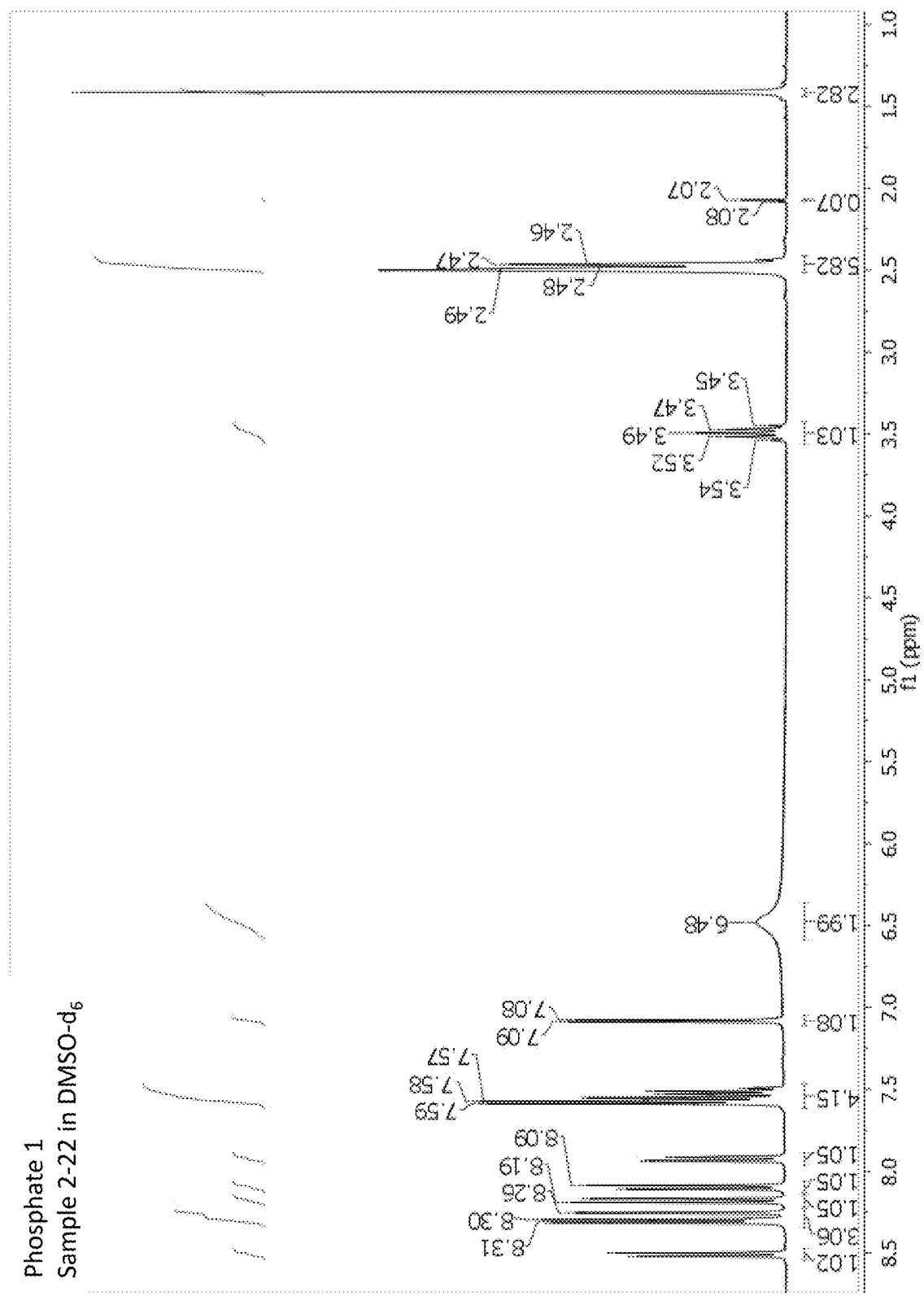
FIG. 60 shows the $^1$H NMR in DMSO-$d_6$ of Phosphate 1 (Sample 2-22).

The $^1$H NMR spectrum of the sample was consistent with linsitinib but did show some peak shifting compared to the free base, suggestive of salt formation; however, the stoichiometry of the potential salt was not determined. Residual acetonitrile was also observed in the spectrum (FIG. 60). A minor weight loss of 0.3% was observed upon heating likely attributable to the trace acetonitrile observed in the $^1$H NMR spectrum indicating the sample is anhydrous/unsolvated (FIG. 60). A broad, overlapping endotherm-exotherm is observed around 160 and 181° C. in the DSC, respectively that could be attributable to a potential melt/recrystallization event. A final major endotherm is observed at 229 that is likely attributable to a melt/decomposition event based on the change in weight observed in the TGA at that temperature. (FIG. 61). Characterization results indicate that Phosphate 1 is anhydrous/unsolvated.

Example 10: Linsitinib Crystalline Salt Form HCl 1

Figure 64:
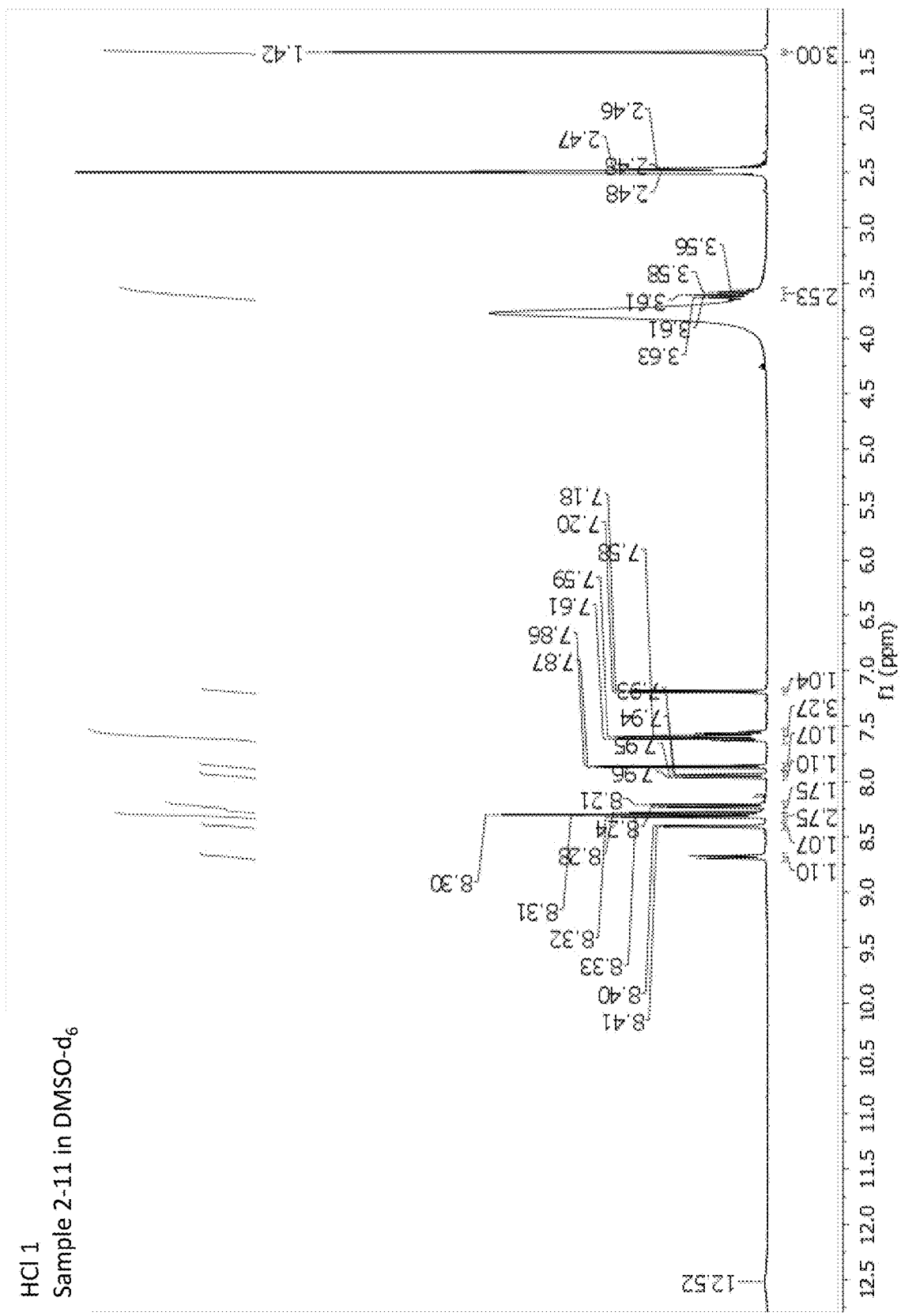
FIG. 64 shows the $^1$H NMR in DMSO-$d_6$ of HCl 1 (Sample 2-11).

HCl 1 was generated via evaporation of a solution containing 1:1 linsitinib:acid in tetrahydrofuran (THF)/water at 70° C. PXRD analysis of the sample after capped storage at room temperature for 17 days showed no significant changes indicating the sample is physically stable under these conditions. No evidence of organic solvent was observed in the $^1$H NMR spectrum of the sample (FIG. 64). The spectrum showed peak shifting compared to the as-received linsitinib free base suggestive of salt formation however the stoichiometry of the potential salt was not determined. Thermal analysis showed consistent weight loss upon heating including 12.5% weight loss to 76° C. with a corresponding broad endotherm at 104° C. in the DSC (FIG. 65). The weight loss is likely due to water and potentially evolution of hydrochloric acid.

Example 11: Scale Up of Selected Crystalline Salts of Linsitinib

Three salts were selected for solubility assessment, Phosphate 1, L-Malate 1, and Esylate 1. The phosphate and malate were selected based on their unsolvated/anhydrous nature. While Esylate 1 appeared hydrated, hydrates may often be developable if they have suitable physical properties. Thermal analysis also suggested the potential for additional forms of the salt to exist. Ethanesulfonic acid is also a stronger acid compared to phosphoric and L-Malic acid and may have an impact on the corresponding aqueous solubility (see Section 3.5).

In order to generate sufficient material for the solubility data, the salts were prepared at about 1.5 g and about 2.0 g scale. The salts were prepared using conditions that were similar to those used to prepare the salts initially at small scale. Each of the scale up experiments successfully generated the targeted salt on the basis of PXRD.

Esylate 1 Scale Up

For the 1.5 g scale up of Esylate 1, 1.5002 g of linsitinib was combined with 20 mL of isopropanol and 305.6 µL of ethanesulfonic acid (95% w/v) and heated to 75° C., producing a yellow slurry. The sample was seeded with a small amount of Esylate 1 and stirred overnight producing a yellow slurry. The suspension was cooled and filtered producing light-yellow solids. Samples were dried overnight under ambient conditions producing an off-white slightly sticky powder. 1.8738 g of material was recovered.

For the 2.0 g scale up of Esylate 1, 2.0014 g of linsitinib (A combination of TCL18673 and TCL17230 used as starting material) and 25 mL of isopropanol were added to a flask and stirred at 75° C. 407.6 μL of ethanesulfonic acid (95% w/v) was added dropwise producing a thick light-yellow slurry within a few minutes. The sample was seeded with a spatula tip of Esylate 1. The sample was stirred overnight at 75° C. producing a yellow slurry. The sample was vacuum filtered and the solids were allowed to air dry in the hood overnight producing off-white/yellow solids. 2.4960 g of material was recovered.

L-Malate 1 Scale Up

For the 1.5 g scale up of L-Malate 1, 1.5006 g of linsitinib was combined with 0.4774 g of L-malic acid and 25 mL of acetonitrile producing a yellow slurry. The sample was seeded with a small amount of L-Malate 1. A yellow slurry was produced after overnight stirring at room temperature. The solids were isolated via vacuum filtration producing damp solids that were allowed to dry overnight at ambient conditions. Solid chunks were produced which were gently ground with a spatula to produce an off-white powder. 1.7289 g of material was recovered.

For the 2.0 g scale up of L-Malate 1, 2.0095 g of linsitinib (TCL17230 used as starting material) was added to a flask with a stir bar, 0.6393 g of malic acid and 35 mL of acetonitrile. Stirring the sample resulted in a yellow slurry that was seeded with a small spatula tip of L-Malate 1. The sample was allowed to stir overnight at room temperature producing an off-white slurry. The solids were isolated via vacuum filtration. The isolated solids were allowed to dry in the hood overnight resulting in off-white/slightly yellow solids. 2.6167 g of material was recovered.

Phosphate 1 Scale Up

For the 1.5 g scale up of Phosphate 1, 1.5004 g of linsitinib was added to 25 mL of acetonitrile. The sample was heated to 70° C. before 241.4 μL of phosphoric acid (85% w/w aqueous solution). The sample was seeded with Phosphate 1 (Sample 2-22) and left to stir overnight at room temperature producing a yellow slurry. The solids were vacuum filtered producing yellow solids that were left to dry overnight at ambient conditions. Brittle solid chunks were produced which were crushed to a yellow powder using a spatula. 1.6696 g of material were produced.

TABLE 26

Scale-up of selected salts

| Coformer | Conditions | Result |
|---|---|---|
| Ethanesulfonic acid (1.5 g scale) | Slurry in isopropanol, 75° C., 1 day | Esylate 1 |
| Ethanesulfonic acid (2.0 g scale) | Slurry in IPA at 75° C., 1 day | Esylate 1 |
| L-Malic acid (1.5 g scale) | Slurry in acetonitrile at RT, 1 day | L-Malate 1 |
| L-Malic acid (2.0 g scale) | Slurry in acetonitrile at RT, 1 day | L-Malate 1 |
| Phosphoric acid (1.5 g scale) | Slurry in acetonitrile, 75° C., 1 day | Phosphate 1 |

Example 12: Linsitinib Free Base Crystalline Polymorph Form B

An attempt to make a cocrystal via an equimolar slurry of linsitinib and benzamide generated a unique crystalline phase. 25.2 mg of linsitinib and 8.0 mg of benzamide were contacted with 0.5 mL of ethanol producing an off-white slurry. The sample was allowed to slurry at room temperature for 3 days producing a light-yellow suspension. Yellow solids were produced after filtration and drying of the material overnight at ambient.

Figure 73:
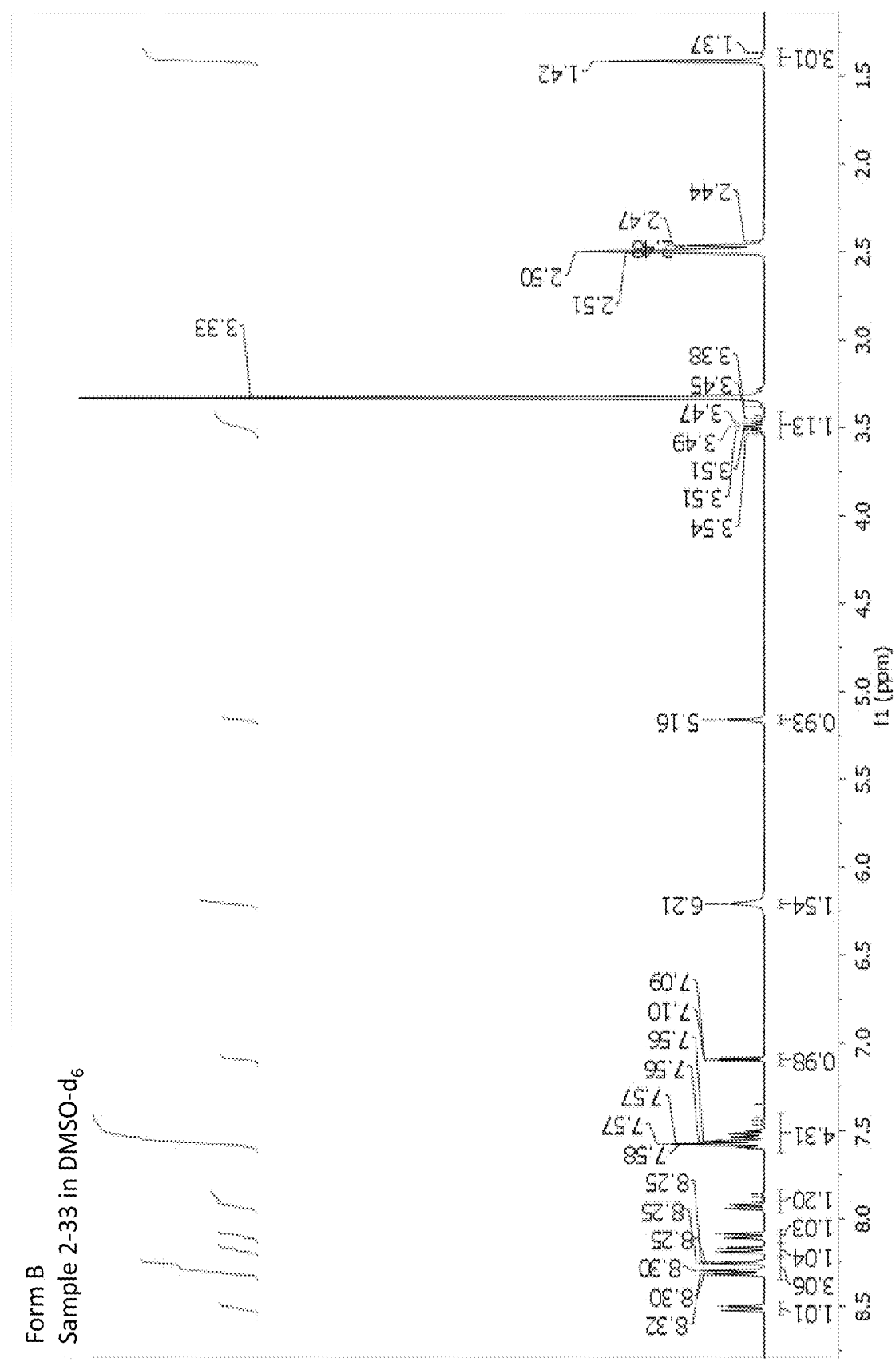
FIG. 73 shows the $^1$H NMR in DMSO-$d_6$ of Form B free base from benzamide coformer (Sample 2-33 after 23 days of storage at RT).

The product was analyzed by powder x-ray diffraction spectroscopy. The PXRD pattern was visually similar to previously identified Form B, as shown in FIG. 71 and FIG. 72. The sample was further characterized by $^1$H NMR spectroscopy (FIG. 73) and confirmed the presence of the linsitinib and the absence of the benzamide. No residual solvent was observed in the spectrum. Thermal analysis of the sample (FIG. 74) showed a 3.7% weight loss to 75° C. with a corresponding broad endotherm observed in the DSC trace at 89° C. An additional weight loss of 1.1% was observed to 150° C. along with a large endotherm potentially attributable to melting around 247° C. Form B was a reported mono-hydrate and the weight loss observed is similar to a theoretical mono-hydrate (4.1%).

Example 13: Linsitinib Free Base Crystalline Polymorph Form H

An attempt to make a cocrystal via an equimolar slurry of linsitinib and 4-aminosalicylic acid generated a unique crystalline phase. In one instance, 24.9 mg of linsitinib, 10.0 mg of 4-aminosalicylic acid, and 0.5 mL of methanol were combined producing an off-white suspension. After stirring for 3 days, an off-white/light-brown suspension was observed. The sample was filtered producing pale purple solids and a clear brown filtrate. After overnight drying at ambient conditions, shrinking of the solids was observed and a light brown powder was produced upon crushing using a spatula.

Form H was observed from several other cocrystal screening experiments, each involving methanol as the organic solvent. Form H was also obtained as a physical mixture with the starting coformer in experiments with adenine, L-arginine, L-threonine.

Thermal analysis of Form H showed a 4.0% weight loss to 100° C. with a corresponding broad shallow endotherm at 93° C. in the DSC (FIG. 77). Additional endotherms and exotherms were observed in the DSC thermogram including overlapping major endotherms at 243 and 247° C. which may be due in part to decomposition based on the weight change in the TGA.

The weight loss was anticipated to be associated with methanol, however $^1$H NMR analysis of the sample indicated that there was no organic solvent in the sample. The NMR analysis was conducted after the thermal analysis and it was speculated that potentially the solvent was lost upon storage at ambient temperature. Reanalysis of the material was consistent with the initial data indicating that the weight loss is likely due to water. The weight loss is consistent with a theoretical mono-hydrate of linsitinib free base.

Example 14: Linsitinib Free Base Crystalline Polymorph Form I

Linsitinib Form I was originally generated from a salt formation attempt with 2-hydroxyethanesulfonic acid in acetonitrile. In one instance, 25.0 mg of linsitinib was slurried with 8.8 mg of 2-hydroxyethanesulfonic acid sodium salt in 0.5 mL of acetonitrile at room temperature. The slurry was initially observed to be white but turned light yellow after one hour of stirring. The solids were isolated after 6 days of stirring at room temperature. The solids were dried overnight at ambient and produced white solids.

Form I was also observed when a sample of Form J generated from a cocrystal attempt with vanillin (see section 3.3.4 below for additional details) was stored at room temperature in a capped vial for 20 days. $^1$H NMR spectroscopy of the sample indicated that the sample had a minor (<0.1 mol/mol) amount of residual vanillin. The $^1$H NMR spectrum also confirmed the presence of linsitinib free base (FIG. 75). No organic solvent was observed in the spectrum. Thermal analysis of Form I showed 1.8% weight loss upon heating to 163° C. (FIG. 81). The DSC shows the presence of several thermal events indicating a complex thermal profile including an exotherm at 173° C. that may be due to recrystallization of the sample. Additional investigation such as hot-stage microscopy would be needed to confirm the nature of these events. The weight loss observed suggests that Form I may be hydrated and the weight loss observed would be consistent with a potential hemi-hydrate (2.1% theoretical).

Example 15: Linsitinib Free Base Crystalline Polymorph Form J

Form J was generated from a cocrystal attempt with vanillin in acetone. 25.8 mg of linsitinib and 10.2 mg of vanillin were combined with 0.5 mL of acetone producing an off-white slurry that was allowed to stir at room temperature for 3 days. The slurry turned yellow during the equilibration and the solids were isolated from the suspension via filtration. Solids were allowed to dry overnight at ambient conditions producing light yellow solids.

Figure 85:
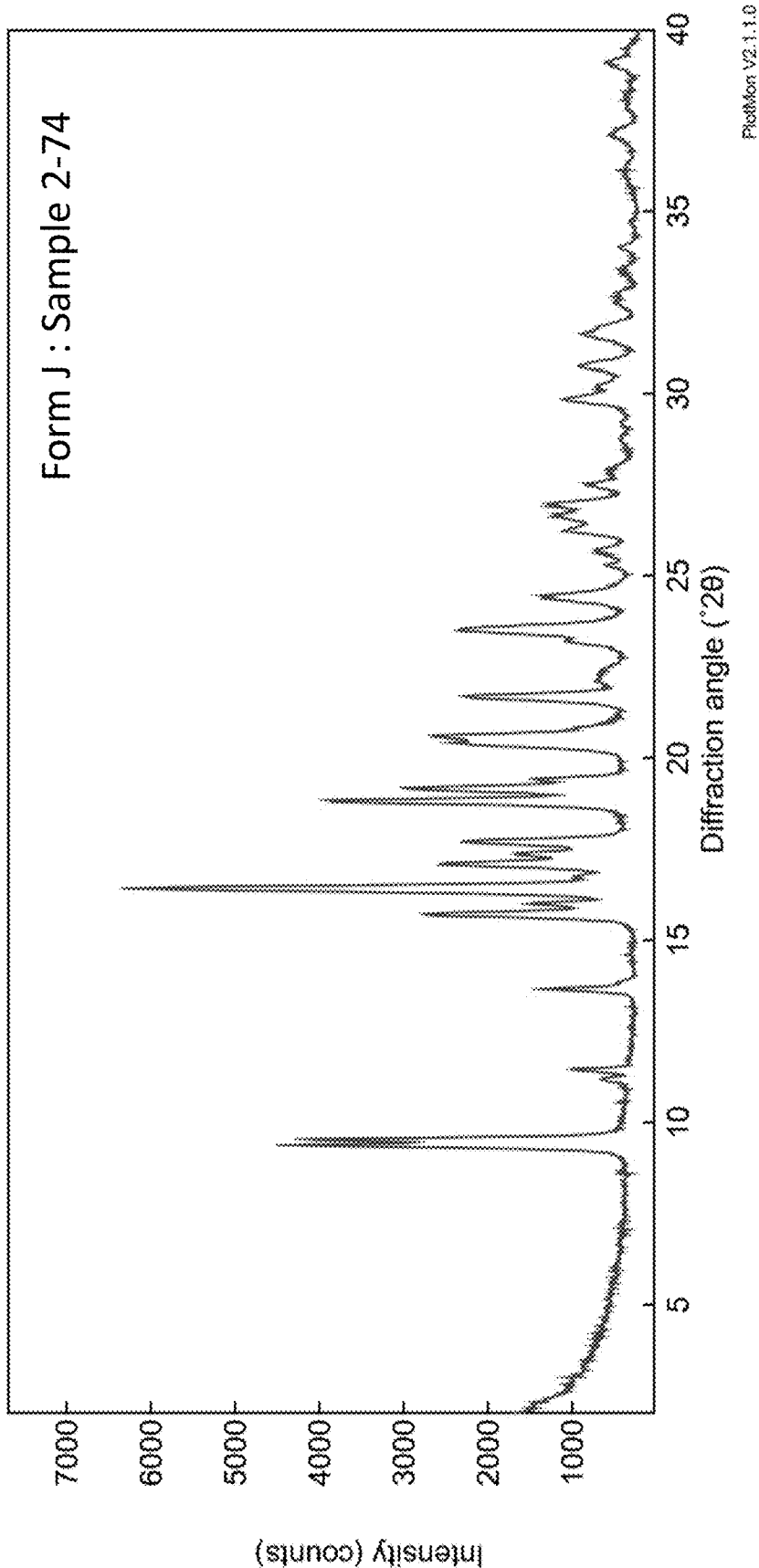
FIG. 85 shows the PXRD of Form J from Vanillin (Sample 2-74).

The sample was initially analyzed by PXRD and stored at ambient temperature in a capped vial. (FIG. 85). After storage under at ambient for 20 days the sample was reanalyzed by PXRD and found to have converted to Form I indicating that Form J is metastable under ambient storage.

Example 16: Linsitinib Free Base Crystalline Polymorph Form K

Form K was generated once during a cocrystal attempt with sorbic acid in acetone. 25.2 mg of linsitinib, 7.4 mg of sorbic and 0.5 mL of acetone were all combine to produce a yellow slurry at room temperature. After 6 days of stirring, a dark yellow slurry was generated. Yellow solids were obtained after isolation via filtration and overnight drying at ambient conditions.

Figure 87:
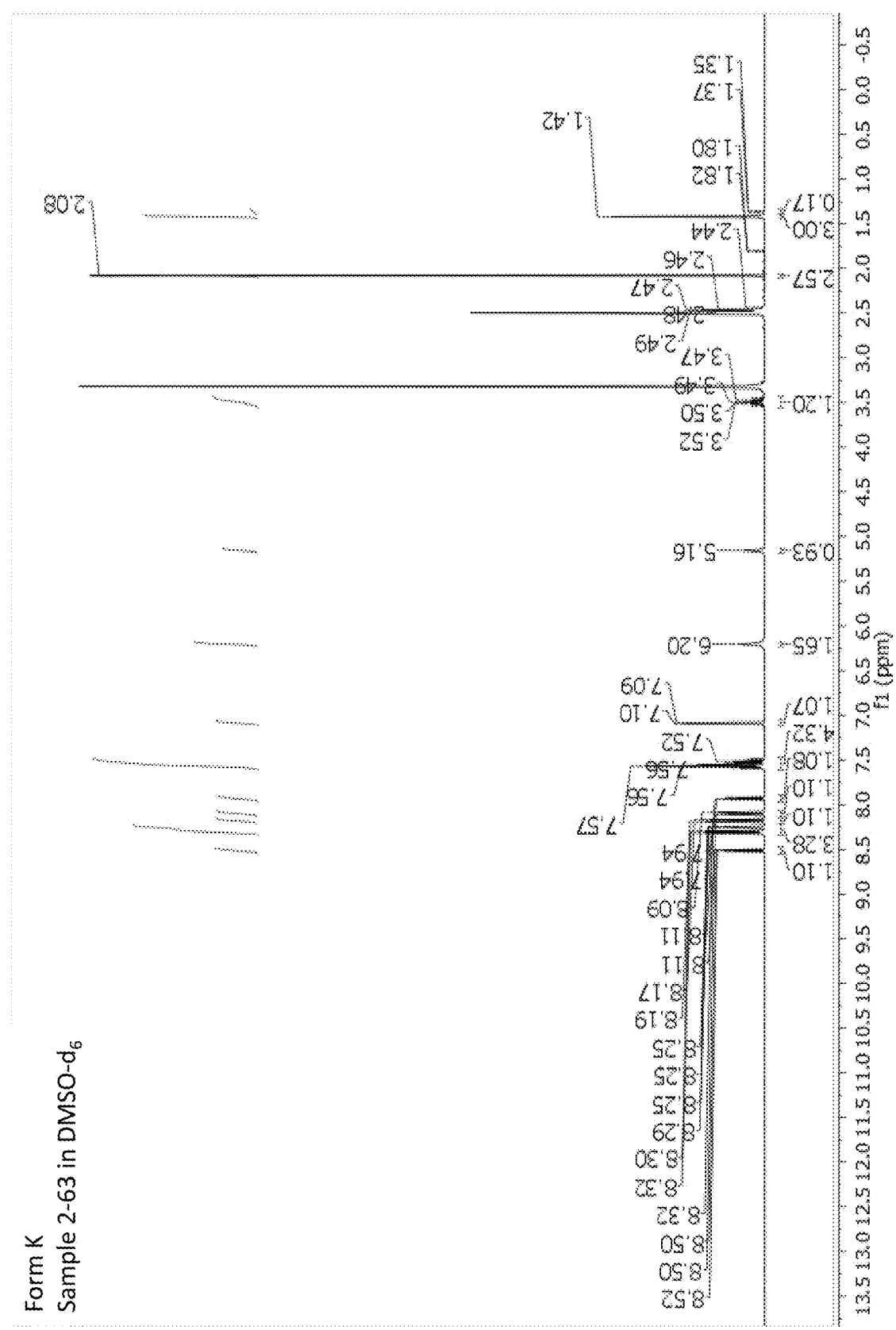
FIG. 87 shows the $^1$H NMR in DMSO-$d_6$ of Form K free base from sorbic acid (Sample 2-63).

The $^1$H NMR spectrum was consistent with linsitinib with no evidence of the sorbic acid present (FIG. 87). The spectrum also showed the presence of 0.4 equivalents of acetone.

Thermal analysis of the sample (FIG. 88) showed a step change weight loss of 4.6% (equivalent to 0.4 mols of acetone) upon heating. Additional thermal events are observed in the DSC including an overlapped endotherm and exotherm at 156 and 174° C. respectively which could suggest possible recrystallization of the sample though additional investigation would be needed to confirm the nature of the events. Similar to Form H, double endothermic events were observed at 241° C. and 247° C.

Example 17: Solubility of Crystalline Linsitinib Salt Forms

The pH-solubility of selected salts (Phosphate 1, L-Malate 1, Esylate 1, and Esylate 2) was evaluated and compared with linsitinib free base. The solubility analysis was conducted in a manner consistent with a previous study that was performed with linsitinib free base. Aqueous solutions were prepared between pH 1.5 and pH 6.5 in 0.5 pH unit increments via titration of the solution using NaOH and HCl. For each salt or the free base, an attempt was made to reach saturation in each of the solutions by adding sufficient material to the solution such that excess solids remained. If saturation was achieved, the pH of the solution was measured and adjusted to the target pH and additional material was added if needed. The samples were then equilibrated overnight. The final pH of the solution was measured, the solids were filtered and selected samples were analyzed by PXRD. The concentration of linsitinib in the filtrate was quantitated by HPLC (diluted as needed). In some cases, significant drift (+1 pH unit or more) of the final pH from the target pH was observed after the overnight equilibration.

Figure 89:
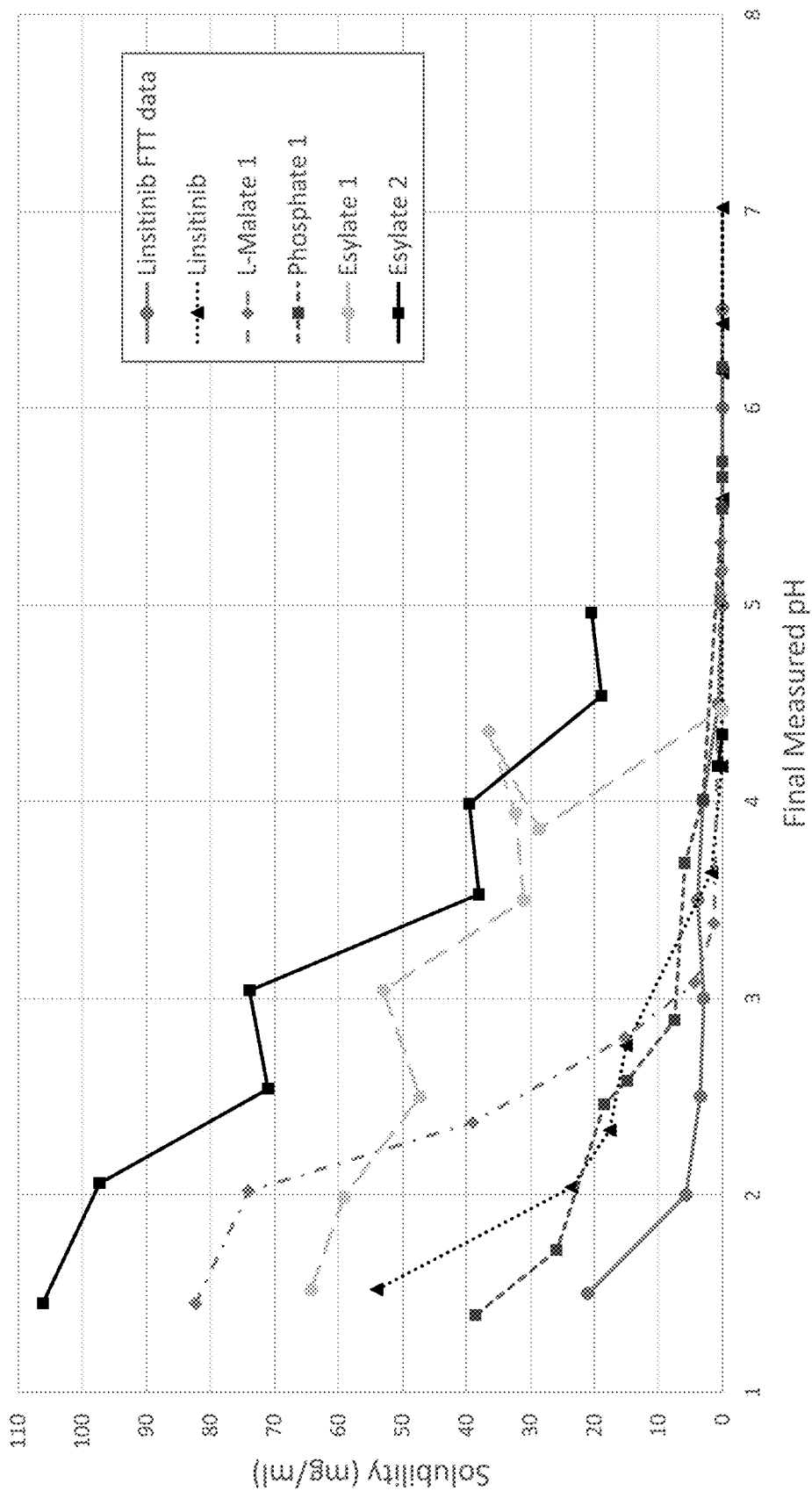
FIG. 89 show the pH-solubility profile of linsitinib free base and its salts. Data points circled in black were experiments where no solids were present after 24 hours and are not equilibrium solubility values.

A summary of the solubility data along with previously collected data for the free base is shown in Table 27. The pH-solubility data is shown graphically in FIG. 89. The profiles of each of the samples were consistent with a basic compound showing poor solubility at higher pH and significantly improved solubility at more acidic conditions. The high solubility at low pH suggests that linsitinib (in any form) is likely to rapidly dissolve in the acidic environment of the stomach. Indeed, it should be noted that in the majority of the low pH systems, higher initial dissolution/solubility was observed followed by precipitation of the material from solution upon longer equilibration. In some cases, precipitation did not occur and saturation of the system was not achieved.

TABLE 27

| pH-Solubility (mg/mL) of Linsitinib Free Base and Salts | | | | | | | | |
|---|---|---|---|---|---|---|---|---|
| | pH 1.5 | | pH 2.0 | | pH 2.5 | | pH 3.0 | |
| | Final pH | Solubility | Final pH | Solubility | Final pH | Solubility | Final pH | Solubility |
| Linsitinib FTT data | 1.5 | 21.0397 | 2.0 | 5.7281 | 2.5 | 3.4777 | 3.0 | 2.9329 |
| Linsitinib | 1.52 | 54.0170 | 2.04 | 23.5669 | 2.33 | 17.6118 | 2.76 | 15.0455 |
| L-Malate 1 | 1.45 | 82.3339* | 2.02 | 74.0499* | 2.37 | 39.0410 | 2.80 | 15.3379 |
| Phosphate 1 | 1.39 | 38.5732 | 1.72 | 25.9110 | 2.46 | 18.4479 | 2.58 | 14.9046 |
| Esylate 1 | 1.52 | 64.2843* | 1.99 | 59.1411* | 2.50 | 47.2960* | 3.04 | 52.9793* |
| Esylate 2 | 1.45 | 106.19 | 2.06 | 97.33 | 2.54 | 71.00 | 3.04 | 73.90 |

TABLE 27-continued

| | pH 3.5 | | pH 4.0 | | pH 4.5 | | pH 5.0 | |
|---|---|---|---|---|---|---|---|---|
| | Final pH | Solubility | Final pH | Solubility | Final pH | Solubility | Final pH | Solubility |
| Linsitinib FTT data | 3.5 | 3.8629 | 4.0 | 3.0302 | 4.5 | 0.6117 | 5.0 | 0.0074 |
| Linsitinib | 3.64 | 1.7264 | 4.18 | 0.1158 | 5.54 | 0.0051 | 6.18 | 0.0012 |
| L-Malate 1 | 3.08 | 4.2948 | 3.38 | 1.3359 | 5.05 | 0.3367 | 5.16 | 0.2743 |
| Phosphate 1 | 2.89 | 7.5028 | 3.69 | 5.8685 | 4.01 | 3.0382 | 5.49 | 0.0458 |
| Esylate 1 | 3.50 | 31.0107* | 3.94 | 32.3308* | 4.36 | 36.5639* | 3.86 | 28.6723 |
| Esylate 2 | 3.53 | 38.04 | 3.99 | 39.56 | 4.54 | 18.90 | 4.96 | 20.46 |

| | pH 5.5 | | pH 6.0 | | PH 6.5 | |
|---|---|---|---|---|---|---|
| | Final pH | Solubility | Final pH | Solubility | Final pH | Solubility |
| Linsitinib FTT data | 5.5 | 0.0010 | 6.0 | 0.0011 | 6.5 | 0.0012 |
| Linsitinib | 6.43 | 0.0017 | 7.02 | 0.0010 | 6.43 | 0.0012 |
| L-Malate 1 | 5.32 | 0.1918 | 5.50 | 0.1216 | 5.18 | 0.0165 |
| Phosphate 1 | 5.73 | 0.0350 | 5.65 | 0.0046 | 6.21 | 0.0010 |
| Esylate 1 | 4.47 | 0.0517 | 9.08 | — | 4.46 | 0.0296 |
| Esylate 2 | 5.48 | | 4.18 | 0.70 | 4.34 | 0.002 |

*Vials were clear solutions with no precipitate after 24 hours. Concentrations reported are not equilibrium values.

L-Malate 1, Esylate 1 and Esylate 2 showed significantly higher solubility at lower pH (<3) than the free base or Phosphate 1. Esylate 1 and 2 showed the highest solubility compared to the free base and other salts between pH 3 and pH 4. The data indicates that these salts may offer solubility enhancement compared to the free base at these higher pHs which could be important if higher pH stomach conditions are anticipated (as occurs with some patient populations).

Figure 90:
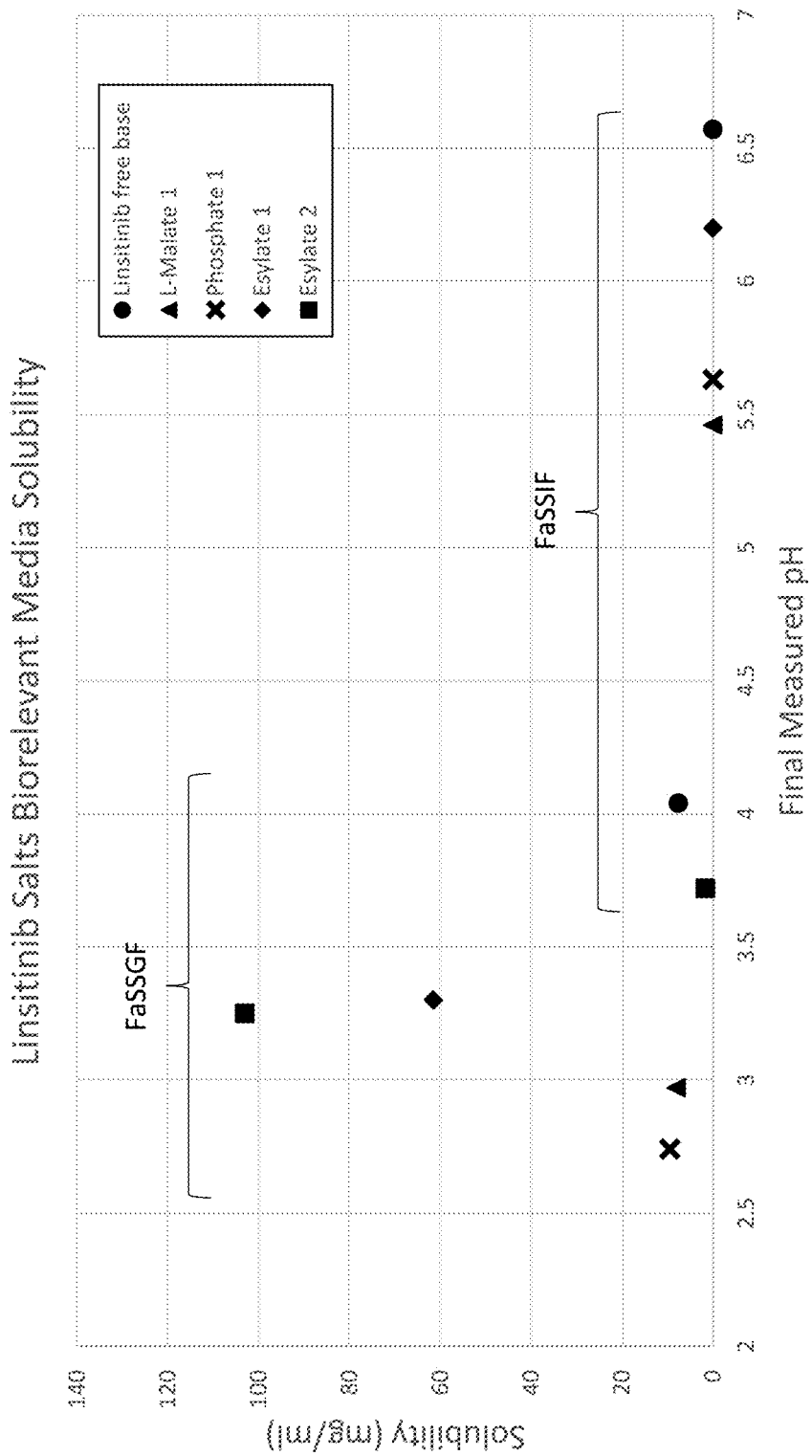
FIG. 90 shows the solubility of linsitinib free base and its salts in biorelevant media.

In addition to the pH-solubility data, a comparison of the equilibrium solubility of linsitinib free base and salts in two bio-relevant media (Table 28), fasted state simulated gastric fluid (FaSSGF pH 1.6) and intestinal fluid (FaSSIF pH 6.5) was completed. The results are summarized in Table 4. Similar to the pH-solubility data, the solubility in FaSSGF (pH 1.6) was significantly higher than FaSSIF (pH 6.5) for each material tested (FIG. 90). The solubility for L-Malate 1 and Phosphate 1 were largely comparable to the solubility of the free base; however, Esylate 1 and Esylate 2 showed the highest solubility by a significant margin. A saturated solution of Esylate 1 was not achieved during this study and therefore the equilibrium solubility could be higher than determined. It should be noted that variability of almost a full pH unit was noted among the samples making a direct comparison more challenging. No clear trend was observed in the FaSSIF data with some of the salts (L-Malate 1) showing higher solubility than the free base while others showed lower solubility (Esylate 1).

The solubility results suggest a solubility advantage of L-Malate 1 and Esylate 2 compared to the free base.

TABLE 28

Solubility (mg/mL) of Linsitinib Free Base and Salts in Bio-relevant Media

| | FaSSGF (pH 1.6) | | FaSSIF (pH 6.5) | |
|---|---|---|---|---|
| Compound | Final pH | Solubility | Final pH | Solubility |
| Linsitinib free base | 4.04 | 7.672 | 6.57 | 0.025 |
| L-Malate 1 | 2.97 | 8.130 | 5.46 | 0.044 |
| Phosphate 1 | 2.74 | 9.513 | 5.63 | 0.009 |
| Esylate 1 | 3.30 | 61.572$^a$ | 6.20 | 0.006 |
| Esylate 2 | 3.25 | 103.10 | 3.72 | 1.62 |

$^a$Sample was not visually saturated with compound (clear solution). Solubility could be higher than concentration determined The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A crystalline Form 2 of linsitinib esylate salt having the structure of Formula II:

(II)

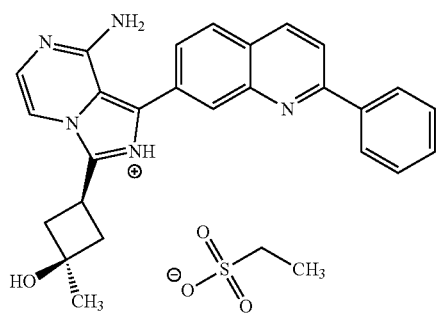

wherein the crystalline Form 2 of linsitinib esylate salt is characterized by a powder x-ray diffraction (PXRD) pattern comprising at least three peaks selected from the group consisting of 6.74±0.20°2θ, 8.92±0.20°2θ, 10.26±0.20°2θ, 11.04 0.20°2θ, 14.76±0.20°2θ, 16.80±0.20°2θ, 17.60±0.20°2θ, 17.90±0.20°2θ, 18.56 0.20°2θ, 20.24±0.20°2θ, 20.56±0.20°2θ, 20.74±0.20°2θ, 24.58±0.20°2θ, 25.80±0.20°2θ, 26.12±0.20°2θ, and 27.34±0.20°2θ, as determined on a diffractometer using Cu-Kα radiation.

2. The crystalline Form 2 of linsitinib esylate salt according to claim 1, which is further characterized by a powder x-ray diffraction (PXRD) pattern comprising at least six peaks selected from the group consisting of 6.74±0.20°2θ, 8.92±0.20°2θ, 10.26±0.20°2θ, 11.04±0.20°2θ, 14.76±0.20°2θ, 16.80±0.20°2θ, 17.60±0.20°2θ, 17.90±0.20°2θ, 18.56±0.20°2θ, 20.24±0.20°2θ, 20.56±0.20°2θ, 20.74±0.20°2θ, 24.58±0.20°2θ, 25.80±0.20°2θ, 26.12±0.20°2θ, and 27.34±0.20°2θ, as determined on a diffractometer using Cu-Kα radiation.

3. The crystalline Form 2 of linsitinib esylate salt according to claim 1, which is further characterized by a powder x-ray diffraction (PXRD) pattern comprising at least ten peaks selected from the group consisting of 6.74±0.20°2θ, 8.92±0.20°2θ, 10.26±0.20°2θ, 11.04±0.20°2θ, 14.76±0.20°2θ, 16.80±0.20°2θ, 17.60±0.20°2θ, 17.90±0.20°2θ, 18.56±0.20°2θ, 20.24±0.20°2θ, 20.56±0.20°2θ, 20.74±0.20°2θ, 24.58±0.20°2θ, 25.80±0.20°2θ, 26.12±0.20°2θ, and 27.34±0.20°2θ, as determined on a diffractometer using Cu-Kα radiation.

4. The crystalline Form 2 of linsitinib esylate salt according to claim 1, which is further characterized by a powder x-ray diffraction (PXRD) pattern comprising peaks at 6.74±0.20°2θ, 8.92±0.20°2θ, 10.26±0.20°2θ, 11.04±0.20°2θ, 14.76±0.20°2θ, 16.80±0.20°2θ, 17.60±0.20°2θ, 17.90±0.20°2θ, 18.56±0.20°2θ, 20.24±0.20°2θ, 20.56±0.20°2θ, 20.74±0.20°2θ, 24.58±0.20°2θ, 25.80±0.20°2θ, 26.12±0.20°2θ, and 27.34±0.20°2θ, as determined on a diffractometer using Cu-Kα radiation.

5. The crystalline Form 2 of linsitinib esylate salt according to claim 1, which is further characterized by a powder x-ray diffraction (PXRD) pattern resembling that of FIG. 8, as determined on a diffractometer using Cu-Kα radiation.

6. The crystalline Form 2 of linsitinib esylate salt according to claim 1, which is further characterized by a DSC thermogram resembling that of FIG. 10.

7. The crystalline Form 2 of linsitinib esylate salt according to claim 1, which is further characterized by a TGA signal resembling that of FIG. 10.

8. The crystalline Form 2 of linsitinib esylate salt according to claim 1 having an orthorhombic crystal structure.

9. The crystalline Form 2 of linsitinib esylate salt according to claim 1 having a P2$_1$2$_1$2$_1$ space group.

10. The crystalline Form 2 of linsitinib esylate salt according to claim 1 having a unit cell with the following parameters:

| | |
|---|---|
| a (Å) | 7.4100(8) |
| b (Å) | 17.4900(17) |
| c (Å) | 19.769(2) |
| α (°) | 90 |
| β (°) | 90 |
| γ (°) | 90 |
| volume (Å3) | 2562.0(5). |

11. A composition comprising the crystalline Form 2 of linsitinib esylate salt according to claim 1, wherein the crystalline Form 2 of linsitinib esylate salt is present at a level of at least about 95% or more by weight of the total amount of linsitinib esylate salt in the composition.

12. A pharmaceutical composition comprising:
the crystalline Form 2 of linsitinib esylate salt according to claim 1; and
a pharmaceutically acceptable excipient.

13. A pharmaceutical composition comprising:
the crystalline Form 2 of linsitinib esylate salt according to claim 3; and
a pharmaceutically acceptable excipient.

14. A method of treating a condition mediated by human insulin-like growth factor-1 receptor (IGF-1R) or insulin receptor (IR), comprising administering to a subject in need thereof a therapeutically effective amount of the crystalline Form 2 of linsitinib esylate salt according to claim 1.

15. A method of treating thyroid eye disease in a subject in need thereof, comprising administering to a subject in need thereof a therapeutically effective amount of the crystalline Form 2 of linsitinib esylate salt according to claim 1.

16. A crystalline Form 1 of linsitinib L-malate salt having the structure (III)

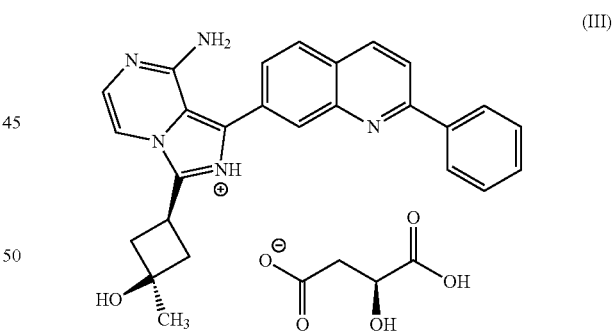

wherein the crystalline Form 1 of linsitinib L-malate salt is characterized by a powder x-ray diffraction (PXRD) pattern comprising at least three peaks selected from the group consisting of 5.42±0.2° 2θ, 8.68±0.2° 2θ, 11.88±0.2° 2θ, 12.40±0.2° 2θ, 16.24±0.2° 2θ, 17.36±0.2° 2θ, 17.96±0.2° 2θ, 18.22±0.2° 2θ, 19.20±0.2° 2θ, 20.88±0.2° 2θ, 22.08±0.2° 2θ, 22.58±0.2° 2θ, 22.90±0.2° 2θ, 23.86±0.2° 2θ, 24.44±0.2° 2θ, 24.92±0.2° 2θ, 25.66±0.2° 2θ, 26.1±0.2° 2θ, 28.58±0.2° 2θ, or 29.44±0.2° 2θ, as determined on a diffractometer using Cu-Kα radiation.

17. The crystalline Form 1 of linsitinib L-malate salt according to claim 16, which is further characterized by a powder x-ray diffraction (PXRD) pattern comprising at least six peaks selected from the group consisting of 5.42±0.2° 2θ, 8.68±0.2° 2θ, 11.88±0.2° 2θ, 12.40±0.2° 2θ, 16.24±0.2° 2θ, 17.36±0.2° 2θ, 17.96±0.2° 2θ, 18.22±0.2° 2θ, 19.20±0.2° 2θ, 20.88±0.2° 2θ, 22.08±0.2° 2θ, 22.58±0.2° 2θ, 22.90±0.2° 2θ, 23.86±0.2° 2θ, 24.44±0.2° 2θ, 24.92±0.2° 2θ, 25.66±0.2° 2θ, 26.1±0.2° 2θ, 28.58±0.2° 2θ, or 29.44±0.2° 2θ, as determined on a diffractometer using Cu-Kα radiation.

18. The crystalline Form 1 of linsitinib L-malate salt according to claim 16, which is further characterized by a powder x-ray diffraction (PXRD) pattern comprising at least ten peaks selected from the group consisting of 5.42±0.2°2θ, 8.68±0.2°2θ, 11.88±0.2°2θ, 12.40±0.2°2θ, 16.24±0.2°2θ, 17.36±0.2°2θ, 17.96±0.2°2θ, 18.22±0.2°2θ, 19.20±0.2°2θ, 20.88±0.2°2θ, 22.08±0.2°2θ, 22.58±0.2°2θ, 22.90±0.2°2θ, 23.86±0.2°2θ, 24.44±0.2°2θ, 24.92±0.2°2θ, 25.66±0.2°2θ, 26.1±0.2°2θ, 28.58±0.2°2θ, or 29.44±0.2°2θ, as determined on a diffractometer using Cu-Kα radiation.

19. The crystalline Form 1 of linsitinib L-malate salt according to claim 16, which is further characterized by a powder x-ray diffraction (PXRD) pattern comprising peaks at 5.42±0.2°2θ, 8.68±0.2°2θ, 11.88±0.2°2θ, 12.40±0.2°2θ, 16.24±0.2°2θ, 17.36±0.2°2θ, 17.96±0.2°2θ, 18.22±0.2°2θ, 19.20±0.2°2θ, 20.88±0.2°2θ, 22.08±0.2°2θ, 22.58±0.2°2θ, 22.90±0.2°2θ, 23.86±0.2°2θ, 24.44±0.2°2θ, 24.92±0.2°2θ, 25.66±0.2°2θ, 26.1±0.2°2θ, 28.58±0.2°2θ, and 29.44±0.2°2θ, as determined on a diffractometer using Cu-Kα radiation.

20. The crystalline Form 1 of linsitinib L-malate salt according to claim 16, which is further characterized by a powder x-ray diffraction (PXRD) pattern resembling that of FIG. 33, as determined on a diffractometer using Cu-Kα radiation.

21. The crystalline Form 1 of linsitinib L-malate salt according to claim 16, which is further characterized by a DSC thermogram resembling that of FIG. 35.

22. The crystalline Form 1 of linsitinib L-malate salt according to claim 16, which is further characterized by a TGA signal resembling that of FIG. 35.

23. A composition comprising the crystalline Form 1 of linsitinib L-malate salt according to claim 16, wherein the crystalline Form 1 of linsitinib L-malate salt is present at a level of at least about 95% or more by weight of the total amount of linsitinib L-malate salt in the composition.

24. A pharmaceutical composition comprising:
the crystalline Form 1 of linsitinib L-malate salt according to claim 16; and
a pharmaceutically acceptable excipient.

25. A pharmaceutical composition comprising:
the crystalline Form 1 of linsitinib L-malate salt according to claim 18; and
a pharmaceutically acceptable excipient.

26. A method of treating a condition mediated by human insulin-like growth factor-1 receptor (IGF-1R) or insulin receptor (IR), comprising administering to a subject in need thereof a therapeutically effective amount of the crystalline Form 1 of linsitinib L-malate salt according to claim 16.

27. A method of treating thyroid eye disease in a subject in need thereof, comprising administering to a subject in need thereof a therapeutically effective amount of the crystalline Form 1 of linsitinib L-malate salt according to claim 16.

* * * * *

UNITED STATES PATENT AND TRADEMARK OFFICE
CERTIFICATE OF CORRECTION

PATENT NO. : 11,976,074 B1
APPLICATION NO. : 18/341620
DATED : May 7, 2024
INVENTOR(S) : Ronald Dadino et al.

It is certified that error appears in the above-identified patent and that said Letters Patent is hereby corrected as shown below:

In the Claims

Column 81, Claim 1, Line 20:
"11.04 0.20 °2θ,"
Should read:
--11.04±0.20 °2θ,--.

Column 81, Claim 1, Lines 21-22:
"18.56 0.20 °2θ,"
Should read:
--18.56±0.20 °2θ,--.

Column 82, Claim 16, Line 38:
"the structure"
Should read:
--the structure of formula III:--.

Signed and Sealed this
Twenty-third Day of July, 2024

Katherine Kelly Vidal
*Director of the United States Patent and Trademark Office*